United States Patent
Nagano et al.

(10) Patent No.: US 10,189,843 B2
(45) Date of Patent: Jan. 29, 2019

(54) FUSED PYRAZOLE DERIVATIVE HAVING AUTOTAXIN INHIBITORY ACTIVITY

(71) Applicants: The University of Tokyo, Tokyo (JP); TOHOKU UNIVERSITY, Miyagi (JP); Shionogi & Co., Ltd., Osaka (JP)

(72) Inventors: Tetsuo Nagano, Tokyo (JP); Takayoshi Okabe, Tokyo (JP); Hirotatsu Kojima, Tokyo (JP); Mitsuyasu Kawaguchi, Tokyo (JP); Osamu Nureki, Tokyo (JP); Ryuichiro Ishitani, Tokyo (JP); Hiroshi Nishimasu, Tokyo (JP); Junken Aoki, Sendai (JP); Chiaki Fujikoshi, Toyonaka (JP); Manabu Katou, Toyonaka (JP); Masahide Odan, Toyonaka (JP); Nobuyuki Tanaka, Toyonaka (JP); Yusuke Tateno, Toyonaka (JP); Junji Yamane, Toyonaka (JP)

(73) Assignees: THE UNIVERSITY OF TOKYO, Tokyo (JP); TOHOKU UNIVERSITY, Miyagi (JP); SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 15/120,763

(22) PCT Filed: Feb. 26, 2015

(86) PCT No.: PCT/JP2015/055693
§ 371 (c)(1),
(2) Date: Aug. 23, 2016

(87) PCT Pub. No.: WO2015/129821
PCT Pub. Date: Sep. 3, 2015

(65) Prior Publication Data
US 2016/0376278 A1 Dec. 29, 2016

(30) Foreign Application Priority Data

Feb. 27, 2014 (JP) ................................ 2014-037591
Aug. 29, 2014 (JP) ................................ 2014-176146

(51) Int. Cl.
C07D 487/04 (2006.01)
C07D 491/147 (2006.01)
C07D 519/00 (2006.01)
C07D 487/18 (2006.01)

(52) U.S. Cl.
CPC ......... C07D 487/04 (2013.01); C07D 487/18 (2013.01); C07D 491/147 (2013.01); C07D 519/00 (2013.01)

(58) Field of Classification Search
CPC . C07D 487/04; C07D 487/18; C07D 491/147
See application file for complete search history.

(56) References Cited

U.S. PATENT DOCUMENTS

| 7,476,666 B2 | 1/2009 | Wai et al. | |
| 2007/0082908 A1* | 4/2007 | Nakahira | C07D 487/04 514/243 |
| 2008/0015187 A1 | 1/2008 | Wai et al. | |
| 2009/0312335 A1 | 12/2009 | Wai et al. | |
| 2012/0225844 A1* | 9/2012 | Conn | A61K 31/40 514/63 |
| 2013/0345203 A1 | 12/2013 | Conn et al. | |
| 2013/0345204 A1 | 12/2013 | Conn et al. | |

(Continued)

FOREIGN PATENT DOCUMENTS

| CN | 101367819 | 2/2009 |
| JP | 4-191736 | 7/1992 |

(Continued)

OTHER PUBLICATIONS

Schafer et al 'Failure is an option: learning from unsuccessful proof-of-concept trials' Drug Discovery Today. 12(21/22), p. 913-916, 2008.*
J. G. Cannon 'Analog Design' Burgers Medicinal Chemistry and Drug Discovery, Fifth Edition, vol. 1., p. 783-802, 1995.*
Hong et al 'From bench to clinic and back: Perspective on the 1st IQPC Translational Research conference' Journal of Translational Medicine, 2(44), p. 1-8, 2004.*
International Search Report dated Mar. 24, 2015 in International Application No. PCT/JP2015/055693.

(Continued)

*Primary Examiner* — Craig D Ricci
*Assistant Examiner* — Christopher R Stone
(74) *Attorney, Agent, or Firm* — Wenderoth, Lind & Ponack, L.L.P.

(57) ABSTRACT

The present invention provides a compound of formula (1), wherein $R^1$, $R^2$, $R^3$, $R^{4a}$, $R^{4b}$, $R^{5a}$ and $R^{5b}$ are as defined in the description, which has an autotaxin inhibitory activity, a pharmaceutical composition comprising the compound as an active ingredient, and a method of prevention or treatment of a disease involving autotaxin, which is characterized by administering the compound.

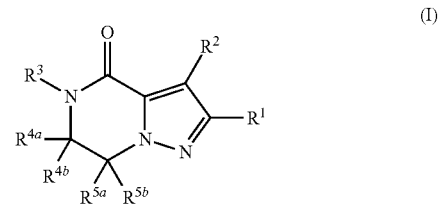

(I)

11 Claims, No Drawings

(56) References Cited

U.S. PATENT DOCUMENTS

| | | |
|---|---|---|
| 2013/0345205 A1 | 12/2013 | Conn et al. |
| 2014/0057870 A1 | 2/2014 | Conn et al. |
| 2016/0002247 A1 | 1/2016 | Nagano et al. |

FOREIGN PATENT DOCUMENTS

| | | |
|---|---|---|
| WO | 2005-120516 A2 | 12/2005 |
| WO | 2005/120516 A3 | 12/2005 |
| WO | 2006/030847 | 3/2006 |
| WO | 2006/050803 | 5/2006 |
| WO | 2007/050510 A2 | 5/2007 |
| WO | 2007/050510 A3 | 5/2007 |
| WO | 2011/151461 | 12/2011 |
| WO | 2012/083224 | 6/2012 |
| WO | 2013/192346 | 12/2013 |
| WO | 2013/192347 | 12/2013 |
| WO | 2013/192350 | 12/2013 |
| WO | 2014/195311 | 12/2014 |
| WO | 2015/073767 | 5/2015 |

OTHER PUBLICATIONS

International Preliminary Report on Patentability dated Aug. 30, 2016 in International Application No. PCT/JP2015/055693.

Sayda M. Elbashir et al., "Duplexes of 21—nucleotide RNAs mediate RNA interference in cultured mammalian cells", Nature vol. 411, May 2001, pp. 494-498.

Tjeerd Barf et al., "Structure-based lead identification of ATP-competitive MK2 inhibitors", Bioorganic & Medicinal Chemistry Letters 21 (2011) pp. 3818-3822.

H. Marie Langford et al., "Design and synthesis of substituted 4-oxo-4,5,6,7-tetrahydropyrazolo [1,5-α]pyrazine-2-carboxamides, novel HIV-1 integrase inhibitors", Bioorganic & Medicinal Chemistry Letters 18 (2008) pp. 721-725.

O.V. Zaremba et al., "Facile One-Pot Synthesis of the Pyrazolo[1,5-α]Pyrazine Scaffold", Chemistry of Heterocyclic Compounds, vol. 49, No. 6, Sep. 2013, pp. 915-921.

Extended European Search Report dated Aug. 23, 2017 in corresponding European Patent Application No. 15754487.5.

Bourgoin et al., "Autotaxin and lysophospholipids in rheumatoid arthritis", Current Opinion in Investigational Drugs, 2010, vol. 11, No. 5, pp. 515-526, XP008147065, ISSN : 2040-3429.

Zhang et al., "Synthesis and preliminary biological evaluation of novel pyrazolo [1,5 -α]pyrazin-4(5H)-one derivatives as potential agents against A549 lung cancer cells", Bioorganic & Medicinal Chemistry, 2008, vol. 16, pp. 10165-10171.

* cited by examiner

FUSED PYRAZOLE DERIVATIVE HAVING AUTOTAXIN INHIBITORY ACTIVITY

TECHNICAL FIELD

The present invention fused pyrazole derivatives having autotaxin inhibitory activity, as well as pharmaceutical comprising said fused pyrazole derivatives as an active ingredient.

BACKGROUND ART

Lysophosphatidic acid (LPA) is a lipid mediator that exhibits a variety of effects, such as cell proliferation, intracellular calcium influx, cytoskeletal changes, cell migration, via signal transduction through G protein-coupled receptor expressed on cell surface (LPA1-6). It has been reported that the lipid is involved in abnormalities of living body, such as fibrosis, pain, cancer, inflammation, arteriosclerosis (Non-Patent Document 1).

LPA can be biosynthesized by several metabolic pathways, primarily via hydrolysis of lysophosphatidyicholine by autotaxin (ENPP2, ATX). ATX is a secreted protein of ENPP (Ectonucleotide pyrophosphatase and phosphodiesterase) family (ENPP1-7) and referred to as ENPP2. ATX is the only one of this family that has a lysophospholipase D activity and thus is involved in LPA production. It has been reported that inhibiting the enzyme activity of ATX to inhibit LPA production is effective in the treatment of fibrotic diseases (Non-patent Document 1).

Fibrosis can occur in any organ, and the mechanism of its progression is common regardless of the trigger involved.

Animal tissues and organs maintain its structure with fibers such as collagen, and injured tissues and organs are restored to the original condition through the process of wound healing with collagen production. However, in case where the tissue receives immunological, chemical, mechanical, metabolic or other injuries repeatedly or experiences a greater degree of injury, excessive accumulation of fibrous connective tissue may occur. Accumulation of such connective tissue is irreversible, and fibers abnormally increased cause fibrosis that is associated with dysfunction of tissues and organs.

Pathological feature of chronic kidney disease includes renal glomerular fibrosis and tubulointerstitial fibrosis. Dropout and fibrosis of parenchymal cells prevail in the pathology of end-stage renal failure. In chronic kidney disease patients having tubulointerstitial fibrosis, the progress to renal failure is faster as compared to chronic kidney disease patients without such fibrosis.

For preventing and treating chronic kidney disease, treatments with an antihypertensive drug, such as angiotensin receptor antagonists and calcium antagonists, have been practiced, as well as advice on daily living and dietary. However, the effect from such conventional treatments is not enough to be satisfied, and there still exists an ongoing need for new drugs to make prevention and treatment more effective.

Patent Document 1 to 3 and 6 disclose dihydropyrazolopyradinone derivatives that are mGluR5 receptor allosteric modulators.

Non-patent Document 2 discloses dihydropyrazolopyradinone derivatives having an inhibitory activity on MK2.

Patent Document 4, 5 and Non-patent Document 3 disclose dihydropyrazolopyradinone having an inhibitory activity on HIV integrase.

However, it is not described or suggested that such compounds inhibit autotaxin or may be a therapeutic agent for chronic kidney disease.

On the other hand, Patent Document 7 discloses imidazopyridinone derivatives having an inhibitory activity on autotaxine.

PRIOR ART DOCUMENTS

Patent Documents

[Patent Document 1] WO2013/192350
[Patent Document 2] WO2013/192346
[Patent Document 3] WO2012/83224
[Patent Document 4] WO2007/50510
[Patent Document 5] WO2005/120516
[Patent Document 6] WO2014/195311
[Patent Document 7] WO2014/133112

Non-Patent Documents

[Non-Patent Document 1] Nature, vol. 411, pp. 494-498 (2001)
[Non-patent Document 2] Bioorganic & Medicinal Chemistry Letters, vol. 21, issue: 12, pp. 3818-3822
[Non-Patent Document 3] Bioorganic & Medicinal Chemistry Letters, vol. 18, issue: 2, pp. 721-725

SUMMARY OF INVENTION

Problem to be Solved by the Invention

The object of the present invention is to provide fused pyrazole derivatives having an excellent inhibitory activity on autotaxine.

Means for Solving the Problem

The present invention is based on the inventor's discovery of the fused pyrazole derivatives having an excellent inhibitory activity on autotaxin.

The present invention relates to the following.

(1) A compound of formula (I) or a pharmaceutically acceptable salt thereof:

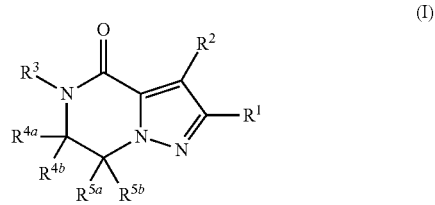

wherein
$R^1$ is substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted alkyl, substituted or unsubstituted alkenyl, substituted or unsubstituted alkynyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted carbamoyl, substituted or unsubstituted alkyloxy, substituted or unsubstituted alkenyloxy, substituted or unsubstituted alkynyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy or substituted or unsubstituted amino;

$R^2$ is hydrogen, halogen, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl;

$R^3$ is hydrogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstitulted aromatic carbocyclylsulfonyl, substituted or unsubstituted non-aromatic heterocyclylsulfonyl or substituted or unsubstituted aromatic heterocyclylsulfonyl;

$R^{4a}$ and $R^{4b}$ are each independently hydrogen, halogen, hydroxy, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, $R^{5a}$ is hydrogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy, $R^{5b}$ is substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy, or $R^{4b}$ and $R^{5b}$ may be taken together to form a bond, or $R^{4b}$ and $R^{5b}$ may be taken together to form substituted or unsubstituted aromatic carbocycle or substituted or unsubstituted non-aromatic heterocycle, provided that (i) a compound wherein $R^1$ is substituted or unsubstituted phenyloxymethyl or substituted or unsubstituted pyridyloxymethyl, $R^2$ is hydrogen, $R^{5a}$ is hydrogen, and $R^{5b}$ is substituted or unsubstituted methyl, (ii) a compound wherein $R^3$ is hydrogen or methyl, and either one of $R^{5a}$ and $R^{5b}$ or each of them are each independently unsubstituted methyloxy or unsubstituted ethyloxy, and (iii) the compounds represented as follows:

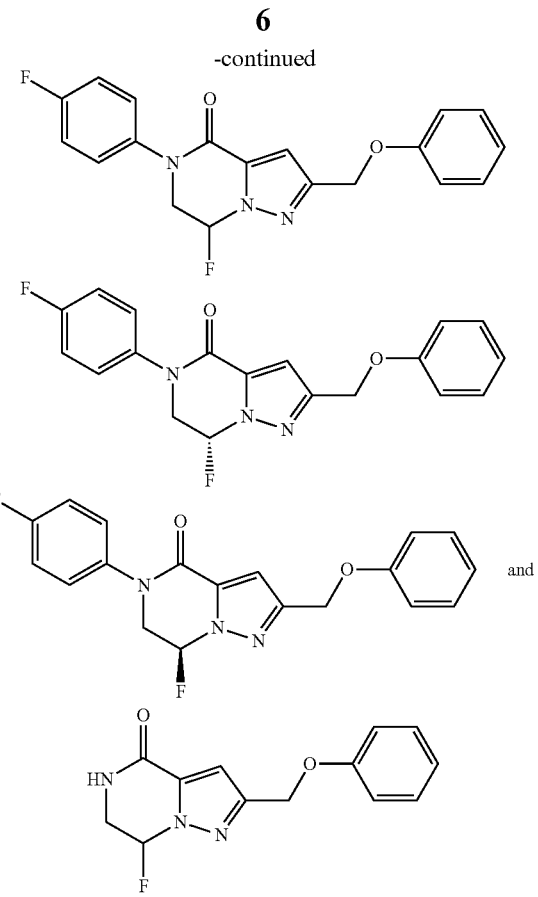

are excluded.

(2) The compound according to (1), wherein $R^1$ is substituted or unsubstituted aromatic carbocyclyl, substituted or unsubstituted non-aromatic carbocyclyl, substituted or unsubstituted non-aromatic heterocyclyl, substituted or unsubstituted alkenyl, substituted or unsubstituted alkynyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted carbamoyl, substituted or unsubstituted alkenyloxy, substituted or unsubstituted alkynyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy or substituted or unsubstituted amino, or a pharmaceutically acceptable salt thereof.

(3) The compound according to (1), wherein $R^1$ is substituted or unsubstituted non-aromatic carbocyclyl, substituted or unsubstituted aromatic carbocyclyl or substituted or unsubstituted non-aromatic heterocyclyl, or a pharmaceutically acceptable salt thereof.

(4) The compound according to (1), wherein $R^1$ is substituted or unsubstituted aromatic carbocyclyl, or a pharmaceutically acceptable salt thereof.

(5) The compound according to any one of (1) to (4), wherein $R^2$ is hydrogen, or a pharmaceutically acceptable salt thereof.

(6) The compound according to any one of (1) to (5), wherein $R^3$ is alkyl substituted with one or more substitutent(s) selected from the Substituent group A (wherein the Substituent group A consists of hydroxy, carboxy, substituted or unsubstituted alkyloxy, substituted or unsubstituted alkenyloxy, substituted or unsubstituted alkynyloxy, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted carbamoyl, substituted or unsubstituted carbonyl and substituted or unsubstituted sulfamoyl), alkenyl substituted with one or more substitutent(s) selected from the Substituent group A or alkynyl substituted with one or more substitutent(s) selected from the Substituent group A, substituted or unsubstituted aromatic carbocyclyl or substituted or unsubstituted aromatic heterocyclyl, or a pharmaceutically acceptable salt thereof.

(7) The compound according to (6), wherein substituent(s) selected from the Substituent group A is(are) any one of hydroxy, carboxy, aromatic carbocyclyl optionally substituted with one or more substituent(s) selected from the Substituent group α, aromatic heterocyclyl optionally substituted with carboxy, carbamoyl optionally substituted with one or more substituent(s) selected from the Substituent group β, carbonyl optionally substituted with one or more substituent(s) selected from the Substituent group γ, and amino optionally substituted with one or more substituent(s) selected from the Substituent group δ,
wherein
the Substituent group α consists of hydroxy, carboxy, cyano, alkyl, hydroxyalkyl, carboxyalkyl, carboxy(alkyl), carbamoyl, alkyloxycarbonyl, alkyloxycarbonylalkyl, aromatic carbocyclylsulfonylalkyl, alkyloxy, alkylcarbonyloxy, alkylaminoalkyloxy, aromatic carbocyclyloxy, alkylcarbonyl, hydroxy non-aromatic heterocyclylcarbonyl, alkylcarbonylamino, alkylsulfonyl and non-aromatic heterocyclylsulfonyl,
the substituent group β consists of alkyl, carboxyalkyl, aromatic carbocyclylalkyl, aromatic carbocyclylalkyl(carboxy), carboxyalkyl(alkyl), alkylaminoalkyl, alkylaminoalkyl(alkyl), alkylcarbamoylalkyl, carboxy non-aromatic carbocyclylalkyl, aromatic carbocyclyl(carboxy)alkyl, carboxy aromatic carbocyclylalkyl, carboxy aromatic carbocyclyl, carboxyalkyl aromatic carbocyclyl, cyano non-aromatic carbocyclyl, carboxy non-aromatic carbocyclyl, aromatic heterocyclyl, non-aromatic carbocyclyl, aromatic carbocyclyl, carboxy aromatic carbocyclyl, alkyloxycarbonyl non-aromatic carbocyclyl and alkyloxycarbonyl,
the Substituent group γ consists of alkyloxy, non-aromatic heterocyclylalkyloxy, carbamoyl aromatic carbocyclyl, carboxy aromatic heterocyclyl, non-aromatic heterocyclyl, hydroxy non-aromatic heterocyclyl, alkyl non-aromatic heterocyclyl, hydroxyalkyl non-aromatic heterocyclyl, carboxyalkyl non-aromatic heterocyclyl, aromatic carbocyclylalkyl non-aromatic heterocyclyl, non-aromatic heterocyclylalkyl non-aromatic heterocyclyl, non-aromatic heterocyclylcarbonyl non-aromatic heterocyclyl, alkyloxycarbonyl non-aromatic heterocyclyl, carboxy non-aromatic heterocyclyl, carbamoyl non-aromatic heterocyclyl, alkylamino non-aromatic heterocyclyl, oxo non-aromatic heterocyclyl and aromatic carbocyclyl non-aromatic heterocyclyl,
the Substituent group δ consists of alkyl, carboxyalkyl, alkylcarbonyl and alkyloxy carbonyl, or a pharmaceutically acceptable salt thereof.

(8) The compound according to any one of (1) to (7), wherein $R^{4a}$ and $R^{4b}$ are hydrogen, or a pharmaceutically acceptable salt thereof.

(9) The compound according to any one of (1) to (7), wherein $R^{4b}$ and $R^{5b}$ are taken together to form substituted or unsubstituted non-aromatic carbocycle or substituted or unsubstituted non-aromatic heterocycle, or a pharmaceutically acceptable salt thereof.

(10) The compound according to any one of (1) to (8), wherein $R^{5a}$ is hydrogen, substituted or unsubstituted alkyl, substituted or unsubstituted alkenyl or substituted or unsubstituted alkynyl, $R^{5b}$ is substituted or unsubstituted alkyl, substituted or unsubstituted alkenyl or substituted or unsubstituted alkynyl, or a pharmaceutically acceptable salt thereof.

(11) The compound according to any one of (1) to (8), wherein $R^{5a}$ is hydrogen or substituted or unsubstituted alkyl, $R^{5b}$ is substituted or unsubstituted C2 to C10 alkyl, or a pharmaceutically acceptable salt thereof.

(12) The compound according to any one of (1) to (8), wherein $R^{5a}$ is hydrogen, $R^{5b}$ is substituted or unsubstituted C2 to C10 alkyl, or a pharmaceutically acceptable salt thereof.

(13) The compound according to (1), wherein $R^1$ is substituted or unsubstituted aromatic carbocyclyl, substituted or unsubstituted non-aromatic heterocyclyl or substituted or unsubstituted non-aromatic heterocyclylcarbonyl, wherein the substituent(s) is(are) each selected from a group consisting of halogen, cyano, carboxy, trihaloalkyl, cyanoalkyl, trihaloalkyloxy and alkylcarbonylamino,
$R^2$ is hydrogen,
$R^3$ is hydrogen, alkyl substituted with one or more substituent(s) selected from the Substituent group A, aromatic carbocyclyl optionally substituted carboxy, or aromatic heterocyclyl, the said substituent(s) selected from the Substituent group A is(are) hydroxy, carboxy, aromatic carbocyclyl optionally substituted with the Substituent group α, aromatic heterocyclyl optionally substituted with carboxy, carbamoyl optionally substituted with one or more substitutent(s) selected from the Substituent group β, carbonyl optionally substituted with one or more substitutent(s) selected from the the Substituent group γ, or amino optionally substituted with one or more substitutent(s) selected from the Substituent group δ,
wherein, the said substitutent(s) selected from the Substituent group α is(are) any one of a group consisting of hydroxy, carboxy, cyano, alkyl, hydroxyalkyl, carboxyalkyl, carbamoyl, alkyloxycarbonyl, alkyloxycarbonylalkyl, aromatic carbocyclylsulfonylalkyl, alkylcarbonyloxy, alkylaminoalkyloxy, aromatic carbocyclyloxy, alkylcarbonyl, hydroxy non-aromatic heterocyclylcarbonyl, alkylcarbonylamino, alkylsulfonyl, and non-aromatic heterocyclylsulfonyl,
the said substituent(s) selected from the Substituent group A is(are) any one of a group consisting of alkyl, carboxyalkyl, aromatic carbocyclylalkyl, aromatic carbocyclylalkyl(carboxy), carboxyalkyl(alkyl), alkylaminoalkyl, alkylaminoalkyl(alkyl), alkylcarbamoylalkyl, carboxy non-aromatic carbocyclylalkyl, carboxy aromatic carbocyclylalkyl, aromatic carbocycle(carboxy)alkyl, carboxy aromatic carbocyclylalkyl, carboxyalkyl aromatic carbocyclyl, cyano non-aromatic carbocyclyl, carboxy non-aromatic carbocyclyl, aromatic heterocyclyl, aromatic carbocyclyl, carboxy aromatic carbocyclyl, or alkyloxy carbonyl non-aromatic carbocyclyl,
the said substituent(s) selected from the Substituent group γ is(are) any one of a group consisting of alkyloxy, non-aromatic heterocyclylalkyloxy, non-aromatic heterocyclyl, hydroxy non-aromatic heterocyclyl, alkyl non-aromatic heterocyclyl, hydroxyalkyl non-aromatic heterocyclyl, carboxyalkyl non-aromatic heterocyclyl, aromatic carbocyclylalkyl non-aromatic heterocyclyl, non-aromatic heterocyclylalkyl non-aromatic heterocyclyl, non-aromatic heterocyclylcarbonyl non-aromatic heterocyclyl, alkyloxycarbonyl non-aromatic heterocyclyl, carboxy non-aromatic heterocyclyl, carbamoyl non-aromatic heterocyclyl, alkylamino non-aromatic heterocyclyl, oxo non-aromatic heterocyclyl or aromatic carbocycle non-aromatic heterocyclyl, the said substituent(s) selected from the Substituent group δ is(are) alkyl carbonyl or alkyloxycarbonyl, $R^{4a}$ and $R^{4b}$ are each hydrogen, $R^{5a}$ is hydrogen or unsubstituted alkyl, $R^{5b}$ is substituted or unsubstituted alkyl, wherein the substituent(s) is(are) hydroxy, halogen, alkyloxy optionally substituted with halogen, aromatic carbocyclyl or aromatic carbocyclylalkyloxy, or $R^{4a}$ and $R^{5a}$ are each hydrogen, $R^{4b}$ and $R^{5b}$ are taken together to form substituted or unsubstituted non-aromatic carbocycle or substituted or unsubstituted non-aromatic heterocycle, or a pharmaceutically acceptable salt thereof.

(14) A pharmaceutical composition comprising the compound according to any one of (1) to (13) or a pharmaceutically acceptable salt thereof as an active ingredient.

(15) The pharmaceutical composition according to (14), which possesses an autotaxin inhibitory activity.

(16) A method for the prevention or treatment of a disease involving autotaxin, which is characterized by administering the compound according to any one of (1) to (13) or a pharmaceutically acceptable salt thereof.

(17) The compound according to any one of (1) to (13) for the prevention or treatment of a disease involving autotaxin or a pharmaceutically acceptable salt thereof.

(18) Use of a compound according to any one of (1) to (13) or a pharmaceutically acceptable salt thereof for the manufacture of a medicament for the prevention or treatment of a disease involving autotaxin.

(1') A compound of formula (I) or a pharmaceutically acceptable salt thereof:

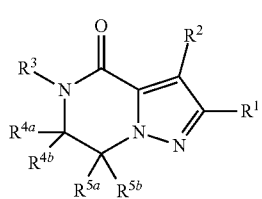

wherein
$R^1$ is substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted alkyl, substituted or unsubstituted alkenyl, substituted or unsubstituted alkynyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted carbamoyl, substituted or unsubstituted alkyloxy, substituted or unsubstituted alkenyloxy, substituted or unsubstituted alkynyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy or substituted or unsubstituted amino, $R^2$ is hydrogen, halogen, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, $R^3$ is hydrogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, R$^{4a}$ and R$^{4b}$ are each independently hydrogen, halogen, hydroxy, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclyithio, substituted or unsubstituted aromatic carbocyclthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, R$^{5b}$ is hydrogen, halogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy, R$^{5b}$ is halogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy, or R$^{4b}$ and R$^{5b}$ may be taken together to form a bond, R$^{5b}$ may be taken together with the substituent on R$^1$ to form substituted or unsubstituted non-aromatic carbocycle or substituted or unsubstituted non-aromatic heterocycle, or R$^{4b}$ and R$^{5b}$ may be taken together to form substituted or unsubstituted non-aromatic carbocycle or substituted or unsubstituted non-aromatic heterocycle, provided that (i) a compound wherein R$^1$ is substituted or unsubstituted phenyloxymethyl or substituted or unsubstituted pyridyloxymethyl, R$^2$ is hydrogen, R$^{5a}$ is hydrogen or substituted or unsubstituted methyl, and R$^{5b}$ is substituted or unsubstituted methyl, (ii) a compound wherein R$^3$ is hydrogen or unsubstituted methyl, and either one of R$^{5a}$ and R$^{5b}$ or each of them are each independently unsubstituted methyloxy or unsubstituted ethyloxy, and (iii) the compounds represented as follows:

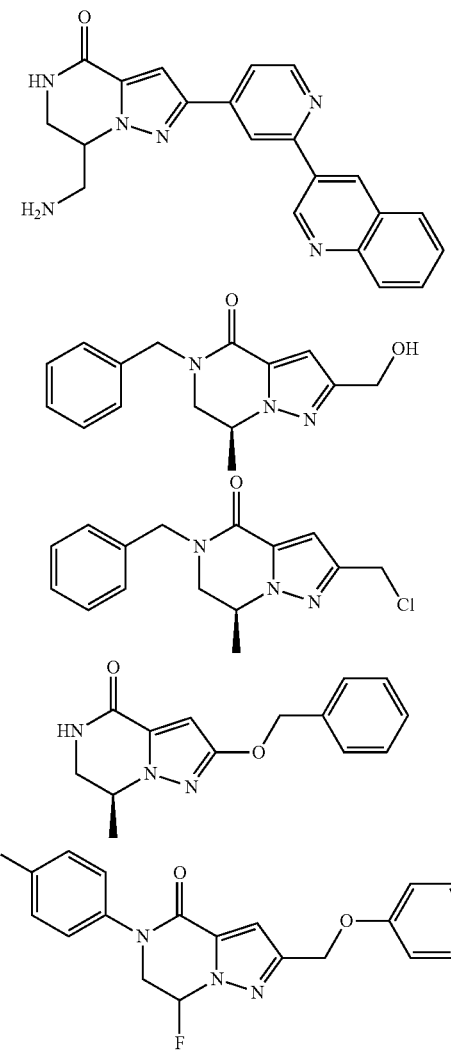

-continued

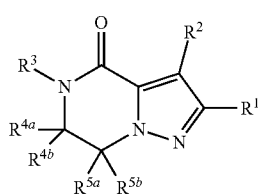

are excluded.

(1″) A compound of formula (I) or a pharmaceutically acceptable salt thereof:

$$\text{(I)}$$

wherein

R¹ is substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted alkyl, substituted or unsubstituted alkenyl, substituted or unsubstituted alkynyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted carbamoyl, substituted or unsubstituted alkyloxy, substituted or unsubstituted alkenyloxy, substituted or unsubstituted alkynyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy or substituted or unsubstituted amino, R² is hydrogen, halogen, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsufinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, R³ is hydrogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, R⁴ᵃ and R⁴ᵇ are each independently hydrogen, halogen, hydroxy, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclithio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, $R^{5a}$ is hydrogen, halogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy, $R^{5b}$ is halogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy, or $R^{4b}$ and $R^{5a}$ may be taken together to form a bond, $R^{5b}$ and the substituent on the $R^1$ may be taken together to form substituted or unsubstituted non-aromatic carbocycle or substituted or unsubstituted non-aromatic heterocycle, or $R^{4b}$ and $R^{5b}$ may be taken together to form substituted or unsubstituted non-aromatic carbocycle or substituted or unsubstituted non-aromatic heterocycle, provided that (i) a compound, wherein $R^1$ is substituted or unsubstituted phenyloxymethyl or substituted or unsubstituted pyridyloxymethyl, $R^2$ is hydrogen, $R^{5a}$ is hydrogen or substituted or unsubstituted methyl, and $R^{5b}$ is substituted or unsubstituted methyl, (iii) a compound, wherein $R^3$ is hydrogen or unsubstituted methyl, and either one of $R^{5a}$ and $R^{5b}$ or each of them are each independently unsubstituted methyloxy or unsubstituted ethyloxy, and (iii) the compounds represented as follows:

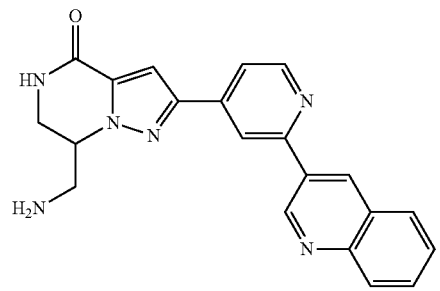

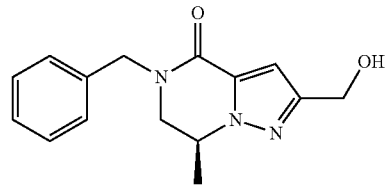

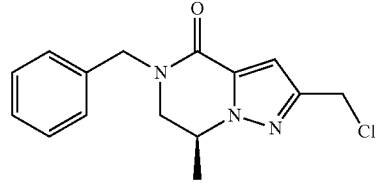

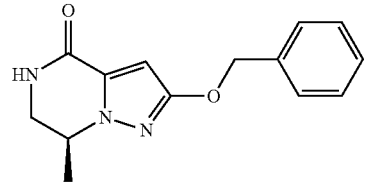

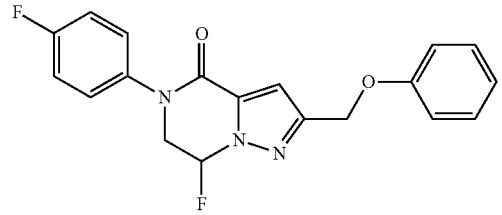

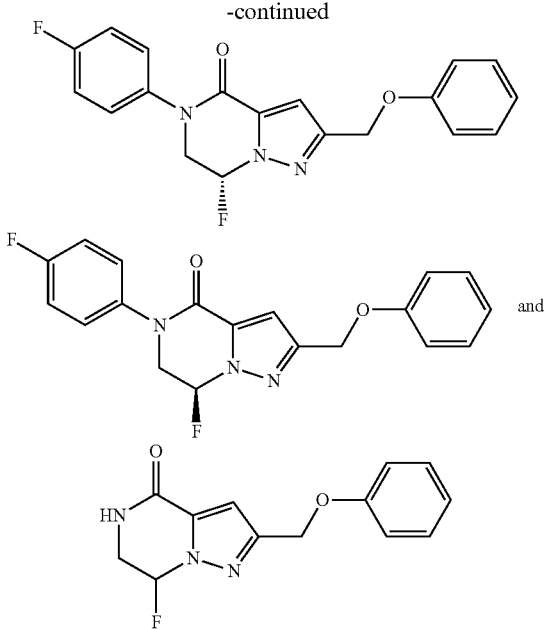

are excluded.

(2') The compound according to (1') or (1"), wherein $R^1$ is substituted or unsubstituted aromatic carbocyclyl, substituted or unsubstituted non-aromatic carbocyclyl, substituted or unsubstituted non-aromatic heterocyclyl, substituted or unsubstituted alkenyl, substituted or unsubstituted alkynyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted carbamoyl, substituted or unsubstituted alkenyloxy, substituted or unsubstituted alkynyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy or substituted or unsubstituted amino, or a pharmaceutically acceptable salt thereof.

(3') The compound according to (1') or (1"), wherein $R^1$ is substituted or unsubstituted non-aromatic carbocyclyl, substituted or unsubstituted aromatic carbocyclyl or substituted or unsubstituted non-aromatic heterocyclyl, or a pharmaceutically acceptable salt thereof.

(4') The compound according to (1') or (1"), wherein $R^1$ is substituted or unsubstituted aromatic carbocyclyl, or a pharmaceutically acceptable salt thereof.

(4") The compound according to (1') or (1"), wherein $R^1$ is substituted or unsubstituted phenyl, or a pharmaceutically acceptable salt thereof.

(4''') The compound according to (1) or (1"), wherein $R^1$ is substituted phenyl, wherein the substituent(s) is(are) each one or more substituent(s) selected from the group consisting of halogen, cyano, formyl, carboxy, trihaloalkyl, cyanoalkyl, hydroxyalkyl, trihaloalkyloxy, alkyloxyalkyl, alkylcarbamoylalkyl, alkylaminoalkyl, dialkylaminoalkyl, amino, alkylamino, cyanoalkylamino, alkylcarbonylamino, monohalo-alkylcarbonylamino, trihaloalkylcarbonylamino, non-aromatic carbocyclylcarbonyl amino, hydroxyalkylcarbonylamino, alkylaminocarbonylamino, dialkylaminocarbonylamino, alkylsulfonylamino, aromatic heterocycle amino, trihaloalkylcarbamoyl, alkyloxyalkylcarbamoyl, and aromatic carbocyclyl, or a pharmaceutically acceptable salt thereof.

(4"") The compound according to (1') or (1"), wherein $R^1$ is substituted phenyl, wherein the substituent(s) is(are) each one or more substituents selected from the group consisting of halogen, cyano, formyl, carboxy, trihaloalkyl, cyanoalkyl, hydroxyalkyl, alkenyl, alkyloxy, trihaloalkyloxy, alkyloxyalkyl, alkylcarbamoylalkyl, alkylaminoalkyl, dialkylaminoalkyl, amino, alkylamino, dialkylamino, cyanoalkylamino, trihaloalkylamino, alkylcarbonylamino, monohaloalkylcarbonylamino, trihaloalkylcarbonylamino, non-aromatic carbocyclylcarbonylamino, hydroxyalkylcarbonylamino, alkyloxycarbonylamino, alkyloxyalkylcarbonylamino, alkylaminocarbonylamino, dialkylaminocarbonylamino, alkylsulfonylamino, aromatic heterocyclylamino, trihaloalkylcarbamoyl, alkyloxyalkylcarbamoyl, pentafuluorothio, and aromatic carbocyclyl, or a pharmaceutically acceptable salt thereof.

(5') The compound according to any one of (1') to (4""), wherein $R^2$ is hydrogen, or a pharmaceutically acceptable salt thereof.

(6') The compound according to any one of (1') to (5'), wherein $R^3$ is alkyl substituted with one or more substituent(s) selected from the Substituent group A', wherein the Substituent group A' consists of hydroxy, carboxy, substituted or unsubstituted alkyloxy, substituted or unsubstituted alkenyloxy, substituted or unsubstituted alkynyloxy, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkylcarbonyl, substituted or unsubstituted alkenylcarbonyl, substituted or unsubstituted alkynylcarbonyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted amino, substituted or unsubstituted carbamoyl, substituted or unsubstituted carbonyl, and substituted or unsubstituted sulfamoyl, alkenyl substituted with one or more substituent(s) selected from the Substituent group A', alkynyl substituted with one or more substituent(s) selected from the Substituent group A', substituted or unsubstituted aromatic carbocyclyl, or substituted or unsubstituted aromatic heterocyclyl, or a pharmaceutically acceptable salt thereof.

(6") The compound according to any one of (1') to (5'), wherein $R^3$ is alkyl substituted with one or more substituent(s) is(are) selected from the Substituent group A" (wherein the Substituent group A" is hydroxy, carboxy, substituted or unsubstituted alkyloxy, substituted or unsubstituted alkenyloxy, substituted or unsubstituted alkynyloxy, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted aromatic carbocyclyloxy, substituted or unsubstituted alkylcarbonyl, substituted or unsubstituted alkenylcarbonyl, substituted or unsubstituted alkynylcarbonyl, substituted or unsubstituted aromatic carbocyclylcarbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted alkyloxycarbonyl, substituted or unsubstituted amino, substituted or unsubstituted carbamoyl, substituted or unsubstituted carbonyl and substituted or unsubstituted sulfamoyl), alkenyl substituted with one or more the substituent(s) selected from the Substituent group A″, or alkynyl substituted with one or more substituent(s) selected from the Substituent group A″, substituted or unsubstituted aromatic carbocyclyl, or substituted or unsubstituted aromatic heterocyclyl, or a pharmaceutically acceptable salt thereof.

(7′) The compound according to (6′) or (6″), wherein the substituent(s) selected from the Substituent group A′ or the Substituent group A″ is(are) hydroxy, carboxy, aromatic carbocyclyl optionally substituted with one or more substituent(s) selected from the Substituent group α′, substituted or unsubstituted non-aromatic heterocyclyl, aromatic heterocyclyl optionally substituted with carboxy, carbamoyl optionally substituted with one or more substituent(s) selected from the Substituent group β′, carbonyl optionally substituted with one or more substituent(s) selected from the Substituent group γ′, and amino optionally substituted with one or more substituent(s) selected from the substituent group δ′, wherein
the Substituent group α′ consists of hydroxy, carboxy, cyano, alkyl, hydroxyalkyl, carboxyalkyl, carboxy(alkyl), carbamoyl, alkyloxycarbonyl, alkyloxycarbonylalkyl, aromatic carbocyclylsulfonylalkyl, alkyloxy, alkylcarbonyloxy, alkyaminoalkyloxy, aromatic carbocyclyloxy, alkylcarbonyl, hydroxy non-aromatic heterocyclylcarbonyl, alkylcarbonylamino, alkylsulfonyl and non-aromatic heterocyclylsulfonyl, the Substituent group β′ consists of alkyl, cyanoalkyl, dicyanoalkyl, carboxyalkyl, hydroxyalkyl, di(hydroxy)alkyl, trihalo(hydroxy)alkyl, hydroxyalkyloxyalkyl, aromatic carbocyclylalkyl, aromatic carbocyclyl(cyano)alkyl, hydroxy aromatic carbocyclylalkyl, aromatic heterocyclylalkyl, hydroxy aromatic heterocyclylalkyl, aromatic carbocyclylalkyl(carboxy), oxo non-aromatic heterocyclylalkyl, hydroxyalkyl non-aromatic heterocyclylalkyl, carboxy alkyl(alkyl), alkylaminoalkyl, alkylaminoalkyl(alkyl), carbamoylalkyl, alkylcarbamoylalkyl, dialkylcarbamoylalkyl, carboxy non-aromatic carbocyclylalkyl, aromatic carbocyclyl(carboxy)alkyl, aromatic carbocyclyl(hydroxy)alkyl, carboxy aromatic carbocyclylalkyl, carboxy aromatic carbocyclyl, carboxyalkyl aromatic carbocyclyl, cyano non-aromatic carbocyclyl, hydroxy non-aromatic carbocyclyl, carboxy non-aromatic carbocyclyl, aromatic heterocyclyl, non-aromatic carbocyclyl, aromatic carbocyclyl, carboxy aromatic carbocyclyl, aromatic heterocyclyl, non-aromatic carbocyclyl, aromatic carbocyclyl, carboxy aromatic carbocyclyl, alkyloxycarbonyl non-aromatic carbocyclyl, and alkyloxycarbonyl, the Substituent group γ′ consists of alkyloxy, non-aromatic heterocyclylalkyloxy, carbamoyl aromatic carbocyclyl, carboxy aromatic heterocyclyl, non-aromatic heterocyclyl, hydroxy non-aromatic heterocyclyl, cyano non-aromatic heterocyclyl, alkyl non-aromatic heterocyclyl, dialkyl non-aromatic heterocyclyl, hydroxyalkyl non-aromatic heterocyclyl, hydroxyalkyloxy non-aromatic heterocyclyl, carboxyalkyl non-aromatic heterocyclyl, aromatic carbocyclylalkyl non-aromatic heterocyclyl, non-aromatic heterocyclylalkyl non-aromatic heterocyclyl, non-aromatic heterocyclylcarbonyl non-aromatic heterocyclyl, alkyloxycarbonyl non-aromatic heterocyclyl, carboxy non-aromatic heterocyclyl, carbamoyl non-aromatic heterocyclyl, cyanoalkylcarbamoyl non-aromatic carbocycle group, alkylamino non-aromatic heterocyclyl, oxo non-aromatic heterocyclyl, and aromatic carbocycle non-aromatic heterocyclyl, the Substituent group δ′ consists of alkyl, carboxyalkyl, alkylcarbonyl, cyanoalkylcarbonyl and alkyloxycarbonyl, or a pharmaceutically acceptable salt thereof.

(7″) The compound according to (6′) or (6″), wherein the substituent(s) selected from the Substituent group A′ or the Substituent group A″ is(are) hydroxy, carboxy, aromatic carbocyclyl optionally substituted with one or more substituent(s) selected from the Substituent group α″, non-aromatic heterocyclyl optionally substituted with one or more substituent(s) selected from the Substituent group α″, aromatic heterocyclyl optionally substituted with carboxy, carbamoyl optionally substituted with one or more substituent(s) selected from the Substituent group β″, carbonyl optionally substituted with one or more substituent(s) selected from the Substituent group γ″, and amino optionally substituted with one or more substituent(s) selected from the Substituent group δ″, wherein
the Substituent group α″ consists of hydroxy, carboxy, cyano, alkyl, hydroxyalkyl, carboxyalkyl, carboxy(alkyl), cyanoalkyl, carbamoyl, alkyloxycarbonyl, alkyloxycarbonylalkyl, aromatic carbocyclylsulfonylalkyl, alkyloxy, alkylcarbonyloxy, alkylaminoalkyloxy, dialkylaminoalkyloxy, aromatic carbocyclyloxy, alkylcarbonyl, hydroxy non-aromatic heterocyclylcarbonyl, alkylcarbonylamino, alkylsulfonyl, and non-aromatic heterocyclylsulfonyl, the Substituent group β″ consists of alkyl, cyano alkyl, dicyanoalkyl, carboxyalkyl, hydroxyalkyl, di(hydroxy)alkyl, trihalo(hydroxy)alkyl, hydroxyalkyloxyalkyl, aromatic carbocyclylalkyl, aromatic carbocyclyl(cyano)alkyl, hydroxy aromatic carbocyclylalkyl, aromatic heterocyclylalkyl, hydroxy aromatic heterocyclylalkyl, aromatic carbocyclylalkyl(carboxy), oxo non-aromatic heterocyclylalkyl, hydroxyalkyl non-aromatic heterocyclylalkyl, carboxyalkyl (alkyl), alkylaminoalkyl, dialkylaminoalkyl, alkylaminoalkyl(alkyl), carbamoylalkyl, alkylcarbamoylalkyl, dialkylcarbamoylalkyl, carboxy non-aromatic carbocyclylalkyl, aromatic carbocyclyl(carboxy)alkyl, aromatic carbocyclyl(hydroxy)alkyl, carboxy aromatic carbocyclylalkyl, carboxy aromatic carbocyclyl, carboxyalkyl aromatic carbocyclyl, cyano non-aromatic carbocyclyl, hydroxy non-aromatic carbocyclyl, carboxy non-aromatic carbocyclyl, aromatic heterocyclyl, non-aromatic carbocyclyl, aromatic carbocyclyl, carboxy aromatic carbocyclyl, aromatic heterocyclyl, non-aromatic carbocyclyl, aromatic carbocyclyl, carboxy aromatic carbocyclyl, alkyloxycarbonyl non-aromatic carbocyclyl and alkyloxycarbonyl, the substituent group γ″ consists of alkyl, alkyloxy, non-aromatic heterocyclylalkyloxy, carbamoyl aromatic carbocyclyl, non-aromatic carbocyclyl, carboxy aromatic heterocyclyl, non-aromatic heterocyclyl, hydroxy non-aromatic heterocyclyl, cyano non-aromatic heterocyclyl, alkyl non-aromatic heterocyclyl, dialkyl non-aromatic heterocyclyl, hydroxyalkyl non-aromatic heterocyclyl, hydroxyalkyloxy non-aromatic heterocyclyl, carboxyalkyl non-aromatic heterocyclyl, aromatic carbocyclylalkyl non-aromatic heterocyclyl, non-aromatic heterocyclylalkyl non-aromatic heterocyclyl, non-aromatic heterocyclylcarbonyl non-aromatic heterocyclyl, alkyloxycarbonyl non-aromatic heterocyclyl, carboxy non-aromatic heterocyclyl, carbamoyl non-aromatic heterocyclyl, cyanoalkyl carbamoyl non-aromatic carbocycle group, cyano non-aromatic carbocyclylcarbamoyl non-aromatic heterocycly, alkylamino non-aromatic heterocyclyl, dialkylamino non-aromatic heterocyclyl, oxo non-aromatic heterocyclyl, and aromatic carbocyclyl non-aromatic heterocyclyl, the Substituent group δ" consists of alkyl, carboxyalkyl, alkylcarbonyl, hydroxyalkylcarbonyl, cyanoalkylcarbonyl and alkyloxycarbonyl, or a pharmaceutically acceptable salt thereof.

(8') The compound according to any one of (1') to (7"), wherein $R^{4a}$ and $R^{4b}$ are hydrogen, or a pharmaceutically acceptable salt thereof.

(9') The compound according to any one of (1') to (7"), wherein $R^{4b}$ and $R^{5b}$ are taken together to form substituted or unsubstituted non-aromatic carbocycle or substituted or unsubstituted non-aromatic heterocycle, or a pharmaceutically acceptable salt thereof.

(10') The compound according to any one of (1') to (8'), wherein $R^{5a}$ is hydrogen, substituted or unsubstituted alkyl, substituted or unsubstituted alkenyl or substituted or unsubstituted alkynyl, $R^{5b}$ is substituted or unsubstituted alkyl, substituted or unsubstituted alkenyl or substituted or unsubstituted alkynyl, or a pharmaceutically acceptable salt thereof.

(11") The compound according to any one of (1') to (8'), wherein $R^{5a}$ is hydrogen or substituted or unsubstituted alkyl, $R^{5b}$ is substituted or unsubstituted C2-C10 alkyl, or a pharmaceutically acceptable salt thereof.

(12') The compound according to any one of (1') to (8'), wherein $R^{5a}$ is hydrogen, $R^{5b}$ is substituted or unsubstituted C2-C10 alkyl, or a pharmaceutically acceptable salt thereof.

(12") The compound according to any one of (1') to (8'), wherein $R^{5a}$ is hydrogen, $R^{5b}$ is substituted alkyl, wherein the substituent(s) is(are) selected from the group consisting of hydroxy, halogen, alkyloxy optionally substituted with halogen, aromatic carbocyclyl and aromatic carbocyclylalkyloxy, or a pharmaceutically acceptable salt thereof.

(13') The compound according to any one of (1'), wherein $R^1$ is substituted or unsubstituted aromatic carbocyclyl, substituted or unsubstituted non-aromatic heterocyclyl or substituted or unsubstituted non-aromatic heterocyclylcarbonyl, wherein the substituent(s) is(are) each selected from the group consisting of halogen, cyano, carboxy, trihaloalkyl, cyanoalkyl, trihaloalkyloxy and alkylcarbonylamino, $R^2$ is hydrogen, $R^3$ is hydrogen, alkyl substituted with one or more substituent(s) selected from the Substituent group A, aromatic carbocyclyl optionally substituted with carboxy, trihaloalkyl or oxo non-aromatic heterocyclyl optionally substituted with cyanoalkyl, or aromatic heterocyclyl, the substituent(s) selected from the said substituent group A' is(are) hydroxy, carboxy, aromatic carbocyclyl optionally substituted with one or more substituent(s) selected from the Substituent group α', non-aromatic heterocyclyl, oxo non-aromatic heterocyclyl optionally substituted with one or more substituent(s) selected from the Substituent group α', aromatic heterocyclyl optionally substituted with carboxy, carbamoyl optionally substituted with one or more substituent(s) selected from the Substituent group β', carbonyl optionally substituted with one or more substituent(s) selected from the Substituent group γ', or amino optionally substituted with one or more substitutent(s) selected with the Substituent group δ', wherein the substituent(s) selected from the said Substituent group α' is(are) hydroxy, carboxy, cyano, alkyl, hydroxyalkyl, carboxyalkyl, carbamoyl, alkyloxycarbonyl, alkyloxycarbonylalkyl, aromatic carbocyclylsulfonylalkyl, alkylcarbonyloxy, alkylaminoalkyloxy, aromatic carbocyclyloxy, alkylcarbonyl, hydroxy non-aromatic heterocyclylcarbonyl, alkylcarbonylamino, alkylsulfonyl or non-aromatic heterocyclylsulfonyl, the substituent(s) selected from the said substituent group β' is(are) alkyl, cyanoalkyl, carboxalkyl, hydroxyalkyl, aromatic carbocyclylalkyl, aromatic heterocyclylalkyl, aromatic carbocyclylalkyl(carboxy), oxo non-aromatic heterocyclylalkyl, carboxyalkyl(alkyl), alkylaminoalkyl, alkylaminoalkyl(alkyl), alkylcarbamoylalkyl, carboxy non-aromatic carbocyclylalkyl, carboxy aromatic carbocyclylalkyl, aromatic carbocyclyl(carboxy)alkyl, carboxy aromatic carbocyclylalkyl, carboxyalkyl aromatic carbocyclyl, cyano non-aromatic carbocyclyl, carboxy non-aromatic carbocyclyl, aromatic heterocyclyl, aromatic carbocyclyl, carboxy aromatic carbocyclyl, or alkyloxycarbonyl non-aromatic carbocyclyl, the substituent(s) selected from the said Substituent group γ' is(are) alkyloxy, non-aromatic heterocyclylalkyloxy, non-aromatic heterocyclyl, hydroxy non-aromatic heterocyclyl, cyano non-aromatic heterocyclyl, alkyl non-aromatic heterocyclyl, hydroxyalkyl non-aromatic heterocyclyl, carboxylalkyl non-aromatic heterocyclyl, aromatic carbocyclylalkyl non-aromatic heterocyclyl, non-aromatic heterocyclylalkyl non-aromatic heterocyclyl, non-aromatic heterocyclylcarbonyl non-aromatic heterocyclyl, alkyloxycarbonyl non-aromatic heterocyclyl, carboxy non-aromatic heterocyclyl, carbamoyl non-aromatic heterocyclyl, cyanoalkylcarbamoyl non-aromatic carbocyclyl, alkylamino non-aromatic heterocyclyl, oxo non-aromatic heterocyclyl or aromatic carbocyclyl non-aromatic heterocyclyl, the substituent(s) selected from the said Substituent group δ' is(are) alkylcarbonyl, cyanoalkylcarbonyl or alkyloxycarbonyl, $R^{4a}$ and $R^{4b}$ are hydrogen, $R^{5a}$ is hydrogen or unsubstituted alkyl, $R^{5b}$ is substituted or unsubstituted alkyl, wherein the substituent(s) is(are) hydroxy, halogen, alkyloxy optionally substituted with halogen, aromatic carbocyclyl or aromatic carbocyclylalkyloxy, or $R^{4a}$ and $R^{5a}$ are hydrogen, $R^{4b}$ and $R^{5b}$ are taken together to form substituted or unsubstituted non-aromatic carbocycle or substituted or unsubstituted non-aromatic heterocycle, or a pharmaceutically acceptable salt thereof.

(13") The compound according to (1"), wherein $R^1$ is substituted or unsubstituted aromatic carbocyclyl, substituted or unsubstituted non-aromatic heterocyclyl or substituted or unsubstituted non-aromatic heterocyclylcarbonyl, wherein the substituent(s) is(are) each selected from the group consisting of halogen, cyano, formyl, carboxy, hydroxyalkyl, trihaloalkyl, cyanoalkyl, alkylaminoalkyl, alkylaminocarbonylalkyl, alkyloxy, trihaloalkyloxy, amino, alkylamino, trihaloalkylamino, cyanoalkylamino, alkylcarbonylamino, hydroxyalkylcarbonylamino, haloalkylcarbonylamino, trihaloalkylcarbonylamino, alkyloxycarbonylamino, alkyloxyalkylcarbonylamino, non-aromatic carbocyclylcarbonylamino, alkylsulfonylamino, aromatic carbocyclyl, pentafuluorothio, and aromatic heterocyclyl, $R^2$ is hydrogen, $R^3$ is hydrogen, alkyl substituted with one or more substituent(s) selected from the Substituent group A", aromatic carbocyclyl optionally substituted with carboxy, oxo non-aromatic heterocyclyl optionally substituted trihaloalkyl or cyanoalkyl, or aromatic heterocyclyl, the substituent(s) selected from the Substituent group A" is(are) hydroxy, carboxy, aromatic carbocyclyl optionally substituted with one or more substituent(s) selected from the Substituent group α", non-aromatic heterocyclyl, oxo non-aromatic heterocyclyl optionally substituted with one or more substituent(s) selected form the Substituent group α", aromatic heterocyclyl optionally substituted with carboxy, carbamoyl optionally substituted with one or more substituent(s) selected with the Substituent group β", carbonyl optionally substituted with one or more substituent(s) selected from a substituent group γ", or amino optionally substituted with one or more substituent(s) selected from the Substituent group δ", wherein the substituent(s) selected from the Substituent group α" is(are) hydroxy, carboxy, cyano, alkyl, hydroxyalkyl, carboxyalkyl, cyanoalkyl, carbamoyl, alkyloxycarbonyl, alkyloxycarbonylalkyl, aromatic carbocyclylsulfonylalkyl, alkylcarbonyloxy, alkylaminoalkyloxy, dialkylaminoalkyloxy, aromatic carbocyclyloxy, alkylcarbonyl, hydroxy non-aromatic heterocyclylcarbonyl, alkylcarbonylamino, alkylsulfonyl or non-aromatic heterocyclylsulfonyl, the substituent(s) selected from the Substituent group β" is(are) alkyl, cyanoalkyl, carboxyalkyl, hydroxyalkyl, aromatic carbocyclylalkyl, aromatic heterocyclylalkyl, aromatic carbocyclylalkyl(carboxy), oxo non-aromatic heterocyclylalkyl, carboxyalkyl(alkyl), alkylaminoalkyl, dialkylaminoalkyl, alkylaminoalkyl(alkyl), alkylcarbamoylalkyl, carboxy non-aromatic carbocyclylalkyl, carboxy aromatic carbocyclylalkyl, aromatic carbocyclyl(carboxy) alkyl, carboxy aromatic carbocyclylalkyl, carboxyalkyl aromatic carbocyclyl, cyano non-aromatic carbocyclyl, carboxy non-aromatic carbocyclyl, aromatic heterocyclyl, aromatic carbocyclyl, carboxy aromatic carbocyclyl, or alkyloxycarbonyl non-aromatic carbocyclyl, the substituent(s) selected from the Substituent group γ" is(are) alkyl, alkyloxy, non-aromatic heterocyclylalkyloxy, non-aromatic carbocyclyl, non-aromatic heterocyclyl, hydroxy non-aromatic heterocyclyl, cyano non-aromatic heterocyclyl, alkyl non-aromatic heterocyclyl, hydroxyalkyl non-aromatic heterocyclyl, carboxyalkyl non-aromatic heterocyclyl, aromatic carbocyclylalkyl non-aromatic heterocyclyl, non-aromatic heterocyclylalkyl non-aromatic heterocyclyl, non-aromatic heterocyclylcarbonyl non-aromatic heterocyclyl, alkyloxycarbonyl non-aromatic heterocyclyl, carboxy non-aromatic heterocyclyl, carbamoyl non-aromatic heterocyclyl, cyanoalkylcarbamoyl non-aromatic carbocycyl, cyano non-aromatic carbocyclylcarbamoyl non-aromatic heterocyclyl, alkylamino non-aromatic heterocyclyl, oxo non-aromatic heterocyclyl or aromatic carbocyclyl non-aromatic heterocyclyl, the s substituent(s) selected from the Substituent group δ" is(are) alkylcarbonyl, cyanoalkylcarbonyl, hydroxyalkylcarbonyl or alkyloxycarbonyl, $R^{4a}$ and $R^{4b}$ are hydrogen, $R^{5a}$ is hydrogen or unsubstituted alkyl, $R^{5b}$ is substituted or unsubstituted alkyl, wherein the substituent(s) is(are) hydroxy, halogen, alkyloxy optionally substituted with halogen, non-aromatic carbocyclyl, aromatic carbocyclyl or aromatic carbocyclylalkyloxy, or $R^{4a}$ and $R^{5a}$ are hydrogen, $R^{4b}$ and $R^{5b}$ are taken together to form substituted or unsubstituted non-aromatic carbocycle or substituted or unsubstituted non-aromatic heterocycle, or a pharmaceutically acceptable salt thereof.

(14') A pharmaceutical composition comprising the compound according to any one of (1') to (13") or a pharmaceutically acceptable salt thereof as an active ingredient.

(15') The pharmaceutical composition according to (14'), which has an autotaxin inhibitory activity.

(16') A method for the prevention or treatment of a disease involving autotaxin, which is characterized by administering the compound according to any one of (1') to (13") or a pharmaceutically acceptable salt thereof.

(17') The compound according to any one of (1') to (13") for the prevention or treatment of a disease involving autotaxin or a pharmaceutically acceptable salt thereof.

(18') Use of a compound according to any one of (1') to (13') or a pharmaceutically acceptable salt thereof for the manufacture of a medicament for the prevention or treatment of a disease involving autotaxin.

(19') An autotaxin inhibitor comprising a compound of formula (I):

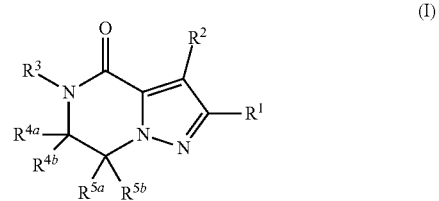

wherein
$R^1$ is substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted alkyl, substituted or unsubstituted alkenyl, substituted or unsubstituted alkynyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted carbamoyl, substituted or unsubstituted alkyloxy, substituted or unsubstituted alkenyloxy, substituted or unsubstituted alkynyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy or substituted or unsubstituted amino, $R^2$ is hydrogen, halogen, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, $R^3$ is hydrogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, or substituted or unsubstituted aromatic heterocyclylsulfonyl, $R^{4a}$ and $R^{4b}$ are each independently hydrogen, halogen, hydroxy, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl, or substituted or unsubstituted aromatic heterocyclylsulfonyl, $R^5$ is hydrogen, halogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy, $R^{5b}$ is halogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, or $R^{4b}$ and $R^{5b}$ may be taken together to form a bond, or $R^{4b}$ and $R^{5b}$ may be taken together to form substituted or unsubstituted non-aromatic carbocycle or substituted or unsubstituted non-aromatic heterocycle, or a pharmaceutically acceptable salt thereof.

Effect of the Invention

The compound of the present invention exhibits excellent autotaxin inhibitory activity, and is useful as the prevention or treatment of a disease involving especially autotaxin.

DESCRIPTION OF EMBODIMENTS

The definitions of the terms as used herein are as follows. Unless specified otherwise, these terms are used alone or in combination with another term in the meaning as defined.

"Halogen" includes fluorine, chlorine, bromine and iodine. Fluorine and chlorine are particularly preferable.

"Alkyl" means a straight or branched hydrocarbon group having 1 to 10 carbon atoms, and includes alkyl of 1 to 6 carbon atoms, alkyl of 1 to 4 carbon atoms, and alkyl of 1 to 3 carbon atoms and the like. Examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, n-decyl and the like.

Specific examples of "alkyl" for $R^3$ include methyl, ethyl, n-propyl, isopropyl, n-butyl, isobutyl, sec-butyl, tert-butyl and the like. In particular, methyl, ethyl, n-propyl, or n-butyl is preferred.

Specific examples of "alkyl" for $R^{5a}$ and $R^{5b}$ include methyl, ethyl, n-propyl, isopropyl, n-butyl, isobutyl, sec-butyl, tert-butyl, n-pentyl, isohexyl and the like. In particular, methyl, ethyl, n-propyl, n-butyl, n-pentyl, methylbutyl, n-hexyl, isohexyl, or ethylpentyl is preferred.

The preferred example of "alkyl" for $R^{5a}$ is particularly methyl or ethyl.

The preferred example of "alkyl" for $R^{5b}$ is particularly methyl, ethyl, n-propyl, isopropyl, n-butyl, or n-pentyl, more preferred is n-butyl or n-pentyl.

The alkyl moiety of "alkyloxy", "alkyloxycarbonyl", "alkylcarbonyl", "alkylsulfinyl", "alkylsulfonyl", "alkylthio", "alkylamino", "alkylaminoalkyl", "alkylaminoalkyl (alkyl)", "alkylaminoalkyloxy", "alkylaminocarbonylamino", "alkylaminocarbonylalkyl", "alkylamino non-aromatic heterocyclyl", "alkyloxyalkyl", "alkyloxyalkylcarbonylamino", "alkyloxycarbonylalkyl", "alkyloxycarbonyl non-aromatic carbocyclyl", "alkylcarbamoylalkyl", "alkylcarbonylamino", "alkylcarbonyloxy", "alkylsulfonylamino", "alkyl non-aromatic heterocyclyl", "oxo non-aromatic heterocyclylalkyl", "carbamoylalkyl", "carboxy(alkyl)", "carboxyalkyl", "carboxyalkyl(alkyl)", "carboxyalkyl non-aromatic heterocyclyl", "carboxyalkyl aromatic carbocyclyl", "carboxy non-aromatic carbocyclylalkyl", "carboxy aromatic carbocyclylalkyl", "di(hydroxy)alkyl", "cyanoalkyl", "cyanoalkylamino", "dialkylaminoalkyl", "dialkylaminoalkylcarbonylamino", "dialkylcarbamoylalkyl", "dialkyl non-aromatic heterocyclyl", "dicyanoalkyl", "trihalo(hydroxy)alkyl", "trihaloalkyl", "trihaloalkyloxy", "haloalkylcarbonylamino", "trihaloalkylcarbonylamino", "hydroxyalkyl", "hydroxyalkyloxyalkyl", "hydroxyalkyloxy non-aromatic heterocyclyl", "hydroxyalkylcarbonylamino", "hydroxyalkyl non-aromatic heterocyclylalkyl", "hydroxyalkyl non-aromatic heterocyclyl", "hydroxy aromatic carbocyclylalkyl", "hydroxy aromatic heterocyclylalkyl", "monohaloalkylcarbonylamino", "non-aromatic heterocyclylalkyloxy", "non-aromatic heterocyclylalkyl non-aromatic heterocyclyl", "aromatic carbocyclyl(carboxy)alkyl", "aromatic carbocyclyl(cyano)alkyl", "aromatic carbocyclyl(hydroxy)alkyl", "aromatic carbocyclylalkyl", "aromatic carbocyclylalkyl(carboxy)", "aromatic carbocyclylalkyl non-aromatic heterocyclyl", "aromatic carbocyclylsulfonylalkyl", "aromatic heterocyclylalkyl", "dialkylamino", "trihaloalkylamino", "alkyloxycarbonylamino", "dialkylaminoalkyloxy", "dialkylamino non-aromatic heterocyclyl", "hydroxyalkylcarbonyl" is as defined above "alkyl".

Namely, the examples of "alkyloxy" include methyloxy, ethyloxy, n-propyloxy, isopropyloxy, tert-butyloxy, n-octyloxy, isobutylmethylhexyloxy, n-nonyloxy and the like, in particular, methyloxy, ethyloxy, n-propyloxy and the like are preferred.

In particular, the preferred example of "alkyloxy" for $R^{5b}$ is methyloxy or ethyloxy.

"Haloalkyl" and "haloalkyloxy" mean respectively alkyl and alkyloxy substituted with 1 to 5, preferably 1 to 3, "halogen" at a substitutable position. Specific examples of "haloalkyl" for $R^{5b}$ include monohaloalkyl, dihaloalkyl, and trihaloalkyl. In particular, trifluorometyl, trifluoroethyl, and heptafluorobutyl are preferred.

"Alkenyl" means a linear or branched hydrocarbon group having 2 to 10 carbon atoms and one or more double bonds at any position, and includes alkenyl of 2 to 8 carbon atoms, alkenyl of 3 to 6. Examples include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like.

The alkenyl moiety of "alkenyloxy", "alkenyloxycarbonyl", "alkenyl carbonyl", "alkenylsulfinyl", "alkenylsulfonyl" and "alkenylthio" has the same meaning as defined above "alkenyl".

"Alkynyl" means a linear or branched hydrocarbon group having 2 to 10 carbon atoms and one or more triple bonds at any position, and includes alkynyl of 2 to 6 carbon atoms, alkynyl of 2 to 4 carbon atoms. Examples include ethynyl, propynyl, butynyl, pentynyl, hexynyl, heptynyl, octynyl, nonynyl, decynyl and the like. Also, the alkynyl may further have a double bond, as well as one or more triple bonds at anyl position.

The alkynyl moiety of "alkynyloxy", "alkynyloxycarbonyl", "alkynylcarbonyl", "alkynylsulfinyl", "alkynylsulfonyl" and "alkynylthio" has the same meaning as defined above "alkynyl".

"Non-aromatic carbocyclyl" includes cyclic saturated hydrocarbon group having 3 to 8 carbon atoms, groups wherein such cyclic saturated hydrocarbon ring is fused with further one or two 3- to 8-membered rings and cyclic unsaturated aliphatic hydrocarbon groups having 3 to 8 carbon atoms, and groups wherein such cyclic unsaturated aliphatic hydrocarbon ring is fused with further one or two 3- to 8-membered rings.

Specific examples of the cyclic saturated hydrocarbon group having 3 to 8 carbon atoms include cyclopropyl, cyclobutyl, cyclopentyl, cyclohexyl, cycloheptyl, cyclooctyl. In particular, a cyclic saturated hydrocarbon group having 3 to 6 carbon atoms and a cyclic saturated hydrocarbon group having 5 or 6 carbon atoms are preferred.

Specific examples of the ring to be fused with the cyclic saturated hydrocarbon group having 3 to 8 carbon atoms include non-aromatic carbocyclic rings, such as cycloalkane ring (for example: cyclohexane, cyclopentane etc.) and cycloalkene ring (for example: cyclohexene, cyclopentene etc.); non-aromatic heterocyclic rings, such as piperidine ring, piperazine ring and morpholine ring etc. The cyclic saturated hydrocarbon group having 3 to 8 carbon atoms should be involved in the linkage of such fused ring.

Specific examples of the ring to be fused with the cyclic unsaturated aliphatic hydrocarbon group having 3 to 8 carbon atoms include carbocyclic rings: such as aromatic carbocyclic rings (for example: benzene ring, naphthalene ring) and non-aromatic carbocyclic rings (for example: cycloalkane rings such as cyclohexane ring and cyclopentane ring, cycloalkene rings such as cyclohexene ring and cyclopentene ring); and heterocyclic rings: such as aromatic heterocyclic rings (for example: pyridine ring, pyrimidine ring, pyrrole ring, imidazole ring) and non-aromatic heterocyclic rings (for example: piperidine ring, piperazine ring, morpholine ring). The cyclic unsaturated aliphatic hydrocarbon group having 3 to 8 carbon atoms should be involved in the linkage of such fused ring.

Examples of the non-aromatic carbocyclic group include the following groups. These groups may have a substituent at any substitutable position.

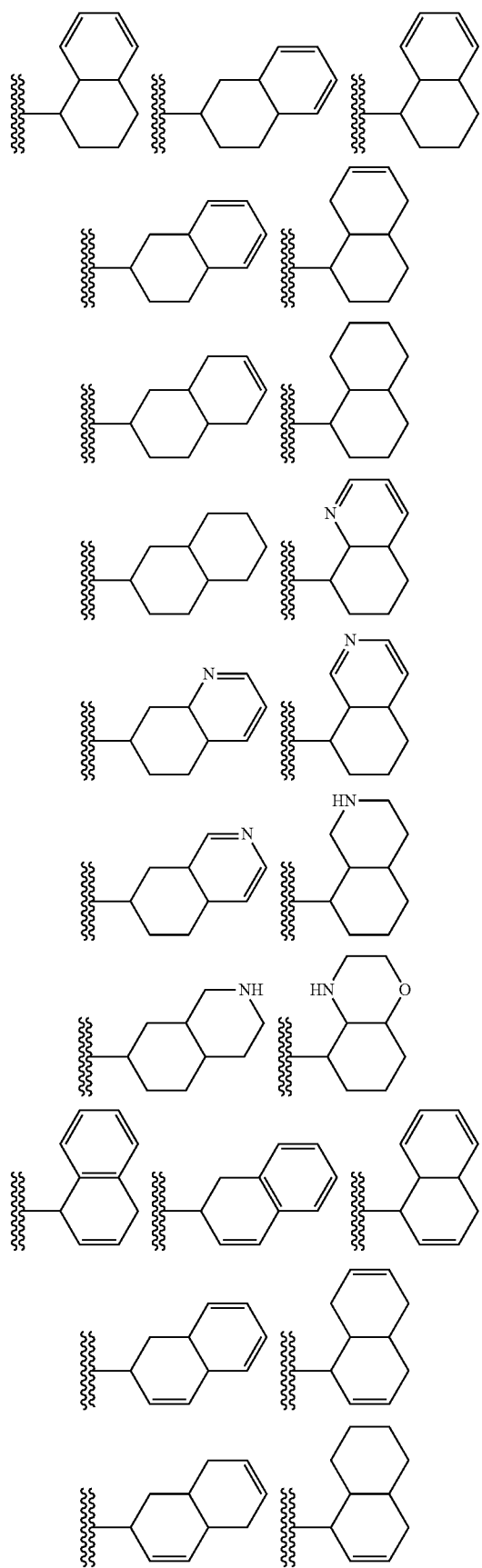

Specific examples of "non-aromatic carbocyclic group" for R¹ include cycloalkyl, cycloalkenyl and the like. In particular, cyclopropyl, cyclobutyl, cyclopentyl, cyclohexyl, cyclopentenyl, cyclohexenyl and the like are preferable.

Specific examples of "non-aromatic carbocyclyl for R³ include cycloalkyl, cycloalkenyl and the like. In particular, cyclopropyl, cyclobutyl, cyclopentyl, cyclohexyl, cyclopentenyl, cyclohexenyl and the like are preferable.

The non-aromatic carbocyclic ring moiety of "non-aromatic carbocyclyloxy", "non-aromatic carbocyclyloxycarbonyl", "non-aromatic carbocyclylcarbonyl", "non-aromatic carbocyclylsulfinyl", "non-aromatic carbocyclylsulfonyl", "non-aromatic carbocyclylthio", "alkyloxycarbonyl non-aromatic carbocyclyl", "carboxy non-aromatic carbocyclylalkyl", "carboxy non-aromatic carbocyclyl", "cyano non-aromatic carbocyclyl", "hydroxy non-aromatic carbocyclyl", "non-aromatic carbocyclylcarbonylamino", "cyano non-aromatic carbocyclylcarbamoyl non-aromatic heterocyclyl" and the like is as defined above "non-aromatic carbocycle".

"Aromatic carbocyclyl" includes monocyclic or polycyclic aromatic carbocyclic groups and groups wherein such monocyclic or polycyclic aromatic carbocyclic ring is fused with further one or two 3- to 8-membered rings. Specific examples of the monocyclic or polycyclic aromatic carbocyclic group include phenyl, naphthyl, anthryl and phenanthryl. Particularly, phenyl is preferred.

Specific examples of the ring to be fused with the monocyclic or polycyclic aromatic carbocyclic group include non-aromatic carbocycle such as cycloalkane rings (for example: cyclohexane ring, cyclopentane ring etc.), cycloalkene rings (for example: cyclohexene ring, cyclopentene ring etc.), and non-aromatic heterocycle (for example: piperidine ring, piperazine ring, morpholine ring etc). The monocyclic or polycyclic aromatic carbocyclyl should be involved in the linkage of such fused ring.

Examples of the aromatic carbocyclic groups include the following groups. These groups may have a substituent at any possible position.

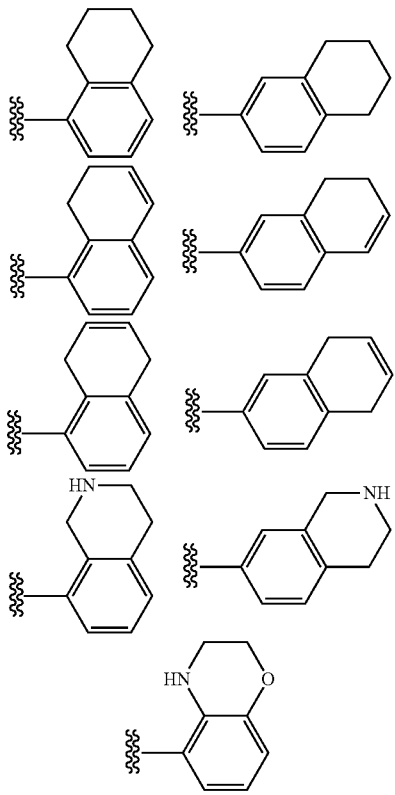

Specific examples of "aromatic carbocyclyl" for $R^1$ include phenyl, naphthyl, anthryl and phenanthryl and the like. In particular, phenyl is preferred.

The aromatic carbocycle moiety of "aromatic carbocyclyloxy", "aromatic carbocyclyloxycarbonyl", "aromatic carbocyclylcarbonyl", "aromatic carbocyclylsulfinyl", "aromatic carbocyclylsulfonyl", "aromatic carbocyclylthio", "carbamoyl aromatic carbocyclyl", "carboxyalkyl aromatic carbocyclyl", "carboxy aromatic carbocyclyl", "carboxy aromatic carbocyclylalkyl", "carboxy aromatic carbocyclyl", "aromatic carbocyclyl(carboxy)alkyl", "aromatic carbocyclylalkyl", "aromatic carbocyclylalkyl non-aromatic heterocyclyl", "aromatic carbocyclylsulfonylalkyl", "aromatic carbocyclyl non-aromatic heterocyclyl", "aromatic carbocyclyl(cyano)alkyl", "hydroxy aromatic carbocyclylalkyl", "aromatic carbocyclyl(hydroxy)alkyl" is as defined above "aromatic carbocycle".

"Aromatic heterocyclyl" means monocyclic or polycyclic aromatic heterocyclic groups having one or more heteroatoms selected from O, S and N in the ring and groups wherein such monocyclic or polycyclic aromatic heterocyclyl is fused with further one or two 3- to 8-membered rings.

Preferred examples of the monocyclic aromatic heterocyclyl include 5- or 6-membered aromatic heterocyclyl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl and the like.

Preferred examples of the polycyclic aromatic heterocyclyl include aromatic heterocyclyl fused with a 5- or 6-membered ring, such as bicyclic aromatic heterocyclyl (for example: indolyl, isoindolyl, indazolyl, indolizinyl, quinolinyl, isoquinolinyl, cinnolinyl, phthalazinyl, quinazolinyl, naphthyridinyl, quinoxalinyl, purinyl, puteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyradinopyridazinyl, oxazolopyridyl, thiazolopyridyl etc.); and tricyclic aromatic heterocyclyl (for example: carbazolyl, acridinyl, xanthenyl, phenothiazinyl, phenoxathiinyl, phenoxazinyl, dibenzofuryl etc.). Any ring of the polycyclic aromatic heterocyclyl may be involved in the linkage.

Specific examples of the ring to be fused the monocyclic or polycyclic aromatic heterocyclic groups include non-aromatic carbocycle such as cycloalkane rings (for example: cyclohexane ring, cyclopentane ring etc.), cycloalkene rings (for example: cyclohexene ring, cyclo pentene ring etc.), non-aromatic heterocycle (for example, piperidine ring, piperazine ring, morpholine ring etc.). The monocyclic or polycyclcic aromatic heterocyclyl should be involved in the linkage of such fused ring.

Examples of the aromatic heterocyclic groups include the following groups. These groups may have a substituent at any possible position.

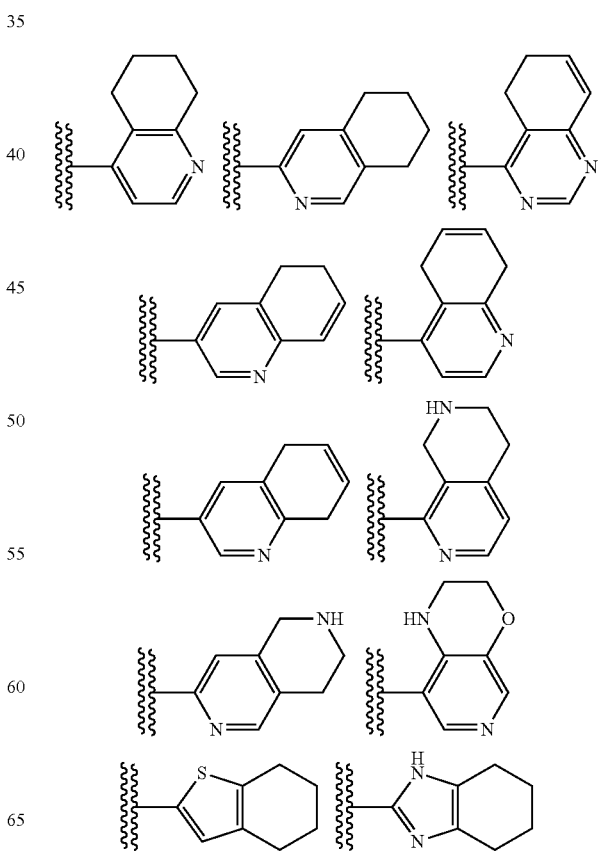

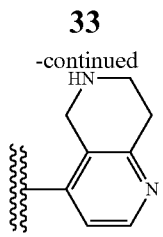

Specific examples of "aromatic heterocyclyl" for $R^1$ include pyrrolyl, imidazolyl, pyrazolyl, pyridyl, pyridadinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl and the like. In particular, pyridyl is preferred. Moreover, 2-pyridyl and 3-pyridyl are more preferred.

Specific examples of "aromatic heterocyclyl" for $R^3$ include pyrrolyl, imidazolyl, pyrazolyl, pyridyl, pyridazinyl, pyrimidinyl, pyrazinyl, triazolyl, triazinyl, tetrazolyl, isoxazolyl, oxazolyl, ocadiazolyl, isothiazolyl, thiazolyl, thiadiazolyl, furyl, thienyl and the like. In particular, pyridyl is preferred.

The aromatic heterocyclyl moiety of "aromatic heterocyclyloxy", "aromatic heterocyclyloxycarbonyl", "aromatic heterocyclylcarbonyl", "aromatic heterocyclylsulfinyl", "aromatic heterocyclylsulfonyl", "aromatic heterocyclylthio", "aromatic heterocyclylalkyl", "hydroxy aromatic heterocyclylalkyl", "aromatic heterocyclylamino" and the like is as defined above "aromatic heterocycle".

"Non-aromatic heterocyclyl" means monocyclic or polycyclic non-aromatic heterocyclyl having one or more heteroatoms selected from O, S and N in the ring and groups wherein such non-aromatic heterocyclic ring is fused with further one or two 3- to 8-membered rings.

Specific examples of the monocyclic non-aromatic heterocyclyl include dioxanyl, thiiranyl, oxiranyl, oxathioranyl, azetidinyl, thianyl, pyrrolidinyl, pyrrolinyl, imidazolidinyl, imidazolinyl, pyrazolidinyl, pyrazolinyl, piperidyl, piperidino, piperazinyl, piperazino, morpholinyl, morpholino, oxadiadinyl, dihydropyridyl, thiomorpholinyl, thiomorpholino, tetrahydrofuryl, tetrahydropyranyl, tetrahydrothiazolyl, tetrahydroisothiazolyl, oxazolidyl, thiazolidyl and the like.

Specific examples of the non-aromatic heterocyclyl include indolinyl, isoindolinyl, chromanyl, isochromanyl, isomannyl and the like. Any ring of the polycyclic non-aromatic heterocyclyl may be involved in the linkage.

Examples of the non-aromatic heterocyclyl include the following groups.

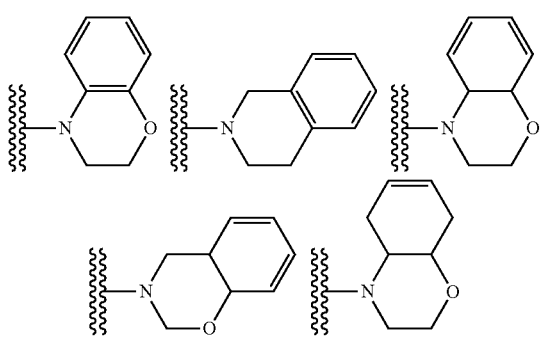

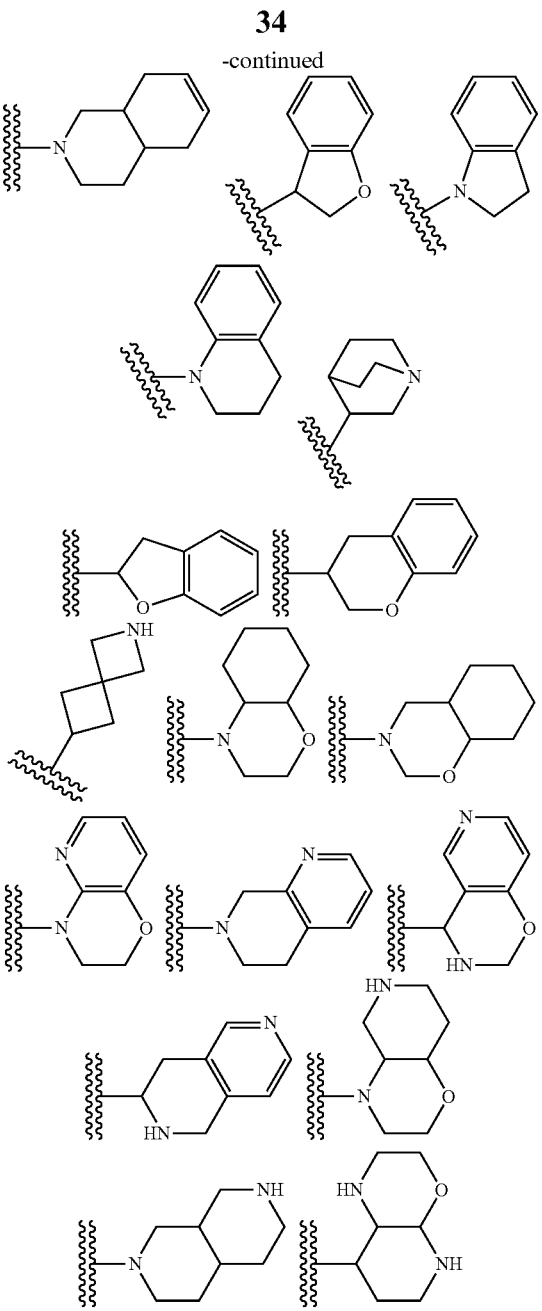

Specific examples of "non-aromatic heterocycle formula" for $R^1$ include azethidinyl, piperidyl, piperidino, piperazinyl, piperadino, morpholinyl, morpholino and the like. In particular, pirrolidinyl, piperidinyl, piperazinyl, morpholinyl, morpholino, azepanyl, isoindolinyl and the like are preferred. More preferable are azetidinyl, piperidinyl, isoindolinyl and the like.

The non-aromatic heterocyclic ring moiety of "non-aromatic heterocyclyloxy", "non-aromatic heterocyclyloxycarbonyl", "non-aromatic heterocyclylcarbonyl", "non-aromatic heterocyclylsulfinyl", "non-aromatic heterocyclylsulfonyl", "non-aromatic heterocyclylthio", "alkylamino non-aromatic heterocyclyl", "alkyl non-aromatic heterocyclyl", "oxo non-aromatic heterocyclyl", "carbamoyl non-aromatic heterocyclyl", "carboxyalkyl non-aromatic heterocyclyl", "carboxy non-aromatic heterocyclyl", "hydroxyalkyl non-aromatic heterocyclyl", "hydroxy non-aromatic heterocyclylcarbonyl", "hydroxy non-aromatic heterocyclyl", "non-aromatic heterocyclylalkyloxy", "non-aromatic heterocyclylalkyl non-aromatic heterocyclyl", "non-aromatic heterocyclylcarbonyl non-aromatic heterocyclyl", "non-aromatic heterocyclylsulfonyl", "oxo non-aromatic heterocyclylalkyl", "hydroxyalkyl non-aromatic heterocyclylalkyl", "cyano non-aromatic heterocyclyl", "dialkyl non-aromatic heterocyclyl", "hydroxyalkyloxy non-aromatic heterocyclyl", "cyano non-aromatic carbocyclylcarbamoyl non-aromatic heterocyclyl", "dialkylamino non-aromatic heterocyclyl", "cyano non-aromatic carbocyclylcarbamoyl non-aromatic heterocyclyl" and the like is as defined above "non-aromatic heterocycle".

The substituted or unsubstituted non-aromatic carbocyclyl or substituted or unsubstituted non-aromatic heterocyclyl are optionally substituted with one or two oxo, thioxo or substituted or unsubstituted imino.

Examples of the substituent group for "substituted alkyl", "substituted alkenyl", "substituted alkynyl", "substituted non-aromatic carbocyclyl", "substituted aromatic carbocyclyl", "substituted aromatic heterocyclyl" or "substituted non-aromatic heterocyclyl" include halogen, hydroxy, mercapto, nitro, nitroso, cyano, azido, formyl, amino, carboxy, alkyl, haloalkyl, alkenyl, alkynyl, non-aromatic carbocyclyl, aromatic carbocyclyl, aromatic heterocyclyl, non-aromatic heterocyclyl, substituted carbamoyl, substituted sulfamoyl, substituted amidino, a group of formula: —O—$R^x$, a group of formula: —O—C(=O)—$R^x$, a group of formula: —C(=O)—$R^x$, a group of formula: —C(=O)—O—$R^x$, a group of formula: —S—$R^x$ or a group formula: —$SO_2$—$R^x$ wherein $R^x$ is alkyl, haloalkyl, alkenyl, alkynyl, non-aromatic carbocyclyl, aromatic carbocyclyl, aromatic heterocyclyl, non-aromatic heterocyclyl, carbamoyl, sulfamoyl or amidino. One or more of these substituents may occur at any substitutable position.

Specific examples of the substituent for "substituted alkyl" in $R^3$ include hydroxy, carboxy, aromatic carbocyclyl optionally substituted with one or more substituent(s) selected from the above Substituent group α", aromatic heterocyclyl optionally substituted with carboxy, carbamoyl optionally substituted with one or more substituent(s) selected from the above Substituent group β", carbonyl optionally substituted with one or more substituent(s) selected from the Substituent group γ", amino optionally substituted with one or more substituent(s) selected from the substituent group δ" and the like.

Specific examples of the substituent for "substituted alkyl" in $R^{5a}$ and $R^{5b}$ include hydroxy, halogen, alkyloxy optionally substituted with halogen, aromatic carbocyclyl, aromatic carbocyclylalkyloxy and the like.

Specific examples of the substituent for "substituted aromatic carbocyclyl", "substituted non-aromatic heterocyclyl", and "substituted non-aromatic heterocyclylcarbonyl" in $R^1$ include halogen, cyano, formyl, carboxy, trihaloalkyl, cyanoalkyl, hydroxyalkyl, alkenyl, alkyloxy, trihaloalkyloxy, alkyloxyalkyl, alkylcarbamoylalkyl, alkylaminoalkyl, dialkylaminoalkyl, amino, alkylamino, dialkylamino, cyanoalkylamino, trihaloalkylamino, alkylcarbonylamino, monohaloalkylcarbonylamino, trihaloalkylcarbonylamino, hydroxyalkylcarbonylamino, alkyloxycarbonylamino, alkyloxyalkylcarbonylamino, non-aromatic carbocyclylcarbonylamino, alkylamino carbonylamino, dialkylaminocarbonylamino, alkylsulfonylamino, aromatic heterocycyamino, trihaloalkylcarbamoyl, alkyloxyalkylcarbamoyl, dialkylaminocarbonylamino, pentafluorothio, aromatic carbocyclyl and the like.

Specific examples of the substituent of the substituent for "substituted amino", "substituted carbamoyl", "substituted sulfamoyl", "substituted amidino" or "substituted imino" include hydroxy, cyano, formyl, alkyl, haloalkyl, alkenyl, alkynyl, non-aromatic carbocyclyl, aromatic carbocyclyl, aromatic heterocyclyl, non-aromatic heterocyclyl, carbamoyl, sulfamoyl, amidino, a group of formula: —O—R, a group of formula: —C(=O)—R, a group of formula: —C(=O)—O—R, or a group of formula: —$SO_2$—R, wherein R include alkyl, haloalkyl, alkenyl, alkynyl, non-aromatic carbocyclyl, aromatic carbocyclyl, aromatic heterocyclyl or non-aromatic heterocyclyl. One or two of these substituents may occur at any substitutable position.

Specific examples of the substituent for "substituted amino" in $R^4$ include alkyl, hydroxy alkyl, alkyloxy alkyl, carboxyalkyl, alkylaminoalkyl, aromatic carbocyclylalkyl, alkyloxy aromatic carbocyclylalkyl, alkyloxycarbonylalkyl, carboxy aromatic carbocyclylalkyl, alkylamino aromatic carbocyclylalkyl, methylene dioxy aromatic carbocyclylalkyl, aromatic heterocyclylalkyl, alkyl aromatic heterocyclylalkyl, non-aromatic heterocyclylalkyl, alkyl non-aromatic heterocyclylamino, alkylcarbonylaminoalkyl, non-aromatic carbocyclyl, alkylaminosulfonyl and the like.

"Pentafluorothio" means a group represented by the formula:

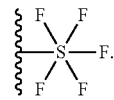

In the case of "$R^{4b}$ and $R^{5a}$ may be taken together to form a bond" in formula (I), formula (I) is represented by the following formula:

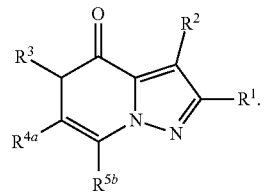

Preferred embodiments of $R^1$, $R^2$, $R^3$, $R^{4a}$, $R^{4b}$, $R^{5a}$ and $R^{5b}$ in a compound represented by formula (I):

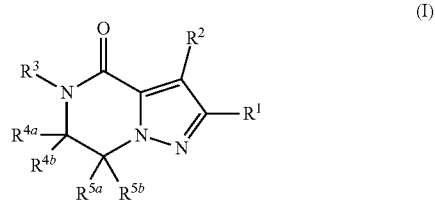

(I)

are described below. Compounds having possible combination of the substituents in the following embodiments are preferable.

$R^1$ includes substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted alkyl, substituted or unsubstituted alkenyl, substituted or unsubstituted alkynyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted carbamoyl, substituted or unsubstituted alkyloxy, substituted or unsubstituted alkenyloxy, substituted or unsubstituted alkynyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy or substituted or unsubstituted amino.

Preferable embodiments of $R^1$ include substituted or unsubstituted aromatic carbocyclyl, substituted or unsubstituted non-aromatic carbocyclyl, substituted or unsubstituted non-aromatic heterocyclyl, substituted or unsubstituted alkenyl, substituted or unsubstituted alkynyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted carbamoyl, substituted or unsubstituted alkenyloxy, substituted or unsubstituted alkynyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy or substituted or unsubstituted amino.

The other preferable embodiments of $R^1$ include substituted or unsubstituted non-aromatic carbocyclyl, substituted or unsubstituted aromatic carbocyclyl or substituted or unsubstituted non-aromatic heterocyclyl.

The other more preferable embodiments of $R^1$ include non-aromatic carbocyclyl optionally substitute with one or more substituent(s) selected from the Substituent group B (halogen, cyano, formyl, carboxy, hydroxyalkyl, cyanoalkyl, trihaloalkyl, alkyloxyalkyl, alkylcarbamoylalkyl, alkylaminoalkyl, dialkylaminoalkyl, alkylaminocarbonylamino, alkyloxy, trihaloalkyloxy, amino, alkylamino, cyanoalkylamino, alkylcarbonylamino, monohaloalkylcarbonylamino, trihaloalkylcarbonylamino, hydroxyalkylcarbonylamino, alkylaminocarbonylamino, dialkylaminoalkylcarbonylamino, non-aromatic carbocyclylcarbonylamino, alkylaminocarbonylamino, alkyloxyalkylcarbonylamino, alkylsulfonylamino, aromatic heterocyclylamino, trihaloalkylcarbamoyl, alkyloxyalkylcarbamoyl and aromatic carbocyclyl), aromatic carbocyclyl optionally substituted with one or more substituent(s) selected with the Substituent group B, non-aromatic heterocyclyl optionally substituted with one or more substituent(s) selected with a substituent group B, and non-aromatic heterocyclyl optionally substituted with one or more substituent(s) selected from a substituent group B.

The other more preferable embodiments of $R^1$ include aromatic carbocyclyl substituted with one or more substituent(s) selected from the Substituent group B or unsubstituted aromatic carbocyclyl.

The other more preferable embodiments of $R^1$ include phenyl substituted with one or more substituent(s) selected from the Substituent group C consisting of halogen, cyano, formyl, carboxy, trihaloalkyl, cyanoalkyl, hydroxyalkyl, alkenyl, alkyloxy, trihaloalkyloxy, alkyloxyalkyl, alkylcarbamoylalkyl, alkylaminoalkyl, dialkylaminoalkyl, amino, alkylamino, dialkylamino, cyanoalkylamino, trihaloalkylamino, alkylcarbonylamino, monohaloalkylcarbonylamino, trihaloalkylcarbonylamino, non-aromatic carbocyclylcarbonylamino, hydroxyalkylcarbonylamino, alkyloxycarbonylamino, alkyloxyalkylcarbonylamino, alkylaminocarbonylamino, dialkylaminocarbonylamino, alkylsulfonylamino, aromatic heterocycloylamino and trihaloalkylcarbamoyl, alkyloxyalkylcarbamoyl and aromatic carbocyclyl.

The other more preferable embodiments of $R^1$ include a group represented by formula:

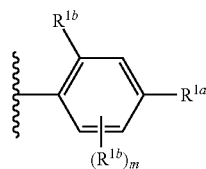

wherein $R^{1a}$ is halogen, cyano, substituted alkyl, substituted or unsubstituted alkenyl, substituted or unsubstituted alkynyl, substituted alkyloxy, substituted or unsubstituted alkenyloxy, substituted or unsubstituted alkynyloxy, substituted or unsubstituted alkylthio, substituted or unsubstituted alkenylthio, or substituted or unsubstituted alkynylthio, $R^{1b}$ is halogen, cyano, hydroxy, formyl, carboxy, substituted or unsubstituted alkyl, substituted or unsubstituted alkenyl, substituted or unsubstituted alkynyl, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted alkyloxy, substituted or unsubstituted alkenyloxy, substituted or unsubstituted alkynyloxy, substituted or unsubstituted aromatic carbocyclyloxy, substituted or unsubstituted aromatic heterocyclyloxy, substituted or unsubstituted non-aromatic carbocyclyloxy, substituted or unsubstituted non-aromatic heterocyclyloxy, substituted or unsubstituted alkyl carbonyl, substituted or unsubstituted alkenyl carbonyl, substituted or unsubstituted alkynyl carbonyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkenyloxycarbonyl, substituted or unsubstituted alkynyloxy carbonyl, substituted or unsubstituted aromatic carbocyclyloxy carbonyl, substituted or unsubstituted aromatic heterocyclyloxycarbonyl, substituted or unsubstituted non-aromatic carbocyclyloxycarbonyl, substituted or unsubstituted non-aromatic heterocyclyloxycarbonyl, substituted or unsubstituted carbamoyl, substituted or unsubstituted alkylthio, substituted or unsubstituted alkenylthio, substituted or unsubstituted alkynylthio, substituted or unsubstituted aromatic carbocyclylthio, substituted or unsubstituted aromatic heterocyclylthio, substituted or unsubstituted non-aromatic carbocyclylthio, substituted or unsubstituted non-aromatic heterocyclylthio, substituted or unsubstituted alkylsulfinyl, substituted or unsubstituted alkenylsulfinyl, substituted or unsubstituted alkynylsulfinyl, substituted or unsubstituted aromatic carbocyclylsulfinyl, substituted or unsubstituted aromatic heterocyclylsulfinyl, substituted or unsubstituted non-aromatic carbocyclylsulfinyl, substituted or unsubstituted non-aromatic heterocyclylsulfinyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted aromatic heterocyclylsulfonyl, substituted or unsubstituted non-aromatic carbocyclylsulfonyl, substituted or unsubstituted non-aromatic heterocyclylsulfonyl, substituted or unsubstituted carbamoyl, substituted or unsubstituted sulfamoyl or substituted or unsubstituted amino, m is integer of 0 to 3.

The other preferable embodiments of $R^{1a}$ include halogen, cyano, trihaloalkyl, alkyloxy, and trihaloalkyloxy.

The other more preferable embodiments of $R^{1b}$ include halogen, formyl, cyanoalkyl, hydroxyalkyl, alkyloxyalkyl, alkylaminoalkyl, dialkylaminoalkyl, alkenyl, amino, alkylamino, cyanoalkylamino, trihaloalkylamino, alkylcarbonylamino, haloalkylcarbonylamino, trihaloalkylcarbonylamino, hydroxyalkylcarbonylamino, alkyloxyalkylcarbonylamino, alkyloxycarbonylamino, alkylaminocarbonylamino, dialkylaminoalkylcarbonylamino, non-aromatic carbocyclylcarbonylamino, alkylsulfonylamino, and aromatic carbocyclylamino.

$R^2$ is hydrogen, halogen, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyl oxy carbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl.

Preferable embodiment of $R^2$ includes hydrogen.

$R^3$ is hydrogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl.

Preferable embodiments of $R^3$ include alkyl substituted with one or more substituent(s) selected from the above Substituent group A", alkenyl substituted with one or more substituent(s) selected from the above Substituent group A", alkynyl substituted with one or more substituent(s) selected from the above Substituent group A", substituted or unsubstituted aromatic carbocyclyl or substituted or unsubstituted aromatic heterocyclyl.

The other preferable embodiment of the said one or more substituent(s) selected from the Substituent group A" in $R^3$ include hydroxy, carboxy, aromatic carbocyclyl optionally substituted with one or more substituent(s) selected from the above Substituent group α", substituted or unsubstituted non-aromatic heterocyclyl, aromatic heterocyclyl optionally substituted with carboxy, carbamoyl optionally substituted with one or more substituent(s) selected from the above the Substituent group β", carbonyl optionally substituted with one or more substituent(s) selected from the above Substituent group γ" and amino optionally substituted with one or more substituent(s) selected from the above Substituent group δ".

$R^{4a}$ and $R^{4b}$ are each independently hydrogen, halogen, hydroxy, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl.

Preferable embodiment of $R^{4a}$ and $R^{4b}$ include that both of them is hydrogen.

Preferable embodiment of $R^{4a}$ and $R^{5b}$ include that they are taken together to form substituted or unsubstituted non-aromatic heterocycle.

The other preferable embodiments of $R^{4b}$ and $R^{5b}$ include that they are taken together to form a bond.

Preferable embodiments of $R^{4b}$ and $R^5$ include that they are taken together to form substituted or unsubstituted non-aromatic carbocycle or substituted or unsubstituted non-aromatic heterocycle.

$R^{5a}$ is hydrogen, halogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyl oxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy.

Preferable embodiments of $R^{5a}$ include hydrogen, substituted or unsubstituted alkyl, substituted or unsubstituted alkenyl or substituted or unsubstituted alkynyl.

The other more preferable embodiment(s) of $R^{5a}$ include hydrogen or substituted or unsubstituted alkyl.

The other more preferable embodiments of $R^{5a}$ include hydrogen.

$R^{5b}$ is halogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy.

Preferable embodiments of $R^{5b}$ include substituted or unsubstituted alkyl, substituted or unsubstituted alkenyl or substituted or unsubstituted alkynyl.

The other preferable embodiments of $R^{5b}$ include substituted or unsubstituted C2 to C10 alkyl.

The other more preferable embodiments of $R^{5b}$ include substituted or unsubstituted alkyl, wherein the substituent is hydroxy, halogen, alkyloxy optionally substituted with halogen, aromatic carbocyclyl or aromatic carbocyclylalkyloxy.

Preferred embodiments of the invention are described below.

Preferred embodiments of the substituents for $R^1$, $R^2$, $R^3$, $R^4$, $R^{4b}$, $R^{5a}$ and $R^{5b}$ in formula (I) are described in (Ia) to (Iz) and (Ia') to (Ie'). Compounds having possible combination of the following embodiments are preferable.

$R^1$ is, preferably, (Ia) substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted alkyl, substituted or unsubstituted alkenyl, substituted or unsubstituted alkynyl, substituted or unsubstituted aromatic carbocyclylcarbonyl, substituted or unsubstituted aromatic heterocyclylcarbonyl, substituted or unsubstituted non-aromatic carbocyclylcarbonyl or substituted or unsubstituted non-aromatic heterocyclylcarbonyl, substituted or unsubstituted carbamoyl, substituted or unsubstituted alkyloxy, substituted or unsubstituted alkenyloxy, substituted or unsubstituted alkynyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy or substituted or unsubstituted amino, (Ib) substituted or unsubstituted aromatic carbocyclyl, substituted or unsubstituted aromatic heterocyclyl, substituted or unsubstituted non-aromatic carbocyclyl or substituted or unsubstituted non-aromatic heterocyclyl, (Ic) substituted or unsubstituted aromatic carbocyclyl or substituted or unsubstituted aromatic heterocyclyl, (Id) substituted or unsubstituted alkyl, substituted or unsubstituted alkenyl or substituted or unsubstituted alkynyl, (Ie) substituted or unsubstituted aromatic carbocyclylcarbonyl, substituted or unsubstituted aromatic heterocyclylcarbonyl, substituted or unsubstituted non-aromatic carbocyclylcarbonyl or substituted or unsubstituted non-aromatic heterocyclylcarbonyl or substituted or unsubstituted carbamoyl, or (If) substituted or unsubstituted alkyloxy, substituted or unsubstituted alkenyloxy, substituted or unsubstituted alkynyloxy, substituted or unsubstituted aromatic carbocyclyloxy, substituted or unsubstituted non-aromatic carbocyclyloxy, substituted or unsubstituted aromatic heterocyclyloxy, substituted or unsubstituted non-aromatic heterocyclyloxy or substituted or unsubstituted amino, (If') non-aromatic carbocyclyl optionally substituted with one or more substituent(s) selected from the Substituent group B consisting of halogen, cyano, formyl, carboxy, hydroxy alkyl, cyano alkyl, trihaloalkyl, alkyloxyalkyl, alkylcarbamoylalkyl, alkylaminoalkyl, dialkylaminoalkyl, alkylaminocarbonylamino, alkyloxy, trihaloalkyloxy, amino, alkylamino, cyanoalkylamino, alkylcarbonyl amino, monohaloalkylcarbonylamino, trihaloalkylcarbonylamino, hydroxyalkylcarbonylamino, alkylaminocarbonylamino, dialkylaminoalkylcarbonylamino, non-aromatic carbocyclylcarbonyl amino, alkylaminocarbonylamino, alkyloxyalkylcarbonylamino, alkylsulfonylamino, aromatic heterocyclylamino, trihaloalkylcarbamoyl, alkyloxyalkylcarbamoyl and aromatic carbocyclyl, aromatic carbocyclyl optionally substituted with one or more substituent(s) selected from the Substituent group B, non-aromatic heterocyclyl optionally substituted with one or more substituent(s) selected from the Substituent group B, non-aromatic heterocyclyl optionally substituted with one or more substituent(s) selected from the Substituent group B, (If″) aromatic carbocyclyl optionally substituted with one or more substituent(s) selected from the Substituent group B, (If‴) phenyl substituted with one or more substituent(s) selected form the Substituent group C consisting of halogen, cyano, formyl, carboxy, trihaloalkyl, cyanoalkyl, hydroxyalkyl, alkenyl, alkyloxy, trihaloalkyloxy, alkyloxyalkyl, alkylcarbamoylalkyl, alkylaminoalkyl, dialkylaminoalkyl, amino, alkylamino, dialkylamino, cyanoalkylamino, trihaloalkylamino, alkylcarbonylamino, monohaloalkylcarbonylamino, trihaloalkylcarbonylamino, non-aromatic carbocyclylcarbonylamino, hydroxyalkylcarbonylamino, alkyloxycarbonylamino, alkyloxyalkylcarbonylamino, alkylaminocarbonylamino, dialkylaminocarbonylamino, alkylsulfonylamino, aromatic heterocyclylamino and trihaloalkylcarbamoyl, alkyloxyalkylcarbamoyl and aromatic carbocyclyl, (If″″) a group represented by formula:

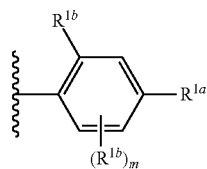

wherein $R^{1a}$ is halogen, cyano, substituted alkyl, substituted or unsubstituted alkenyl, substituted or unsubstituted alkynyl, substituted alkyloxy, substituted or unsubstituted alkenyloxy, substituted or unsubstituted alkynyloxy, substituted or unsubstituted alkylthio, substituted or unsubstituted alkenylthio, substituted or unsubstituted alkynylthio, $R^{1b}$ is halogen, cyano, hydroxy, formyl, carboxy, substituted or unsubstituted alkyl, substituted or unsubstituted alkenyl, substituted or unsubstituted alkynyl, substituted or unsubstituted aromatic carbocyclyl, substituted or unsubstituted aromatic heterocyclyl, substituted or unsubstituted non-aromatic carbocyclyl, substituted or unsubstituted non-aromatic heterocyclyl, substituted or unsubstituted alkyloxy, substituted or unsubstituted alkenyloxy, substituted or unsubstituted alkynyloxy, substituted or unsubstituted aromatic carbocyclyloxy, substituted or unsubstituted aromatic heterocyclyloxy, substituted or unsubstituted non-aromatic carbocyclyloxy, substituted or unsubstituted non-aromatic heterocyclyloxy, substituted or unsubstituted alkylcarbonyl, substituted or unsubstituted alkenyl carbonyl, substituted or unsubstituted alkynyl carbonyl, substituted or unsubstituted aromatic carbocyclylcarbonyl, substituted or unsubstituted aromatic heterocyclylcarbonyl, substituted or unsubstituted non-aromatic carbocyclylcarbonyl, substituted or unsubstituted non-aromatic heterocyclylcarbonyl, substituted or unsubstituted alkyloxycarbonyl, substituted or unsubstituted alkynyloxycarbonyl, substituted or unsubstituted alkynyloxycarbonyl, substituted or unsubstituted aromatic carbocyclyloxycarbonyl, substituted or unsubstituted aromatic heterocyclyloxycarbonyl, substituted or unsubstituted non-aromatic carbocyclyloxycarbonyl, substituted or unsubstituted non-aromatic heterocyclyloxy carbonyl, substituted or unsubstituted carbamoyl, substituted or unsubstituted alkylthio, substituted or unsubstituted alkenylthio, substituted or unsubstituted alkynylthio, substituted or unsubstituted aromatic carbocyclylthio, substituted or unsubstituted aromatic heterocyclylthio, substituted or unsubstituted non-aromatic carbocyclylthio, substituted or unsubstituted non-aromatic heterocyclylthio, substituted or unsubstituted alkylsulfinyl, substituted or unsubstituted alkenylsulfinyl, substituted or unsubstituted alkynylsulfinyl, substituted or unsubstituted aromatic carbocyclylsulfinyl, substituted or unsubstituted aromatic heterocyclylsulfinyl, substituted or unsubstituted non-aromatic carbocyclylsulfinyl, substituted or unsubstituted non-aromatic heterocyclylsulfinyl, substituted or unsubstituted alkylsulfonyl, substituted or unsubstituted alkenylsulfonyl, substituted or unsubstituted alkynylsulfonyl, substituted or unsubstituted aromatic carbocyclylsulfonyl, substituted or unsubstituted aromatic heterocyclylsulfonyl, substituted or unsubstituted non-aromatic carbocyclylsulfonyl, substituted or unsubstituted non-aromatic heterocyclylsulfonyl, substituted or unsubstituted carbamoyl, substituted or unsubstituted sulfamoyl or substituted or unsubstituted amino, m is an integer of 0 to 3, (If″″′) a group represented by formula:

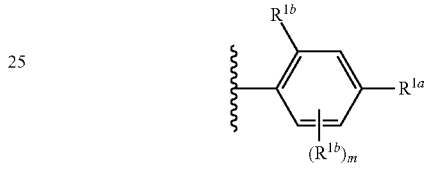

wherein $R^{1a}$ is halogen, cyano, trihaloalkyl, alkyl oxy, trihaloalkyloxy, $R^{1b}$ is halogen, formyl, cyanoalkyl, hydroxyalkyl, alkyloxyalkyl, alkylaminoalkyl, dialkylaminoalkyl, alkenyl, amino, alkylamino, cyanoalkylamino, trihaloalkylamino, alkylcarbonylamino, haloalkylcarbonylamino, trihaloalkylcarbonylamino, hydroxyalkylcarbonylamino, alkyloxyalkylcarbonylamino, alkyloxycarbonylamino, alkylaminoalkylcarbonylamino, dialkylaminoalkylcarbonylamino, non-aromatic carbocyclylcarbonyl amino, alkylsulfonylamino, aromatic carbocyclylamino, m is an integer of 0 to 3.

$R^2$ is, preferably, (Ig) hydrogen, halogen, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, (Ih) hydrogen, halogen, cyano, formyl, carboxy, substituted or unsubstituted alkyl, substituted or unsubstituted alkenyl or substituted or unsubstituted alkynyl, or (Ii) hydrogen.

$R^3$ is, preferably, (Ij) hydrogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, (Ik) substituted or unsubstituted alkyl, substituted or unsubstituted alkenyl or substituted or unsubstituted alkynyl, (Il) substituted or unsubstituted non-aromatic carbocyclyl or substituted or unsubstituted aromatic carbocyclyl, substituted or unsubstituted non-aromatic heterocyclyl or substituted or unsubstituted aromatic heterocyclyl, (Im) substituted or unsubstituted alkyl carbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, (In) alkyl substituted with one or more substituent(s) selected from the above Substituent group A", alkenyl substituted with one or more substituent(s) selected from the above Substituent group A or alkynyl substituted with one or more substituent(s) selected from the above Substituent group A, (Io) alkyl substituted with one or more substituent(s) selected from the above Substituent group A", (Ip) alkyl substituted with a substituent selected form the Substituent group D, wherein the Substituent group D is hydroxy, carboxy, aromatic carbocyclyl optionally substituted with one or more substituent(s) selected from the above Substituent group α", aromatic heterocyclyl optionally substituted with carboxy, carbamoyl optionally substituted with one or more substituent(s) selected from the above Substituent group β", carbonyl optionally substituted with one or more substituent(s) selected from the above Substituent group γ", and amino optionally substituted with one or more substituent(s) selected from the above Substituent group δ", or (Ip') alkyl substituted with one or more substituent(s) selected from the above Substituent group A", wherein the substituent(s) selected from the Substituent group A" is hydroxy, carboxy, aromatic carbocyclyl optionally substituted with one or more substituent(s) selected from the Substituent group α", non-aromatic heterocyclyl optionally substituted with one or more substituent(s) selected from the Substituent group α", aromatic heterocyclyl optionally substituted with carboxy, carbamoyl optionally substituted with one or more substituent(s) selected from the Substituent group β", carbonyl optionally substituted with one or more substituent(s) selected from the Substituent group γ" and amino optionally substituted with one or more substituent(s) selected from the Substituent group δ".

$R^{4a}$ and $R^{4b}$ are, preferably, (Iq) each independently hydrogen, halogen, hydroxy, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenyl sulfonyl, substituted or unsubstituted alkynyl sulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, $R^{4b}$ and $R^{5b}$ are taken together to form a bond, or $R^{4b}$ and $R^{5b}$ are taken together to form substituted or unsubstituted non-aromatic carbocycle or substituted or unsubstituted non-aromatic heterocycle; (Ir) each independently hydrogen, halogen, hydroxy, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkylsulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkylsulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl, (Is) each independently hydrogen, halogen, hydroxy, cyano, formyl, carboxy, substituted or unsubstituted alkyl, substituted or unsubstituted alkenyl, substituted or unsubstituted alkynyl or substituted or unsubstituted amino, (It) each independently hydrogen, substituted or unsubstituted non-aromatic carbocyclyl, substituted or unsubstituted aromatic carbocyclyl, substituted or unsubstituted non-aromatic heterocyclyl or substituted or unsubstituted aromatic heterocyclyl, (Iu) $R^{4b}$ and $R^{5b}$ are taken together to form substituted or unsubstituted non-aromatic carbocycle or substituted or unsubstituted non-aromatic heterocycle, (Iv) $R^{4b}$ and $R^{5b}$ are taken together to form a bond, or (Iw) $R^{4a}$ and $R^{4b}$ are hydrogen.

$R^{5a}$ is, preferably, (Ix) hydrogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy, (Iy) hydrogen, substituted or unsubstituted alkyl, substituted or unsubstituted alkenyl or substituted or unsubstituted alkynyl, or (Iz) hydrogen.

$R^{5b}$ is, preferably, (Ia') substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy, (Ib') substituted or unsubstituted alkyl, substituted or unsubstituted alkenyl or substituted or unsubstituted alkynyl, (Ic') substituted or unsubstituted non-aromatic carbocyclyl, substituted or unsubstituted aromatic carbocyclyl, substituted or unsubstituted non-aromatic heterocyclyl or substituted or unsubstituted aromatic heterocyclyl, (Id') substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy, or (Ie') substituted or unsubstituted C2 to C10 alkyl.

The compounds or its pharmaceutically acceptable salt are also preferable embodiments of the present invention.

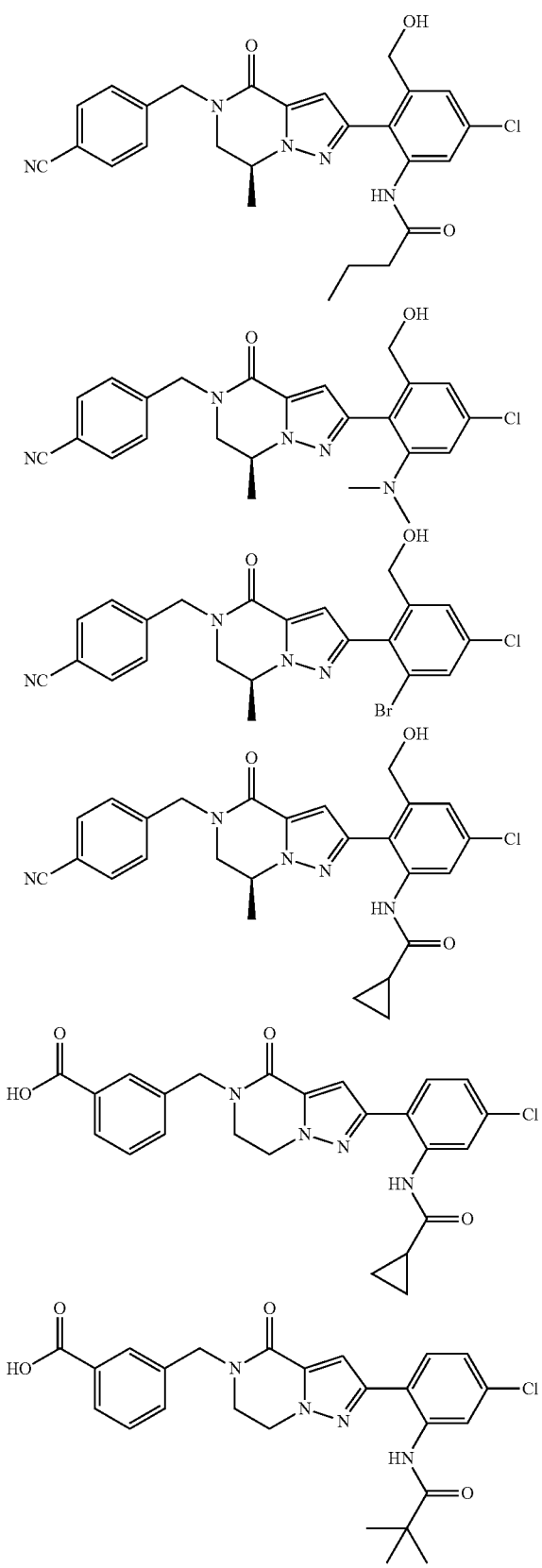

The compounds of the present invention are not limited to specific isomers and include all possible isomers (e.g., keto-enol isomers, imine-enamine isomers, diastereisomers; enantioisomer, rotamers and the like, racemates or mixture thereof.

One or more hydrogen, carbon and/or other atoms in the compounds of the present invention may be replaced with isotopes of hydrogen, carbon and/or other atoms respectively. Examples of the isotopes include hydrogen, carbon, nitrogen, oxygen, phosphorus, sulfur, fluorine, iodine and chlorine, such as $^2H$, $^3H$, $^{11}C$, $^{13}C$, $^{14}C$, $^{15}N$, $^{18}O$, $^{17}O$, $^3P$, $^{32}P$, $^{35}S$, $^{18}F$, $^{123}I$ and $^{31}Cl$ respectively. The compounds of the present invention include compounds replaced with these isotopes. The compounds replaced with the above isotopes are useful as pharmaceuticals and include all of radiolabeled compounds of the compound of the present invention. The present invention also includes a method of radiolabeling in the manufacture of the radiolabeled compounds. Such radiolabeled compounds are useful in the studies for metabolized drug pharmacokinetics and binding assay and also as a diagnostic tool.

A radiolabeled compound of the compounds of the present invention can be prepared using methods well-known in the art. For example, a tritium-labeled compound of formula (I) can be prepared by introducing a tritium into a compound of formula (I), through a catalytic dehalogenation using a tritium. This method comprises reacting with an appropriately-halogenated precursor of the compound of formula (I) with tritium gas in the presence of an appropriate catalyst, such as Pd/C, and in the presence or absent of a base. The other appropriate methods for preparing a tritium-labeled compound can be found in "Isotopes in the Physical and Biomedical Sciences, Vol. 1, Labeled Compounds (Part A), Chapter 6 (1987)". A $^{14}C$-labeled compound can be prepared by using a raw material having $^{14}C$ carbon.

Pharmaceutically acceptable salts of the compounds of the present invention include, for example, salts with alkaline metals such as lithium, sodium, potassium and the like; alkaline earth metals such as calcium, barium and the like; magnesium; transition metals such as zinc, iron and the like; ammonium; organic bases such as trimethylamine, trimethylamine, dicyclohexylamine, ethanolamine, diethanolamine, triethanolamine, meglumine, ethylenediamine, pyridine, picoline, quinolone and the like; amino acids; or inorganic acids such as hydrochloric acid, sulfuric acid, nitric acid, carbonic acid, hydrobromic acid, phosphoric acid, hydroiodic acid and the like; and organic acids such as formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethane sulfonic acid and the like, particularly salts with hydrochloric acid, sulfuric acid, phosphoric acid, tartaric acid and methanesulfonic acid. These salts can be formed according to conventional methods.

The compounds of the present invention or pharmaceutically acceptable salts thereof may exist in a form of solvate (e.g., hydrate and the like) and/or crystal polymorphs. The present invention encompasses those various solvates and crystal polymorphs. The "solvates" may be those wherein any numbers of solvent molecules (e.g. water molecules and the like) are coordinated with the compounds of the present invention. When the compounds of the present invention or pharmaceutically acceptable salts thereof are allowed to stand in the atmosphere, the compounds may absorb water, resulting in attachment of adsorbed water or formation of hydrates. Recrystallization of the compounds of the present invention or pharmaceutically acceptable salts thereof may produce crystal polymorphs.

The compounds of the present invention may form prodrugs. Such prodrugs are encompassed by the present invention. Prodrugs are derivatives of the compounds of the invention with a chemically or metabolically degradable group(s), and the compounds are converted to pharmaceutically active compounds of the invention through solvolysis or under physiological conditions in vivo. The prodrugs include compounds that are converted to a compound of the invention through enzymatic oxidation, reduction, hydrolysis or the like under physiological conditions in vivo, compounds that are converted to a compound of the invention through hydrolysis by gastric acid, and the like. Methods for selecting and preparing suitable prodrug derivatives are described in, for example, "Design of Prodrugs, Elsevier, Amsterdam, 1985". The prodrugs themselves may have some activity.

In case where the compound of the present invention or a pharmaceutically acceptable salt thereof has hydroxyl group(s), the prodrugs may be acyloxy derivatives and sulfonyloxy derivatives that are prepared by, for example, reacting a compound having hydroxyl group(s) with suitable acyl halide, suitable acid anhydride, suitable sulfonyl chloride, suitable sulfonyl anhydride or mixed anhydride, or by reacting with a condensing agent. Examples include $CH_3COO\!-\!$, $C_2H_5COO\!-\!$, $t\text{-BuCOO}\!-\!$, $C_{15}H_{31}COO\!-\!$, $PhCOO\!-\!$, $(m\text{-NaOOCPh})COO\!-\!$, $NaOOCCH_2CH_2COO\!-\!$, $CH_3CH(NH_2)COO\!-\!$, $CH_2N(CH_3)_2COO\!-\!$, $CH_3SO_3\!-\!$, $CH_3CH_2SO_3\!-\!$, $CF_3SO_3\!-\!$, $CH_2FSO_3\!-\!$, $CF_3CH_2SO_3\!-\!$, $p\text{-}CH_3\text{-}O\text{-}PhSO_3\!-\!$, $PhSO_3\!-\!$, and $p\text{-}CH_3PhSO_3\!-\!$.

"Chronic kidney disease" means a condition where either or both of (1) kidney disorder (urine abnormalities such as proteinuria, e.g. microalbuminuria, abnormal urinary sediment, abnormal finding of clinical imaging such as single kidney and polycystic kidney disease, decreased renal function such as increased serum creatinine, electrolyte abnormalities such as hypokalemia due to tubular damage, and abnormal finding of renal tissue biopsy) and (2) deterioration in renal function less than 60 mL/min/1.73 m² of GFR (glomerular filtration rate) is present for over three months.

The compounds of the present invention are produced according to general procedures as described below. Also, the compounds of the invention can be prepared according to other methods based on the knowledge in organic chemistry.

Preparation of Compound a2

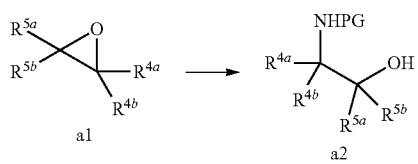

wherein
PG is an amino protecting group such as Boc etc., the other symbols are as defined above.

The compound a1 is reacted with ammonium hydroxide, and then reacted with a protecting agent to obtain Compound a2.

Examples of the solvent include 2-propanol, dichloromethane, tetrahydrofuran, N,N-dimethylformamide, ethanol, water, toluene, acetonitrile, 1,4-dioxane and the like, and these solvents may be used alone or in combination.

Ammonium hydroxide may be used in 1 to 50 mole equivalents, preferably 5 to 30 mole equivalents of Compound a1.

The reaction temperature may be room temperature to 200° C., preferably 50° C. to 150° C., and the reaction can be conducted in sealed tube as required.

The reaction time may be 0.1 to 24 hours, preferably 1 to 12 hours.

Examples of the amino-protecting agent include $(Boc)_2O$, Fmoc-Cl, benzyloxy chloride, benzyl bromide and the like, and the amount of the amino protecting agent may be 1 to 50 mole equivalents, preferably 1 to 10 mole equivalents of Compound a1.

Examples of the solvent for protecting amino group include dichloromethane, tetrahydrofuran, ethyl acetate, water, 1,2-dimethoxyethane, N,N-dimethylformamide, acetonitrile, 1,4-dioxane, acetone and the like, and these solvents may be used alone or in combination.

The reaction temperature for protecting amino group may be 0° C. to 100° C., preferably room temperature.

The reaction time for protecting amino group may be 0.1 to 24 hours, preferably 1 to 5 hours.

Preparation of Compound a4

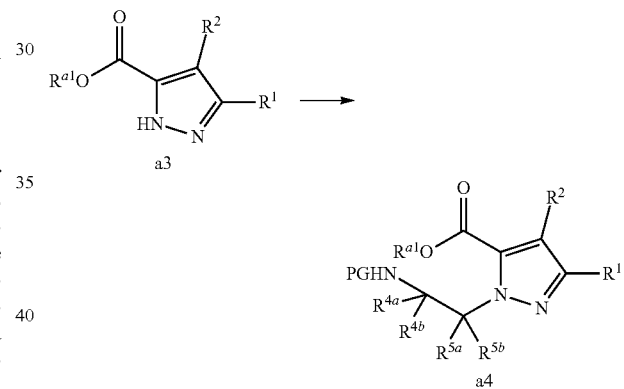

wherein
$R^{a1}$ is substituted or unsubstituted alkyl, substituted or unsubstituted alkenyl or substituted or unsubstituted alkynyl, the other symbols are as defined above.

Compound a4 can be obtained by reacting the solution of Compound a3 with Compound a2 in the presence of triphenylphosphine and a condensing agent.

Examples of the reaction solvent include tetrahydrofuran, dichloromethane, ethyl acetate, water, methanol, N,N-dimethylformamide, acetonitrile, 1,4-dioxane, toluene and the like, and these solvents may be used alone or in combination.

Triphenylphosphine may be used in 1 to 10 mole equivalents, preferably 1 to 3 mole equivalent of Compound a3.

Examples of the condensing agent include isopropyl azodicarboxylate, di-tert-butyl azodicarboxylate, diethyl azodicarboxylate, aluminium oxide, sulfuric acid, diphosphorus pentaoxide, sulfur trioxide, dicyclohexyl carbodimide and the like. The amount of the condensing agent may be 1 to 10 mole equivalents, preferably 1 to 3 mole equivalents of Compound a3.

The reaction temperature may be 0° C. to reflux temperature, preferably 0° C. to room temperature.

The reaction time may be 0.1 to 24 hours, preferably 1 to 5 hours.

Preparation of Compound a5

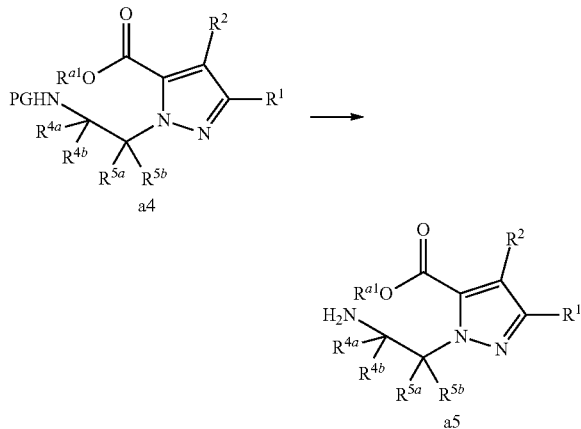

wherein each symbols is as defined above.

Compound 5a can be obtained by reacting the solution of Compound a4 with a deprotecting agent. The various salts of Compound 5a can be obtained as to the deprotecting agent.

Examples of the reaction solvent include ethyl acetate, methanol, water, ethanol, 2-propanol, dichloromethane, THF, 1,4-dioxane, tetrahydrofuran and the like, and these solvents may be used alone or in combination.

Examples of the deprotecting agent include hydrochloric acid/ethyl acetate, sodium hydroxide, palladium carbon, trichloroethyl chloroformate, piperidine, morpholine, tetrabutyl ammoniumfluoride and the like. The amount of the deprotecting agent may be 1 to 100 mole equivalents, preferably 1 to 20 mole equivalents of Compound a4.

The reaction temperature may be 0° C. to reflux temperature, preferably room temperature.

The reaction time may be 0.1 to 24 hours, preferably 1 to 5 hours.

Preparation of Compound a6

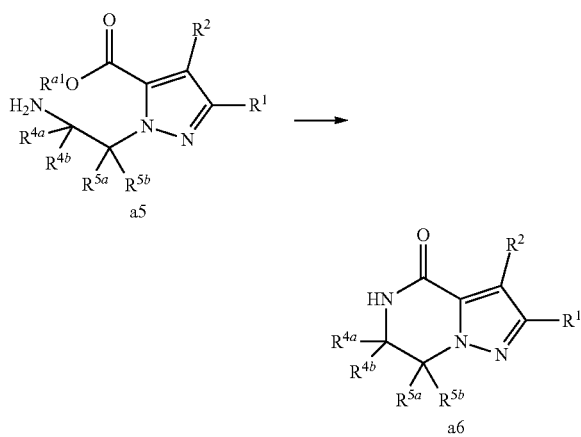

wherein each symbols is as defined above.

Compound a6 can be obtained by heating Compound a5. The salt of Compound a5 can be heating in the presence of base.

Examples of the reaction solvent include ethanol, water, dichloromethane, tetrahydrofuran, N,N-dimethylformamide, methanol, 1,4-dioxane, acetonitrile, toluene, ethyl acetate and the like, and these solvents may be used alone or in combination.

Examples of the base include triethylamine, diisopropylethylamine, sodium hydroxide, potassium carbonate and the like. The amount of the base may be 1 to 10 mole equivalents, preferably 1 to 5 mole equivalents of Compound a4.

The reaction temperature may be 50° C. to reflux temperature, preferably reflux temperature.

The reaction time may be 0.1 to 24 hours, preferably 1 to 5 hours.

Preparation of Compound a7

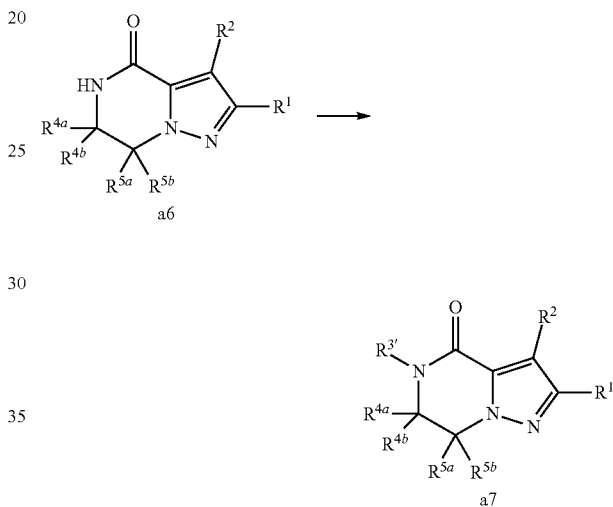

wherein $R^{3'}$ is substituted or unsubstituted alkyl, substituted or unsubstituted alkenyl or substituted or unsubstituted alkynyl, the other symbols are as defined above.

Compound a7 can be obtained by reacting Compound a6 with an electrophile in the presence of base.

Examples of the reaction solvent include tetrahydrofuran, ethanol, water, dichloromethane. N, N-dimethylformamide, methanol, 1,4-dioxane, acetonitrile, toluene, ethyl acetate and the like, and the solvent may be used alone or in combination.

Examples of the electrophile include halide, mesylate, tosylate and the like. The amount of the electrophile may be 1 to 10 mole equivalents, preferably 1 to 5 mole equivalents of Compound a6.

Examples of base may be potassium tert-butoxide, sodium hydride, potassium carbonate, cesium carbonate, triethylamine, diisopropylethylamine, DBU and the like. The amount of the base may be 1 to 10 mole equivalents, preferably 1 to 5 mole equivalents of Compound a6.

The reaction temperature may be under ice-cooling to reflux temperature, preferably under ice-cooling to room temperature.

The reaction time may be 0.1 to 24 hours, preferably 0.1 to 5 hours.

Preparation of Compound a9

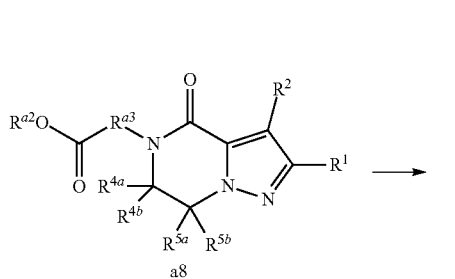

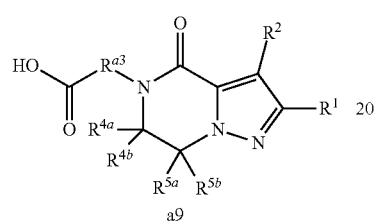

wherein $R^{a2}$ is substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl or substituted or unsubstituted aromatic heterocyclyl, $R^{a3}$ is substituted or unsubstituted alkylene, substituted or unsubstituted alkenylene, substituted or unsubstituted alkynylene, substituted or unsubstituted non-aromatic carbocyclediyl, substituted or unsubstituted aromatic carbocyclediyl, substituted or unsubstituted non-aromatic heterocyclediyl, substituted or unsubstituted aromatic heterocyclediyl, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted carbamoyl, substituted or unsubstituted sulfamoyl, substituted or unsubstituted alkylsulfonyl, substituted or unsubstituted alkenyl sulfonyl, substituted or unsubstituted alkynyl sulfonyl, the other symbols are as defined above.

Compound a9 can be obtained by hydrolyzing Compound a8.

Examples of the reaction solvent include tetrahydrofuran, ethanol, water, dichloromethane, N,N-dimethylformamide, methanol, 1,4-dioxane, acetonitrile, toluene, ethyl acetate and the like, these solvents may be used alone or in combination.

Examples of base include sodium hydroxide, lithium hydroxide, potassium hydroxide and the like. The amount of the base may be 1 to 10 mole equivalents, preferably 1 to 5 mole equivalents of Compound a8.

The reaction temperature may be under ice-cooling to reflux temperature, preferably room temperature.

The reaction time may be 0.1 to 24 hours, preferably 0.1 to 5 hours.

Preparation of Compound a10

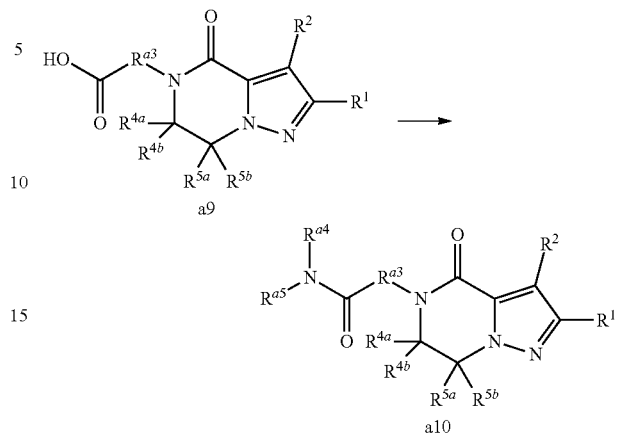

wherein $R^{a4}$ and $R^{a5}$ are each independently hydrogen, substituted or unsubstituted alkyl, substituted or unsubstituted alkenyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, or $R^{a4}$ and $R^{a5}$ are taken together with the nitrogen atom bonded them to form substituted or unsubstituted nitrogen-containing non-aromatic heterocyclyl, the other symbols are as defined above.

Compound a10 can be obtained by reacting Compound a9 with amine in the presence of condensing agents.

Examples of the reaction solvent include N,N-dimethylformamide, ethanol, water, dichloromethane, tetrahydrofuran, methanol, 1,4-dioxane, acetonitrile, toluene, ethyl acetate and the like, and these solvents may be used alone or in combination.

Examples of the base include triethylamine, potassium tert-butoxide, potassium carbonate, cesium carbonate, diisopropylethylamine, DBU and the like. The amount of the base may be 1 to 10 mole equivalents, preferably 1 to 5 mole equivalents of Compound a9.

Examples of the condensing agent include HATU, WSC, DCC and the like. The amount of the condensing agent may be 1 to 10 mole equivalents, preferably 1 to 5 mole equivalents of Compound a9.

The amine may be used in 1 to 10 mole equivalents, preferably 1 to 5 mole equivalents of Compound a9.

The reaction temperature may be under ice-cooling to reflux temperature, preferably room temperature.

The reaction time may be 0.1 to 24 hours, preferably 1 to 5 hours.

Preparation of Compound a11

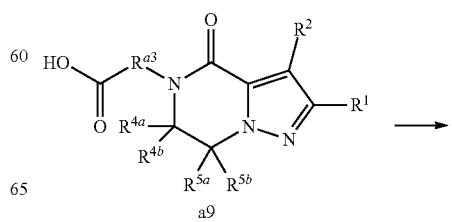

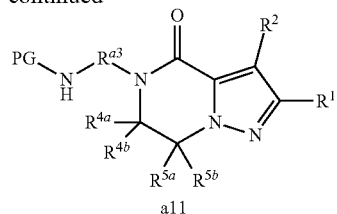

wherein each symbols is as defined above.

Compound a11 can be obtained by reacting Compound a9 with DPPA in the presence of base.

Examples of the reaction solvent include tert-buthanol, water, dichloromethane, N,N-dimethylformamide, ethanol, tetrahydrofuran, methanol, 1,4-dioxane, acetonitrile, toluene, ethyl acetate, benzene and the like, and these solvents may be used alone or in combination.

Examples of the base include triethylamine, diisopropylethylamine, and the like. The amount of the base may be 1 to 10 mole equivalents, preferably 1 to 3 mole equivalents of Compound a9.

The amount of DPPA may be 1 to 10 mole equivalents, preferably 1 to 5 mole equivalents of Compound a9.

The reaction temperature may be room temperature to reflux temperature, preferably reflux temperature.

The reaction time may be 1 to 24 hours, preferably 1 to 5 hours.

Preparation of Compound a12

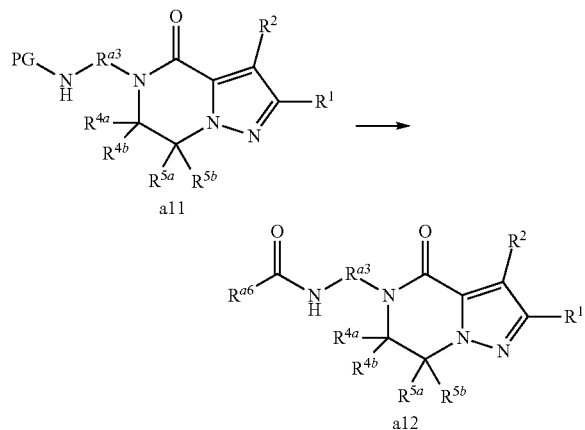

wherein $R^{a6}$ is substituted or unsubstituted alkyl, substituted or unsubstituted alkenyl, substituted or unsubstituted non-aromatic carbocyclyl, substituted or unsubstituted aromatic carbocyclyl, substituted or unsubstituted non-aromatic heterocyclyl or substituted or unsubstituted aromatic heterocyclyl, the other symbols are as defined above.

Compound a12 can be obtained by reacting acid anhydride or acid halide in the presence of base after reacting Compound a11 with deprotecting agents.

Examples of the reaction solvent for deprotecting reaction include ethyl acetate, water, dicloromethane, N, N-dimethylformamide, ethanol, tetrahydrofuran, methanol, 1,4-dioxane, acetonitrile, toluene and the like, and these solvents may be used alone or in combination.

Examples of the deprotecting agent include hydrochloric acid/ethyl acetate, methane sulfonic acid, trifluoroacetic acid, sulfuric acid, iodotrimethylsilane, aluminium trichloride, bromocatechol borane, trimethylsilyl chloride, trimethylsilyl triflate and the like. The amount of the deprotecting agent may be 1 to 100 mole equivalents, preferably 1 to 50 mole equivalents of Compound a11.

Examples of the base include triethylamine, cesium carbonate, potassium carbonate, diisopropylethylamine, sodium hydroxide, potassium hydroxide, sodium carbonate and the like.

The amount of the base may be 1 to 10 mole equivalents, preferably 1 to 5 mole equivalents of Compound a11.

The amount of the acid anhydride or acid halide may be 1 to 5 mole equivalents, preferably 1 to 3 mole equivalents of Compound a11.

Examples of the reaction solvent include methanol, water, dichloromethane, N,N-dimethylformamide, ethanol, tetrahydrofuran, 1,4-dioxane, acetonitrile, toluene, ethyl acetate and the like, and these solvents may be used alone or in combination.

The reaction temperature may be 0° C. to reflux temperature, preferably room temperature.

The reaction time may be 1 to 24 hours, preferably 1 to 12 hours.

Preparation of Compound a13

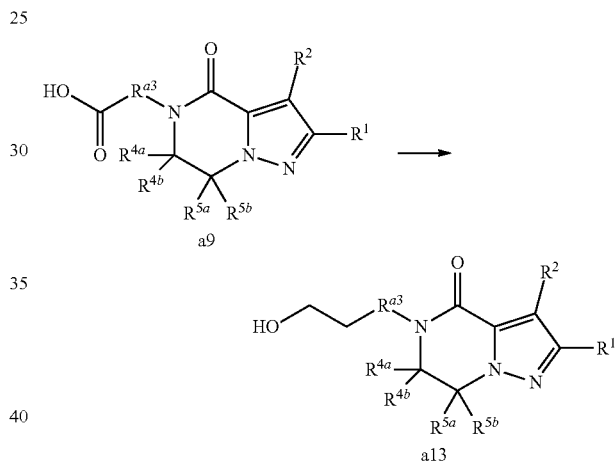

wherein each symbols is as defined above.

Compound a13 can be obtained by reacting Compound a9 with reductants in the presence of bases and ethyl chloroformate.

Examples of the reaction solvent include tetrahydrofuran, diethylether, 1,4-dioxane and the like, and these solvents may be used alone or in combination.

Examples of the base include triethylamine, diisopropylethylamine, sodium hydrogen carbonate, sodium hydroxide and the like. The amount of the base may be 1 to 10 equivalents, preferably 1 to 3 mole equivalents of Compound a9.

Examples of the reductant include sodium borohydride, lithium aluminium hydride, sodium triacetoxyborohydride and the like. The amount of the reductant may be 1 to 10 mole equivalents, preferably 1 to 5 mole equivalents of Compound a9.

Ethyl chloroformate may be used in 1 to 10 mole equivalents, preferably 1 to 3 mole equivalents of Compound a9.

The reaction temperature may be under ice-cooling to reflux temperature, preferably under ice-cooling to room temperature.

The reaction time may be 0.1 to 24 hours, preferably 0.1 to 5 hours.

Preparation of Compound a15

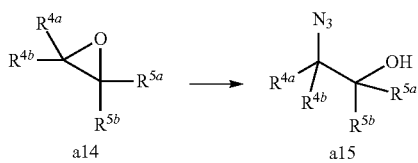

wherein each symbols is as defined above.

Compound a15 can be obtained by reacting Compound a14 with azido compounds in the presence of additives.

Examples of the reaction solvent include methanol, water, diethylether, dicholoromethane, tetrahydrofuran, N,N-dimethylformamide, ethanol, toluene, acetonitrile, benzene and the like, and these solvents may be used alone or in combination.

Examples of azido compounds include sodium azido, trimethylsilyl azido, lithium azido and the like. The amount of the azido compounds may be 1 to 50 mole equivalents, preferably 1 to 10 mole equivalents of Compound a14.

Examples of additives include ammonium chloride, zinc dicholoride, tetrabutylammonium chloride, titanium tetraisopropoxide, boran trifluoride/ether, cerium trichloride, cerium ammonium nitrate and the like. The amount of the additives may be 1 to 20 mole equivalents, preferably 1 to 10 mole equivalents of Compound a14.

The reaction temperature may be room temperature to reflux temperature, preferably reflux temperature.

The reaction time may be 0.1 to 24 hours, preferably 1 to 5 hours.

Preparation of Compound a17

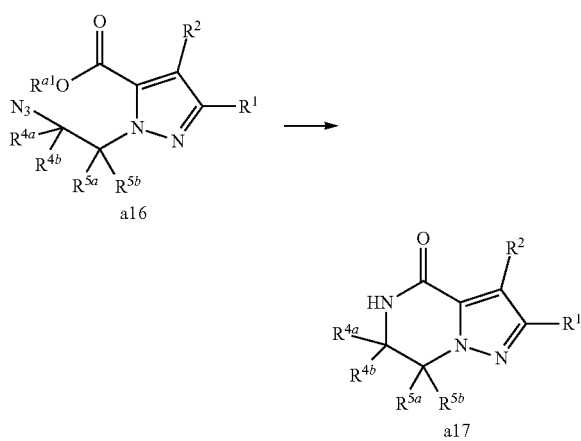

wherein each symbols is as defined above.

Compound a17 can be obtained by heating Compound a16 in the presence of triphenylphosphines.

Examples of the reaction solvent include tetrahydrofuran, water, methanol, ethyl acetate, dichloromethane, N,N-dimethylformamide, ethanol, 1,4-dioxane, acetonitrile, toluene and the like, and these solvents may be used alone or in combination.

Triphenylphosphine may be used in 1 to 10 mole equivalents, preferably 1 to 5 mole equivalents of Compound a16. Polymer bounded triphenylphosphine may be also used as phosphines.

The reaction temperature may be 50° C. to reflux temperature, preferably reflux temperature.

The reaction time may be 1 to 24 hours, preferably 1 to 12 hours.

Preparation of Compound a19

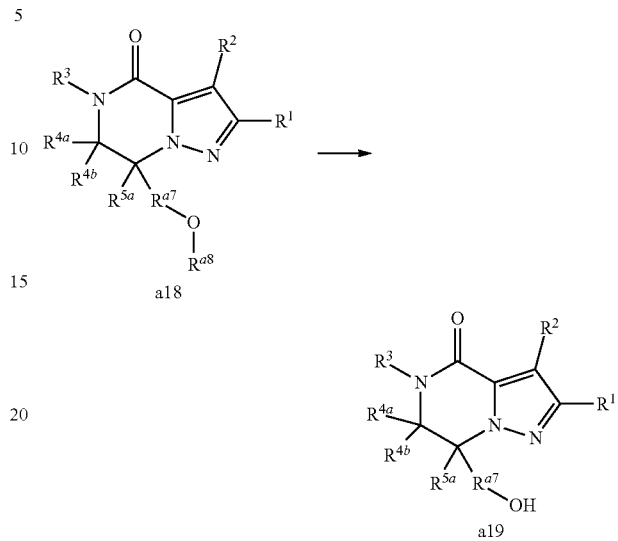

wherein $R^{a7}$ is substituted or unsubstituted alkylene, substituted or unsubstituted alkenylene, substituted or unsubstituted alkynylene, substituted or unsubstituted alkylene oxy, substituted or unsubstituted alkenylene oxy or substituted or unsubstituted alkynylene oxy, $R^{a8}$ is substituted or unsubstituted alkyl, substituted or unsubstituted alkenyl or substituted or unsubstituted alkynyl, the other symbols are as defined above.

Compound a19 can be obtained by deprotecting Compound a18.

Examples of the reaction solvent include dichloromethane, ethanol, methanol, 2-propanol, dichloromethane, 1,2-dichloroethane, acetic acid, tetrahydrofuran, N,N-dimethylformamide, benzene, toluene, acetonitrile, 1,4-dioxane, diethylether and the like, these solvents may be used alone or in combination.

Examples of the deprotecting agent include borane tribromide, palladium carbon, Raney nickel, sodium/ammonia, trimethylsilyl iodide, tin tetrachloride, iron trichloride, chromium trioxide and the like. The amount of the deprotecting agent may be 1 to 20 mole equivalents, preferably 3 to 10 mole equivalents of Compound a18.

The reaction temperature may be under ice-cooling to reflux temperature, preferably room temperature.

The reaction time may be 0.1 to 24 hours, preferably 0.1 to 5 hours.

The compound of the present invention thus obtained may be purified and crystallized in a variety of solvents. Examples of the solvent to be used include alcohols (methanol, ethanol, isopropylalcohol, n-butanol etc.), ether (diethylether, diisopropylether etc.), methyl acetate, ethyl acetate, chloroform, methylene chloride, tetrahydrofuran, N,N-dimethylformamide, toluene, benzene, xylene, acetonitrile, hexane, dioxane, dimethoxyethane, water or a mixture thereof. The compound may be dissolved in the solvent under heating, and the impurities are removed. The solution is then gradually cooled and filtered to collect the precipitated solid or crystal.

The compound of the present invention has autotaxin inhibitory activity. Accordingly, the pharmaceutical composition containing the compound of the present invention is useful as a therapeutic and/or prophylactic agent for diseases involving autotaxin. The diseases involving autotaxin include, for example, urinary extraction failure, chronic kidney disease or renal fibrosis, interstitial pneumonitis or pulmonary fibrosis, scleroderma, pain, fibromyalgia, rheumatoid arthritis, angiogenesis, cancer, formation, growth and propagation of tumor, arteriosclerosis, ocular diseases, choroidal neovascularization and diabetic retinopathy, inflammatory diseases, arthritis, neurodegeneration, restenosis, wound healing, transplant rejection, endometriosis and the like. The pharmaceutical composition containing the compound the the present invention is useful as a therapeutic agent and/or preventive agent for these diseases. More preferably, the pharmaceutical composition containing the compound of the present invention is useful as a therapeutic agent and/or preventive agent for urinary extraction failure, interstitial lung disease or fibroid lung, renal fibrosis, hepatic fibrosis, pachyderma, pain, fibromyalgia syndrome, arthritis and rheumatism, disseminated sclerosis or endometriosis and the like. The compound of the present invention may have a utility as as pharmaceutical, as well as autotaxin inhibitory effect, characterized by any of or all of the features as follows:

a) weak inhibitory effect on CYP enzyme (e.g. CYP1A2, CYP2C9, CYP3A4, etc.);
b) good pharmacokinetics, such as high bioavailability and appropriate clearance;
c) low toxicity (e.g. anemia-induced action);
d) high metabolic stability;
e) high water solubility;
f) high brain migration;
g) free of gastrointestinal disorders (e.g., hemorrhagic enteritis, gastrointestinal ulcers, gastrointestinal bleeding, etc.).

Also, the compound of the present invention has low affinity for ENPP1, ENPP3 to 7 receptors and high selectivity for ENPP2 receptor.

The pharmaceutical composition of the present invention may be administered orally in a formulation as conventionally used including tablets, granules, powders, capsules, pills, solution, syrups, buccal or sublingual. The pharmaceutical composition may be administered parentally in a formulation as conventionally used including injections such as intramuscular or intravenous injection, suppositories, transdermal absorbents, inhalants, etc.

The pharmaceutical composition may be prepared by mixing an effective amount of the compound of the invention with various pharmaceutical additives suitable for the formulation, such as excipients, binders, moistening agents, disintegrants, lubricants, diluents and the like. For injections, an active ingredient together with a suitable carrier may be sterilized to obtain a pharmaceutical composition.

Examples of the excipients include lactose, saccharose, glucose, starch, calcium carbonate, crystalline cellulose and the like. Examples of the binders include methylcellulose, carboxymethylcellulose, hydroxypropylcellulose, gelatin, polyvinylpyrrolidone and the like. Examples of the disintegrants include carboxymethylcellulose, sodium carboxymethylcellulose, starch, sodium alginate, agar, sodium lauryl sulfate and the like. Examples of the lubricants include talc, magnesium stearate, macrogol and the like. For base materials of suppositories, cacao oil, macrogol, methylcellulose and the like may be used. Solubilizing agents, suspending agents, emulsifiers, stabilizers, preservatives, isotonic agents and the like, which are commonly used, may be added when the composition is prepared as solutions, emulsified or suspended injections. Sweetening agents, flavors and the like, which are commonly used, may be added for oral formulation.

The dosage of the pharmaceutical composition of the invention is determined in the light of the age and weight of the patient, the type and severity of the disease to be treated, and the route for administration and the like. In the case of oral administration to adults, the dosage is usually in the range of 0.05 to 100 mg/kg/day, preferably 0.1 to 10 mg/kg/day. In the case of parenteral administration, the dosage is variable depending on the administration route, but is usually 0.005 to 10 mg/kg/day, preferably in the range of 0.01 to 1 mg/kg/day. The dosage may be administered in single or divided doses.

EXAMPLES

The present invention is further explained by the following Examples and Test Examples, which are not intended to limit the scope of the present invention.

The abbreviations as used herein represent the following meaning.
Me: methyl
Et: ethyl
Bu: butyl
Ph: phenyl
$PPh_3$, TPP: triphenylphosphine
AcOEt: ethyl acetate
DMF: N, N-dimethylformamide
TFA: trifluoroacetic acid
DMSO: dimethyl sulfoxide
THF: tetrahydrofuran
DIEA, Hunig's Base: N, N-diisopropylethylamine
TBAF: tetrabutylammonium fluoride
SEM: 2-(trimethylsilyl)ethoxymethyl
OAc: acetoxy group
mCPBA: methachloroperbenzoic acid
NMP: 1-methylpyrrolidine-2-one
LAH: lithium aluminium hydride
DBU: 1, 8-diazabicyclo[5.4.0]undeca-7-ene
DCM: methylene chloride
TEA: triethylamine
TMS: tetramethylsilane
HATU: O-(7-azabenzotriazole-1-yl)-N, N,N',N'-tetramethyluronium hexafluorophosphate
DPPA: diphenylphosphoryl azide
$PdCl_2$(dppf)-DCM: 1,1'-bis(diphenylphosphino)ferrocene-palladium(II)dichloride-dichloromethane complex NMR analysis of the compounds obtained in the Example was carried out at 400 MHz, using deuterated dimethyl sulfoxide (d6-DMSO) or deuterochloroform ($CDCl_3$).

LC/MS was measured under the following conditions.
(Method A)
Column: ACQUITY UPLC BEH C18 (1.7 μm i.d.2.1×50 mm) (Waters)
Flow rate: 0.8 mL/min
UV detection wavelength: 254 nm
Mobile Phase:
[A] 0.1% formic acid in water
[B] 0.1% formic acid in acetonitrile
Gradient: linear gradient from 10% to 100% [B] over 3.5 minutes, and then 100% [B] was maintained for 0.5 minutes.
(Method B)
Column: Shim-pack XR-ODS (2.2 μm, i.d.50×3.0 mm) (Shimadzu)
Flow rate: 1.6 mL/min
UV detection wavelength: 254 nm Mobile Phase:
[A] 0.1% formic acid in water
[B] 0.1% formic acid in acetonitrile
Gradient: linear gradient from 10% to 100% [B] over 3 minutes, and then 100% [B] was maintained for 0.5 minute.
(Method C)
Column: ACQUITY UPLC (registration of trademark) BEH C18
flow rate: 0.55 mL/min
UV detection wavelength: 254 nm
Mobile Phase:
[A] 0.1% formic acid in water
[B] 0.1% formic acid in acetonitrile
Gradient: linear gradient from 10% to 100% [B] over 3 minutes, and then 100% [B] was maintained for 0.5 minute.

Example 1: Preparation of Compound 2

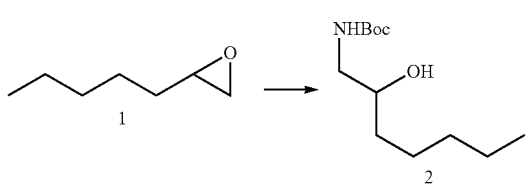

Step 1

To a solution of Compound 1 (300 mg, 2.63 mmol) in 2-propanol (1 mL) was added ammonium hydroxide (2 mL, 51.4 mmol), and the solution was stirred at 100° C. for 4.5 hours in sealed tube, and further stirred at 80° C. for 6 hours. After the reaction mixture was concentrated under reduced pressure, the residue was dissolved in dichloromethane (2 mL), added di-tert-butyl carbonate (0.671 mL, 2.89 mmol), and stirred at room temperature for 1 hour. After the reaction mixture was concentrated under reduced pressure, the residue was purified by silica gel chromatography (chroloform/methanol) to yield Compound 2 (400 mg, yield: 66%) as a colorless oil.

$^1$H-NMR (CDCl$_3$) δ: 4.90 (br s, 1H), 3.74-3.54 (m, 1H), 3.40-3.24 (m, 1H), 3.05-2.95 (m, 1H), 2.24 (br s, 1H), 1.50-1.25 (m, 17H), 0.89 (t, 3H, J=6.8 Hz).

Example 2: Preparation of Compound 8 (I-0001)

Step 1: Preparation of Compound 6

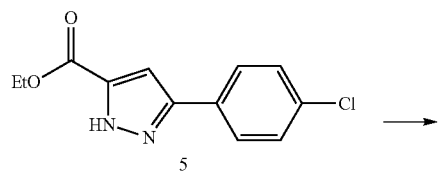

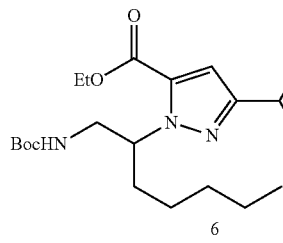

To a solution of Compound 5 (100 mg, 0.399 mmol) in tetrahydrofuran (2 mL) was added triphenylphosphine (126 mg, 0.479 mmol) and Compound 2 (111 mg, 0.479 mmol). The solution was added isopropyl azodicarboxylate (0.093 mL, 0.479 mmol) under ice-cooling, and stirred at room temperature for 1 hour. After the reaction mixture was concentrated under reduced pressure, the residue was purified by silica gel chromatography (hexane/ethyl acetate) to yield Compound 6 (126 mg, yield: 68%) as colorless oil.

1H-NMR (CDCl$_3$) δ: 7.75 (d, 2H, J=8.5 Hz), 7.38 (d, 2H, J=8.5 Hz), 7.09 (s, 1H), 5.50-5.43 (m, 1H), 4.83 (br s, 1H), 4.36 (q, 2H, J=7.1 Hz), 3.62 (t, 2H, J=5.9 Hz), 2.05-1.93 (m, 1H), 1.83-1.72 (m, 1H), 1.45-1.38 (m, 11H), 1.32-1.09 (m, 5H), 0.91-0.79 (m, 5H).

Step 2: Preparation of Compound 7

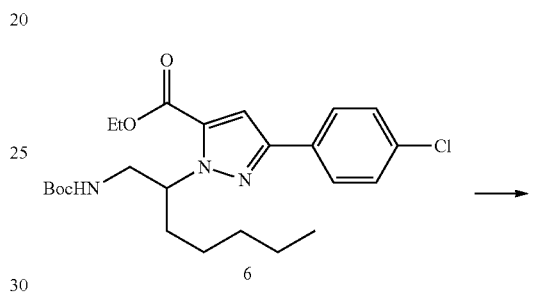

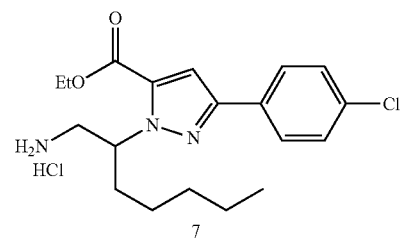

To a solution of Compound 6 (124 mg, 0.267 mmol) in ethyl acetate (1 mL) was added 4 mol/L hydrochrolic acid/ethyl acetate (1 mL, 4.00 mmol), and the solution was stirred at room temperature for 2 hours. The reaction mixture was concentrated under reduced pressure to yield Compound 7 (100 mg, yield: 94%) as a white solid.

$^1$H-NMR (DMSO-D$_6$) δ: 8.00-7.90 (m, 5H), 7.53-7.49 (m, 2H), 5.54-5.46 (m, 1H), 4.36 (q, 2H, J=7.1 Hz), 3.51 (t, 1H, J=11.0 Hz), 1.88-1.77 (m, 2H), 1.35 (t, 3H, J=7.1 Hz), 1.25-1.10 (m, 6H), 0.97 (br s, 1H), 0.78 (t, 3H, J=6.5 Hz).

Step 3: Preparation of Compound 8 (I-0001)

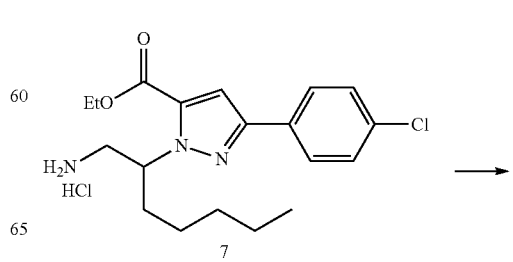

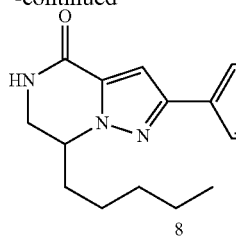

8

To a solution of Compound 7 (98 mg, 0.245 mmol) in ethanol was added trimethylamine (0.136 mL, 0.979 mmol) and the solution was stirred at reflux temperature for 8.5 hours. After the reaction solution was concentrated under reduced pressure, the residue was purified by silica gel chromatography (hexane/ethyl acetate) to yield Compound 8 ((I-0001), 70 mg, yield: 90%) as a white solid.

$^1$H-NMR (CDCl$_3$) δ: 7.75 (dt, 2H, J=9.0, 2.2 Hz), 7.38 (dt, 2H, J=9.0, 2.2 Hz), 7.13 (s, 1H), 6.02 (s, 1H), 4.44 (dt, 1H, J=13.3, 5.0 Hz), 3.91 (dq, 1H, J=12.9, 2.2 Hz), 3.57 (ddd, 1H, J=13.0, 5.0, 3.7 Hz), 2.21-2.13 (m, 1H), 1.89-1.80 (m, 1H), 1.50-1.30 (m, 6H), 0.90 (t, 3H, J=7.3 Hz).

Example 3: Preparation of Compound 9 (I-0002)

Step 1

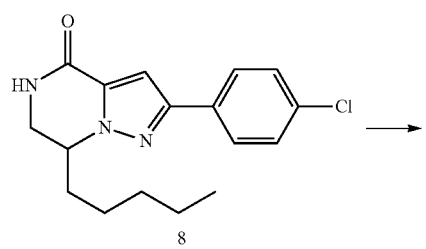

8

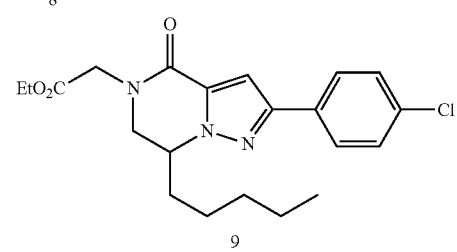

9

To a solution of Compound 8 (63 mg, 0.198 mmol) in tetrahydrofuran (1 mL) was added potassium tert-butoxide (26.7 mg, 0.238 mmol) under ice-cooling, the solution was stirred for 10 minutes. To the solution was added ethyl 2-bromoacetate (0.026 mL, 0.238 mmol) under ice-cooling and stirred for 30 minutes. After the reaction solution was dropwised into 10% citric acid solution, the mixture was extracted with ethyl acetate. The organic layer was washed with water and brine, and dried with anhydrous sodium sulfate. After the organic layer was concentrated under reduced pressure, the residue was purified by silica gel chromatography (hexane/ethyl acetate) to yield Compound 9 ((I-0002), 75 mg, yield: 94%) as a white solid.

$^1$H-NMR (CDCl$_3$) δ: 7.75 (dt, 2H, J=9.0, 2.2 Hz), 7.38 (dt, 2H, J=9.0, 2.2 Hz), 7.13 (s, 1H), 4.53-4.43 (m, 1H), 4.33 (s, 2H), 4.24 (q, 2H, J=7.1 Hz), 4.00 (dd, 1H, J=12.8, 4.5 Hz), 3.62 (dd, 1H, J=12.8, 5.5 Hz), 2.25-2.17 (m, 1H), 1.95-1.82 (m, 1H), 1.51-1.24 (m, 6H), 1.30 (t, 3H, J=7.1 Hz), 0.90 (t, 3H, J=7.0 Hz).

Example 4: Preparation of Compound 10 (I-0003)

Step 1

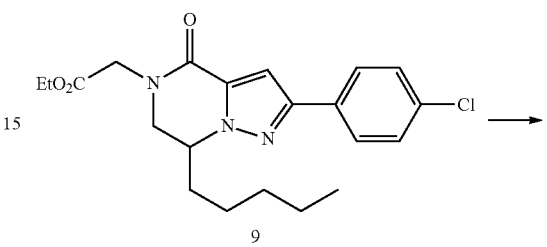

9

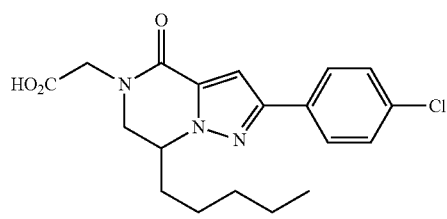

10

To a solution of Compound 9 (65 mg, 0.161 mmol) in tetrahydrofuran (1 mL) and ethanol (1 mL) was added 2 mol/L sodium hydroxide solution (0.241 mL, 0.483 mmol), the solution was stirred at room temperature for 1 hours. The reaction mixture was added 2 mol/L hydrochloric acid solution (0.240 mL, 0.483 mmol) and concentrated under reduced pressure. To the residue was added water, and extracted with ethyl acetate twice, and then the organic layer was dried with anhydrous sodium sulfate. The organic layer was concentrated under reduced pressure to yield Compound 10 ((I-0003), 58 mg, yield: 96%) as a white solid.

$^1$H-NMR (CDCl$_3$) δ: 7.74 (dt, 2H, J=8.9, 2.1 Hz), 7.38 (dt, 2H, J=8.9, 2.1 Hz), 7.14 (s, 1H), 4.54-4.45 (m, 1H), 4.39 (s, 2H), 4.01 (dd, 1H, J=12.7, 4.6 Hz), 3.63 (dd, 1H, J=12.7, 5.5 Hz), 2.25-2.14 (m, 1H), 1.93-1.82 (m, 1H), 1.53-1.21 (m, 7H), 0.89 (t, 3H, J=7.0 Hz).

Example 5: Preparation of Compound 11 (I-0004)

Step 1

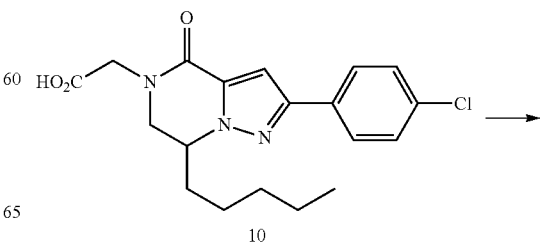

10

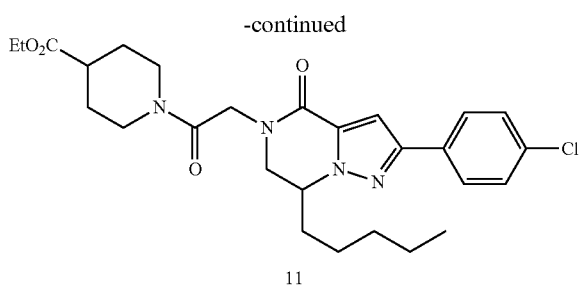

To a solution of Compound 10 (48 mg, 0.128 mmol) in N,N-dimethylformamide (0.5 mL) was added trimethylamine (0.021 mL, 0.153 mmol), HATU (58.3 mg, 0.153 mmol) and ethyl piperidine-4-carboxylate (0.024 mL, 0.153 mmol), the solution was stirred at room temperature for 1.5 hours. To the reaction solution was added 10% citric acid solution, and extracted with ethyl acetate twice. The organic layer was washed with 10% citric acid solution, saturated sodium hydrogen carbonate solution and brine, and dried with anhydrous sodium sulfate. The organic layer was concentrated under reduced pressure, the residue was purified by silica gel chromatography (hexane/ethyl acetate) to yield Compound 11 ((I-0004), 65 mg, yield: 99%) as a white solid.

$^1$H-NMR (CDCl$_3$) δ: 7.74 (d, 2H, J=8.5 Hz), 7.37 (d, 2H, J=8.5 Hz), 7.11 (s, 1H), 4.56-4.22 (m, 4H), 4.16 (q, 2H, J=7.2 Hz), 4.00 (ddd, 1H, J=28.4, 12.6, 4.3 Hz), 3.86 (d, 1H, J=14.1 Hz), 3.75-3.65 (m, 1H), 3.28-3.14 (m, 1H), 2.97-2.85 (m, 1H), 2.56 (br s, 1H), 2.28-2.15 (m, 1H), 1.99 (t, 2H, J=10.8 Hz), 1.89-1.67 (m, 3H), 1.50-1.31 (m, 6H), 1.27 (t, 3H, J=7.2 Hz), 0.90 (t, 3H, J=7.0 Hz).

Example 6: Preparation of Compound 12 (I-0007)

Step 1

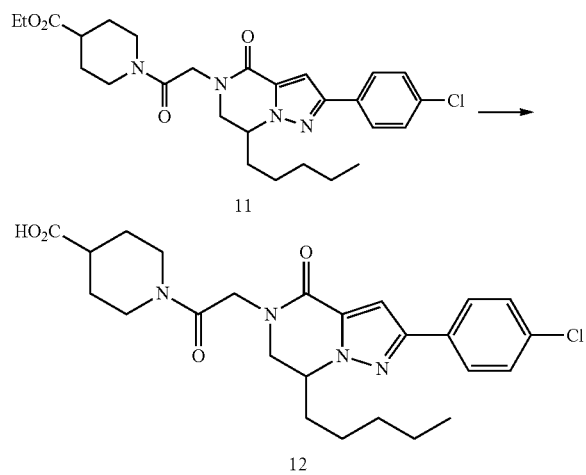

To a solution of Compound 11 (53 mg, 0.103 mmol) in ethanol (1 mL) was added 2 mol/L sodium hydroxide solution (0.154 mL, 0.309 mmol), the solution was stirred at room temperature for 2 hours. To the reaction mixture was added 2 mol/L hydrochloric acid solution (0.150 mL, 0.300 mmol), and concentrated under reduced pressure. To the residue was added water (5 mL), and the mixture was stirred at room temperature for 30 minutes. The precipitated solid was filtered to yield compound 12 ((I-0007), 40 mg, yield: 80%) as a white solid.

$^1$H-NMR (DMSO-D$_6$) δ: 7.90 (2H, d, J=7.5 Hz), 7.48 (2H, d, J=7.8 Hz), 7.28 (1H, s), 4.59-4.49 (1H, m), 4.48-4.34 (2H, m), 4.23-4.12 (1H, m), 4.04-3.92 (1H, m), 3.85-3.74 (1H, m), 3.68-3.59 (1H, m), 3.13 (1H, t, J=11.7 Hz), 2.83-2.71 (1H, m), 2.09-1.93 (1H, m), 1.92-1.73 (3H, m), 1.64-1.48 (1H, m), 1.48-1.34 (3H, m), 1.34-1.23 (4H, m), 0.92-0.82 (3H, m).

Example 7: Preparation of Compound 13 (I-0005)

Step 1

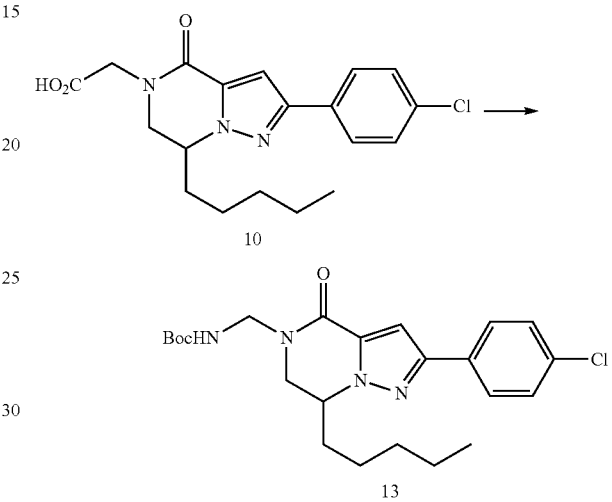

To a solution of Compound 10 (90 mg, 0.239 mmol) in tert-butanol (2 mL) was added triethylamine (0.050 mL, 0.359 mmol) and DPPA (77 uL, 0.359 mmol), the solution was stirred at reflux temperature for 4 hours. The reaction solution was concentrated under reduced pressure, the residue was purified by silica gel chromatography (hexane/ethyl acetate) to yield Compound 13 ((I-0005), 35 mg, yield: 33%) as a white solid.

$^1$H-NMR (CDCl$_3$) δ: 7.74 (dt, 2H, J=9.0, 2.2 Hz), 7.38 (dt, 2H, J=9.0, 2.2 Hz), 7.10 (s, 1H), 5.58 (t, 1H, J=7.0 Hz), 4.85 (dq, 2H, J=30.5, 7.0 Hz), 4.46-4.38 (m, 1H), 4.08 (dd, 1H, J=13.2, 4.4 Hz), 3.85 (dd, 1H, J=13.2, 4.4 Hz), 2.10-1.98 (m, 1H), 1.85-1.73 (m, 1H), 1.53-1.24 (m, 6H), 1.45 (s, 9H), 0.89 (t, 3H, J=7.0 Hz).

Example 8: Preparation of Compound 14 (I-0151)

Step 1

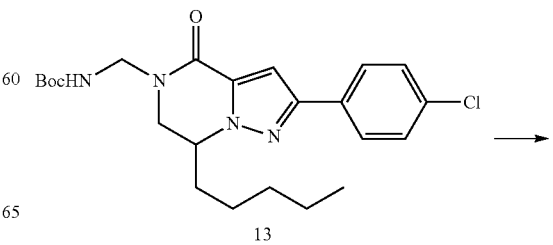

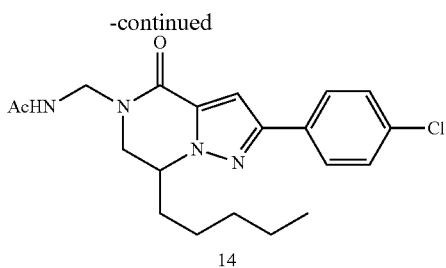

14

To a solution of Compound 13 (30 mg, 0.067 mmol) in ethyl acetate (0.5 mL) and chloroform (0.2 mL) added 4 mol/L hydrochloric acid/ethyl acetate solution (0.5 mL, 2.000 mmol), the mixture was stirred at room temperature for 3.5 hours. The reaction mixture was concentrated under reduced pressure, to the residue was added methanol (1 mL). To the reaction solution was added triethylamine (0.279 mL, 0.201 mmol) and acetic anhydrous (0.00952 uL, 0.101 mmol), and stirred at room temperature for 5 hours. The reaction solution was concentrated under reduced pressure, the residue was purified by silica gel chromatography (hexane/ethyl acetate) to yield Compound 14 ((I-0151), 19 mg, yield: 73%) as a white solid.

$^1$H-NMR (CDCl$_3$) δ: 7.74 (dt, 2H, J=9.0, 2.2 Hz), 7.38 (dt, 2H, J=9.0, 2.2 Hz), 7.10 (s, 1H), 6.58 (t, 1H, J=6.7 Hz), 4.93 (d, 2H, J=6.7 Hz), 4.42 (dt, 1H, J=13.3, 5.3 Hz), 4.08 (dd, 1H, J=13.3, 4.5 Hz), 3.85 (dd, 1H, J=13.3, 5.3 Hz), 2.13-2.02 (m, 1H), 2.02 (s, 3H), 1.82-1.72 (m, 1H), 1.50-1.30 (m, 6H), 0.93-0.88 (m, 3H).

Example 9: Preparation of Compound 15 (I-0006)

Step 1

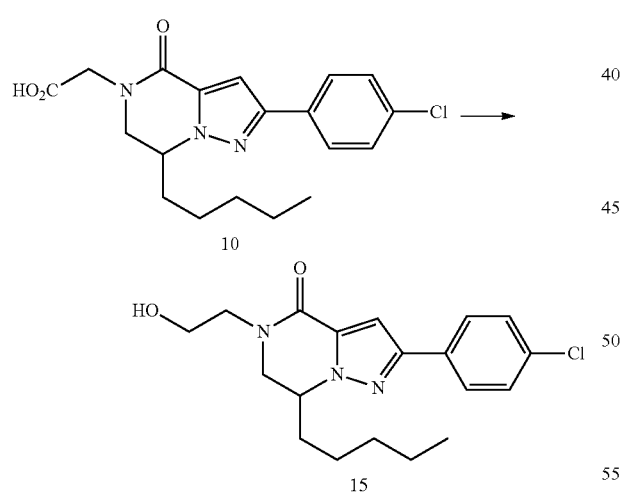

To a solution of Compound 10 (50 mg, 0.133 mmol) in tetrahydrofuran (1 mL) was added triethylamine (0.022 mL, 0.160 mmol). To the mixture was added ethyl chloroformate (0.015 mL, 0.160 mmol) under ice-cooling, and stirred for 30 minutes. To the mixture was added sodium borohydride (15.1 mg, 0.399 mmol), and stirred at room temperature for 30 minutes. To the reaction mixture was added brine, and extracted with ethyl acetate twice. The organic layer was washed with water and brine, dried with anhydrous sodium sulfate, and concentrated under reduced pressure. The residue was purified by silica gel chromatography (hexane/ethyl acetate) to yield Compound 15 ((I-0006), 30 mg, yield: 62%) as colorless oil.

$^1$H-NMR (CDCl$_3$) δ: 7.74 (dt, 2H, J=8.9, 2.1 Hz), 7.38 (dt, 2H, J=8.9, 2.1 Hz), 7.10 (s, 1H), 4.44 (dt, 1H, J=13.4, 5.1 Hz), 4.03 (dd, 1H, J=13.1, 4.5 Hz), 3.92 (t, 2H, J=5.0 Hz), 3.82-3.65 (m, 3H), 2.28-2.09 (m, 2H), 1.88-1.77 (m, 1H), 1.50-1.24 (m, 6H), 0.93-0.88 (m, 3H).

Example 10: Preparation of Compound 19 (I-0024)

Step 1

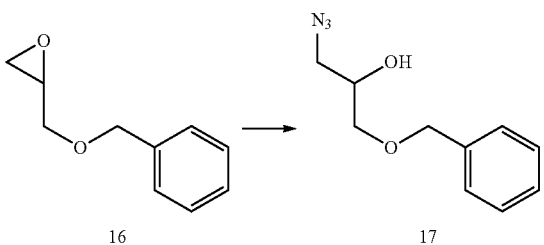 [SMILES: c1ccc(COCC2CO2)cc1 ; [N-]=[N+]=NCC(O)COCc1ccccc1]

To a mixed solution of Compound 16 (0.187 mL, 1.218 mmol) in methanol (1 mL) and water (0.1 mL) was added sodium azide (396 mg, 6.09 mmol) and ammonium chloride (195 mg, 3.65 mmol), the solution was stirred at reflux temperature for 2 hours. To the reaction mixture was added ethyl acetate, the insoluble material was filtered out. The filtrate was concentrated under reduced pressure to yield Compound 17 as a crude compound.

Step 2

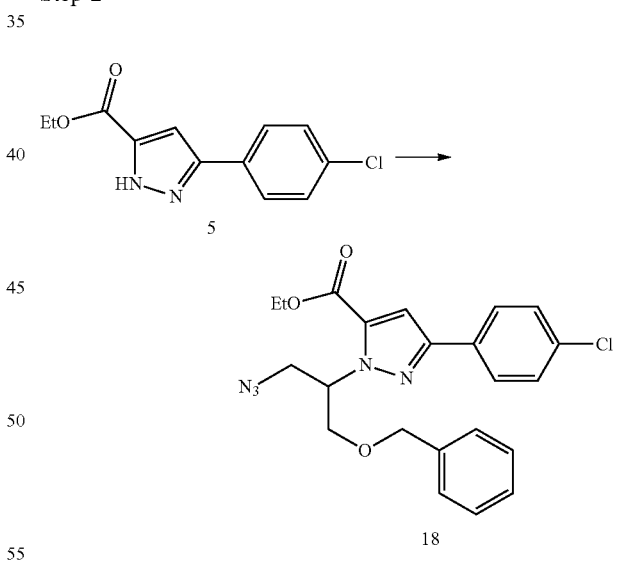

To a solution of Compound 17 obtained in Step 1 in tetrahydrofuran (2 mL) was added Compound 5 (218 mg, 0.870 mmol), diisopropyl azodicarboxylate (0.220 mL, 1.131 mmol) and triphenylphosphine (297 mg, 1.131 mmol), the mixture was stirred at room temperature for 1 hour. The reaction mixture was concentrated under reduced pressure, the residue was purified by silica gel chromatography (hexane/ethyl acetate) to yield Compound 18 (335 mg, yield: 88%) as colorless oil.

$^1$H-NMR (CDCl$_3$) δ: 7.74 (dt, 2H, J=9.0, 2.1 Hz), 7.37 (dt, 2H, J=9.0, 2.1 Hz), 7.32-7.21 (m, 5H), 7.14 (s, 1H), 5.82-5.76 (m, 1H), 4.51 (dd, 2H, J=17.1, 12.0 Hz), 4.37 (q, 2H, J=7.2 Hz), 4.01 (dd, 1H, J=12.8, 8.8 Hz), 3.89 (ddd, 2H, J=24.2, 9.9, 6.6 Hz), 3.74 (dd, 1H, J=12.5, 4.5 Hz), 1.40 (t, 3H, J=7.2 Hz).

Step 3

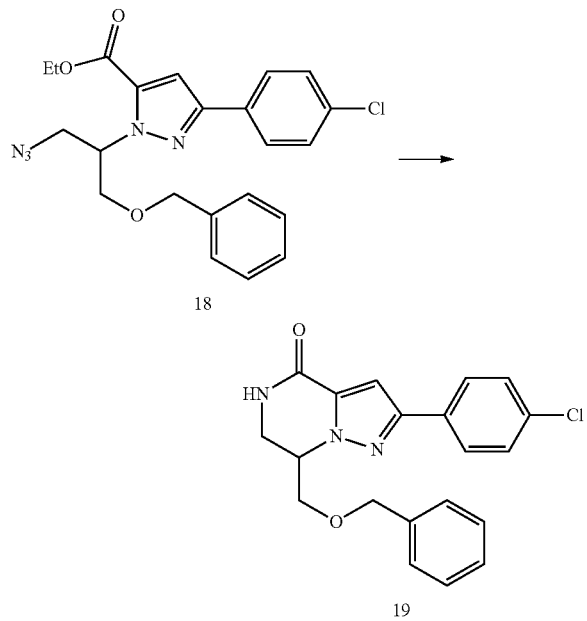

To a mixed solution of Compound 18 obtained in Step 2 in tetrahydrofuran (2 mL) and water (0.4 mL) was added polymer bounded triphenylphosphine (751 mg, 2.251 mmol), the mixture was stirred at reflux temperature for 5 hours. The reaction mixture was cooled to room temperature, and then added ethyl acetate. The insoluble material was filtered out through celite, the filtrate was concentrated under reduced pressure. To the residue was added ethyl acetate (10 mL), the precipitated solid was filtered to yield Compound 19 ((I-0024), 210 mg, yield: 76%) as a white solid.

$^1$H-NMR (CDCl$_3$) δ: 7.73 (d, 2H, J=8.3 Hz), 7.41-7.29 (m, 7H), 7.13 (s, 1H), 5.85 (s, 1H), 4.68 (td, 1H, J=8.8, 4.4 Hz), 4.59 (dd, 2H, J=18.1, 11.8 Hz), 3.98-3.83 (m, 4H).

Example 11: Preparation of Compound 21 (I-0173)

Step 1

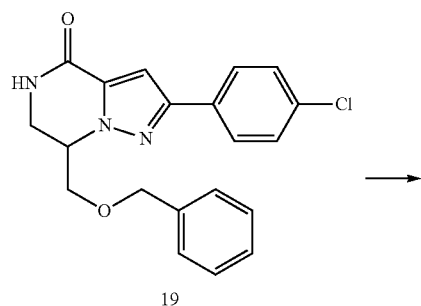

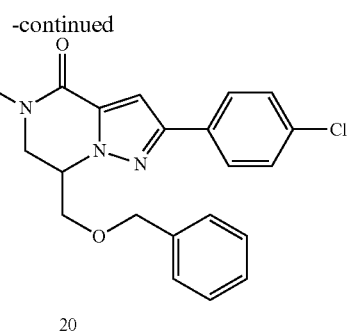

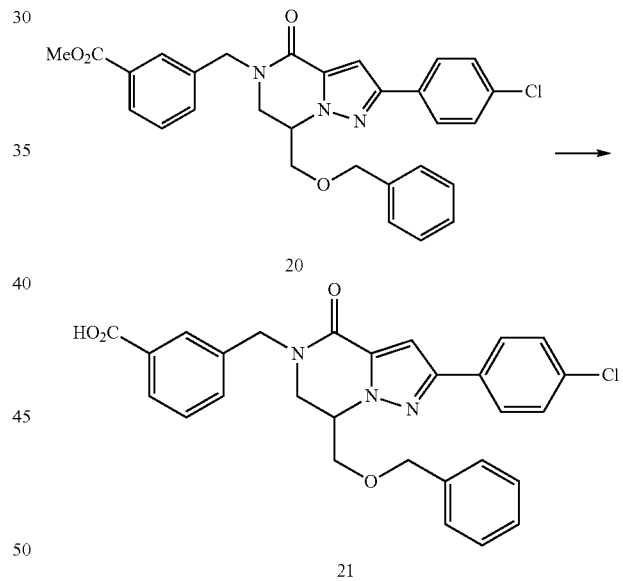

To a solution of Compound 19 (1.0 g, 2.72 mmol) in tetrahydrofuran (2 mL) was added methyl 3-(bromomethyl)benzoate (685 mg, 2.99 mmol) and potassium tert-butoxide (366 mg, 3.26 mmol), the solution was stirred at room temperature for 2 hours. To the reaction solution was added 2 mol/L hydrochloric acid solution, and extracted with ethyl acetate. The organic layer was washed with water, and dried with anhydrous sodium sulfate. The solution was concentrated under reduced pressure to yield a crude Compound 20 (1.62 g, yield: quant.) as tan oil.

LC/MS Method: C, retention time: 2.83 min

Step 2

To a solution of Compound 20 (1.62 g) obtained in step 1 in tetrahydrofuran (16 mL) was added 2 mol/L sodium hydroxide solution (3.92 mL, 7.85 mmol), the solution was stirred at 50° C. for 2 hours. To the reaction solution was added 2 mol/L hydrochloric acid solution (5 mL) and water, and extracted with ethyl acetate. The organic layer was washed with water, dried with anhydrous sodium sulfate, and the solution was concentrated under reduced pressure. The residue was purified by suspending with ethyl acetate and hexane to yield Compound 21 ((I-0173), 855 mg, yield: 54%) as a white solid.

$^1$H-NMR (δ ppm TMS/CDCl$_3$) 7.94 (1H, s), 7.93-7.84 (3H, m), 7.61 (1H, d, J=7.8 Hz), 7.52-7.45 (3H, m), 7.37 (1H, s), 7.31-7.24 (3H, m), 7.18-7.11 (2H, m), 4.92 (1H, d, J=14.9 Hz), 4.82-4.74 (1H, m), 4.60 (1H, d, J=14.9 Hz), 4.35 (2H, dd, J=26.2, 12.0 Hz), 4.06-3.93 (1H, m), 3.78-3.65 (3H, m).

Example 12: Preparation of Compound 22 (I-0174)

Step 1

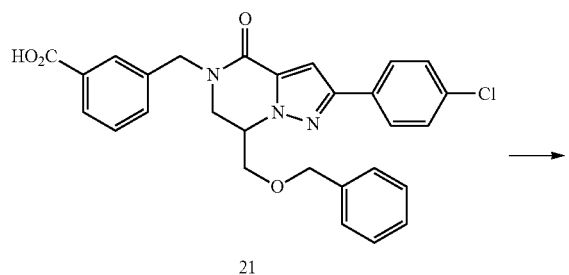

To a suspension of Compound 21 (700 mg, 1.395 mmol) in dichloromethane (5 mL) was added 1.0 mol/L borane tribromide dichloromethane solution (7 mL, 7 mmol), the mixture was stirred at room temperature for 3 hours. To the reaction solution was added water, and extracted with ethyl acetate. The organic layer was washed with water, dried with anhydrous sodium sulfate, and the solution was concentrated under reduced pressure. The residue was purified by suspending with ethyl acetate and hexane to yield Compound 22 ((I-0174), 460 mg, yield: 80%) as a colorless solid.

$^1$H-NMR (δ ppm TMS/DMSO-D$_6$) 7.97-7.85 (4H, m), 7.61 (1H, d, J=7.5 Hz), 7.54-7.45 (3H, m), 7.35 (1H, s), 5.21 (1H, br s), 4.78 (2H, dd, J=26.3, 15.0 Hz), 4.58-4.48 (1H, m), 3.88 (1H, dd, J=13.2, 5.0 Hz), 3.84-3.68 (3H, m).

Example 13: Preparation of Compound 23 (I-0176)

Step 1

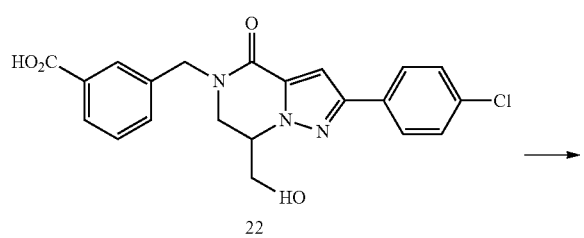

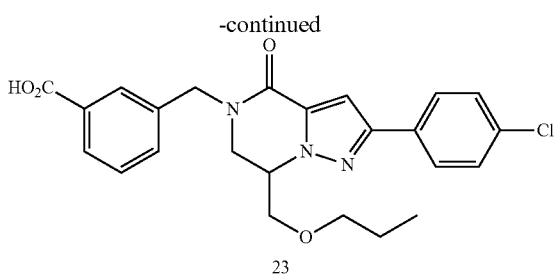

To a suspension of Compound 22 (75 mg, 0.182 mmol) in tetrahydrofuran (5 mL) added sodium hydride (145.6 mg, 3.64 mmol) and 1-iodopropane (618.7 mg, 3.64 mmol), the mixture was stirred at 60° C. for 4 hours. To the reaction mixture was added water, and extracted with ethyl acetate. The organic layer was washed with water, dried with anhydrous sodium sulfate, and the filtrate was concentrated under reduced pressure. The residue was purified by silica gel chromatography (chloroform/methanol) to yield Compound 23 ((I-0176), 32.5 mg, yield: 39%) as colorless oil.

$^1$H-NMR (δ ppm TMS/CDCl$_3$) 8.10-8.03 (2H, m), 7.73 (2H, d, J=8.5 Hz), 7.64 (1H, d, J=7.8 Hz), 7.49 (1H, t, J=7.7 Hz), 7.38 (2H, d, J=8.5 Hz), 7.17 (1H, s), 5.04 (1H, d, J=14.7 Hz), 4.65-4.54 (2H, m), 3.87 (1H, dd, J=13.1, 4.6 Hz), 3.81-3.71 (2H, m), 3.52 (1H, t, J=9.3 Hz), 3.32-3.24 (1H, m), 3.17-3.07 (1H, m), 1.48-1.37 (2H, m), 0.79 (3H, t, J=7.4 Hz).

Example 14: Preparation of Compound 25 (I-0179)

Step 1

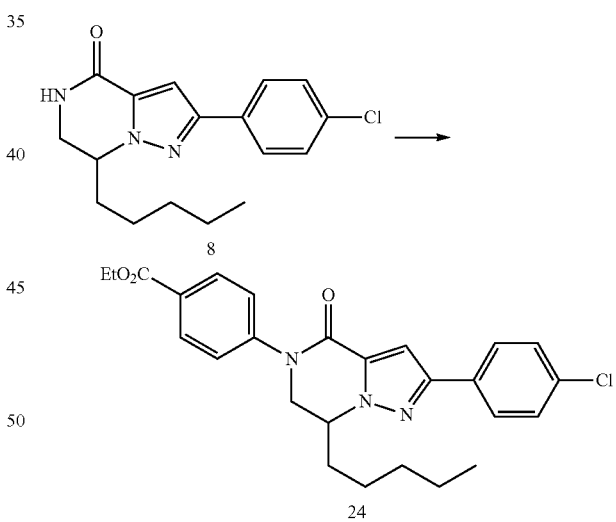

To a solution of Compound 8 (100 mg, 0.315 mmol) in DMA (3 ml) was added cupper(I) iodide (5.99 mg, 0.031 mmol), 2-(dimethylamino)acetic acid (9.73 mg, 0.094 mmol), cesium carbonate (308 mg, 0.944 mmol) and ethyl 4-iodebenzoate (87 mg, 0.315 mmol), the solution was stirred under MW irradiation at 150° C. for 30 minutes. To the reaction mixture was added 2 mol/L hydrochloric acid aqueous solution, and extracted with ethyl acetate. The organic layer was washed with water, dried with anhydrous sodium sulfate, and then the solution was concentrated under reduced pressure to yield crude Compound 24 (209 mg).

Step 2

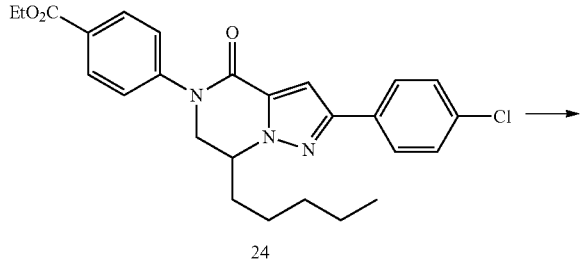
24

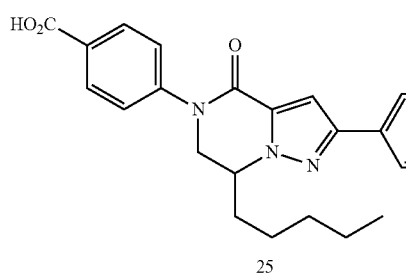
25

To a solution of Compound 24 (209 mg) in tetrahydrofuran (4 ml) was added 2 mol/L sodium hydroxide aqueous solution (400 ul), the solution was stirred at 50° C. for 2 hours. To the reaction mixture was added 2 mol/L hydrochloric acid aqueous solution, and extracted with ethyl acetate. The organic layer was washed with water, dried with anhydrous sodium sulfate, and then the solution was concentrated under reduced pressure. The residue was purified by silica gel chromatography (chloroform/methanol) to yield Compound 25 ((I-0179), 64 mg, yield: 46%) as a colorless solid.

$^1$H-NMR (δ ppm TMS/CDCl$_3$) 8.19 (2H, d, J=8.0 Hz), 7.78 (2H, d, J=7.9 Hz), 7.51 (2H, d, J=8.0 Hz), 7.40 (2H, d, J=7.8 Hz), 7.23 (1H, s), 4.65-4.56 (1H, m), 4.40 (1H, dd, J=12.7, 4.0 Hz), 4.02 (1H, dd, J=12.4, 4.9 Hz), 2.32-2.19 (1H, m), 1.99-1.85 (2H, m), 1.54-1.42 (2H, m), 1.42-1.26 (4H, m), 0.89 (3H, t, J=6.6 Hz).

Example 15: Preparation of Compound 29 (I-0180)

Step 1

Compound 26 was prepared using dimethyl 1H-pyrazole-3,5-dicarboxylate as a starting material according to Example 10.

Step 2

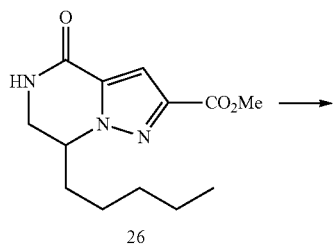
26

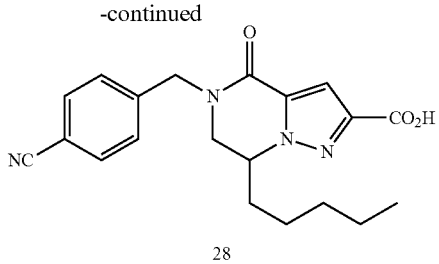
28

To a solution of Compound 26 (530 mg, 2.00 mmol) in tetrahydrofuran (5 mL) was added 4-(bromomethyl)benzonitrile (431 mg, 2.197 mmol) and potassium tert-butoxide (247 mg, 2.197 mmol), the solution was stirred at room temperature for 2 hours. To the reaction mixture was added methanol (5 mL) and 2 mol/L sodium hydroxide aqueous solution (2 mL), and then stirred at room temperature for 20 minutes. To the reaction solution was added 1 mol/L hydrochloric acid aqueous solution, and extracted with ethyl acetate. The organic layer was dried with anhydrous sodium sulfate, and concentrated under reduced pressure. The residue was purified by silica gel chromatography (chloroform/methanol) to yield Compound 28 (404 mg, yield: 55%) as a white solid.

LC/MS Method: B, retention time: 1.86 min, M+H: 367

Step 3

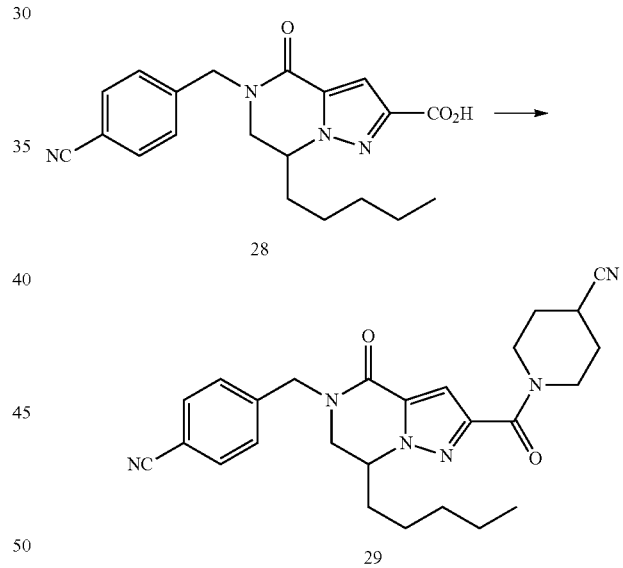

To a solution of Compound 28 (30 mg, 0.082 mmol) in N,N-dimethylformamide (0.5 mL) was added triethylamine (0.034.0 mL, 0.246 mmol), HATU (37.4 mg, 0.098 mmol) and piperidine-4-carbonitrile (13.53 mg, 0.123 mmol), the solution was stirred at room temperature for 1 hour. To the reaction mixture was added water, and extracted with ethyl acetate. The organic layer was dried with anhydrous sodium sulfate. The organic layer was concentrated under reduced pressure, the residue was purified by silica gel chromatography (hexane/ethyl acetate) to yield Compound 29 ((I-0180), 32 mg, yield: 86%) as colorless oil.

LC/MS Method: B, retention time: 2.04 min, M+H: 459

$^1$H-NMR (δ ppm TMS/CDCl$_3$) 8.02 (s, 1H), 7.67 (d, 2H, J=7.5 Hz), 7.45 (d, 2H, J=7.5 Hz), 4.98 (d, 1H, J=15.1 Hz), 4.61 (d, 1H, J=15.1 Hz), 4.39-4.36 (m, 1H), 4.13-3.74 (m, 5H), 3.42 (dd, 1H, J=12.8, 4.5 Hz), 2.05-1.95 (m, 5H), 1.25-1.17 (m, 6H), 0.86 (t, 3H, J=5.8 Hz).

Example 16: Preparation of Compound 32 (I-0182) and Compound 33 (I-0181)

Step 1

Compound 30 was prepared using ethyl 3-bromo-1H-pyrazole-5-carboxylate as a starting material according to Example 10.

Step 2

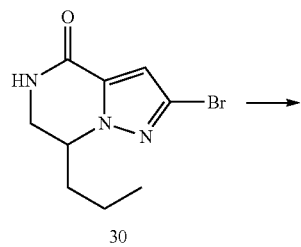

30

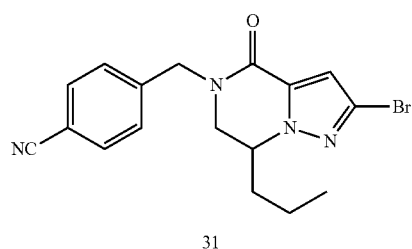

31

To a solution of Compound 30 (350 mg, 1.356 mmol) in tetrahydrofuran (5 mL) was added 4-(bromomethyl)benzonitrile (319 mg, 1.627 mmol) and potassium tert-butoxide (183 mg, 1.627 mmol), the solution was stirred at room temperature for 20 minutes. To the reaction mixture was added methanol (5 mL) and 2 mol/L sodium hydroxide aqueous solution (2 mL), and then stirred at room temperature for 20 minutes. To the reaction mixture was added water, and extracted with ethyl acetate. The organic layer was dried with anhydrous sodium sulfate, and concentrated under reduced pressure. The residue was purified by silica gel chromatography (hexane/ethyl acetate) to yield Compound 31 (520 mg, yield: quant.) as a white solid.

LC/MS Method: B, retention time: 2.14 min, M+H: 373

Step 3

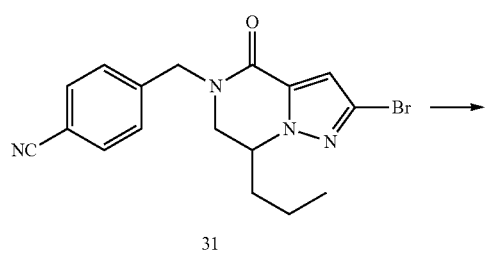

31

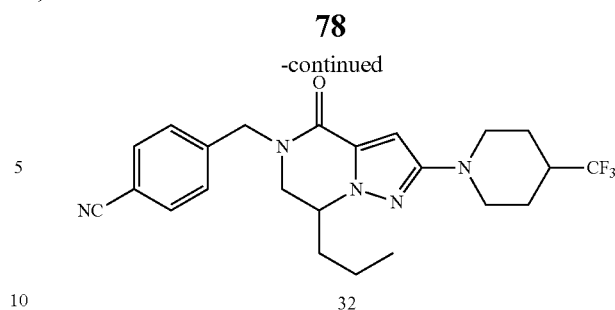

32

A solution of palladium acetate (1.203 mg, 5.36 umol) and RuPhos (7.50 mg, 0.016 mmol) in 1,4-dioxane (0.5 mL) was stirred at room temperature for 15 minutes under nitrogen atmosphere. To the reaction solution was added Compound 31 (20 mg, 0.054 mmol), 4-(trifluoromethyl)piperidine (16.41 mg, 0.107 mmol) and sodium tert-butoxide (7.72 mg, 0.080 mmol) under nitrogen atmosphere, and the mixture was stirred at 100° C. for 1 hours. To the reaction mixture was added water, and extracted with ethyl acetate. The organic layer was dried with anhydrous sodium sulfate. The organic layer was concentrated under reduced pressure, and the residue was purified by silica gel chromatography (hexane/ethyl acetate) to yield Compound 32 ((I-0182), 11.4 mg, yield: 48%) as a white solid.

LC/MS Method: B, retention time: 2.42 min, M+H: 446

$^1$H-NMR (δ ppm TMS/CDCl$_3$) 7.66 (d, 2H, J=7.8 Hz), 7.44 (d, 2H, J=7.8 Hz), 6.29 (s, 1H), 4.94 (d, 1H, J=15.1 Hz), 4.59 (d, 1H, J=15.1 Hz), 4.19-4.17 (m, 1H), 3.84 (t, 2H, J=11.7 Hz), 3.75 (dd, 1H, J=12.8, 4.3 Hz), 3.33 (dd, 1H, J=12.9, 4.6 Hz), 2.70 (t, 2H, J=12.3 Hz), 2.16-2.13 (m, 1H), 1.93-1.90 (m, 3H), 1.75-1.69 (m, 2H), 1.50-1.49 (m, 1H), 1.27-1.13 (m, 2H), 0.85 (t, 3H, J=7.2 Hz).

Step 3

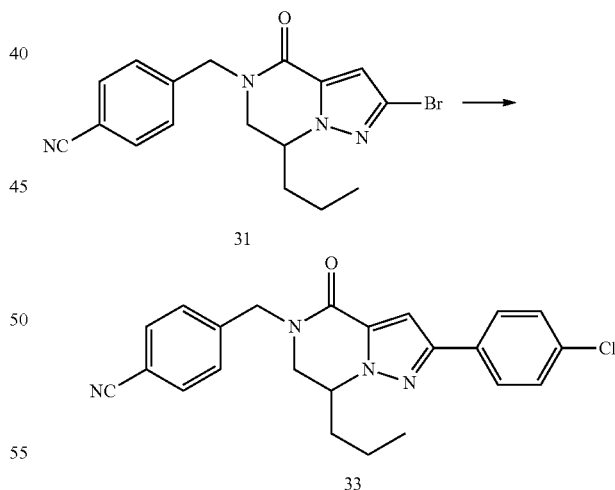

31

33

To a solution of Compound 31 (20 mg, 0.054 mmol) in N,N-dimethylformamide (0.5 mL) was added 4-chlorophenyl boronic acid (12.57 mg, 0.080 mmol), PdCl$_2$(dppf) dichloromethane complex (4.4 mg, 0.0054 mmol) and 2 mol/L sodium carbonate aqueous solution (0.107 mL, 0.214 mmol), the solution was stirred at 100° C. for 1.5 hours. To the reaction mixture was added water, and extracted ethyl acetate. The organic layer was dried with anhydrous sodium sulfate, and concentrated under reduced pressure. The residue was purified by silica gel chromatography (hexane/ethyl acetate) to yield Compound 33 ((I-0181), 14.8 mg, yield: 68%) as a white solid.

LC/MS Method: B, retention time: 2.55 min, M+H: 405

¹H-NMR (δ ppm TMS/CDCl₃) 7.74 (d, 2H, J=7.8 Hz), 7.68 (d, 2H, J=7.8 Hz), 7.47 (d, 2H, J=7.8 Hz), 7.38 (d, 2H, J=8.0 Hz), 7.16 (s, 1H), 4.98 (d, 1H, J=15.3 Hz), 4.64 (d, 1H, J=15.1 Hz), 4.42-4.40 (m, 1H), 3.83 (dd, 1H, J=13.1, 4.3 Hz), 3.42 (dd, 1H, J=13.1, 4.8 Hz), 2.06-1.97 (m, 1H), 1.33-1.22 (m, 2H), 0.89 (t, 3H, J=7.3 Hz).

Example 17: Preparation of Compound 35

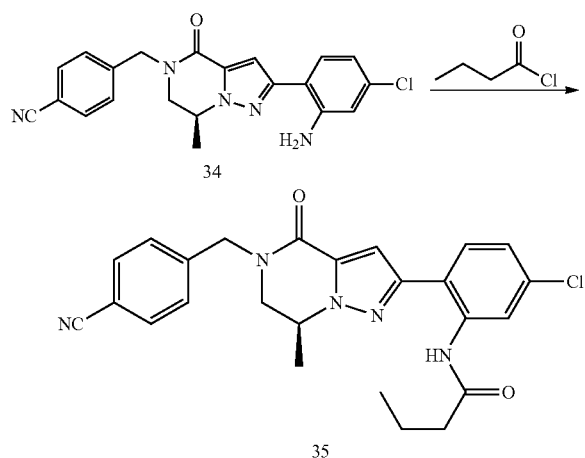

To a compound 34 (20 mg, 0.05 mmol) in dichloromathene (1 mL) was added triethylamine (35 ul, 0.26 mmol) and butyryl chloride (8.2 mg, 0.08 mmol), the solution was stirred at room temperature for 40 minutes. To the reaction solution was added 1 mol/L hydrochloric acid aqueous solution, extracted with ethyl acetate. The organic layer was dried with anhydrous sodium sulfate, and concentrated under reduced pressure. The residue was purified by silica gel chromatography (ethyl acetate/hexane) to yield Compound 35 (18 mg, yield: 76%) as a white solid.

¹H-NMR (CDCl₃) δ: 11.03 (1H, s), 8.78 (1H, s), 7.69 (2H, d, J=7.8 Hz), 7.56 (1H, d, J=8.5 Hz), 7.47 (2H, d, J=7.8 Hz), 7.10 (1H, d, J=8.3 Hz), 4.89-4.80 (2H, m), 4.59-4.57 (1H, m), 3.69 (1H, dd, J=12.8, 4.3 Hz), 3.55-3.49 (1H, m), 2.38 (2H, dd, J=9.8, 5.3 Hz), 1.82-1.77 (2H, m), 1.64 (3H, d, J=6.3 Hz), 1.00 (3H, t, J=7.3 Hz).

LC-MS: m/z=462. [M+H]⁺

Example 18: Preparation of Compound 36

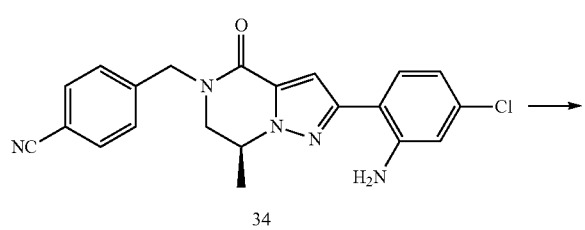

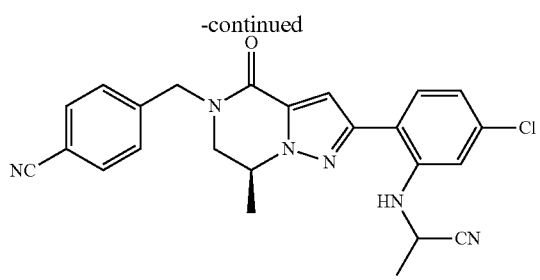

To a solution of Compound 34 (20 mg, 0.05 mmol) in dichloromathene (200 uL) was added water (4.6 ul, 0.26 mmol), acetoaldehyde (28.5 ul, 0.51 mmol) and cyano trimethylsilane (63.3 ul, 0.51 mmol), the solution was stirred at room temperature for 1.5 hours. To the reaction mixture was added water, and extracted with ethyl acetate. The organic layer was dried with anhydrous sodium sulfate, and concentrated under reduced pressure. The residue was purified by silica gel chromatography (ethyl acetate/hexane) to yield Compound 36 (16 mg, yield: 71%).

¹H-NMR (CDCl₃) δ: 7.89-7.87 (1H, m), 7.68 (2H, d, J=7.5 Hz), 7.53 (1H, d, J=8.3 Hz), 7.46 (2H, d, J=7.8 Hz), 7.24 (1H, s), 6.86 (1H, t, J=4.3 Hz), 6.79 (1H, s), 4.90-4.77 (2H, m), 4.58-4.50 (1H, m), 4.40-4.36 (1H, m), 3.69-3.62 (1H, m), 3.52-3.47 (1H, m), 1.77 (3H, d, J=7.0 Hz).

LC-MS: m/z=445. [M+H]⁺

Example 19: Preparation of Compound 37

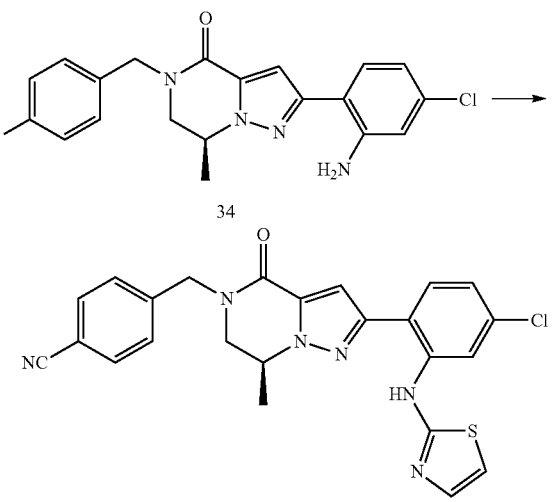

To a solution of Compound 34 (20 mg, 0.05 mmol) in 2-propanol (500 uL) was added 2-bromothiazole (45.5 ul, 0.51 mmol) and p-toluenesulufonic acid hydrate (9.7 mg, 0.05 mmol), the solution was stirred at 120° C. for 1 hours. To the reaction mixture was added water, and extracted with ethyl acetate. The organic layer was dried with anhydrous sodium sulfate, and concentrated under reduced pressure. The residue was purified by silica gel chromatography (ethyl acetate/hexane) to yield Compound 37 (21 mg, yield: 87%) as a gray solid.

¹H-NMR (CDCl₃) δ: 11.23 (1H, s), 8.53 (1H, s), 7.68 (2H, d, J=7.8 Hz), 7.58 (1H, d, J=8.3 Hz), 7.47 (2H, d, J=7.5 Hz), 7.35 (1H, d, J=3.5 Hz), 7.02 (1H, d, J=8.3 Hz), 6.71 (1H, d, J=3.3 Hz), 4.88-4.80 (2H, m), 4.63-4.60 (1H, m), 3.68 (1H, dd, J=12.7, 4.4 Hz), 3.54-3.48 (1H, m), 1.68 (3H, d, J=6.5 Hz).

LC-MS: m/z=475. [M+H]⁺

Example 20: Preparation of Compound 38

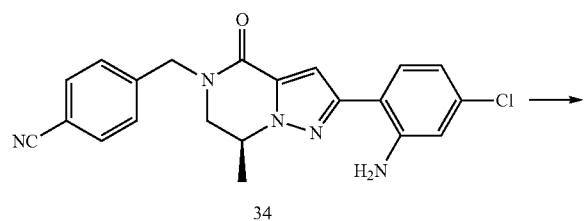
34

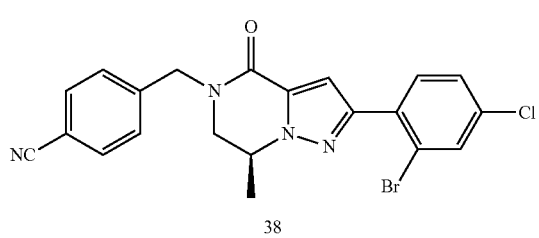
38

To a solution of Compound 34 (50 mg, 0.13 mmol) in acetonitrile (600 uL) was added tert-butyl nitrite (45.9 ul, 0.38 mmol) and copper(I) bromide (54.9 mg, 0.38 mmol), and the solution was stirred at room temperature for 1.5 hours. To the reaction mixture was added water, and extracted with ethyl acetate. The organic layer was dried with anhydrous sodium sulfate, and concentrated under reduced pressure. The residue was purified by silica gel chromatopraphy (ethyl acetate/hexane) to yield Compound 38 (48 mg, yield: 83%) as a yellow solid.

¹H-NMR (CDCl₃) δ: 7.68-7.65 (4H, m), 7.47 (2H, d, J=7.8 Hz), 7.41 (1H, s), 7.35 (1H, d, J=8.3 Hz), 4.83 (2H, s), 4.59-4.55 (1H, m), 3.73-3.70 (1H, m), 3.45 (1H, dd, J=12.5, 8.0 Hz), 1.60-1.58 (3H, m).

LC-MS: m/z=454. [M+H]⁺

Example 21: Preparation of Compound 40

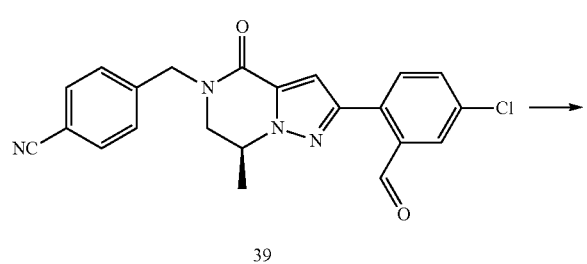
39

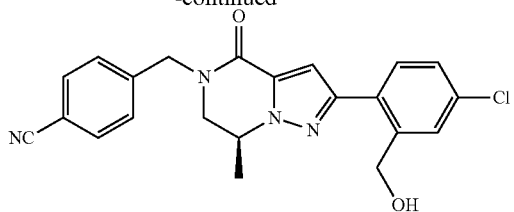
40

To a mixed solution of Compound 39 (20 mg, 0.05 mmol) in tetrahydrofuran (500 uL) and methanol (500 uL) was added sodium borohydride (18.7 mg, 0.49 mmol), and the solution was stirred at room temperature for 50 minutes. To the reaction mixture was added water, and extracted with ethyl acetate. The organic layer was dried with anhydrous sodium sulfate, and concentrated under reduced pressure. The residue was purified by silica gel chromatography (ethyl acetate/hexane) to yield Compound 40 (15 mg, yield: 75%) as a white solid.

1H-NMR (CDCl₃) δ: 7.68 (2H, d, J=7.5 Hz), 7.53 (1H, t, J=4.1 Hz), 7.47 (3H, d, J=8.5 Hz), 7.37 (1H, d, J=8.0 Hz), 7.18 (1H, s), 4.94-4.91 (1H, m), 4.84 (2H, s), 4.62-4.55 (3H, m), 3.73-3.68 (1H, m), 3.52-3.47 (1H, m), 1.62-1.59 (3H, m).

LC-MS: m/z=407. [M+H]⁺

Example 22: Preparation of Compound 41

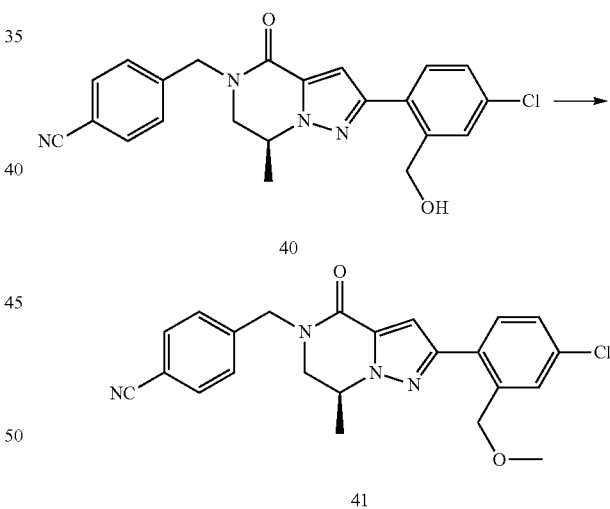
40

41

To a solution of Compound 40 (8 mg, 0.02 mmol) in tetrahydrofuran (800 uL) was added sodium hydride (3.9 mg, 0.10 mmol) under ice-cooling, the solution was stirred for 10 minutes. To the reaction mixture was added methyl iodide (6.2 ul, 0.10 mmol), and stirred at room temperature overnight. To the reaction solution was added water, and extracted with ethyl acetate. The organic layer was dried with anhydrous sodium sulfate, and concentrated under reduced pressure. The residue was purified by reversed phase silica gel chromatography (acetonitrile/water) to yield Compound 41 (6 mg, yield: 73%) as a yellow viscous solid.

1H-NMR (CDCl₃) δ: 7.68 (2H, d, J=8.3 Hz), 7.59 (1H, d, J=2.0 Hz), 7.55 (1H, d, J=8.3 Hz), 7.47 (2H, d, J=8.0 Hz), 7.32 (1H, dd, J=8.3, 2.3 Hz), 7.11 (1H, s), 4.83 (2H, s), 4.62 (2H, s), 4.58-4.56 (1H, m), 3.71 (1H, dd, J=12.9, 4.6 Hz), 3.48-3.46 (1H, m), 3.43 (3H, s), 1.63-1.59 (3H, m).

LC-MS: m/z=421. [M+H]+

Example 23: Preparation of Compound 51 (I-0356)

Step 1

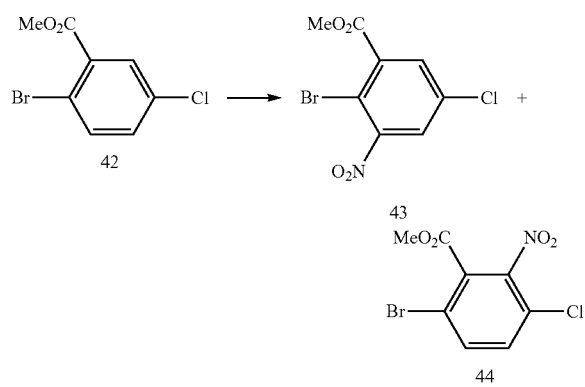

To a solution of Compound 42 (2 g, 8.02 mmol) in tetrahydrofuran (800 uL) was added sulfuric acid (20 ml, 8.02 mmol) at −10° C., the solution was stirred for 40 minutes. The reaction mixture was poured into ice water, and extracted with ethyl acetate. The organic layer was washed with water, dried with anhydrous sodium sulfate, and concentrated under reduced pressure. The residue was purified by silica gel chromatography (ethyl acetate/hexane) to yield the mixture of Compound 43 and 44 (2.2 g, yield: 93%).

LC-MS Method: B, retention time: 2.18 min

Step 2

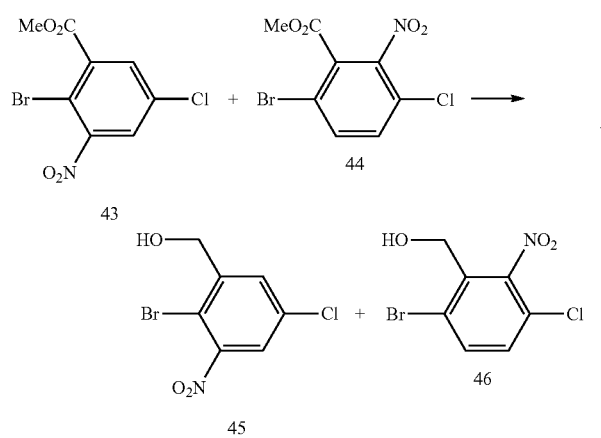

To a solution of the mixture of Compound 43 and 44 (1.7 g, 5.77 mmol) in tetrahydrofuran (20 mL) was added diisobutylaluminium hydride (14.4 ml, 14.4 mmol) at −78° C., and the solution was gradually warmed to 0° C. The reaction mixture was poured into the mixed solvent of ethyl acetate and methanol, and then Rochelle salt aqueous solution was added to the solution. After extracted, the organic layer was washed with water, dried with anhydrous sodium sulfate, and concentrated under reduced pressure. The residue was purified by silica gel chromatography (ethyl acetate/hexane) to yield the mixture of Compound 45 and 46 (1.65 g, yield: quant).

LC/MS Method: B, retention time: 1.79 min, 1.87 min

Step 3

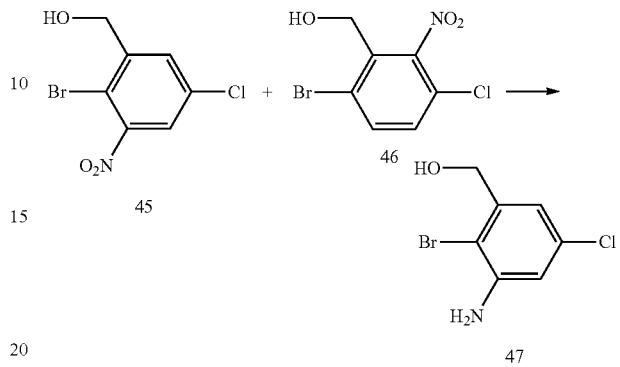

To a mixed solution of the mixture of Compound 45 and 46 (1.55 g, 5.82 mmol) in ethanol (10 mL) and water (2.5 mL) was added ammonium chloride (933 mg, 17.45 mmol) and iron (974 mg, 17.45 mmol), the solution was stirred at 80° C. for 20 minutes. The reaction mixture was filtered, to the filtrate was added water, and extracted with ethyl acetate. The organic layer was dried with anhydrous sodium sulfate, and concentrated under reduced pressure. The residue was purified by suspension with ethyl acetate/hexane to yield Compound 47 (620 mg, yield: 45%) as a white solid.

1H-NMR (DMSO-D6) δ: 6.74 (1H, d, J=2.8 Hz), 6.69 (1H, d, J=2.5 Hz), 5.58 (2H, s), 5.41 (1H, t, J=5.6 Hz), 4.40 (2H, d, J=5.0 Hz).

LC-MS: m/z=235. [M+H]+

Step 4

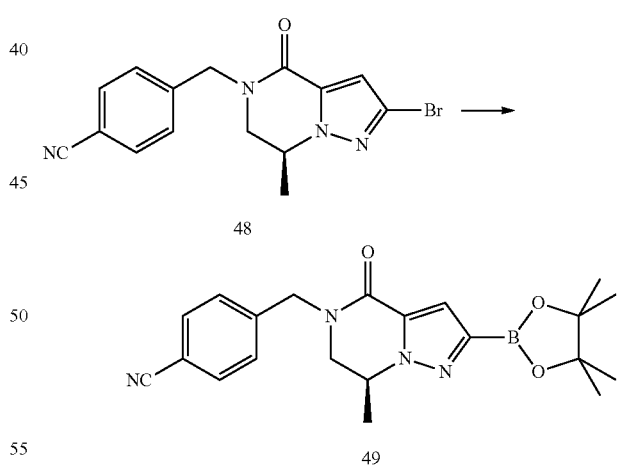

To a solution of Compound 48 (100 mg, 0.29 mmol) in 1,4-dioxane (1.5 mL) was added bis(pinacolate)diboron (176 mg, 0.70 mmol), PdCl$_2$(dppf)-DCM (47.2 mg, 0.06 mmol) and potassium acetate (170 mg, 1.74 mmol), the solution was stirred at 100° C. for 2.5 hours. The reaction mixture was filtered, the filtrate was concentrated under reduced pressure. The residue was purified by diol silica gel chromatography (ethyl acetate/hexane) to yield crude Compound 49 as tan oil.

LC-MS: m/z=311. [M-C$_6$H$_{13}$]+

Step 5
[Chemical Formula 78]

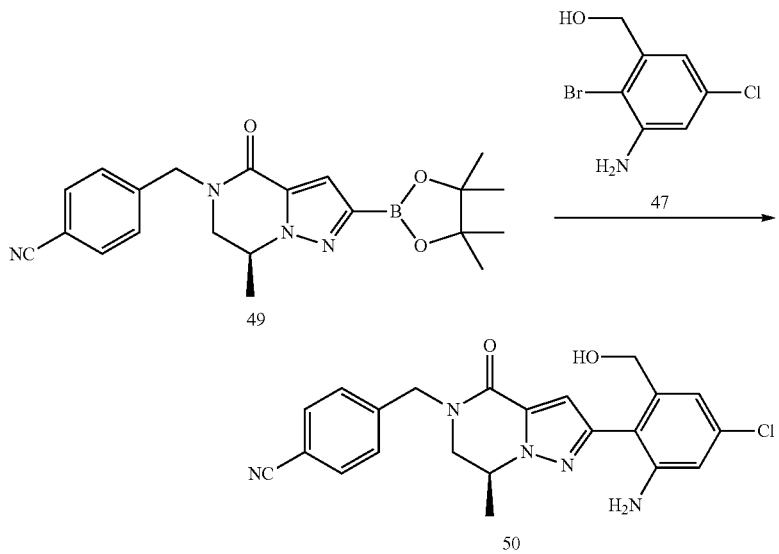

To a solution of Compound 49 (50 mg, 0.13 mmol) in tetrahydrofuran (500 uL) was added Compound 47 (45.2 mg, 0.19 mmol), chloro(2-dicyclohexylphosphino-2',4',6'-triisopropyl-1,1'-biphenyl)[2-(2'-amino-1,1'-biphenyl)]palladium(II) (9.1 mg, 0.01 mmol) and 2 mmol/L tripotassium phosphate aqueous solution (127 ul, 0.26 mmol), the solution was stirred at 60° C. for 45 minutes. To the reaction mixture was added water, and extracted with ethyl acetate. The organic layer was dried with anhydrous sodium sulfate, concentrated under reduced pressure. The residue was purified by silica gel chromatography (chloroform/methanol) to yield Compound 50 (35 mg, yield: 65%) as a tan solid.

1H-NMR (CDCl$_3$) δ: 7.69 (2H, d, J=7.4 Hz), 7.48 (2H, d, J=7.4 Hz), 7.18 (1H, s), 6.88 (1H, s), 6.74 (1H, s), 4.84 (2H, s), 4.59-4.58 (1H, m), 4.26 (2H, d, J=5.9 Hz), 4.05 (2H, s), 3.74-3.68 (2H, m), 3.53-3.48 (1H, m), 1.59 (3H, d, J=6.4 Hz), 1.14-1.13 (1H, m).

LC-MS: m/z=422. [M+H]+

To a solution of Compound 50 (17 mg, 0.04 mmol) in dichloromethane (1 mL) was added acetoaldehyde (4.5 ul, 0.08 mmol), acetic acid (4.6 ul, 0.08 mmol) and sodium triacetoxyborohydride (12.8 mg, 0.06 mmol) at −20° C., the solution was stirred for 40 minutes. To the reaction mixture was added water, and extracted with ethyl acetate. The organic layer was dried with anhydrous sodium sulfate, and concentrated under reduced pressure. The residue was purified by reversed phase silica gel chromatography (acetonitrile/water) to yield Compound 51 (I-0356) (5 mg, yield: 28%).

1H-NMR (CDCl$_3$) δ: 7.69-7.68 (2H, m), 7.49-7.48 (2H, m), 7.13 (1H, s), 6.81 (1H, d, J=2.0 Hz), 6.64 (1H, d, J=2.0 Hz), 4.84 (2H, s), 4.60-4.58 (1H, m), 4.26-4.21 (3H, m), 3.72 (1H, dd, J=12.9, 4.6 Hz), 3.53-3.49 (2H, m), 3.16-3.09 (2H, m), 1.62-1.60 (3H, m), 1.21 (3H, t, J=7.2 Hz).

LC-MS: m/z=450. [M+H]+

Example 24: Preparation of Compound 55 (I-0355)

Step 1

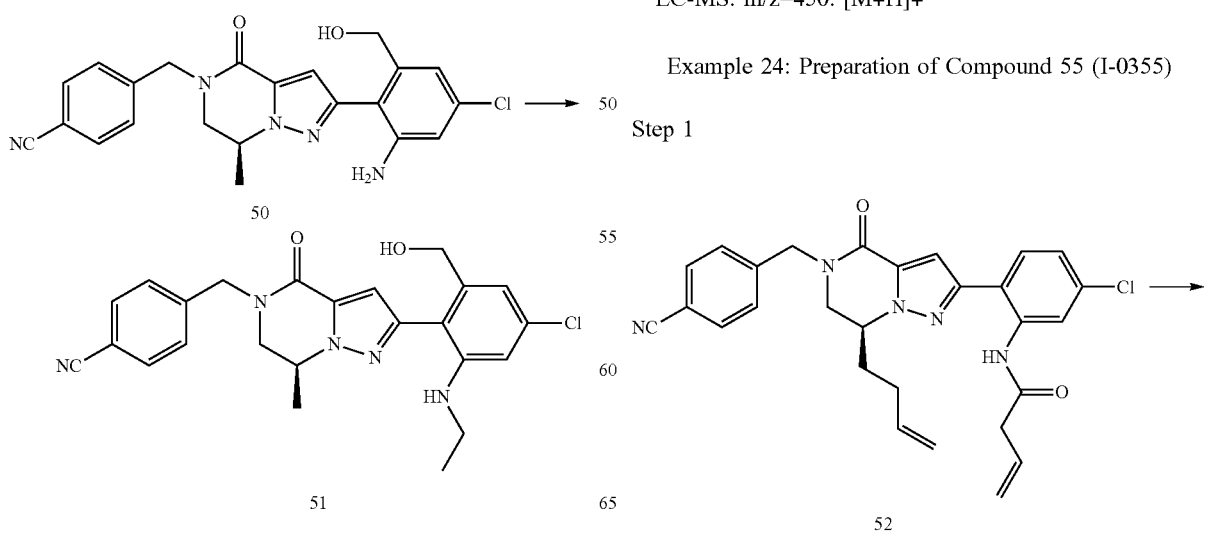

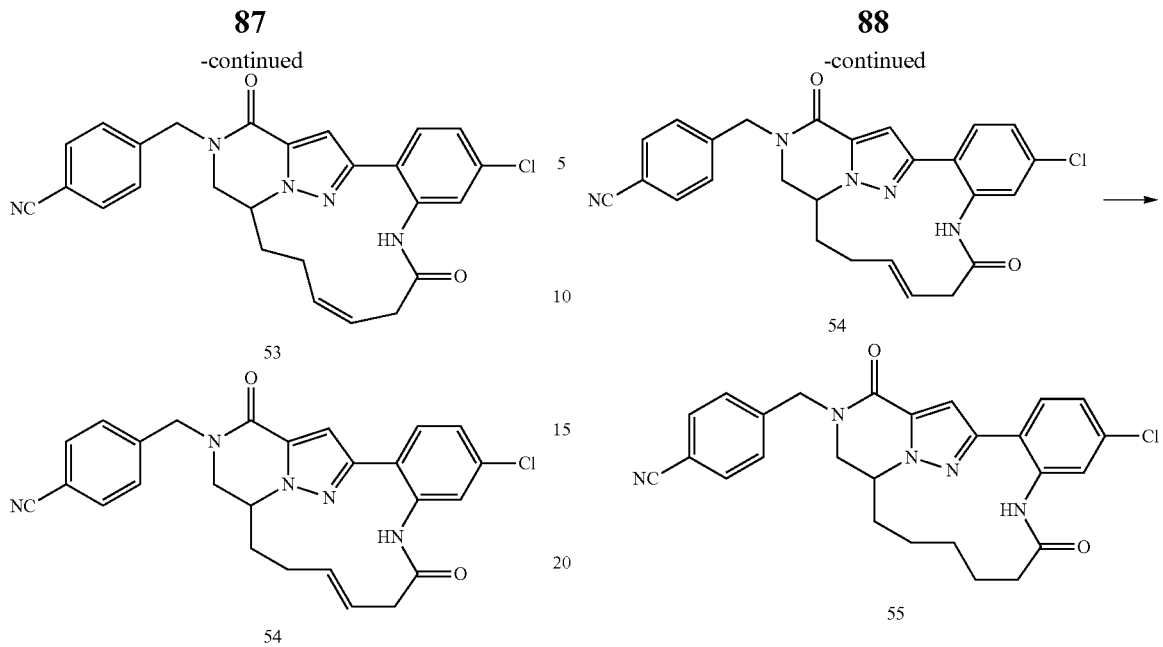

To a solution of Compound 52 (16 mg, 0.03 mmol) in dichloromethane (600 uL) was added Grubbs II catalyst (8.2 mg, 0.001 mmol), the solution was stirred at room temperature for 1 hour. To the reaction mixture was added water, and extracted with ethyl acetate. The organic layer was dried with anhydrous sodium sulfate, and concentrated under reduced pressure. The residue was purified by reversed phase silica gel chromatography (acetonitrile/water) to yield Compound 53 (I-0358) (2 mg, yield: 15%) and Compound 54 (I-0357)(4 mg, yield: 29%).

Compound 53

1H-NMR (CDCl$_3$) δ: 11.11 (1H, s), 8.35 (1H, d, J=2.0 Hz), 7.69 (2H, d, J=8.3 Hz), 7.47-7.44 (3H, m), 7.14-7.12 (1H, m), 7.10 (1H, d, J=3.3 Hz), 5.83-5.77 (2H, m), 4.93 (1H, d, J=15.1 Hz), 4.76-4.70 (2H, m), 4.05-4.00 (1H, m), 3.37 (1H, dd, J=13.1, 3.3 Hz), 3.20 (1H, dd, J=15.8, 9.0 Hz), 3.06-3.03 (1H, m), 2.45-2.39 (1H, m), 2.12-2.09 (2H, m), 1.87-1.80 (1H, m).

LC-MS: m/z=472. [M+H]+

Compound 54

1H-NMR (CDCl$_3$) δ: 11.20 (1H, s), 8.74 (1H, d, J=2.0 Hz), 7.69 (2H, d, J=8.3 Hz), 7.47 (3H, dd, J=8.3, 5.0 Hz), 7.19 (1H, s), 7.11 (1H, dd, J=8.3, 2.3 Hz), 5.85-5.78 (1H, m), 5.71-5.67 (1H, m), 4.83 (2H, dd, J=22.6, 15.3 Hz), 4.47-4.45 (1H, m), 3.59 (2H, d, J=7.3 Hz), 3.13 (2H, d, J=7.3 Hz), 2.56-2.53 (1H, m), 2.38-2.24 (2H, m), 2.02-1.96 (1H, m).

LC-MS: m/z=472. [M+H]+

Step 2

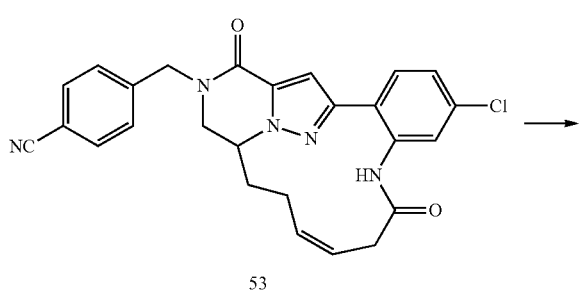

To a solution of the mixture of Compound 53 and 54 (20 mg, 0.04 mmol) in tetrahydrofuran (1 mL) was added Pt/carbon (26.3 mg, 0.13 mmol), the solution was stirred at room temperature for 1 hour under hydrogen atmosphere. The reaction mixture was filtered, the filtrate was concentrated under reduced pressure. The residue was purified by silica gel chromatography (chloroform/methanol), after that purified by suspension with ethyl acetate/hexane to yield Compound 55 (I-0355) (17 mg, yield: 85%) as a gray solid.

1H-NMR (CDCl$_3$) δ: 10.86 (1H, s), 8.47 (1H, d, J=2.3 Hz), 7.68 (2H, d, J=8.3 Hz), 7.52 (1H, d, J=8.3 Hz), 7.46 (2H, d, J=8.3 Hz), 7.20 (1H, s), 7.13 (1H, dd, J=8.4, 2.1 Hz), 4.82 (2H, s), 4.44-4.43 (1H, m), 3.68 (1H, dd, J=12.9, 4.6 Hz), 3.51 (1H, dd, J=12.9, 8.2 Hz), 2.51-2.46 (2H, m), 1.94-1.85 (4H, m), 1.64-1.58 (3H, m), 1.31-1.28 (1H, m).

LC-MS: m/z=474. [M+H]+

Example 25: Preparation of Compound 59

Step 1

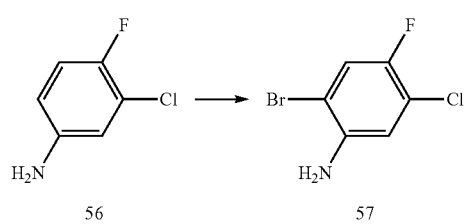 [SMILES: Nc1ccc(F)c(Cl)c1 ; Nc1cc(Cl)c(F)cc1Br]

To a solution of Compound 56 (5 g, 34.3 mmol) in dichloromethane (60 mL) was added pyridine (4.2 ml, 51.5 mmol) under ice-cooling, dropwised a solution of bromine (1.8 ml, 34.3 mmol) in dichloromethane (40 mL), the solution was stirred for 1 hour. To the reaction mixture was added sodium thiosulfate aqueous solution, and extracted with ethyl acetate. The organic layer was dried with anhydrous sodium sulfate, and concentrated under reduced pressure. The residue was purified by silica gel chromatography (ethyl acetate/hexane) to yield Compound 57 (6.4 g, yield: 83%) as an orange solid.

LC-MS: m/z=223. [M+H]+

Step 2

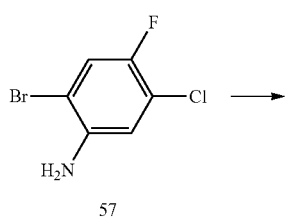

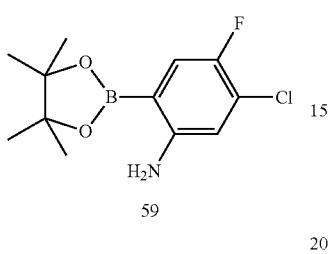

To a solution of Compound 57 (600 mg, 2.67 mmol) in 1,4-dioxane (6 mL) was added bis(pinacolate)diboron (815 mg, 3.21 mmol), PdCl2(dppf)-DCM (218 mg, 0.27 mmol) and potassium acetate (787 mg, 8.02 mmol), and the solution was stirred at 100° C. for 1 hour. The reaction mixture was filtered, the filtrate was concentrated under reduced pressure. The residue was purified by diol silica gel chromatography (ethyl acetate/hexane) to yield crude Compound 59 as black oil.

LC-MS: m/z=188. [M+H]+

Example 26: Preparation of Compound 60

Step 1

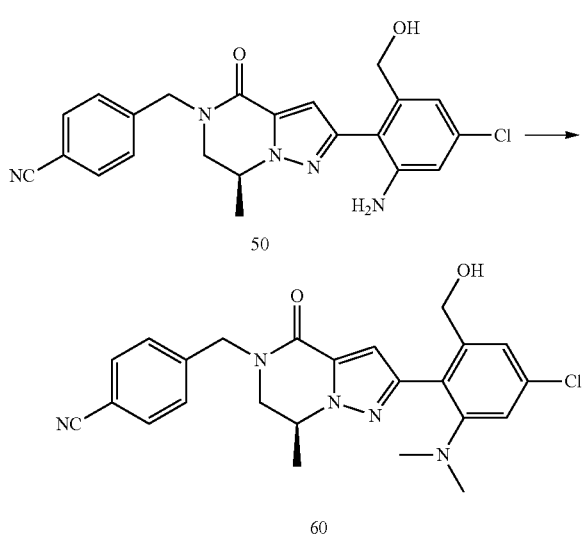

To a solution of Compound 50 (20 mg, 0.047 mmol) in N,N-dimethylformamide (1 mL) was added potassium carbonate (9.8 mg, 0.071 mmol) and methyl iodide (57 ul, 0.91 mmol), the solution was stirred at 70° C. for 3.5 hours. To the reaction mixture was added water, and extracted with ethyl acetate. The organic layer was dried with anhydrous sodium sulfate, and concentrated under reduced pressure. The residue was purified by reversed phase silica gel chromatography (acetonitrile/water) to yield Compound 60 (11.3 mg, yield: 53%) as a yellow viscous solid.

LC/MS Method: B, LC-MS: m/z=450. [M+H]+, retention time: 1.84 min

1H-NMR (CDCl3) δ: 7.69 (2H, d, J=8.0 Hz), 7.49 (2H, d, J=8.0 Hz), 7.27 (2H, d, J=8.5 Hz), 7.06 (1H, d, J=1.8 Hz), 7.01 (1H, d, J=1.8 Hz), 4.84 (2H, dd, J=18.3, 15.3 Hz), 4.61-4.55 (2H, m), 4.23-4.20 (2H, m), 3.73 (1H, dd, J=12.8, 4.5 Hz), 3.48 (1H, dd, J=12.9, 8.2 Hz), 2.54 (6H, s), 1.55 (3H, dd, J=13.4, 6.7 Hz).

Example 27: Preparation of Compound 63

Step 1

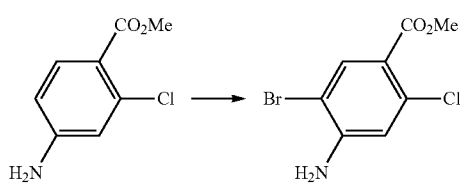

To a solution of Compound 61 (900 mg, 4.85 mmol) in tetrahydrofuran (10 mL) was added N-bromosuccinimide (906 mg, 15.09 mmol) at −20° C., the solution was warmed to room temperature, and stirred for 10 minutes. To the reaction mixture was added 10% sodium thiosulfate aqueous solution, and extracted with ethyl acetate. The organic layer was dried with anhydrous sodium sulfate, and concentrated under reduced pressure. The residue was purified by silica gel chromatography (ethyl acetate/hexane) to yield Compound 62 (600 mg, yield: 47%) as a white solid.

LC/MS Method: B, LC-MS: m/z=263. [M+H]+, retention time: 1.86 min

1H-NMR (DMSO-D6) δ: 7.91 (1H, s), 6.86 (1H, s), 6.38 (2H, s), 3.76 (3H, s).

Step 2

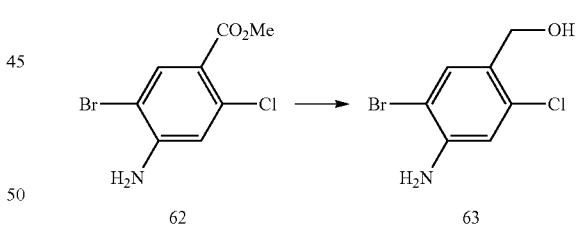

To a solution of Compound 62 (300 mg, 1.13 mmol) in tetrahydrofuran (10 mL) was added 1 mol/L diisobutyl aluminium hydride in hexane solution (5.67 mL, 5.67 mmol) at −78° C. The solution was warmed to 0° C., and stirred for 30 minutes. The reaction mixture was cooled to −78° C., added methanol, and added into the mixed solution of ethyl acetate and potassium sodium tartrate. The mixture was extracted, the organic layer was washed with water, dried with anhydrous sodium sulfate, and concentrated under reduced pressure. The residue was purified by suspension with ethyl acetate/hexane to yield Compound 63 (250 mg, yield: 93%) as a white solid.

LC/MS Method: B, LC-MS: m/z=235. [M+H]+, retention time: 1.35 min

Example 28: Preparation of Compound 65

Step 1

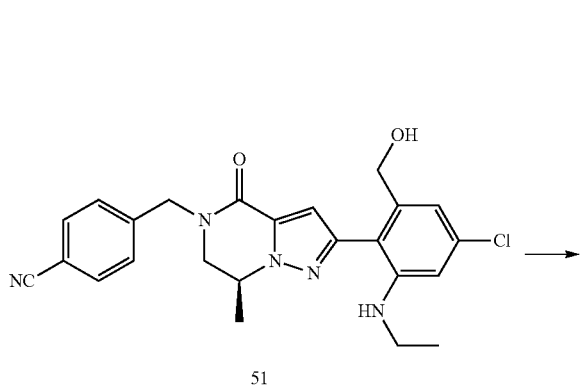

51

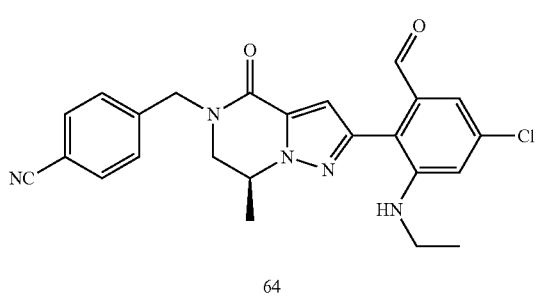

64

To a solution of Compound 51 (22 mg, 0.049 mmol) in dichloromethane (1 mL) was added Dess-Martin reagent (31.1 mg, 0.073 mmol), the solution was stirred at room temperature for 1 hour. To the reaction mixture was added water, extracted with ethyl acetate. The organic layer was dried with anhydrous sodium sulfate, and concentrated under reduced pressure. The residue was purified by silica gel chromatography (ethyl acetate/hexane) to yield Compound 64 (22 mg, yield: 100%) as a yellow amorphous.

LC/MS Method: B, LC-MS: m/z=448. [M+H]+, retention time: 2.35 min

1H-NMR (CDCl3) δ: 9.82 (1H, s), 7.69 (2H, d, J=8.0 Hz), 7.49 (2H, d, J=8.3 Hz), 7.00 (1H, s), 6.83 (1H, d, J=1.8 Hz), 5.02 (1H, s), 4.84 (2H, s), 4.63-4.60 (1H, m), 3.73 (1H, dd, J=12.9, 4.4 Hz), 3.65-3.64 (1H, m), 3.51 (1H, dd, J=13.1, 8.3 Hz), 3.17-3.15 (2H, m), 1.60 (3H, d, J=6.5 Hz), 1.24 (3H, t, J=7.2 Hz).

Step 2

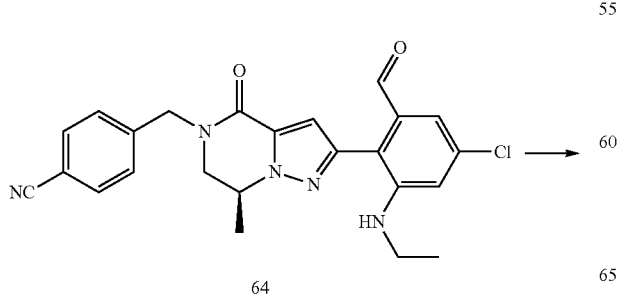

64

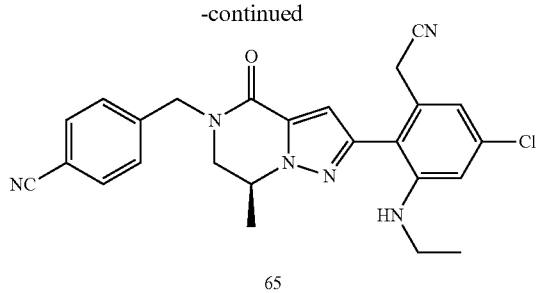

65

To a solution of potassium tert-butoxide (20 mg, 0.179 mmol) in tetrahydrofuran (500 uL) was added p-toluenesulfonyl methyl isocyanide (17.4 mL, 0.089 mmol) at −78° C., the solution was stirred for 10 minutes. To the reaction mixture was added a solution of Compound 64 (20 mg, 0.045 mmol) in tetrahydrofuran (500 uL) an −78° C., and the solution was stirred for 1 hour. To the reaction mixture was added methanol (500 uL), and the solution was stirred at reflux temperature for 30 minutes. To the reaction mixture was added water, and extracted ethyl acetate. The organic layer was dried with anhydrous sodium sulfate, concentrated under reduced pressure. The residue was purified by silica gel chromatography (ethyl acetate/hexane) to yield Compound 65 (4.5 mg, yield: 22%) as yellow oil.

LC/MS Method: B, LC-MS: m/z=458. [M+H]+, retention time: 2.63 min

1H-NMR (CDCl₃) δ: 7.68 (2H, d, J=7.9 Hz), 7.53 (2H, d, J=8.9 Hz), 7.48 (2H, d, J=7.9 Hz), 7.39 (1H, d, J=8.3 Hz), 7.10 (1H, s), 4.99 (1H, d, J=15.2 Hz), 4.65 (1H, d, J=15.1 Hz), 4.43-4.41 (1H, m), 4.14 (2H, s), 3.83 (1H, dd, J=12.9, 4.6 Hz), 3.47 (1H, dd, J=12.9, 5.5 Hz), 2.05-2.03 (1H, m), 1.66-1.62 (3H, m), 1.30-1.14 (6H, m), 0.87 (3H, t, J=6.8 Hz).

Example 29: Preparation of Compound 68

Step 1

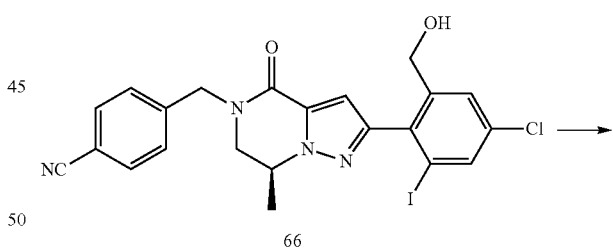

66

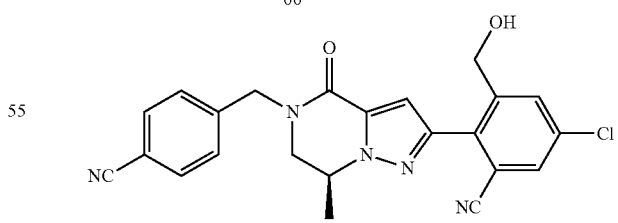

67

To a solution of Compound 66 (14 mg, 0.026 mmol) in N,N-dimethylacetoamide (800 uL) was added copper cyanide (7.06 mg, 0.079 mmol), and the solution was stirred at 150° C. for 30 minutes. To the reaction solution was added water, and extracted with ethyl acetate. The organic layer was dried with anhydrous sodium sulfate, and concentrated under reduced pressure. The residue was purified by silica gel chromatography (methanol/chloroform), and then purified by suspension with ethyl acetate/hexane/diisopropyl ether to yield Compound 67 (12 mg, yield: 57%) as a white solid.

LC/MS Method: B, LC-MS: m/z=432. [M+H]+, retention time: 1.91 min 1H-NMR (CDCl₃) δ: 7.71 (4H, dd, J=15.0, 7.8 Hz), 7.48 (2H, d, J=7.7 Hz), 7.37 (1H, s), 4.84 (2H, s), 4.62-4.60 (1H, m), 4.42 (2H, d, J=7.0 Hz), 4.02-4.00 (1H, m), 3.72 (1H, dd, J=13.2, 4.3 Hz), 3.53-3.51 (1H, m), 1.60 (3H, d, J=6.3 Hz).

Step 2

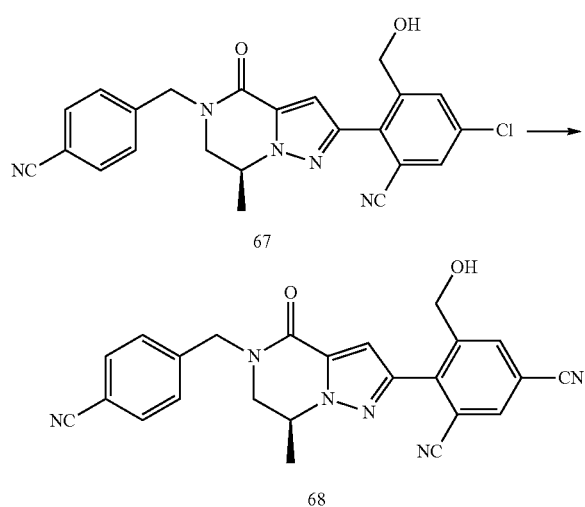

To a solution of Compound 67 (30 mg, 0.069 mmol) in N,N-dimethylacetamide (1 mL) was added zinc (13.6 mg, 0.208 mmol), zinc dicyanide (41.4 mg, 0.097 mmol) and palladium (40.7 mg, 0.021 mmol) under nitrogen atmosphere, the solution was stirred at 100° C. for 2 hours. To the reaction mixture was added water, extracted with ethyl acetate. The organic layer was dried with anhydrous sodium sulfate, and concentrated under reduced pressure. The residue was purified by silica gel chromatography (methanol/chloroform), and purified by reversed phase silica gel chromatography (acetonitrile/water) to yield Compound 68 (10 mg, yield: 34%) as white oil.

LC/MS Method: B, LC-MS: m/z=423. [M+H]+, retention time: 1.91 min

1H-NMR (CDCl₃) δ: 8.03 (2H, dd, J=18.7, 1.6 Hz), 7.69 (2H, d, J=8.3 Hz), 7.49 (2H, d, J=8.3 Hz), 7.42 (1H, s), 4.84 (2H, s), 4.66-4.63 (1H, m), 4.53 (2H, d, J=5.3 Hz), 3.86 (1H, br s), 3.74 (1H, dd, J=13.1, 4.5 Hz), 3.56-3.49 (1H, m).

Example 30: Preparation of Compound 69

Step 1

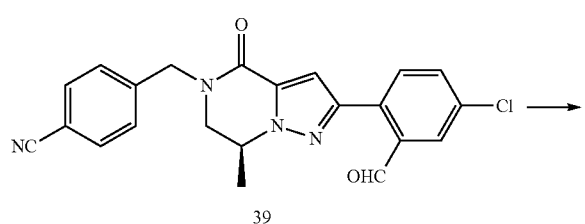

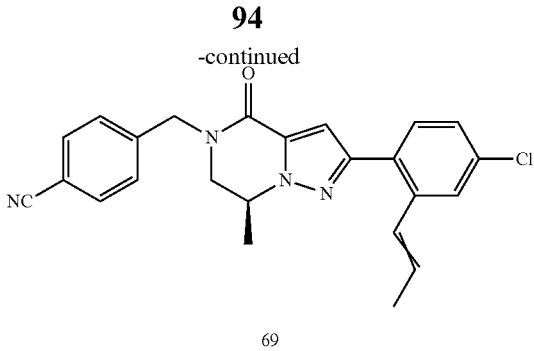

To a solution of Compound 39 (28 mg, 0.069 mmol) in acetonitrile (1 mL) was added propionaldehyde (12 uL, 0.173 mmol), malononitrile (22.8 mg, 0.346 mmol) and acetic acid (16 uL, 0.277 mmol), the solution was stirred at room temperature for 10 minutes. To the reaction mixture was added ammonium acetate (13.3 mg, 0.173 mmol), the solution was stirred at 80° C. for 8 hours. To the reaction mixture was added water, and extracted with ethyl acetate. The organic layer was dried with anhydrous sodium sulfate, and concentrated under reduced pressure. The residue wad purified by silica gel chromatography (ethyl acetate/hexane), and purified by suspension with ethyl acetate/hexane to yield Compound 69 (4 mg, yield: 14%) as a white solid.

LC/MS Method: B, LC-MS: m/z=417. [M+H]+, retention time: 1.55 min

¹H-NMR (CDCl₃) δ: 7.69 (2H, d, J=8.3 Hz), 7.48-7.45 (3H, m), 7.37-7.34 (2H, m), 7.08 (1H, d, J=8.0 Hz), 4.87-4.81 (4H, m), 4.56-4.55 (1H, m), 4.47 (1H, br s), 3.80-3.71 (2H, m), 3.51-3.48 (1H, m), 2.19-2.18 (1H, m), 1.57 (4H, dd, J=6.5, 2.7 Hz), 1.04-0.96 (3H, m).

Example 31: Preparation of Compound 79

Step 2

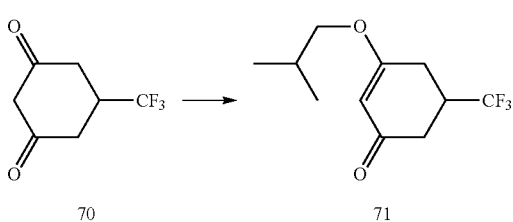 [SMILES: O=C1CC(=O)CC(C(F)(F)F)C1 ; CC(C)COC1=CC(=O)CC(C(F)(F)F)C1]

To a solution of Compound 70 (2.75 g, 15.27 mmol) in toluene (10 mL) was added 2-methylpropane-1-ol (10 mL, 15.27 mmol) and p-toluenesulfonic acid (263 mg, 1.527 mmol), the solution was stirred at reflux temperature for 2 hours. To the reaction mixture was added water, and extracted with ethyl acetate. The organic layer was dried with anhydrous sodium sulfate, and concentrated under reduced pressure. The residue was purified by silica gel chromatography (ethyl acetate/hexane) to yield Compound 71 (3.4 g, yield: 94%) as colorless oil.

LC/MS Method: B, LC-MS: m/z=236, retention time: 2.12 min

Step 2

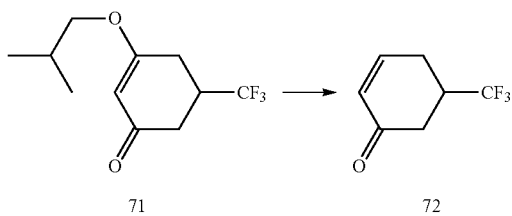 [SMILES: CC(C)COC1=CC(=O)CC(C(F)(F)F)C1 ; O=C1C=CCC(C(F)(F)F)C1]

To a solution of Compound 71 (3.4 g, 14.39 mmol) in tetrahydrofuran (30 mL) was added lithium aluminium hydride (546 mg, 14.39 mmol) under ice-cooling, the solution was stirred for 1 hour. To the reaction mixture was added 2 mol/L hydrochloric acid aqueous solution (36 mL, 72.0 mmol), and stirred at room temperature for 21 hours. To the reaction mixture was added water, and extracted with diethylether. The organic layer was dried with anhydrous sodium sulfate, and concentrated under reduced pressure. The residue was purified by silica gel chromatography (ethyl acetate/hexane) to yield Compound 72 (1.4 g, yield: 59%) as colorless oil.

LC/MS Method: B, LC-MS: m/z=165. [M+H]+, retention time: 1.46 min

1H-NMR (CDCl$_3$) δ: 6.98 (1H, ddd, J=9.9, 6.1, 2.7 Hz), 6.14-6.10 (1H, m), 2.89-2.80 (1H, m), 2.71-2.64 (2H, m), 2.52-2.43 (2H, m).

Step 3

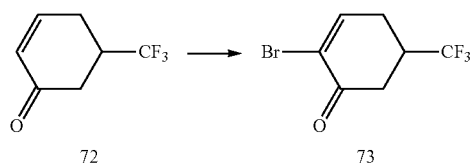 [SMILES: O=C1C=CCC(C(F)(F)F)C1 ; O=C1CC(C(F)(F)F)CC=C1Br]

To a solution of Compound 72 (1.4 g, 8.53 mmol) in dichloromethane (14 mL) was added bromine (484 mL, 9.38 mmol) under ice-cooling, the solution was stirred for 15 minutes. To the reaction solution was added triethylamine (2.01 mL, 14.50 mmol), and stirred at room temperature for 1 hour. To the reaction mixture was added sodium thiosulfate aqueous solution, and extracted with ethyl acetate. The organic layer was dried with anhydrous sodium sulfate, and concentrated under reduced pressure. The residue was purified by silica gel chromatography (ethyl acetate/hexane) to yield Compound 73 (800 mg, yield: 39%) as a white solid.

1H-NMR (CDCl$_3$) δ: 7.40-7.37 (1H, m), 2.97-2.91 (2H, m), 2.75-2.54 (3H, m).

Step 4

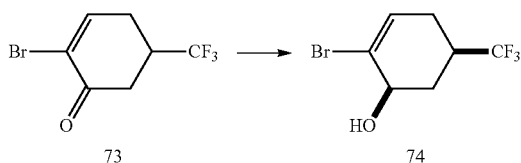 [SMILES: O=C1CC(C(F)(F)F)CC=C1Br ; O[C@@H]1C[C@H](C(F)(F)F)CC=C1Br]

To a solution of Compound 73 (800 mg, 3.29 mmol) in methanol (10 mL) was added cerium chloride (1.35 g, 3.62 mmol), and added sodium borohydride (137 mg, 3.62 mmol) at −25° C., the solution was stirred at −20° C. for 40 minutes. To the reaction solution was added water, and extracted with ethyl acetate. The organic layer was dried with anhydrous sodium sulfate, and concentrated under reduced pressure to yield Compound 74 (780 mg, yield: 97%) as colorless oil.

1H-NMR (CDCl$_3$) δ: 6.15-6.15 (1H, m), 4.35-4.32 (1H, m), 2.54-2.44 (2H, m), 2.30-2.24 (3H, m), 1.73 (1H, td, J=13.1, 10.1 Hz).

Step 5

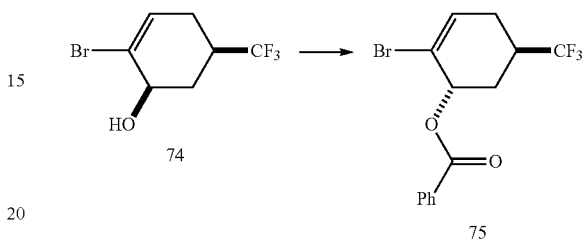

To a solution of Compound 74 (38 mg, 0.155 mmol) in tetrahydrofuran (1 mL) was added benzoic acid (24.6 mg, 0.202 mmol) and isopropyl azodicarboxylate (39.2 uL, 0.202 mmol), and added triphenylphosphine (48.8 mg, 0.186 mmol) under ice-cooling, the solution was stirred at room temperature for 1 hour. The reaction mixture was concentrated under reduced pressure, the residue was purified by silica gel chromatography (ethyl acetate/hexane) to yield Compound 75 (50 mg, yield: 92%) as yellow oil.

1H-NMR (CDCl$_3$) δ: 8.07 (2H, d, J=7.7 Hz), 7.62-7.58 (1H, m), 7.47 (2H, t, J=7.7 Hz), 6.41 (1H, dd, J=5.8, 2.3 Hz), 5.76 (1H, s), 2.64-2.62 (1H, m), 2.50-2.47 (1H, m), 2.37-2.24 (2H, m), 2.03-1.99 (1H, m).

Step 6

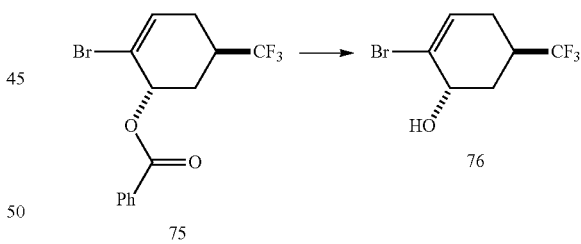

To a solution of Compound 75 (50 mg, 0.143 mmol) in tetrahydrofuran (1 mL) and methanol (500 uL) was added 2 mol/L sodium hydroxide aqueous solution (215 uL, 0.430 mmol), and the solution was stirred at room temperature overnight. To the reaction mixture was added water, and extracted with ethyl acetate. The organic layer was dried with anhydrous sodium sulfate, and concentrated under reduced pressure. The residue was purified by silica gel chromatography (ethyl acetate/hexane) to yield Compound 76 (30 mg, yield: 86%) as yellow oil.

1H-NMR (CDCl$_3$) δ: 6.19 (1H, dd, J=5.8, 2.3 Hz), 4.34 (1H, s), 2.67-2.61 (1H, m), 2.42-2.34 (1H, m), 2.21-2.17 (2H, m), 1.83 (1H, td, J=13.4, 4.1 Hz).

Step 7

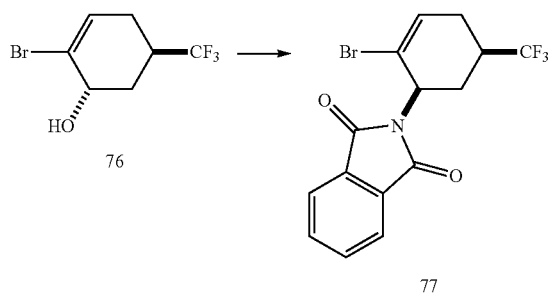 [SMILES: O[C@H]1C[C@H](C(F)(F)F)CC=C1Br ; O=C1c2ccccc2C(=O)N1[C@@H]1C[C@H](C(F)(F)F)CC=C1Br]

To a solution of Compound 76 (30 mg, 0.122 mmol) in tetrahydrofuran (1 mL) was added isoindoline-1,3-dione (21.6 mg, 0.147 mmol) and isopropyl azodicarboxylate (28.6 uL, 0.147 mmol), and added triphenylphosphine (35.3 mg, 0.135 mmol) under ice-cooling. The solution was stirred under ice-cooling for 40 minutes. The reaction mixture was concentrated under reduced pressure, the residue was purified by silica gel chromatography (ethyl acetate/hexane) to yield Compound 77 (30 mg, yield: 66%) as colorless oil.

1H-NMR (CDCl$_3$) δ: 7.88-7.85 (1H, m), 7.77-7.75 (1H, m), 6.34-6.33 (OH, m), 5.09-5.06 (OH, m), 2.67-2.49 (1H, m), 2.43-2.42 (1H, m), 2.28-2.25 (1H, m).

Step 8

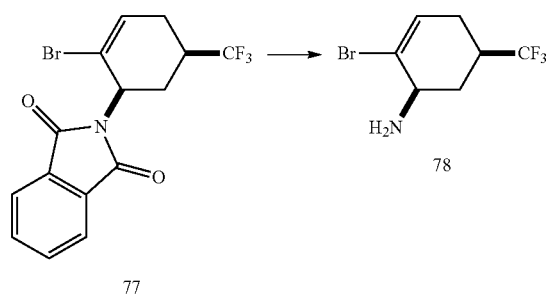 [SMILES: O=C1c2ccccc2C(=O)N1[C@@H]1C[C@H](C(F)(F)F)CC=C1Br ; N[C@@H]1C[C@H](C(F)(F)F)CC=C1Br]

To a solution of Compound 77 (150 mg, 0.401 mmol) in ethanol (1 mL) was added hydrazine hydrate (197 uL, 4.01 mmol), the solution was stirred at 80° C. for 3 hours. After the insoluble material was removed, to the solution was added water, and extracted with ethyl acetate. The organic layer was dried with anhydrous sodium sulfate, and concentrated under reduced pressure to yield Compound 78 (100 mg) as colorless oil. The obtained crude product was used in next step without further purification.

LC/MS Method: B, LC-MS: m/z=243. [M+H], retention time: 0.74 min

Step 9

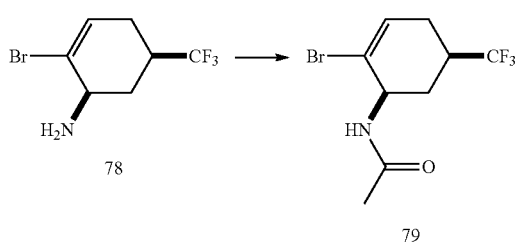

To a solution of Compound 78 (100 mg, 0.410 mmol) in dichloromethane (2 mL) was added pyridine (49.6 uL, 0.615 mmol) and acetic anhydrous (46.5 uL, 0.492 mmol), the solution was stirred at room temperature for 30 minutes. To the reaction solution was added methanol, and concentrated under reduced pressure. The residue was purified by silica gel chromatography (ethyl acetate/hexane) to yield Compound 79 (110 mg, yield: 94%) as a white solid.

LC/MS Method: B, LC-MS: m/z=285. [M+H]+, retention time: 1.59 min

1H-NMR (CDCl$_3$) δ: 6.24-6.23 (1H, m), 5.89 (1H, d, J=8.0 Hz), 4.85-4.81 (1H, m), 2.58-2.45 (2H, m), 2.36-2.28 (1H, m), 2.24-2.16 (1H, m), 2.05 (3H, s), 1.60 (1H, td, J=12.6, 10.6 Hz).

Example 32: Preparation of Compound 82

Step 1

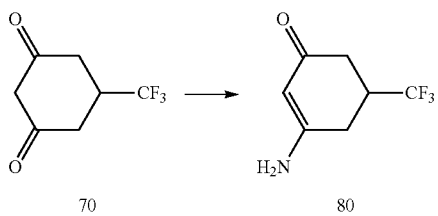 [SMILES: O=C1CC(=O)CC(C(F)(F)F)C1 ; NC1=CC(=O)CC(C(F)(F)F)C1]

To a solution of Compound 70 (450 mg, 2.498 mmol) in toluene (5 mL) was added ammonium acetate (193 mg, 2.498 mmol), the solution was stirred at reflux temperature for 1.5 hours. The reaction mixture was concentrated under reduced pressure to yield Compound 80 (440 mg, yield: 98%).

LC/MS Method: B, LC-MS: m/z=179. [M+H]+, retention time: 0.87 min

1H-NMR (CDCl$_3$) δ: 5.33 (1H, s), 4.61 (2H, s), 2.91-2.81 (2H, m), 2.64-2.55 (2H, m), 2.46-2.43 (1H, m).

Step 2

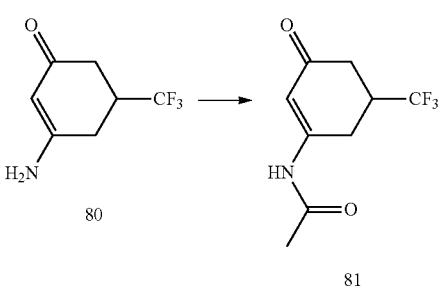

To a solution of Compound 80 (440 mg, 2.456 mmol) in tetrahydrofuran (5 mL) was added pyridine (496 uL, 6.14 mmol) and acetylchloride (351 uL, 4.91 mmol), the solution was stirred at 60° C. for 1 hour. To the reaction solution was added water, and extracted with ethyl acetate. The organic layer was dried with anhydrous sodium sulfate, and concentrated under reduced pressure. The residue was purified by silica gel chromatography (ethyl acetate/hexane) to yield Compound 81 (180 mg, yield: 33%) as a yellow solid.

LC/MS Method: B, LC-MS: m/z=221. [M+H]+, retention time: 1.20 min

¹H-NMR (CDCl₃) δ: 7.98 (1H, s), 6.60 (1H, d, J=1.5 Hz), 2.90-2.62 (4H, m), 2.42-2.38 (1H, m), 2.17 (3H, s).
Step 3

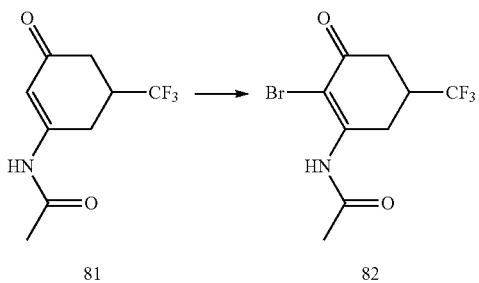 [SMILES: CC(=O)NC1=CC(=O)CC(C(F)(F)F)C1 ; CC(=O)NC1=C(Br)C(=O)CC(C(F)(F)F)C1]

To a solution of Compound 81 (150 mg, 0.678 mmol) in N,N-dimethylformamide (3 mL) was added N-bromosuccinimide (133 mg, 0.746 mmol) under ice-cooling, the solution was stirred at room temperature overnight. To the reaction mixture was added water, and extracted with ethyl acetate. The organic layer was dried with anhydrous sodium sulfate, concentrated under reduced pressure. The residue was purified by silica gel chromatography (ethyl acetate/hexane) to yield Compound 82 (230 mg, yield: quant.) as a yellow solid.

LC/MS Method: B, LC-MS: m/z=301. [M+H]+, retention time: 1.52 min

¹H-NMR (CDCl₃) δ: 8.02-7.99 (1H, m), 3.83-3.78 (1H, m), 3.10 (1H, dd, J=18.6, 11.0 Hz), 2.96-2.81 (2H, m), 2.61 (1H, dd, J=16.1, 12.8 Hz), 2.29 (3H, s).

Example 33: Preparation of Compound 85

Step 1

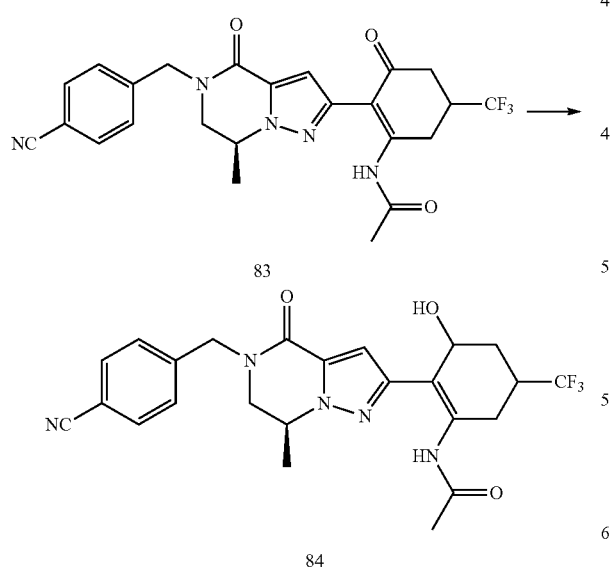

To a solution of Compound 83 (50 mg, 0.103 mmol) in methanol (1 mL) was added sodium borohydride (19.5 mg, 0.515 mmol) at −40° C., the solution was stirred at around −30° C. to 0° C. for 30 minutes. To the reaction mixture was added water, and extracted with ethyl acetate. The organic layer was dried with anhydrous sodium sulfate, and concentrated under reduced pressure. The residue was purified by silica gel chromatography (methanol/chloroform) and purified by suspension with ethyl acetate/isopropylether to yield Compound 84 (20 mg, yield: 40%) as a white solid.

LC/MS Method: B, LC-MS: m/z=488. [M+H]+, retention time: 1.78 min, 1.80 min

1H-NMR (CDCl₃) δ: 10.54-10.53 (1H, m), 7.67 (2H, d, J=8.0 Hz), 7.45 (2H, d, J=8.0 Hz), 7.12-7.10 (1H, m), 4.89-4.75 (3H, m), 4.55-4.49 (1H, m), 3.64 (1H, dd, J=12.8, 4.3 Hz), 3.50-3.33 (2H, m), 2.97-2.93 (1H, m), 2.53-2.37 (2H, m), 2.12-2.12 (3H, m), 2.03-1.99 (1H, m), 1.72-1.53 (7H, m).

Step 2

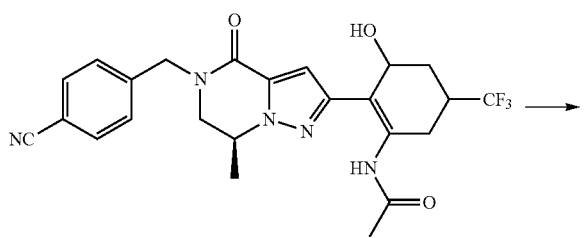

To a solution of Compound 84 (22 mg, 0.045 mmol) in tetrahydrofuran (1.5 mL) was added lithium perchlorate (240 mg, 2.256 mmol) and triethylsilane (36.0 uL, 0.226 mmol), the solution was stirred for 40 minutes under microwave irradiation. The reaction mixture was purified by reversed phase silica gel chromatography (water/acetonitrile) to yield Compound 85 (3 mg, yield: 14%) as a white solid.

LC/MS Method: B, LC-MS: m/z=472. [M+H]+, retention time: 2.12 min

1H-NMR (CDCl₃) δ: 10.80 (1H, s), 7.67 (2H, d, J=8.3 Hz), 7.46 (2H, d, J=8.3 Hz), 6.88 (1H, s), 4.82 (2H, ddd, J=21.1, 15.4, 3.7 Hz), 4.56-4.48 (1H, m), 3.65-3.62 (1H, m), 3.51-3.45 (1H, m), 3.33-3.25 (1H, m), 3.03-2.94 (1H, m), 2.61-2.58 (1H, m), 2.49-2.45 (1H, m), 2.35-2.33 (1H, m), 2.15-2.05 (4H, m), 1.68-1.63 (3H, m).

The following compounds were prepared in a similar manner.

TABLE 1

| Compound No. | Structure | LCMS method | RT (min) | [M + H] |
|---|---|---|---|---|
| 1-0001 | 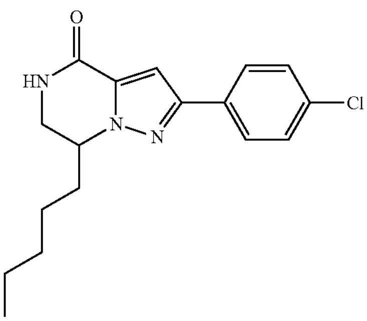 [SMILES: CCCCCC1CNC(=O)c2cc(-c3ccc(Cl)cc3)nn21] | B | 2.42 | 318 |
| 1-0002 | 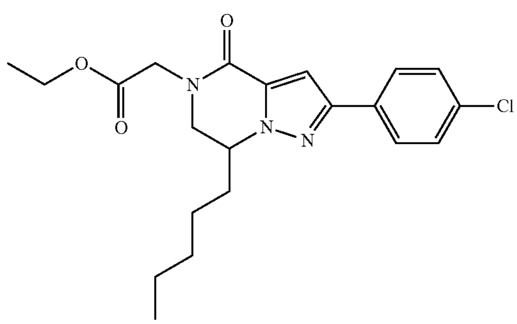 [SMILES: CCCCCC1CN(CC(=O)OCC)C(=O)c2cc(-c3ccc(Cl)cc3)nn21] | B | 2.77 | 404 |
| 1-0003 | 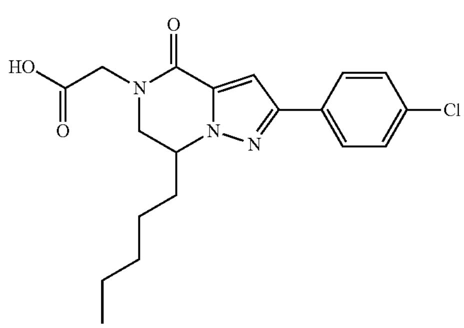 [SMILES: CCCCCC1CN(CC(=O)O)C(=O)c2cc(-c3ccc(Cl)cc3)nn21] | B | 238 | 376 |
| 1-0004 | 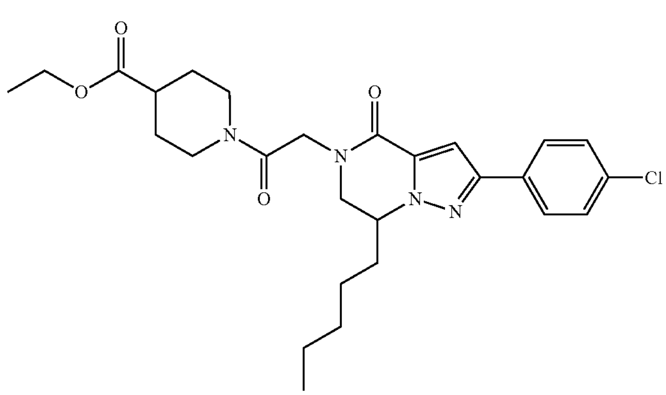 [SMILES: CCCCCC1CN(CC(=O)N2CCC(C(=O)OCC)CC2)C(=O)c2cc(-c3ccc(Cl)cc3)nn21] | B | 2.68 | 516 |

TABLE 1-continued
| Compound No. | Structure | LCMS method | RT (min) | [M + H] |
|---|---|---|---|---|
| 1-0005 | 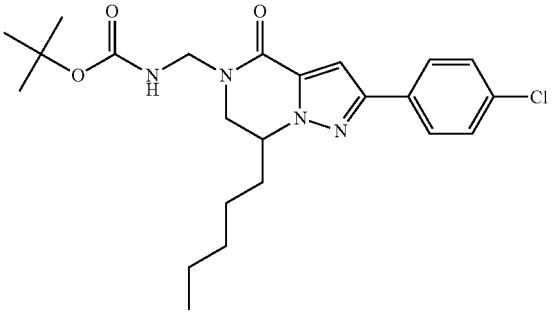 [SMILES: CCCCCC1CN(CNC(=O)OC(C)(C)C)C(=O)c2cc(-c3ccc(Cl)cc3)nn21] | B | 2.36 | 447 |
| 1-0006 | 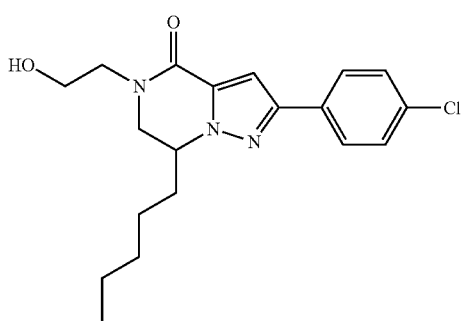 [SMILES: CCCCCC1CN(CCO)C(=O)c2cc(-c3ccc(Cl)cc3)nn21] | D | 4.54 | 362 |
| 1-0007 | 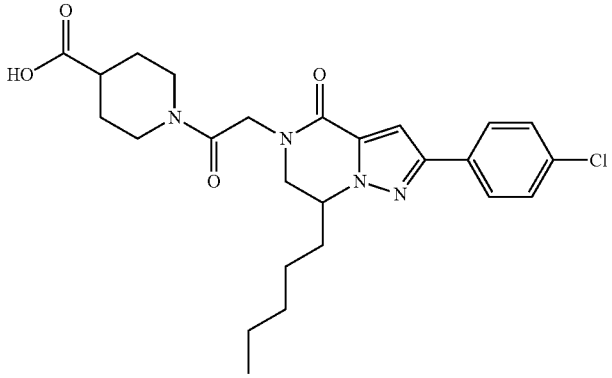 [SMILES: CCCCCC1CN(CC(=O)N2CCC(C(=O)O)CC2)C(=O)c2cc(-c3ccc(Cl)cc3)nn21] | A | 2.33 | 487 |
TABLE 2
| 1-0008 | 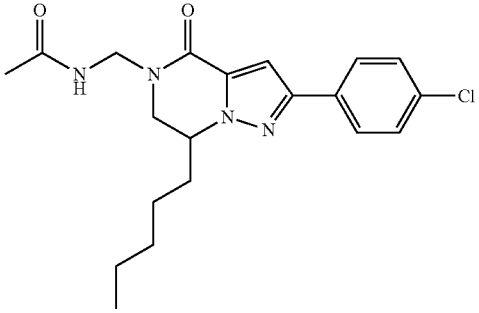 [SMILES: CCCCCC1CN(CNC(C)=O)C(=O)c2cc(-c3ccc(Cl)cc3)nn21] | B | 2.32 | 389 |

TABLE 2-continued

| ID | Structure | Method | RT | MS |
|---|---|---|---|---|
| 1-0009 | (ethyl ester, cyclopentane-fused pyrazolopyrazinone, 4-Cl-phenyl) | B | 2.31 | 374 |
| 1-0010 | (ethyl ester, cyclopentane-fused pyrazolopyrazinone, 4-Cl-phenyl, diastereomer) | B | 2.31 | 374 |
| 1-0011 | (ethyl piperidine-4-carboxylate, acyl, cyclopentane-fused pyrazolopyrazinone, 4-Cl-phenyl) | B | 2.25 | 485 |
| 1-0012 | (piperidine-4-carboxylic acid, acyl, cyclopentane-fused pyrazolopyrazinone, 4-Cl-phenyl) | B | 1.9 | 457 |
| 1-0013 | (piperidine-4-carboxylic acid, acyl, cyclopentane-fused pyrazolopyrazinone, 4-Cl-phenyl, diastereomer) | B | 1.9 | 457 |
| 1-0014 | (ethyl ester, gem-dimethyl pyrazolopyrazinone, 4-Cl-phenyl) | B | 2.32 | 362 |
| 1-0015 | (ethyl piperidine-4-carboxylate, acyl, gem-dimethyl pyrazolopyrazinone, 4-Cl-phenyl) | B | 2.26 | 473 |

TABLE 2-continued
| 1-0016 | 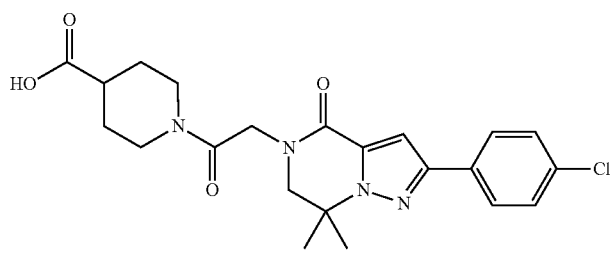 [SMILES: CC1(C)CN(CC(=O)N2CCC(C(=O)O)CC2)C(=O)c2cc(-c3ccc(Cl)cc3)nn21] | B | 1.91 | 445 |
TABLE 3
| 1-0017 | 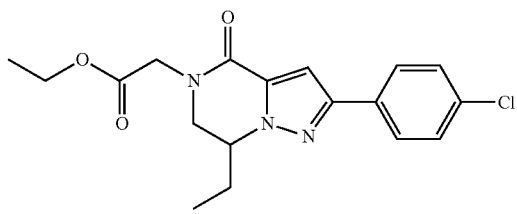 [SMILES: CCOC(=O)CN1CC(CC)n2nc(-c3ccc(Cl)cc3)cc2C1=O] | B | 2.28 | 362 |
| 1-0018 | 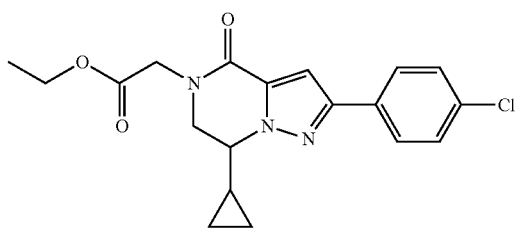 [SMILES: CCOC(=O)CN1CC(C2CC2)n2nc(-c3ccc(Cl)cc3)cc2C1=O] | B | 2.3 | 374 |
| 1-0019 | 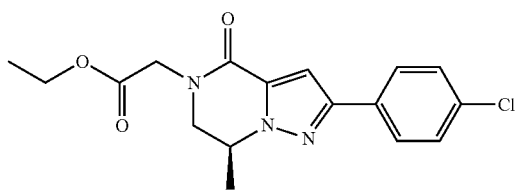 [SMILES: CCOC(=O)CN1C[C@H](C)n2nc(-c3ccc(Cl)cc3)cc2C1=O] | B | 2.15 | 348 |
| 1-0020 | 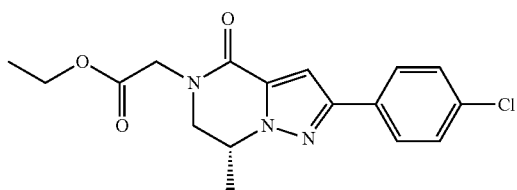 [SMILES: CCOC(=O)CN1C[C@@H](C)n2nc(-c3ccc(Cl)cc3)cc2C1=O] | B | 2.15 | 348 |
| 1-0021 | 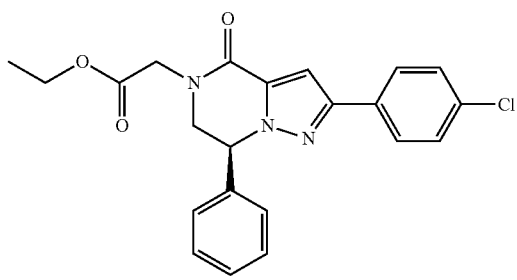 [SMILES: CCOC(=O)CN1C[C@H](c2ccccc2)n2nc(-c3ccc(Cl)cc3)cc2C1=O] | B | 2.37 | 410 |

TABLE 3-continued
| 1-0022 | 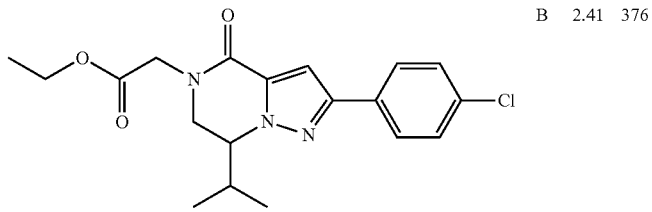 | B | 2.41 | 376 |
| 1-0023 | 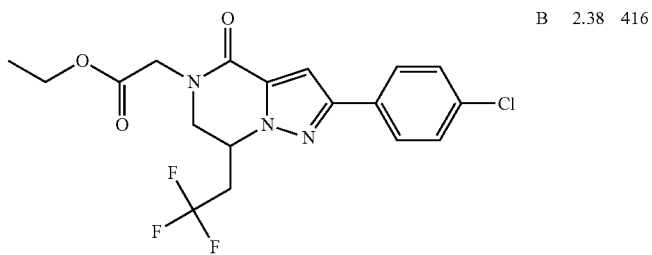 | B | 2.38 | 416 |
| 1-0024 | 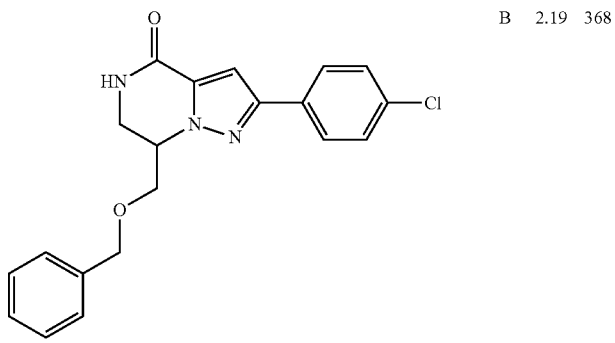 | B | 2.19 | 368 |
TABLE 4
| 1-0025 | 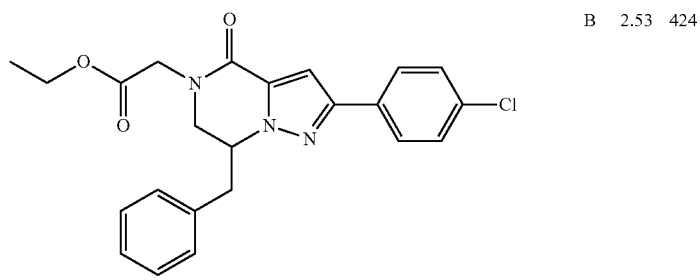 | B | 2.53 | 424 |
| 1-0026 | 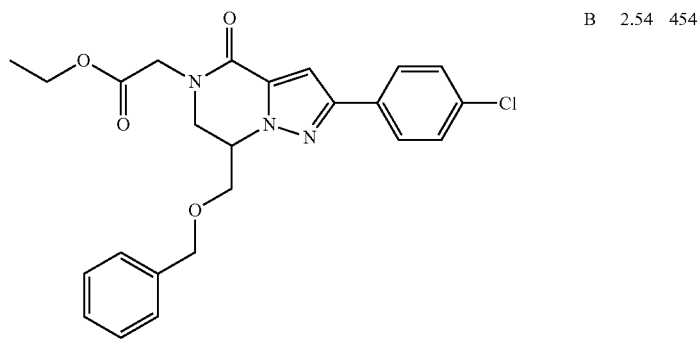 | B | 2.54 | 454 |

TABLE 4-continued

| 1-0027 | | C | 2.07 | 376 |
| 1-0028 | | B | 172 | 459 |
| 1-0029 | | B | 1.62 | 431 |
| 1-0030 | | A | 3.21 | 533 |
| 1-0031 | | A | 3.42 | 513 |
| 1-0032 | | A | 3.03 | 519 |

TABLE 5
| 1-0033 | 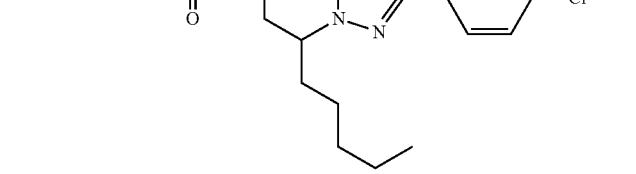 | A | 2.32 | 486 |
| 1-0034 | 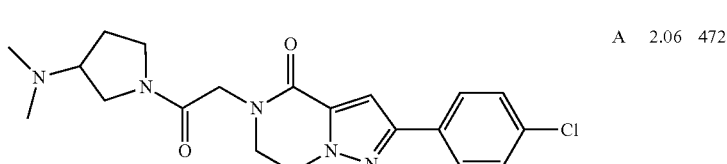 | A | 2.06 | 472 |
| 1-0035 | 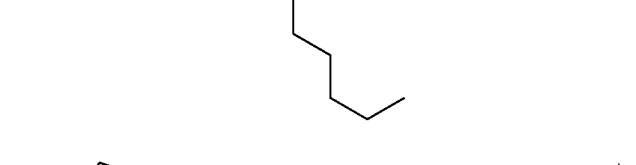 | A | 2.29 | 445 |
| 1-0036 | 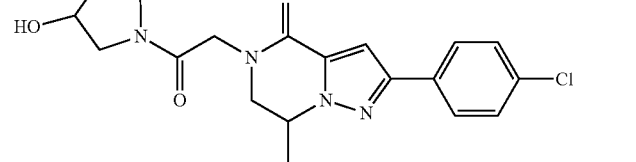 | A | 3.06 | 519 |
| 1-0037 | 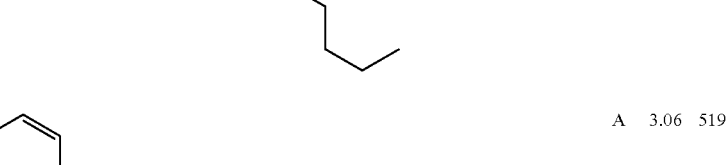 | A | 2.25 | 458 |

TABLE 5-continued
| 1-0038 | 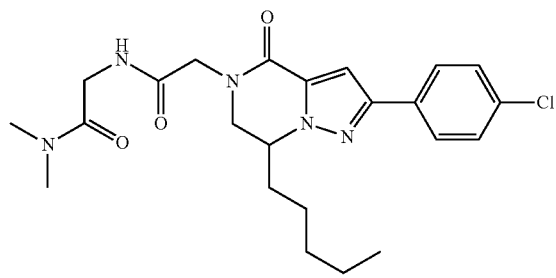 [SMILES: CCCCCC1CN(CC(=O)NCC(=O)N(C)C)C(=O)c2cc(-c3ccc(Cl)cc3)nn21] | A | 2.33 | 460 |
| 1-0039 | 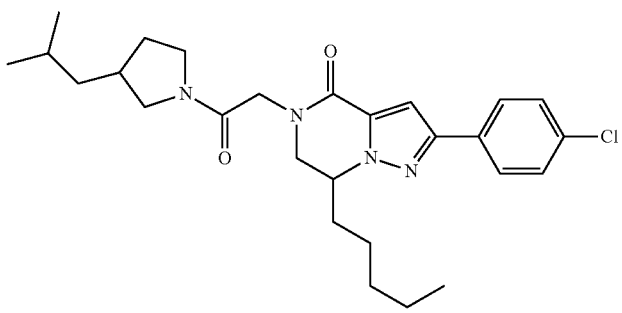 [SMILES: CCCCCC1CN(CC(=O)N2CCC(CC(C)C)C2)C(=O)c2cc(-c3ccc(Cl)cc3)nn21] | A | 3.1 | 485 |
| 1-0040 | 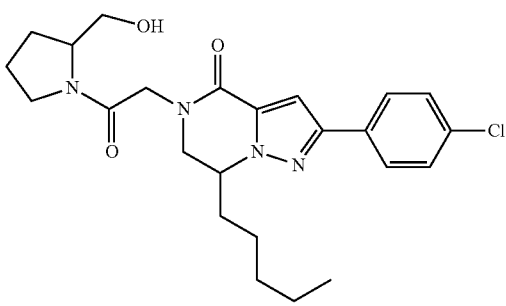 [SMILES: CCCCCC1CN(CC(=O)N2CCCC2CO)C(=O)c2cc(-c3ccc(Cl)cc3)nn21] | A | 2.43 | 459 |
TABLE 6
| 1-0041 | 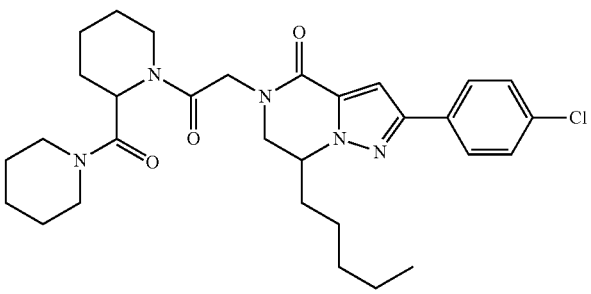 [SMILES: CCCCCC1CN(CC(=O)N2CCCCC2C(=O)N2CCCCC2)C(=O)c2cc(-c3ccc(Cl)cc3)nn21] | A | 2.74 | 554 |
| 1-0042 | 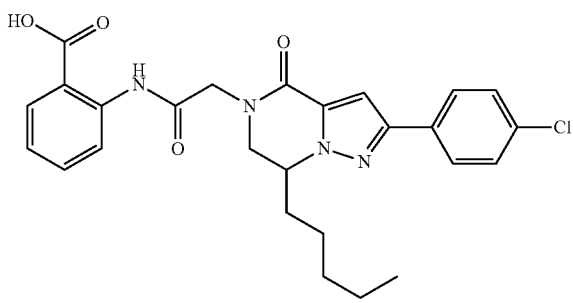 [SMILES: CCCCCC1CN(CC(=O)Nc2ccccc2C(=O)O)C(=O)c2cc(-c3ccc(Cl)cc3)nn21] | A | 2.79 | 495 |

TABLE 6-continued
| 1-0043 | 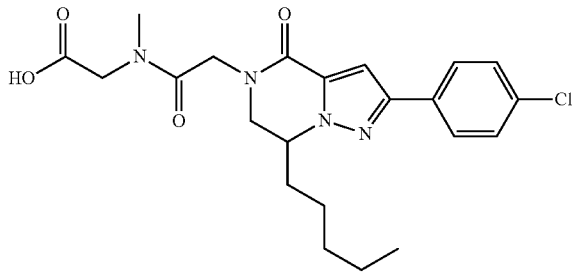 [SMILES: CCCCCC1CN(CC(=O)N(C)CC(=O)O)C(=O)c2cc(-c3ccc(Cl)cc3)nn21] | A | 2.38 | 447 |
| 1-0044 | 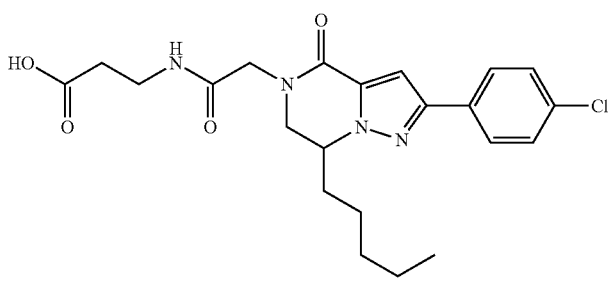 [SMILES: CCCCCC1CN(CC(=O)NCCC(=O)O)C(=O)c2cc(-c3ccc(Cl)cc3)nn21] | A | 2.3 | 447 |
| 1-0045 | 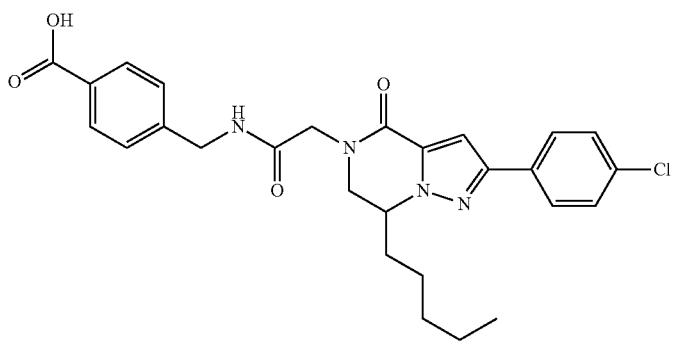 [SMILES: CCCCCC1CN(CC(=O)NCc2ccc(C(=O)O)cc2)C(=O)c2cc(-c3ccc(Cl)cc3)nn21] | A | 2.49 | 509 |
| 1-0046 | 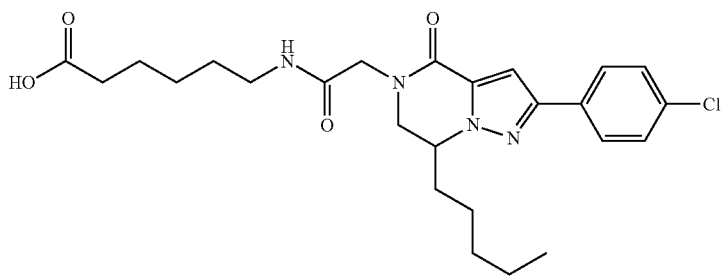 [SMILES: CCCCCC1CN(CC(=O)NCCCCCC(=O)O)C(=O)c2cc(-c3ccc(Cl)cc3)nn21] | A | 2.43 | 489 |
| 1-0047 | 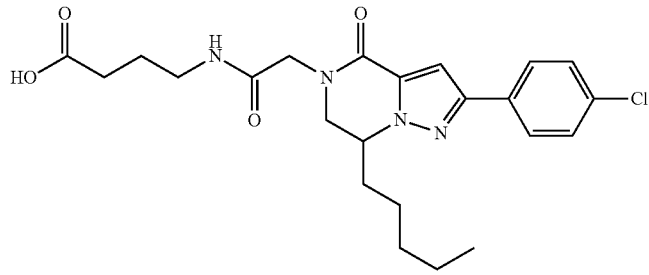 [SMILES: CCCCCC1CN(CC(=O)NCCCC(=O)O)C(=O)c2cc(-c3ccc(Cl)cc3)nn21] | A | 2.33 | 461 |

TABLE 6-continued
| 1-0048 | 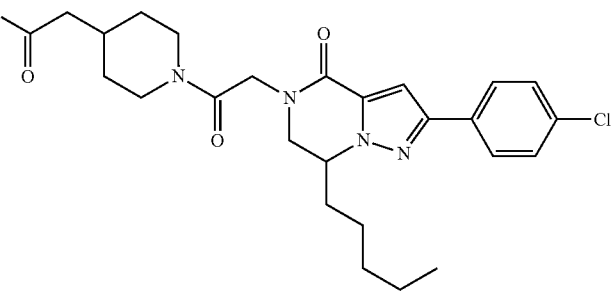 | A | 2.5 | 501 |
TABLE 7
| 1-0049 | 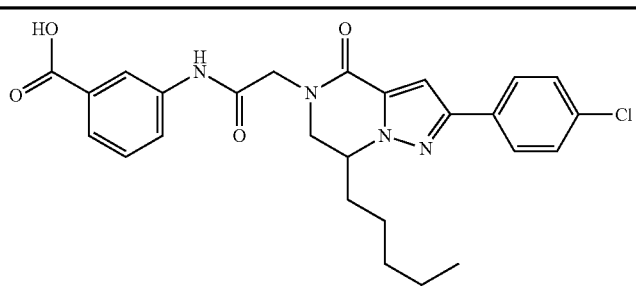 | A | 2.61 | 495 |
| 1-0050 | 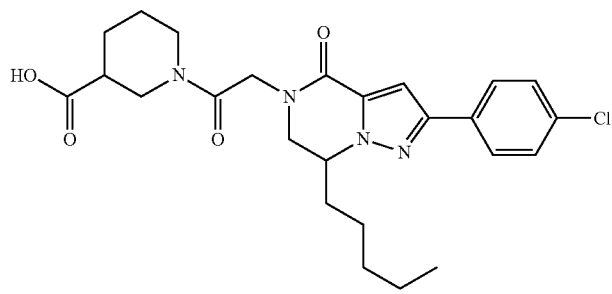 [SMILES: CCCCCC1CN(CC(=O)N2CCCC(C(=O)O)C2)C(=O)c2cc(-c3ccc(Cl)cc3)nn21] | A | 2.48 | 487 |
| 1-0051 | 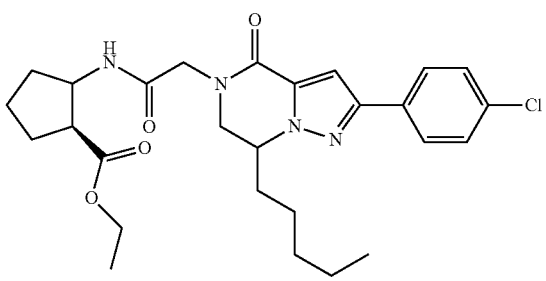 [SMILES: CCCCCC1CN(CC(=O)NC2CCC[C@@H]2C(=O)OCC)C(=O)c2cc(-c3ccc(Cl)cc3)nn21] | A | 2.88 | 515 |
| 1-0052 | 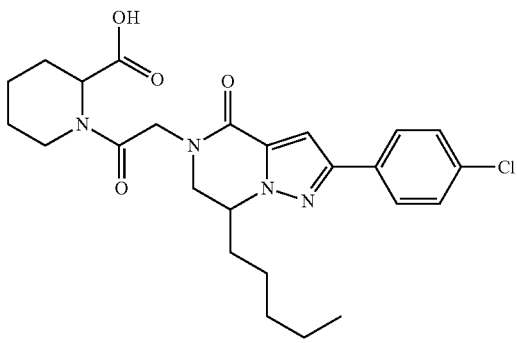 [SMILES: CCCCCC1CN(CC(=O)N2CCCCC2C(=O)O)C(=O)c2cc(-c3ccc(Cl)cc3)nn21] | A | 2.58 | 487 |

TABLE 7-continued
| | | | | |
|---|---|---|---|---|
| 1-0053 | 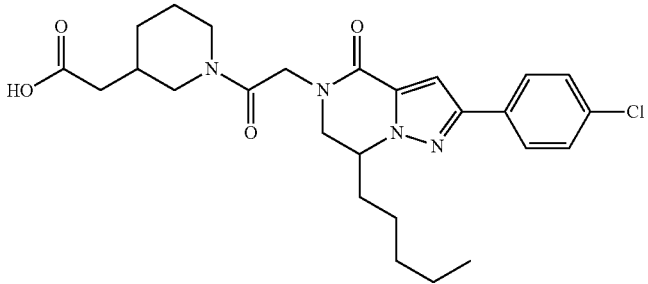 [SMILES: CCCCCC1CN(CC(=O)N2CCCC(CC(=O)O)C2)C(=O)c2cc(-c3ccc(Cl)cc3)nn21] | A | 2.51 | 501 |
| 1-0054 | 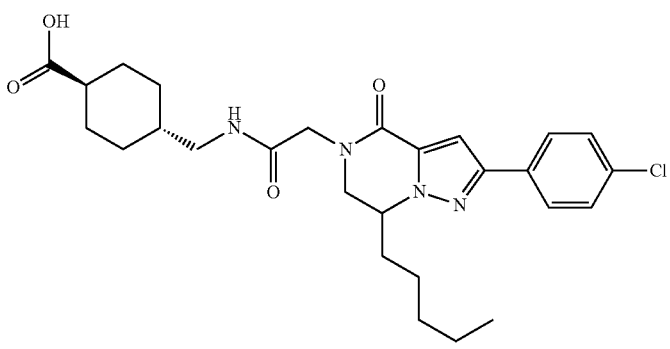 [SMILES: CCCCCC1CN(CC(=O)NC[C@H]2CC[C@H](C(=O)O)CC2)C(=O)c2cc(-c3ccc(Cl)cc3)nn21] | A | 2.48 | 515 |
| 1-0055 | 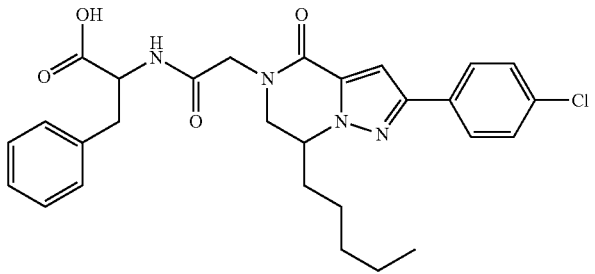 [SMILES: CCCCCC1CN(CC(=O)NC(Cc2ccccc2)C(=O)O)C(=O)c2cc(-c3ccc(Cl)cc3)nn21] | A | 2.7 | 523 |
| 1-0056 | 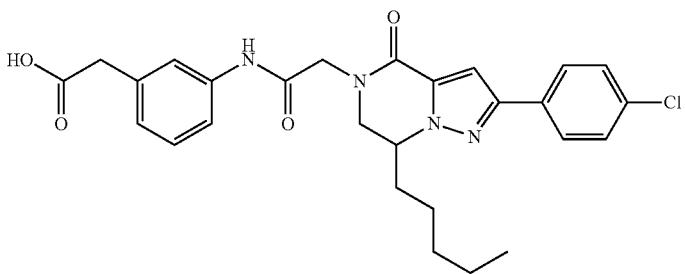 [SMILES: CCCCCC1CN(CC(=O)Nc2cccc(CC(=O)O)c2)C(=O)c2cc(-c3ccc(Cl)cc3)nn21] | A | 2.59 | 509 |
TABLE 8
| | | | | |
|---|---|---|---|---|
| 1-0057 | 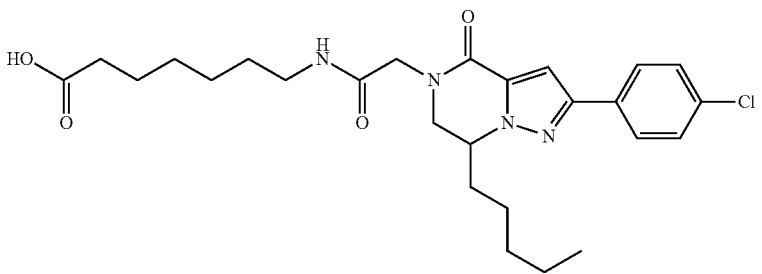 [SMILES: CCCCCC1CN(CC(=O)NCCCCCCC(=O)O)C(=O)c2cc(-c3ccc(Cl)cc3)nn21] | A | 2.5 | 503 |

TABLE 8-continued
| 1-0058 | 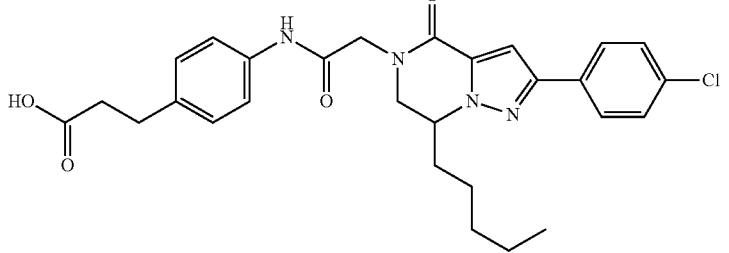 | A | 2.63 | 523 |
| 1-0059 | 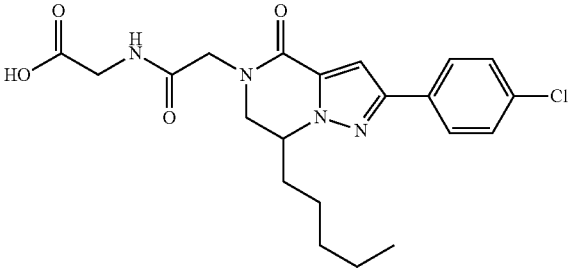 [SMILES: CCCCCC1CN(CC(=O)NCC(=O)O)C(=O)c2cc(-c3ccc(Cl)cc3)nn21] | A | 2.3 | 433 |
| 1-0060 | 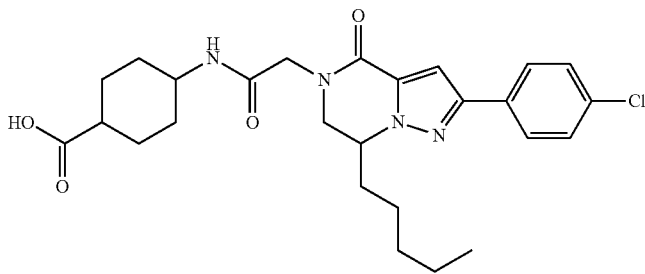 [SMILES: CCCCCC1CN(CC(=O)NC2CCC(C(=O)O)CC2)C(=O)c2cc(-c3ccc(Cl)cc3)nn21] | A | 2.48 | 501 |
| 1-0061 | 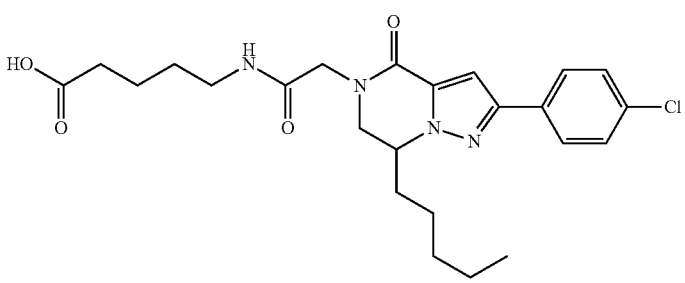 [SMILES: CCCCCC1CN(CC(=O)NCCCCC(=O)O)C(=O)c2cc(-c3ccc(Cl)cc3)nn21] | A | 2.37 | 475 |
| 1-0062 | 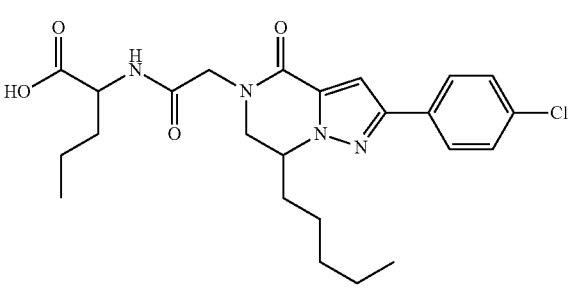 [SMILES: CCCCCC1CN(CC(=O)NC(CCC)C(=O)O)C(=O)c2cc(-c3ccc(Cl)cc3)nn21] | A | 2.57 | 475 |

TABLE 8-continued
| 1-0063 | 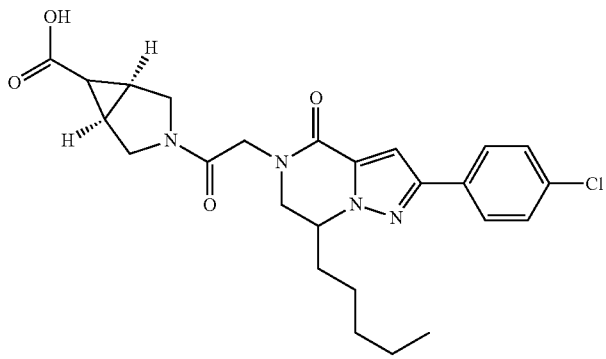 [SMILES: CCCCCC1CN(CC(=O)N2C[C@@H]3C(C(=O)O)[C@@H]3C2)C(=O)c2cc(-c3ccc(Cl)cc3)nn21] | A | 2.43 | 485 |
| 1-0064 | 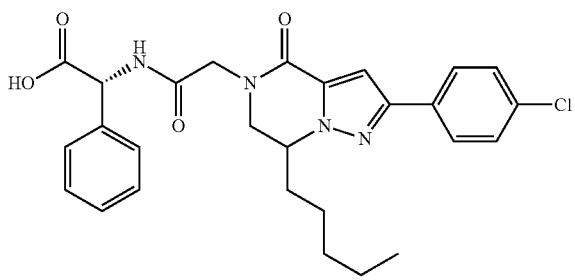 [SMILES: CCCCCC1CN(CC(=O)N[C@@H](C(=O)O)c2ccccc2)C(=O)c2cc(-c3ccc(Cl)cc3)nn21] | A | 2.62 | 509 |
TABLE 9
| I-0065 | 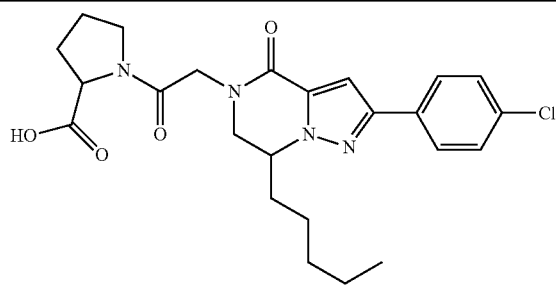 | A | 2.41 | 473 |
| I-0066 | 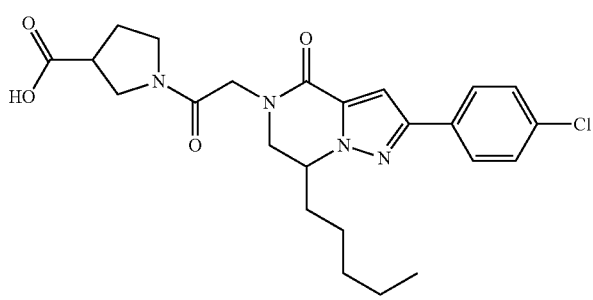 [SMILES: CCCCCC1CN(CC(=O)N2CCC(C(=O)O)C2)C(=O)c2cc(-c3ccc(Cl)cc3)nn21] | A | 2.41 | 473 |
| I-0067 | 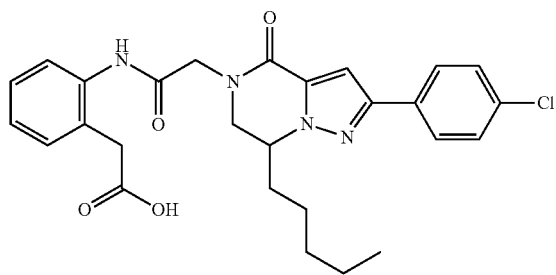 [SMILES: CCCCCC1CN(CC(=O)Nc2ccccc2CC(=O)O)C(=O)c2cc(-c3ccc(Cl)cc3)nn21] | A | 2.58 | 509 |

TABLE 9-continued
| I-0068 | 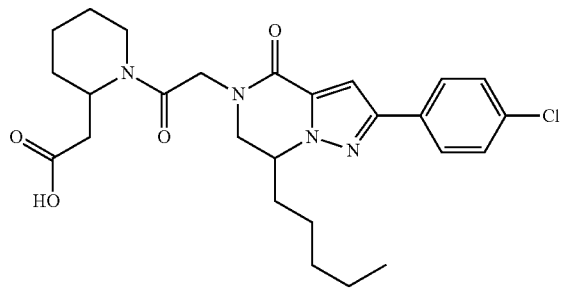 [SMILES: CCCCCC1CN(CC(=O)N2CCCCC2CC(=O)O)C(=O)c2cc(-c3ccc(Cl)cc3)nn21] | A | 2.56 | 501 |
| I-0069 | 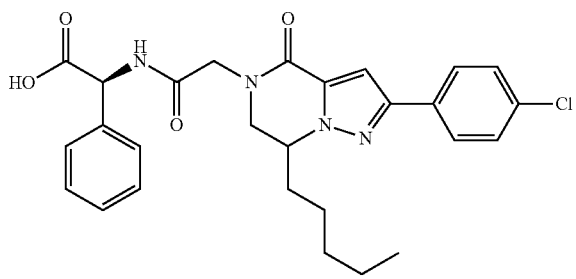 [SMILES: CCCCCC1CN(CC(=O)N[C@H](C(=O)O)c2ccccc2)C(=O)c2cc(-c3ccc(Cl)cc3)nn21] | A | 2.62 | 509 |
| I-0070 | 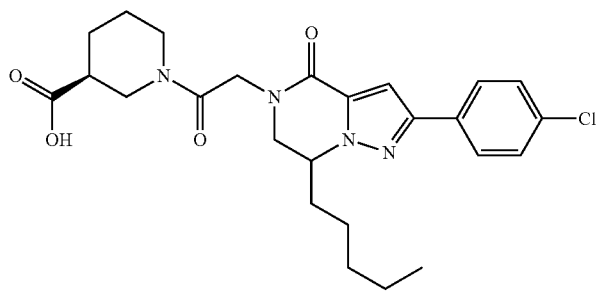 [SMILES: CCCCCC1CN(CC(=O)N2CCC[C@H](C(=O)O)C2)C(=O)c2cc(-c3ccc(Cl)cc3)nn21] | A | 2.49 | 487 |
| I-0071 | 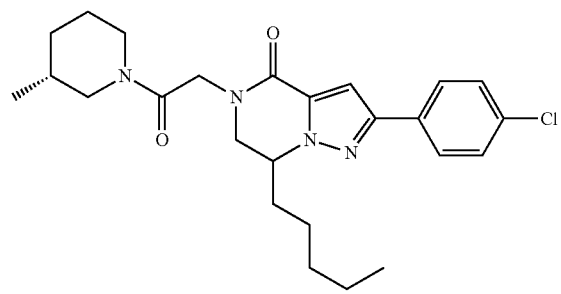 [SMILES: CCCCCC1CN(CC(=O)N2CCC[C@@H](C)C2)C(=O)c2cc(-c3ccc(Cl)cc3)nn21] | A | 2.93 | 457 |
| I-0072 | 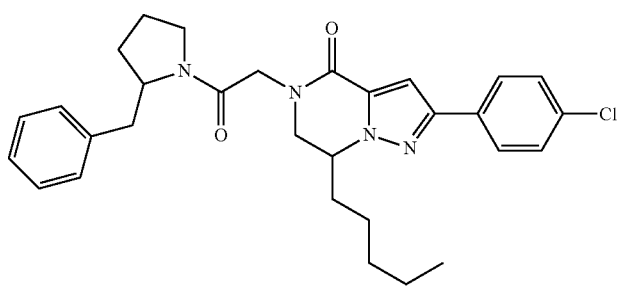 [SMILES: CCCCCC1CN(CC(=O)N2CCCC2Cc2ccccc2)C(=O)c2cc(-c3ccc(Cl)cc3)nn21] | A | 3.08 | 519 |

TABLE 10
| I-0073 | 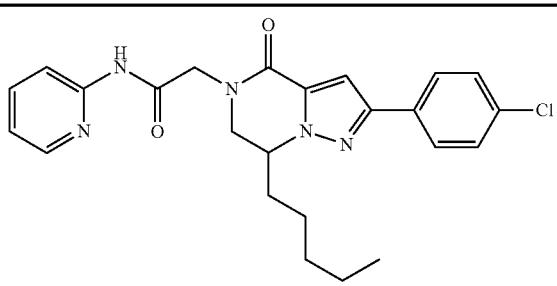 | A | 2.69 | 452 |
| I-0074 | 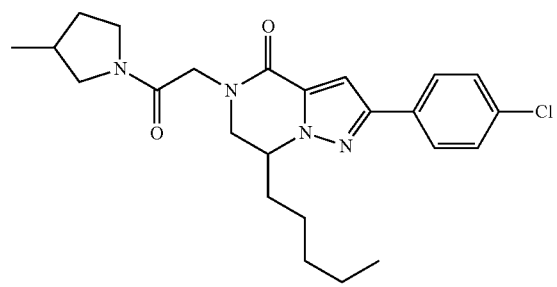 [SMILES: CCCCCC1CN(CC(=O)N2CCC(C)C2)C(=O)c2cc(-c3ccc(Cl)cc3)nn21] | A | 2.72 | 443 |
| I-0075 | 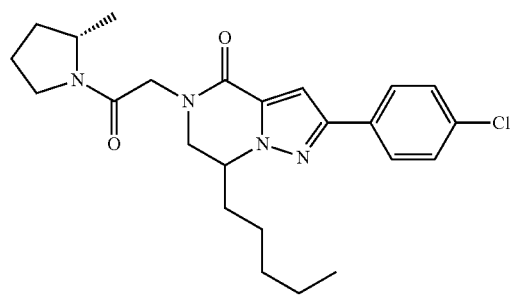 [SMILES: CCCCCC1CN(CC(=O)N2CCC[C@@H]2C)C(=O)c2cc(-c3ccc(Cl)cc3)nn21] | A | 2.75 | 443 |
| I-0076 | 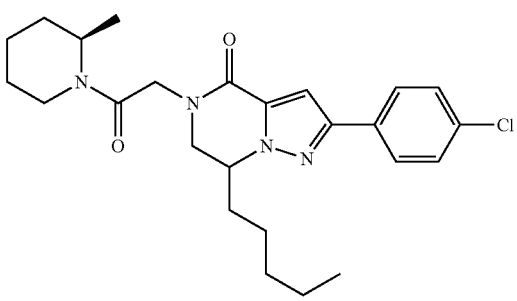 [SMILES: CCCCCC1CN(CC(=O)N2CCCC[C@H]2C)C(=O)c2cc(-c3ccc(Cl)cc3)nn21] | A | 2.9 | 457 |
| I-0077 | 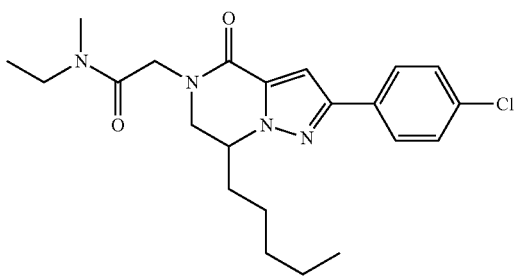 [SMILES: CCCCCC1CN(CC(=O)N(C)CC)C(=O)c2cc(-c3ccc(Cl)cc3)nn21] | A | 2.65 | 417 |

TABLE 10-continued
I-0078 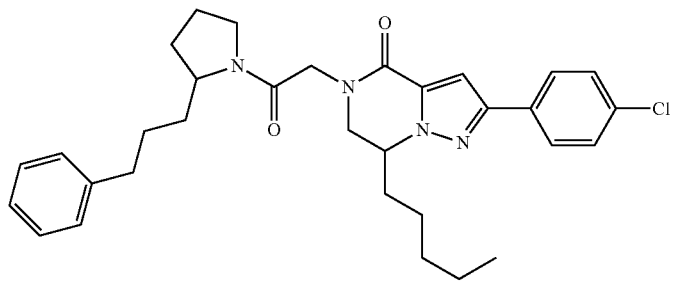 [SMILES: CCCCCC1CN(CC(=O)N2CCCC2CCCc2ccccc2)C(=O)c2cc(-c3ccc(Cl)cc3)nn21] A 3.26 547
I-0079 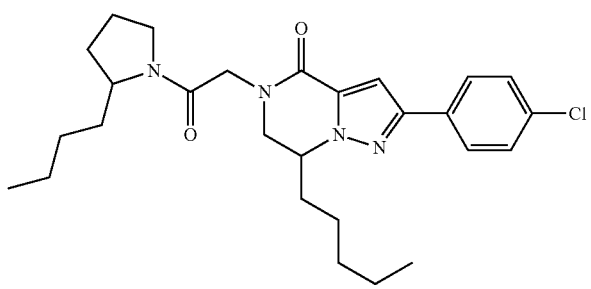 [SMILES: CCCCCC1CN(CC(=O)N2CCCC2CCCC)C(=O)c2cc(-c3ccc(Cl)cc3)nn21] A 3.16 485
I-0080 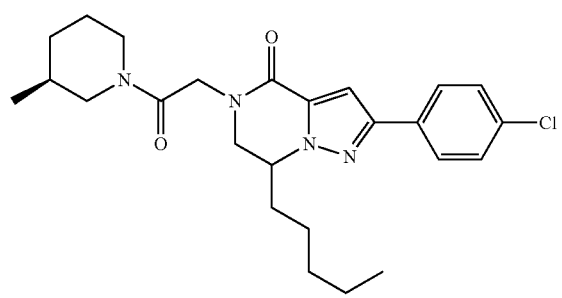 [SMILES: CCCCCC1CN(CC(=O)N2CCC[C@H](C)C2)C(=O)c2cc(-c3ccc(Cl)cc3)nn21] A 2.92 457
TABLE 11
I-0081 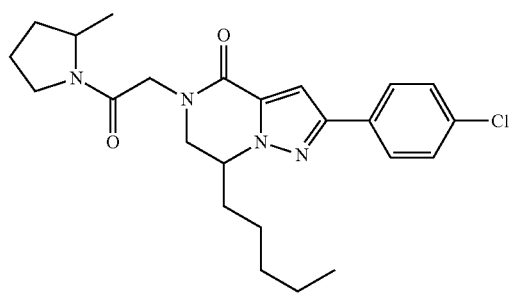 [SMILES: CCCCCC1CN(CC(=O)N2CCCC2C)C(=O)c2cc(-c3ccc(Cl)cc3)nn21] A 2.76 443
I-0082 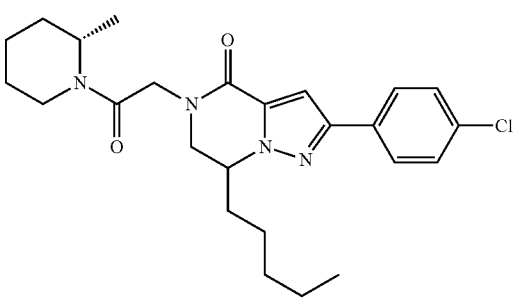 [SMILES: CCCCCC1CN(CC(=O)N2CCCC[C@@H]2C)C(=O)c2cc(-c3ccc(Cl)cc3)nn21] A 2.89 457

TABLE 11-continued
| I-0083 | 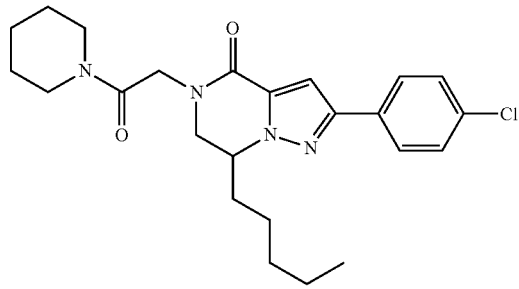 [SMILES: CCCCCC1CN(CC(=O)N2CCCCC2)C(=O)c2cc(-c3ccc(Cl)cc3)nn21] | A | 2.8 | 443 |
| I-0084 | 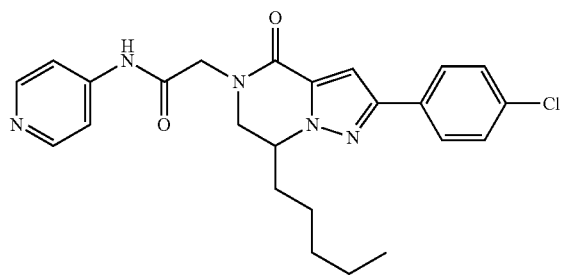 [SMILES: CCCCCC1CN(CC(=O)Nc2ccncc2)C(=O)c2cc(-c3ccc(Cl)cc3)nn21] | A | 2.08 | 452 |
| I-0085 | 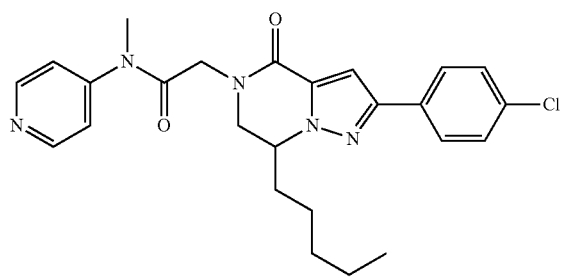 [SMILES: CCCCCC1CN(CC(=O)N(C)c2ccncc2)C(=O)c2cc(-c3ccc(Cl)cc3)nn21] | A | 2.92 | 465 |
| I-0086 | 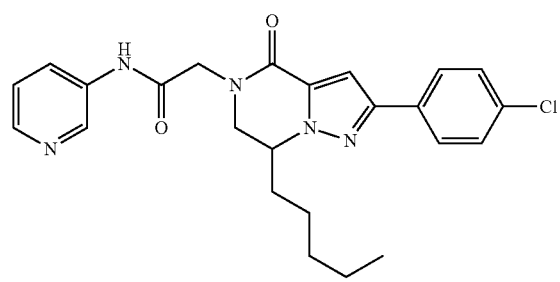 [SMILES: CCCCCC1CN(CC(=O)Nc2cccnc2)C(=O)c2cc(-c3ccc(Cl)cc3)nn21] | A | 2.21 | 452 |
| I-0087 | 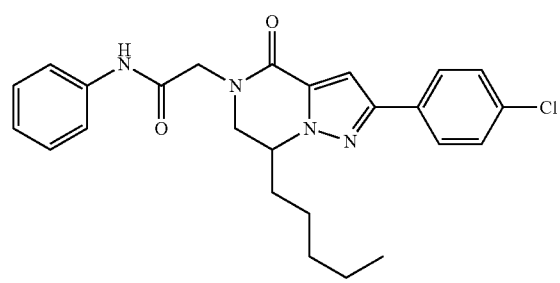 [SMILES: CCCCCC1CN(CC(=O)Nc2ccccc2)C(=O)c2cc(-c3ccc(Cl)cc3)nn21] | A | 2.87 | 451 |

TABLE 11-continued
| I-0088 | 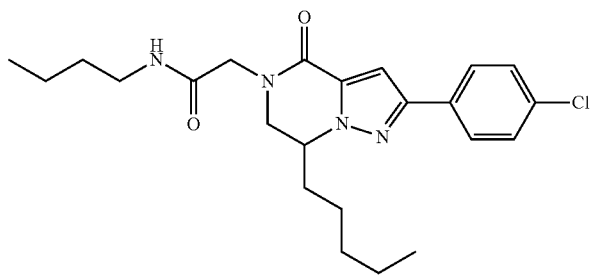 [SMILES: CCCCCC1CN(CC(=O)NCCCC)C(=O)c2cc(-c3ccc(Cl)cc3)nn21] | A | 2.78 | 431 |
TABLE 12
| I-0089 | 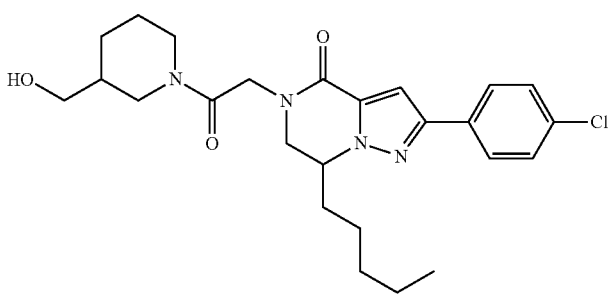 [SMILES: CCCCCC1CN(CC(=O)N2CCCC(CO)C2)C(=O)c2cc(-c3ccc(Cl)cc3)nn21] | A | 2.46 | 473 |
| I-0090 | 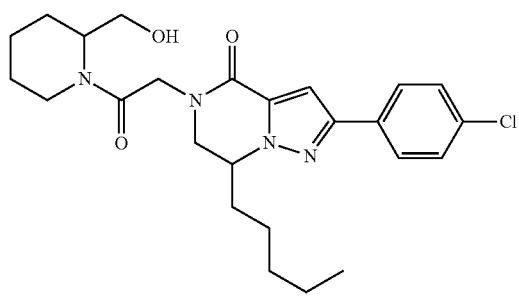 [SMILES: CCCCCC1CN(CC(=O)N2CCCCC2CO)C(=O)c2cc(-c3ccc(Cl)cc3)nn21] | A | 2.52 | 473 |
| I-0091 | 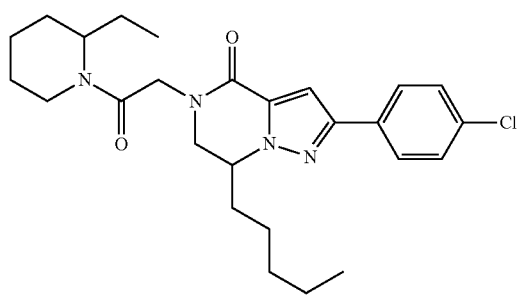 [SMILES: CCCCCC1CN(CC(=O)N2CCCCC2CC)C(=O)c2cc(-c3ccc(Cl)cc3)nn21] | A | 3.02 | 471 |
| I-0092 | 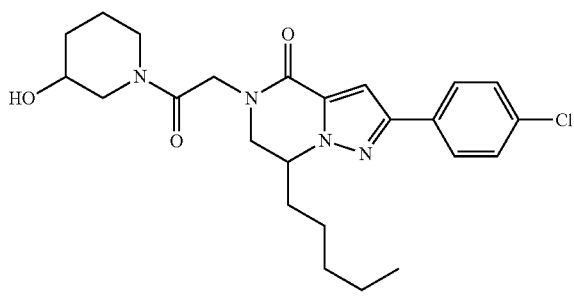 [SMILES: CCCCCC1CN(CC(=O)N2CCCC(O)C2)C(=O)c2cc(-c3ccc(Cl)cc3)nn21] | A | 2.4 | 459 |

TABLE 12-continued
I-0093 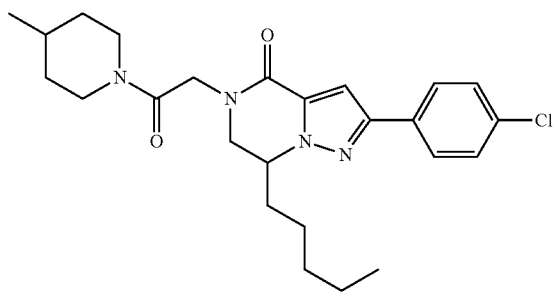 [SMILES: CCCCCC1CN(CC(=O)N2CCC(C)CC2)C(=O)c2cc(-c3ccc(Cl)cc3)nn21] A 2.92 457
I-0094 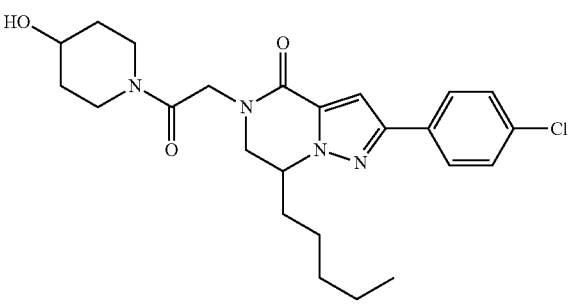 [SMILES: CCCCCC1CN(CC(=O)N2CCC(O)CC2)C(=O)c2cc(-c3ccc(Cl)cc3)nn21] A 2.36 459
I-0095 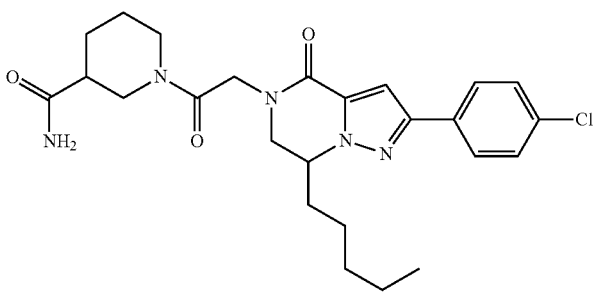 [SMILES: CCCCCC1CN(CC(=O)N2CCCC(C(N)=O)C2)C(=O)c2cc(-c3ccc(Cl)cc3)nn21] A 2.33 486
I-0096 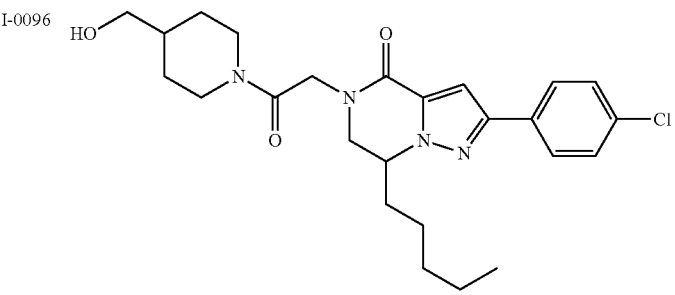 A 2.42 473
TABLE 13
I-0097 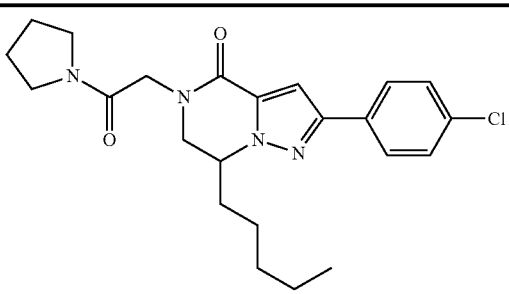 A 2.61 429

TABLE 13-continued
| I-0098 | 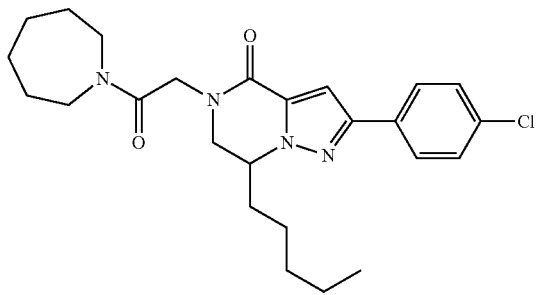 [SMILES: CCCCCC1CN(CC(=O)N2CCCCCC2)C(=O)c2cc(-c3ccc(Cl)cc3)nn21] | A | 2.89 | 457 |
| I-0099 | 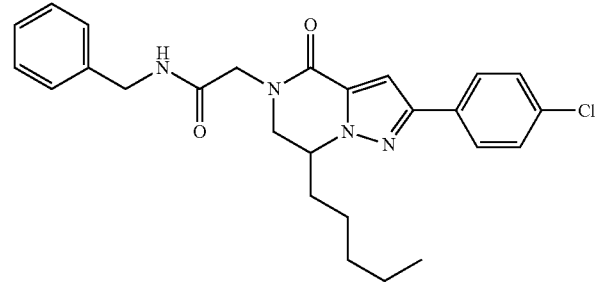 [SMILES: CCCCCC1CN(CC(=O)NCc2ccccc2)C(=O)c2cc(-c3ccc(Cl)cc3)nn21] | A | 2.82 | 463 |
| I-0100 | 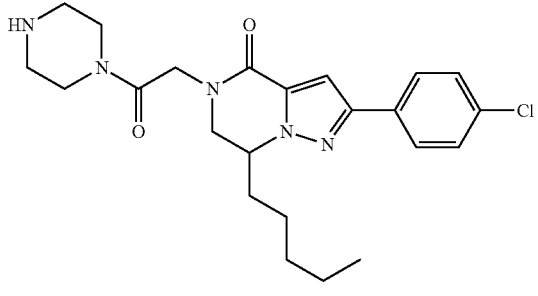 [SMILES: CCCCCC1CN(CC(=O)N2CCNCC2)C(=O)c2cc(-c3ccc(Cl)cc3)nn21] | A | 1.94 | 444 |
| I-0101 | 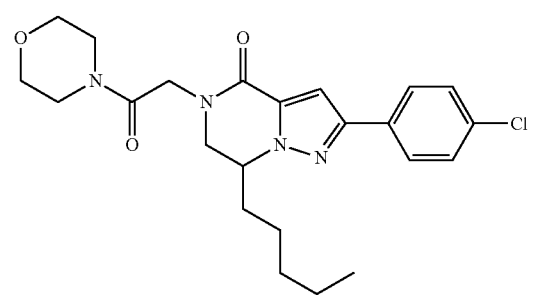 [SMILES: CCCCCC1CN(CC(=O)N2CCOCC2)C(=O)c2cc(-c3ccc(Cl)cc3)nn21] | A | 2.61 | 445 |
| I-0102 | 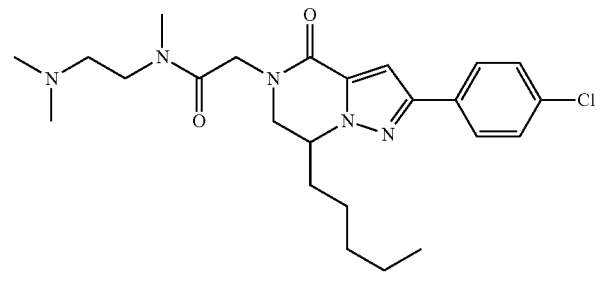 [SMILES: CCCCCC1CN(CC(=O)N(C)CCN(C)C)C(=O)c2cc(-c3ccc(Cl)cc3)nn21] | A | 2,01 | 460 |

TABLE 13-continued
| I-0103 | 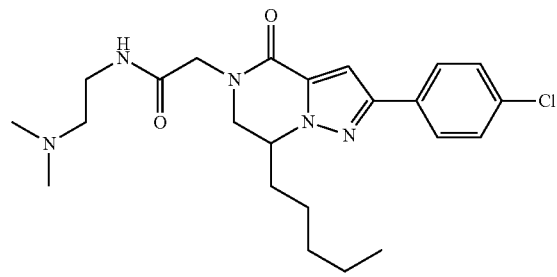 [SMILES: CCCCCC1CN(CC(=O)NCCN(C)C)C(=O)c2cc(-c3ccc(Cl)cc3)nn21] | A | 1.91 | 446 |
| --- | --- | --- | --- | --- |
| I-0104 | 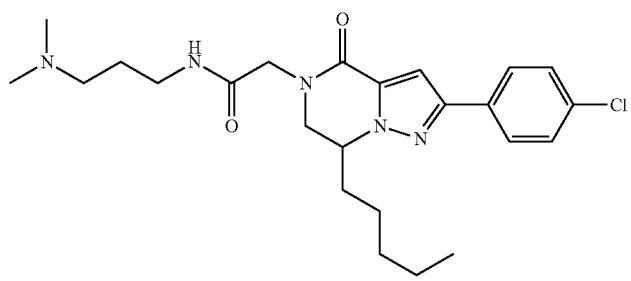 [SMILES: CCCCCC1CN(CC(=O)NCCCN(C)C)C(=O)c2cc(-c3ccc(Cl)cc3)nn21] | A | 1.9 | 460 |
TABLE 14
| I-0105 | 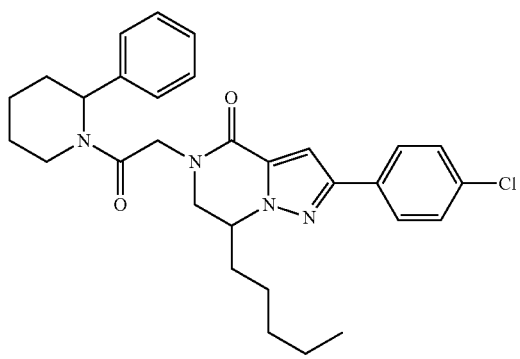 [SMILES: CCCCCC1CN(CC(=O)N2CCCCC2c2ccccc2)C(=O)c2cc(-c3ccc(Cl)cc3)nn21] | A | 3.13 | 519 |
| --- | --- | --- | --- | --- |
| I-0106 | 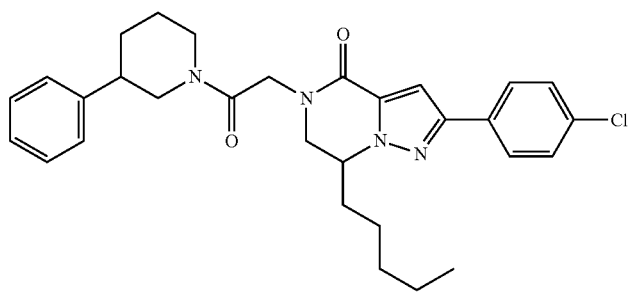 [SMILES: CCCCCC1CN(CC(=O)N2CCCC(c3ccccc3)C2)C(=O)c2cc(-c3ccc(Cl)cc3)nn21] | A | 3.1 | 519 |

TABLE 14-continued
| I-0107 | 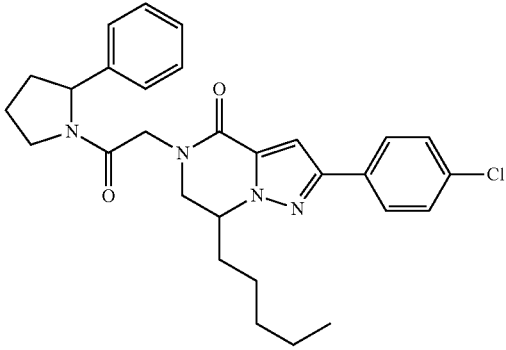 [SMILES: CCCCCC1CN(CC(=O)N2CCCC2c2ccccc2)C(=O)c2cc(-c3ccc(Cl)cc3)nn21] | A | 2.98 | 505 |
| I-0108 | 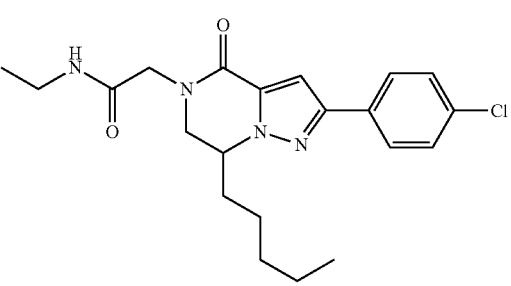 [SMILES: CCCCCC1CN(CC(=O)NCC)C(=O)c2cc(-c3ccc(Cl)cc3)nn21] | A | 2.53 | 403 |
| I-0109 | 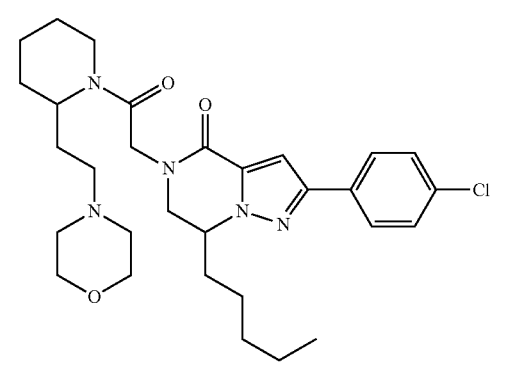 [SMILES: CCCCCC1CN(CC(=O)N2CCCCC2CCN2CCOCC2)C(=O)c2cc(-c3ccc(Cl)cc3)nn21] | A | 2.15 | 556 |
| I-0110 | 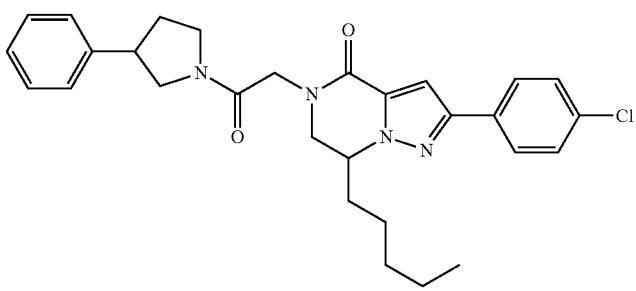 [SMILES: CCCCCC1CN(CC(=O)N2CCC(c3ccccc3)C2)C(=O)c2cc(-c3ccc(Cl)cc3)nn21] | A | 2.95 | 505 |
| I-0111 | 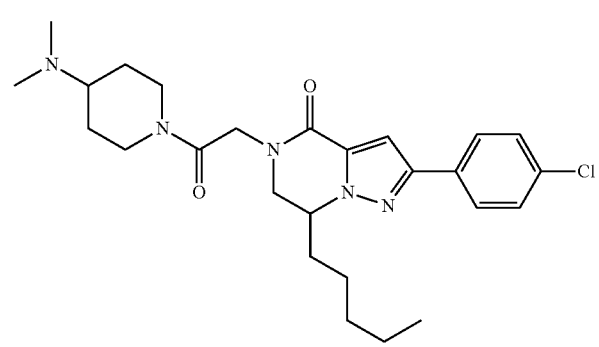 [SMILES: CCCCCC1CN(CC(=O)N2CCC(N(C)C)CC2)C(=O)c2cc(-c3ccc(Cl)cc3)nn21] | A | 1.92 | 486 |

TABLE 14-continued
| I-0112 | 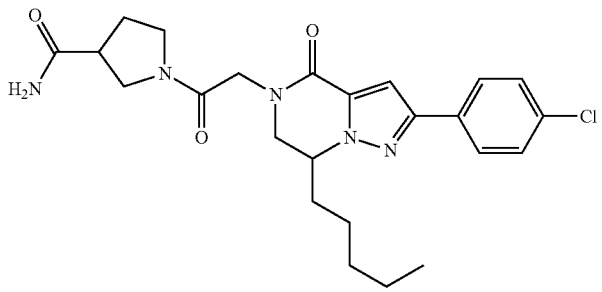 [SMILES: CCCCCC1CN(CC(=O)N2CCC(C(N)=O)C2)C(=O)c2cc(-c3ccc(Cl)cc3)nn21] | A | 2.24 | 472 |
TABLE 15
| I-0113 | 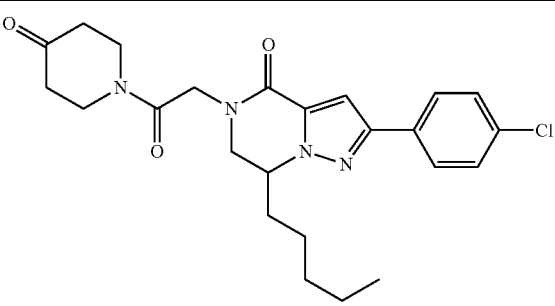 | A | 2.47 | 457 |
| I-0114 | 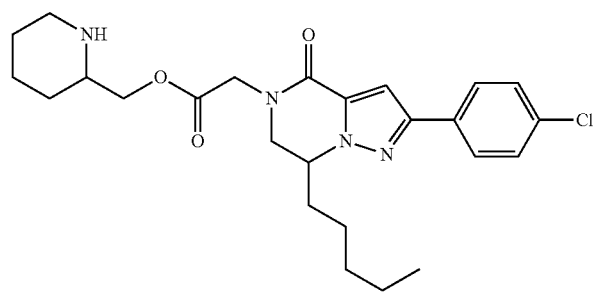 [SMILES: CCCCCC1CN(CC(=O)OCC2CCCCN2)C(=O)c2cc(-c3ccc(Cl)cc3)nn21] | A | 2.21 | 473 |
| I-0115 | 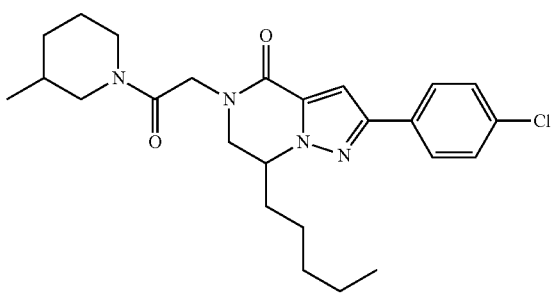 | A | 2.92 | 457 |
| I-0116 | 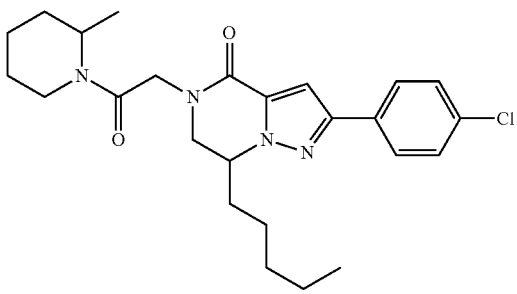 | A | 2.9 | 457 |

TABLE 15-continued
| I-0117 | 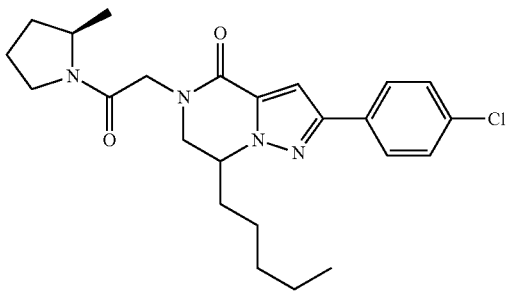 [SMILES: CCCCCC1CN(CC(=O)N2CCC[C@H]2C)C(=O)c2cc(-c3ccc(Cl)cc3)nn21] | A | 2.75 | 443 |
| I-0118 | 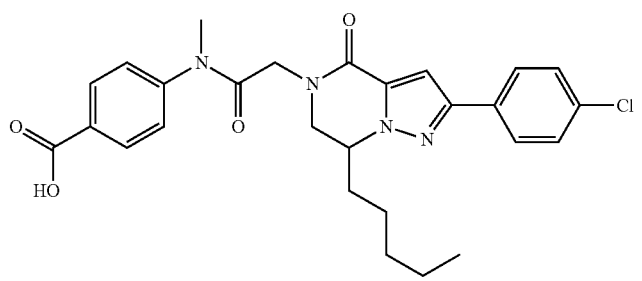 [SMILES: CCCCCC1CN(CC(=O)N(C)c2ccc(C(=O)O)cc2)C(=O)c2cc(-c3ccc(Cl)cc3)nn21] | A | 2.61 | 509 |
| I-0119 | 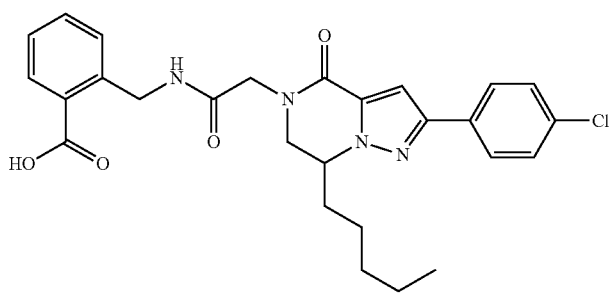 [SMILES: CCCCCC1CN(CC(=O)NCc2ccccc2C(=O)O)C(=O)c2cc(-c3ccc(Cl)cc3)nn21] | A | 2.59 | 509 |
| I-0120 | 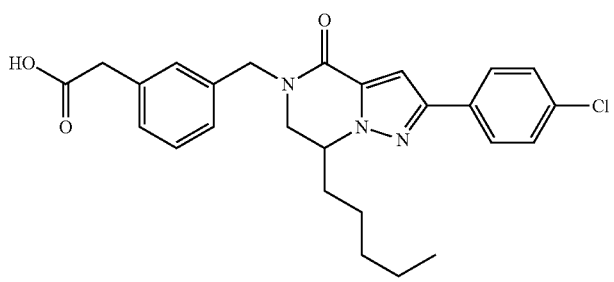 [SMILES: CCCCCC1CN(Cc2cccc(CC(=O)O)c2)C(=O)c2cc(-c3ccc(Cl)cc3)nn21] | A | 2.67 | 466 |
TABLE 16
| I-0121 | 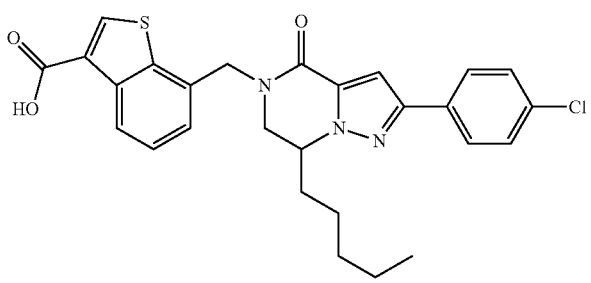 [SMILES: CCCCCC1CN(Cc2cccc3c(C(=O)O)csc23)C(=O)c2cc(-c3ccc(Cl)cc3)nn21] | A | 2.72 | 508 |

TABLE 16-continued
I-0122 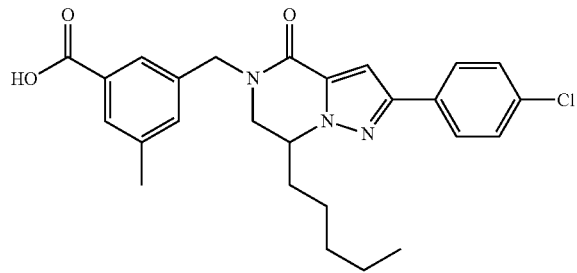 [SMILES: CCCCCC1CN(Cc2cc(C)cc(C(=O)O)c2)C(=O)c2cc(-c3ccc(Cl)cc3)nn21] A 2.74 466
I-0123 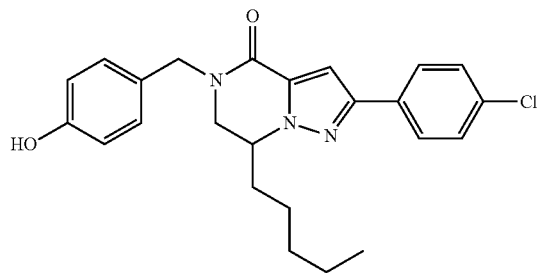 [SMILES: CCCCCC1CN(Cc2ccc(O)cc2)C(=O)c2cc(-c3ccc(Cl)cc3)nn21] A 2.67 424
I-0124 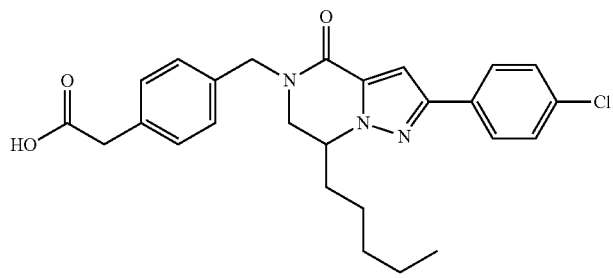 [SMILES: CCCCCC1CN(Cc2ccc(CC(=O)O)cc2)C(=O)c2cc(-c3ccc(Cl)cc3)nn21] A 2.65 466
I-0125 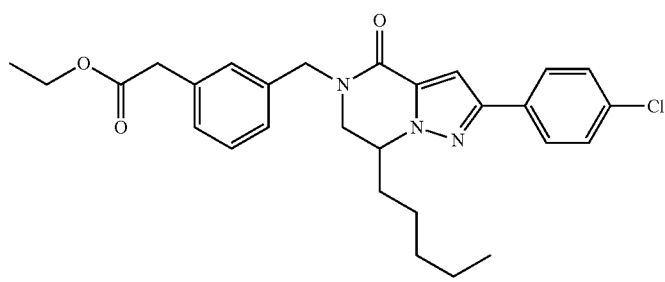 [SMILES: CCCCCC1CN(Cc2cccc(CC(=O)OCC)c2)C(=O)c2cc(-c3ccc(Cl)cc3)nn21] A 3.08 494
I-0126 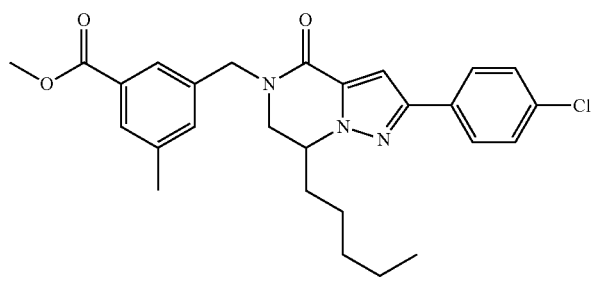 [SMILES: CCCCCC1CN(Cc2cc(C)cc(C(=O)OC)c2)C(=O)c2cc(-c3ccc(Cl)cc3)nn21] A 3.1 480

TABLE 16-continued
| I-0127 | 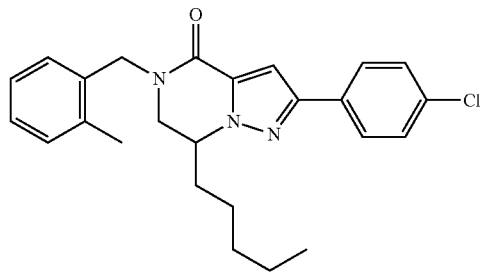 [SMILES: CCCCCC1CN(Cc2ccccc2C)C(=O)c2cc(-c3ccc(Cl)cc3)nn21] | A | 3.18 | 422 |
| I-0128 | 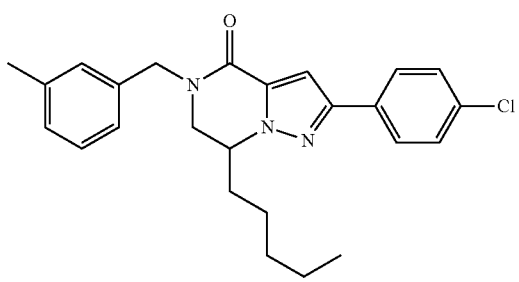 [SMILES: CCCCCC1CN(Cc2cccc(C)c2)C(=O)c2cc(-c3ccc(Cl)cc3)nn21] | A | 3.19 | 422 |
TABLE 17
| I-0129 | 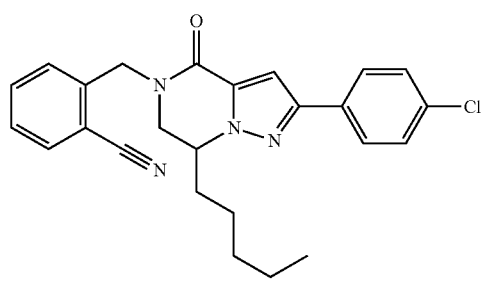 [SMILES: CCCCCC1CN(Cc2ccccc2C#N)C(=O)c2cc(-c3ccc(Cl)cc3)nn21] | A | 2.93 | 433 |
| I-0130 | 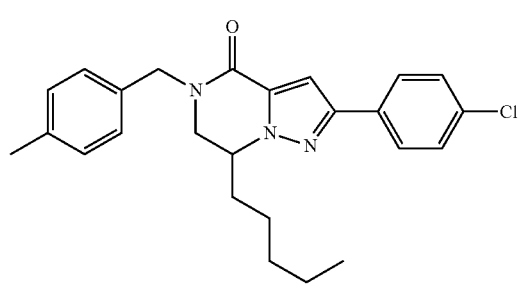 [SMILES: CCCCCC1CN(Cc2ccc(C)cc2)C(=O)c2cc(-c3ccc(Cl)cc3)nn21] | A | 3.2 | 422 |
| I-0131 | 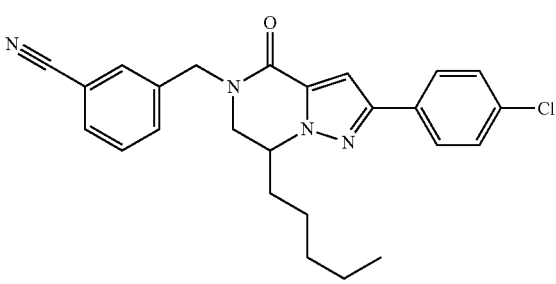 [SMILES: CCCCCC1CN(Cc2cccc(C#N)c2)C(=O)c2cc(-c3ccc(Cl)cc3)nn21] | A | 2.9 | 433 |

TABLE 17-continued
I-0132 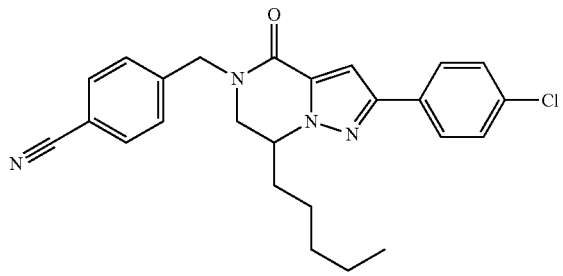 [SMILES: CCCCCC1CN(Cc2ccc(C#N)cc2)C(=O)c2cc(-c3ccc(Cl)cc3)nn21] A 2.9 433
I-0133 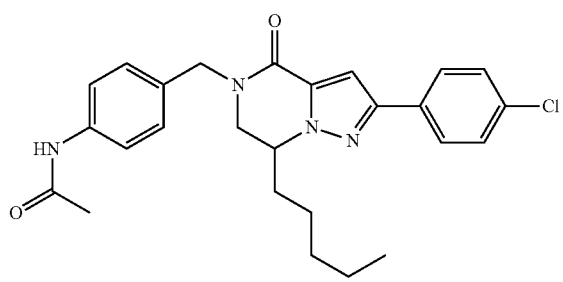 [SMILES: CCCCCC1CN(Cc2ccc(NC(C)=O)cc2)C(=O)c2cc(-c3ccc(Cl)cc3)nn21] A 2.58 465
I-0134 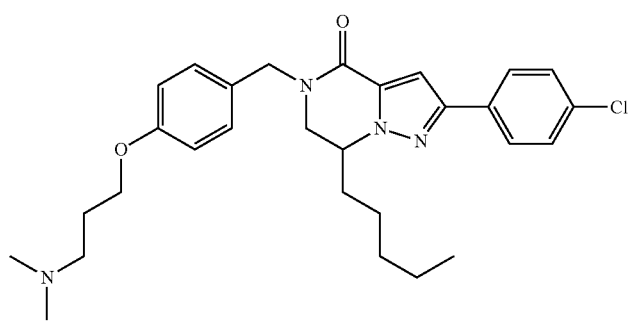 [SMILES: CCCCCC1CN(Cc2ccc(OCCCN(C)C)cc2)C(=O)c2cc(-c3ccc(Cl)cc3)nn21] A 2.16 509
I-0135 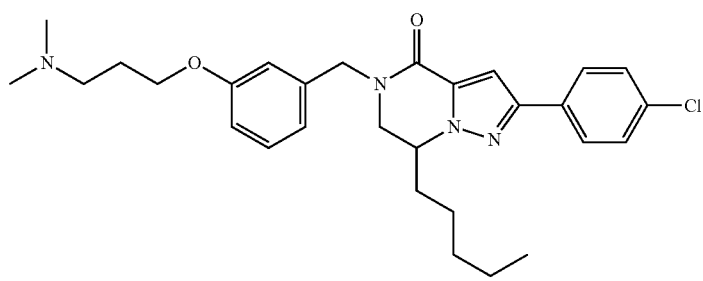 [SMILES: CCCCCC1CN(Cc2cccc(OCCCN(C)C)c2)C(=O)c2cc(-c3ccc(Cl)cc3)nn21] A 2.2 509
I-0136 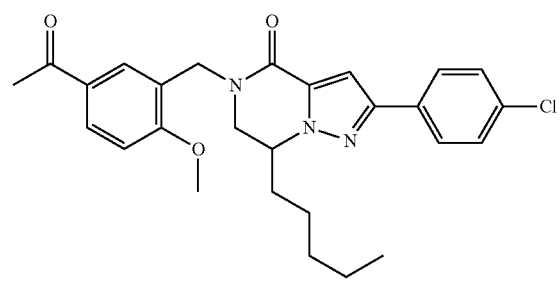 [SMILES: CCCCCC1CN(Cc2cc(C(C)=O)ccc2OC)C(=O)c2cc(-c3ccc(Cl)cc3)nn21] A 2.84 480

TABLE 18

| | | | | |
|---|---|---|---|---|
| I-0137 | | A | 2.43 | 535 |
| I-0138 | | A | 2.25 | 509 |
| I-0139 | | A | 2.95 | 557 |
| I-0140 | | A | 2.93 | 466 |
| I-0141 | | A | 2.68 | 486 |

TABLE 18-continued
| | | | | |
|---|---|---|---|---|
| I-0142 | 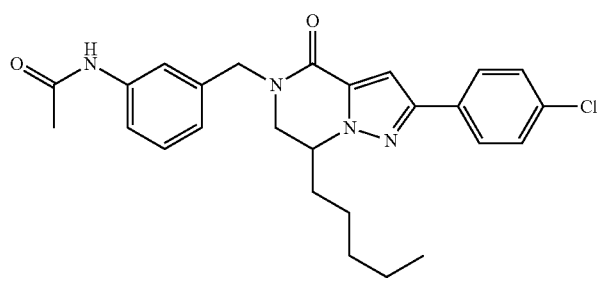 [SMILES: CCCCCC1CN(Cc2cccc(NC(C)=O)c2)C(=O)c2cc(-c3ccc(Cl)cc3)nn21] | A | 2.63 | 465 |
| I-0143 | 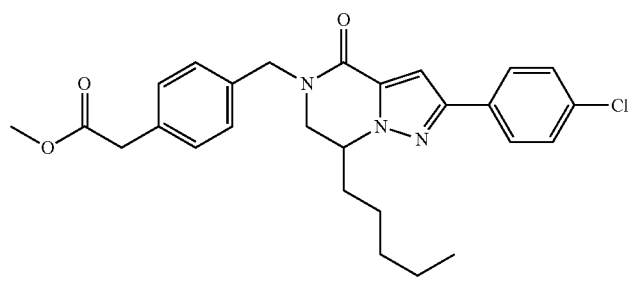 [SMILES: CCCCCC1CN(Cc2ccc(CC(=O)OC)cc2)C(=O)c2cc(-c3ccc(Cl)cc3)nn21] | A | 2.96 | 480 |
| I-0144 | 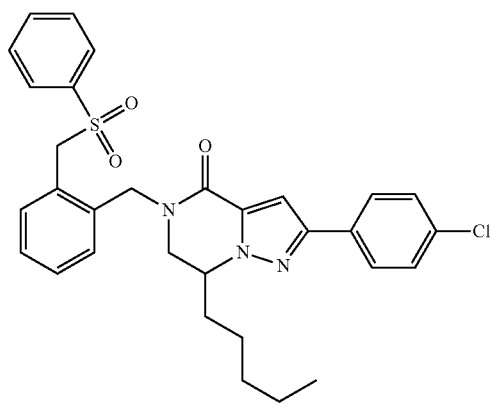 [SMILES: CCCCCC1CN(Cc2ccccc2CS(=O)(=O)c2ccccc2)C(=O)c2cc(-c3ccc(Cl)cc3)nn21] | A | 3.06 | 562 |
TABLE 19
| | | | | |
|---|---|---|---|---|
| I-0145 | 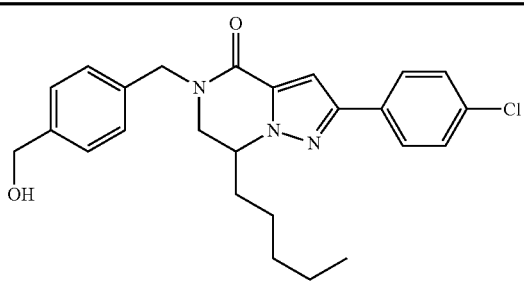 | A | 2.64 | 438 |
| I-0146 | 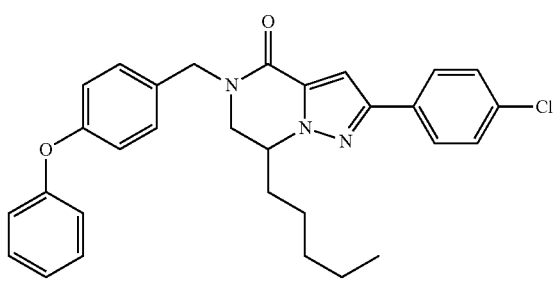 [SMILES: CCCCCC1CN(Cc2ccc(Oc3ccccc3)cc2)C(=O)c2cc(-c3ccc(Cl)cc3)nn21] | A | 3.33 | 500 |

TABLE 19-continued
I-0147 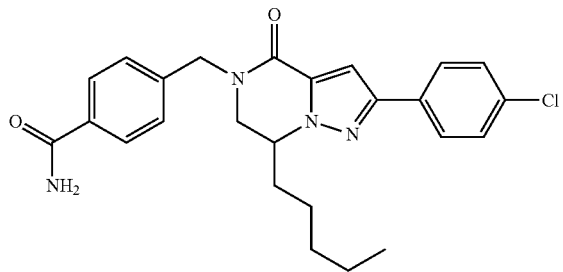 [SMILES: CCCCCC1CN(Cc2ccc(C(N)=O)cc2)C(=O)c2cc(-c3ccc(Cl)cc3)nn21] A 2.43 451
I-0148 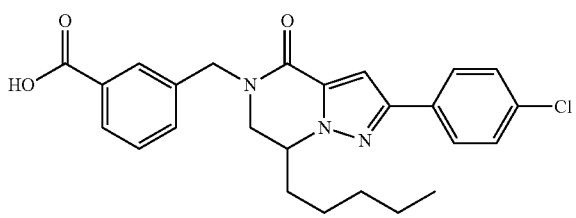 [SMILES: CCCCCC1CN(Cc2cccc(C(=O)O)c2)C(=O)c2cc(-c3ccc(Cl)cc3)nn21] A 2.73 452
I-0149 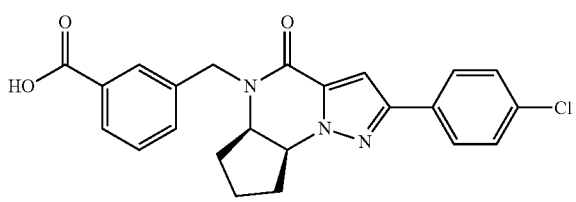 [SMILES: O=C(O)c1cccc(CN2C(=O)c3cc(-c4ccc(Cl)cc4)nn3[C@H]3CCC[C@H]32)c1] A 2.35 422
I-0150 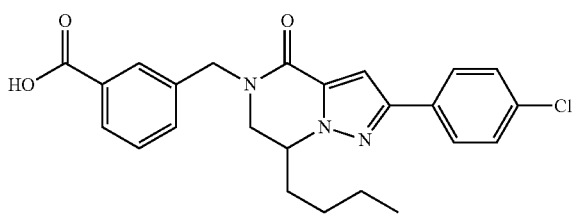 [SMILES: CCCCC1CN(Cc2cccc(C(=O)O)c2)C(=O)c2cc(-c3ccc(Cl)cc3)nn21] A 2.54 438
I-0151 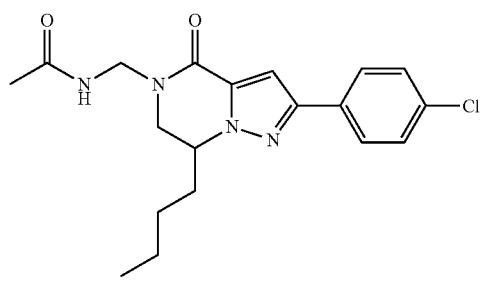 [SMILES: CCCCC1CN(CNC(C)=O)C(=O)c2cc(-c3ccc(Cl)cc3)nn21] A 2.22 375
I-0152 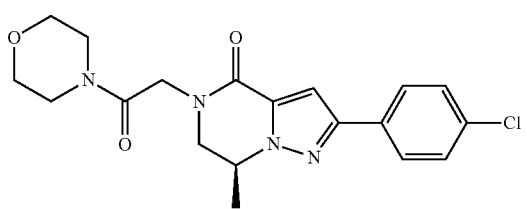 [SMILES: C[C@H]1CN(CC(=O)N2CCOCC2)C(=O)c2cc(-c3ccc(Cl)cc3)nn21] A 2.05 387

TABLE 20

| ID | Structure | | | |
|---|---|---|---|---|
| I-0153 | (structure) | A | 2.08 | 375 |
| I-0154 | (structure) | A | 1.86 | 373 |
| I-0155 | (structure) | A | 1.68 | 391 |
| I-0156 | (structure) | A | 1.64 | 391 |
| I-0157 | (structure) | A | 1.68 | 405 |
| I-0158 | (structure) | A | 1.9 | 431 |
| I-0159 | (structure) | A | 1.81 | 431 |

TABLE 20-continued
| I-0160 | 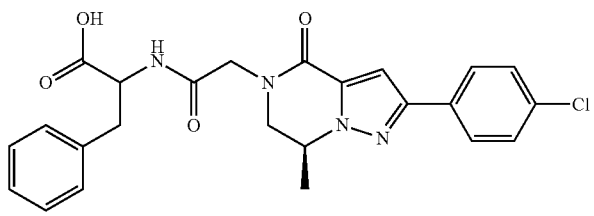 [SMILES: C[C@H]1CN(CC(=O)NC(Cc2ccccc2)C(=O)O)C(=O)c2cc(-c3ccc(Cl)cc3)nn21] | A | 2.08 | 467 |
TABLE 21
| I-0161 | 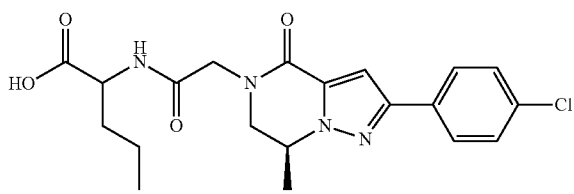 [SMILES: CCCC(NC(=O)CN1C[C@H](C)n2nc(-c3ccc(Cl)cc3)cc2C1=O)C(=O)O] | A | 1.91 | 419 |
| I-0162 | 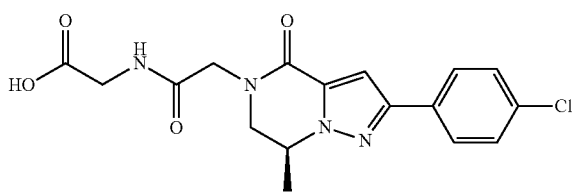 [SMILES: C[C@H]1CN(CC(=O)NCC(=O)O)C(=O)c2cc(-c3ccc(Cl)cc3)nn21] | A | 1.63 | 377 |
| I-0163 | 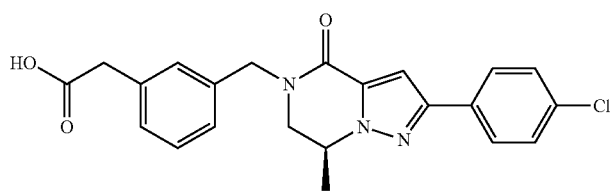 [SMILES: C[C@H]1CN(Cc2cccc(CC(=O)O)c2)C(=O)c2cc(-c3ccc(Cl)cc3)nn21] | A | 2.12 | 410 |
| I-0164 | 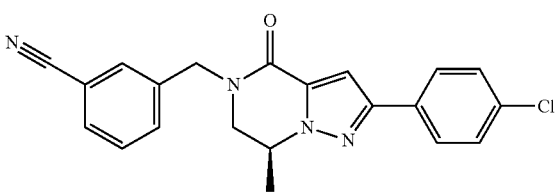 [SMILES: C[C@H]1CN(Cc2cccc(C#N)c2)C(=O)c2cc(-c3ccc(Cl)cc3)nn21] | A | 2.37 | 377 |
| I-0165 | 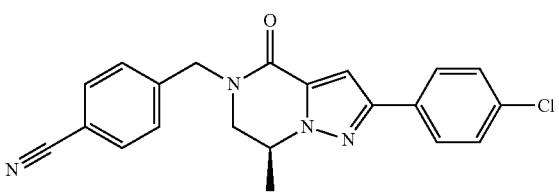 [SMILES: C[C@H]1CN(Cc2ccc(C#N)cc2)C(=O)c2cc(-c3ccc(Cl)cc3)nn21] | A | 2.37 | 377 |
| I-0166 | 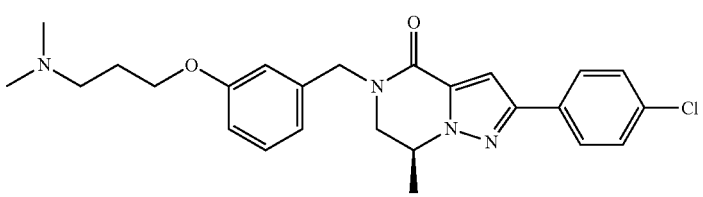 [SMILES: C[C@H]1CN(Cc2cccc(OCCCN(C)C)c2)C(=O)c2cc(-c3ccc(Cl)cc3)nn21] | A | 1.76 | 453 |

TABLE 21-continued
| I-0167 | 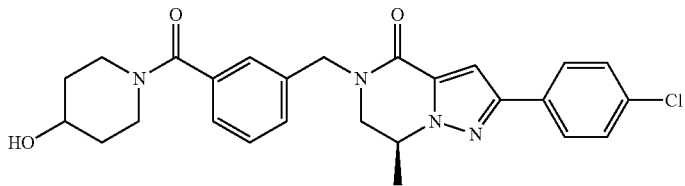 [SMILES: C[C@H]1CN(Cc2cccc(C(=O)N3CCC(O)CC3)c2)C(=O)c2cc(-c3ccc(Cl)cc3)nn21] | A | 1.88 | 479 |
| I-0168 | 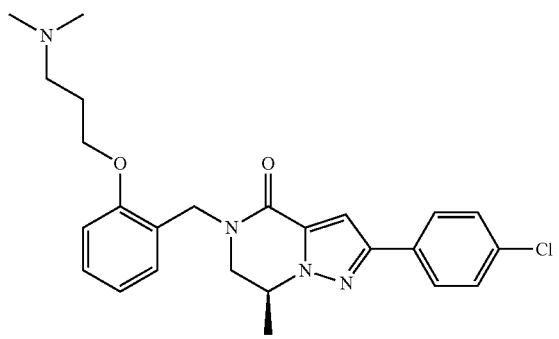 [SMILES: C[C@H]1CN(Cc2ccccc2OCCCN(C)C)C(=O)c2cc(-c3ccc(Cl)cc3)nn21] | A | 1.8 | 453 |
TABLE 22
| I-0169 | 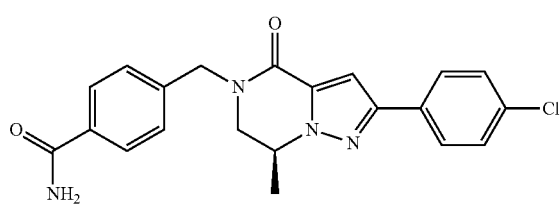 [SMILES: C[C@H]1CN(Cc2ccc(C(N)=O)cc2)C(=O)c2cc(-c3ccc(Cl)cc3)nn21] | A | 1.89 | 395 |
| I-0170 | 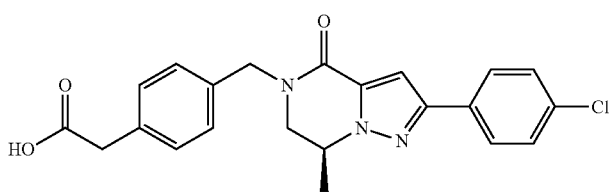 [SMILES: C[C@H]1CN(Cc2ccc(CC(=O)O)cc2)C(=O)c2cc(-c3ccc(Cl)cc3)nn21] | A | 2.12 | 410 |
| I-0171 | 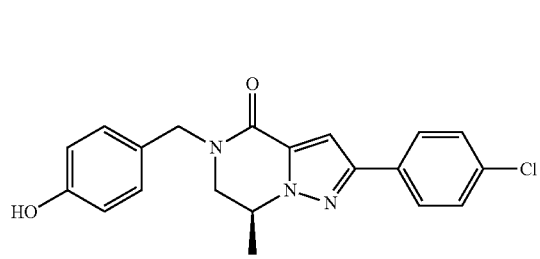 [SMILES: C[C@H]1CN(Cc2ccc(O)cc2)C(=O)c2cc(-c3ccc(Cl)cc3)nn21] | A | 2.12 | 368 |
| I-0172 | 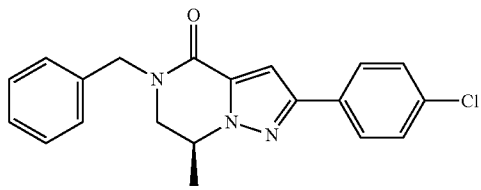 [SMILES: C[C@H]1CN(Cc2ccccc2)C(=O)c2cc(-c3ccc(Cl)cc3)nn21] | A | 2.51 | 352 |

TABLE 22-continued

| ID | Structure | | | |
|---|---|---|---|---|
| I-0173 | (3-carboxybenzyl, benzyloxymethyl substituted pyrazolopyrazinone with 4-Cl-phenyl) | A | 2.51 | 502 |
| I-0174 | (3-carboxybenzyl, hydroxymethyl substituted pyrazolopyrazinone with 4-Cl-phenyl) | A | 1.81 | 412 |
| I-0175 | (3-carboxybenzyl, ethoxymethyl substituted pyrazolopyrazinone with 4-Cl-phenyl) | A | 2.24 | 440 |
| I-0176 | (3-carboxybenzyl, propoxymethyl substituted pyrazolopyrazinone with 4-Cl-phenyl) | A | 2.4 | 454 |

TABLE 23

| ID | Structure | | | |
|---|---|---|---|---|
| I-0177 | (4-cyanobenzyl, benzyloxymethyl substituted pyrazolopyrazinone with 4-Cl-phenyl) | A | 2.73 | 483 |

TABLE 23-continued

| ID | Structure | Class | Val1 | Val2 |
|---|---|---|---|---|
| I-0178 | (4-cyanobenzyl / 2-(4-chlorophenyl) / ethoxymethyl pyrazolopyrazinone) | A | 2.49 | 421 |
| I-0179 | (4-carboxyphenyl / 2-(4-chlorophenyl) / pentyl pyrazolopyrazinone) | A | 2.82 | 438 |
| I-0180 | (4-cyanobenzyl / 2-(4-cyanopiperidinylcarbonyl) / pentyl pyrazolopyrazinone) | B | 2.04 | 459 |
| I-0181 | (4-cyanobenzyl / 2-(4-chlorophenyl) / propyl pyrazolopyrazinone) | B | 2.55 | 405 |
| I-0182 | (4-cyanobenzyl / 2-(4-trifluoromethylphenyl) / propyl pyrazolopyrazinone) | B | 2.42 | 446 |
| I-0183 | (4-cyanobenzyl / 2-(4-chlorophenyl) / butyl pyrazolopyrazinone) | B | 2.66 | 419 |

TABLE 23-continued
| I-0184 | 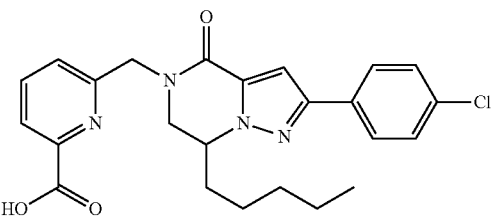 [SMILES: CCCCCC1CN(Cc2cccc(C(=O)O)n2)C(=O)c2cc(-c3ccc(Cl)cc3)nn21] | A | 2.53 | 453 |
TABLE 24
| I-0185 | 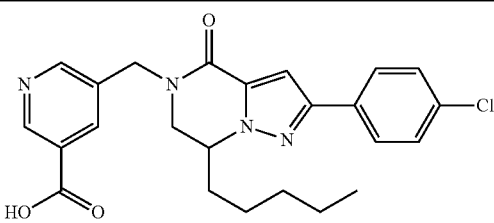 | A | 2.38 | 453 |
| I-0186 | 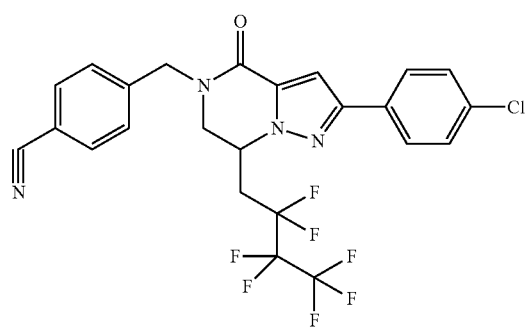 [SMILES: N#Cc1ccc(CN2CC(CC(F)(F)C(F)(F)C(F)(F)F)n3nc(-c4ccc(Cl)cc4)cc3C2=O)cc1] | A | 2.86 | 545 |
| I-0187 | 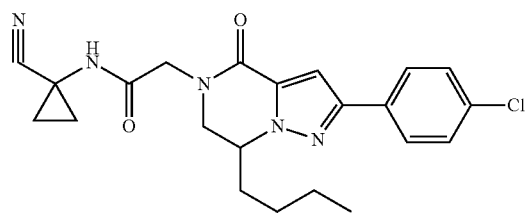 [SMILES: CCCCC1CN(CC(=O)NC2(C#N)CC2)C(=O)c2cc(-c3ccc(Cl)cc3)nn21] | B | 2.27 | 426 |
| I-0188 | 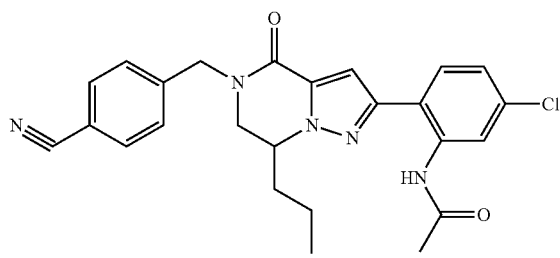 [SMILES: CCCC1CN(Cc2ccc(C#N)cc2)C(=O)c2cc(-c3ccc(Cl)cc3NC(C)=O)nn21] | B | 2.35 | 462 |
| I-0189 | 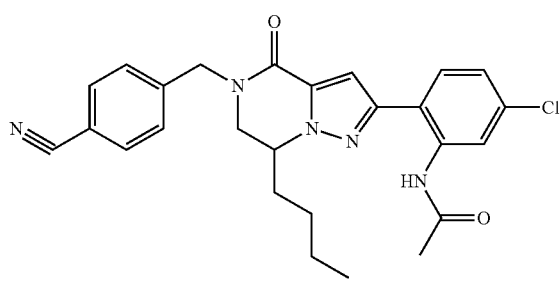 [SMILES: CCCCC1CN(Cc2ccc(C#N)cc2)C(=O)c2cc(-c3ccc(Cl)cc3NC(C)=O)nn21] | B | 2.46 | 476 |

TABLE 24-continued
| | | | | | |
|---|---|---|---|---|---|
| I-0190 | 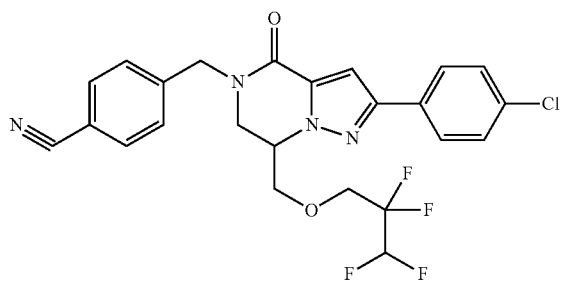 [SMILES: N#Cc1ccc(CN2CC(COCC(F)(F)C(F)F)n3nc(-c4ccc(Cl)cc4)cc3C2=O)cc1] | | B | 2.41 | 507 |
| I-0191 | 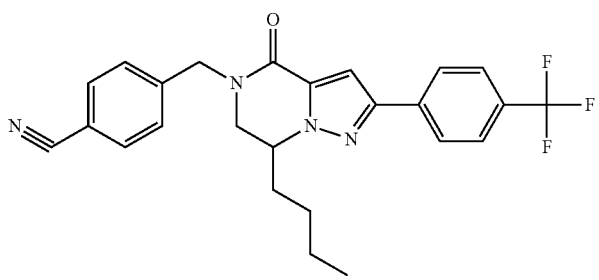 [SMILES: CCCCC1CN(Cc2ccc(C#N)cc2)C(=O)c2cc(-c3ccc(C(F)(F)F)cc3)nn21] | | B | 2.69 | 453 |
| I-0192 | 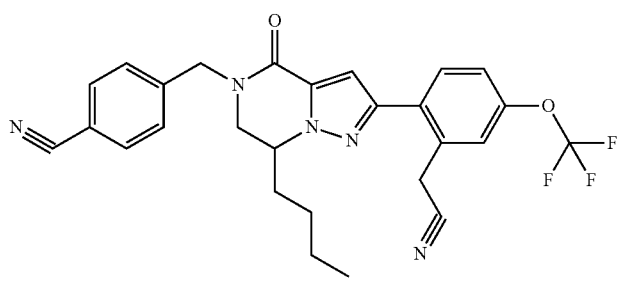 [SMILES: CCCCC1CN(Cc2ccc(C#N)cc2)C(=O)c2cc(-c3ccc(OC(F)(F)F)cc3CC#N)nn21] | | B | 2.55 | 508 |
TABLE 25
| | | | | | |
|---|---|---|---|---|---|
| I-0193 | 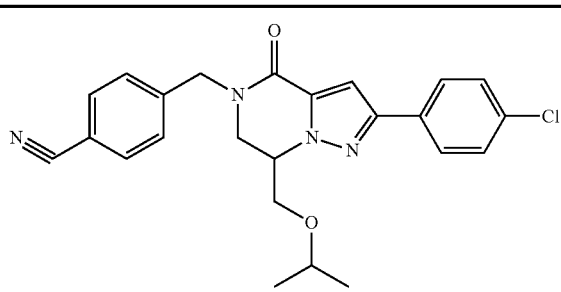 | | B | 2.49 | 435 |
| I-0194 | 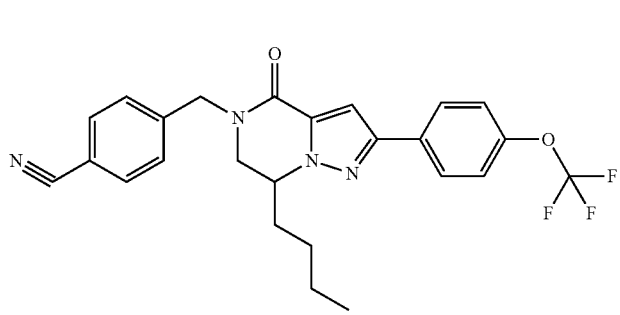 [SMILES: CCCCC1CN(Cc2ccc(C#N)cc2)C(=O)c2cc(-c3ccc(OC(F)(F)F)cc3)nn21] | | B | 2.71 | 469 |

TABLE 25-continued
| I-0195 | 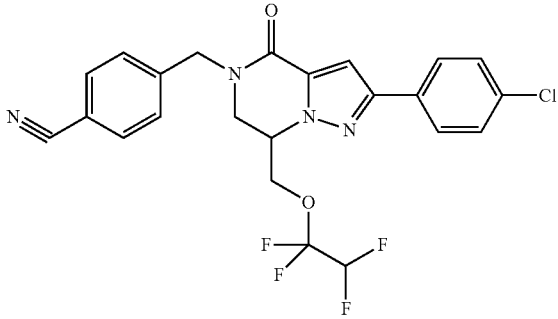 [SMILES: N#Cc1ccc(CN2CC(COC(F)(F)C(F)F)n3nc(-c4ccc(Cl)cc4)cc3C2=O)cc1] | B | 2.4 | 493 |
| I-0196 | 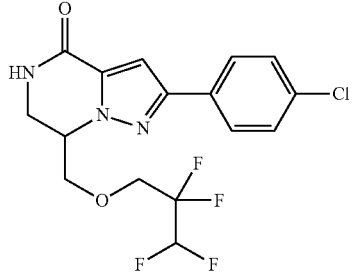 [SMILES: O=C1NCC(COCC(F)(F)C(F)F)n2nc(-c3ccc(Cl)cc3)cc21] | B | 2.05 | 392 |
| I-0197 | 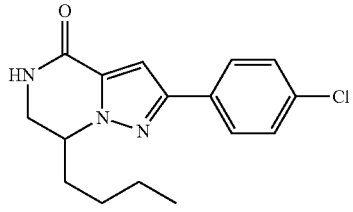 [SMILES: CCCCC1CNC(=O)c2cc(-c3ccc(Cl)cc3)nn21] | B | 2.24 | 304 |
| I-0198 | 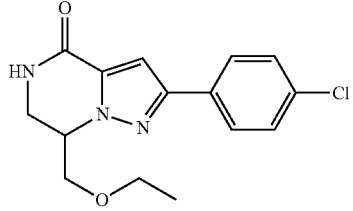 [SMILES: CCOCC1CNC(=O)c2cc(-c3ccc(Cl)cc3)nn21] | B | 1.88 | 306 |
| I-0199 | 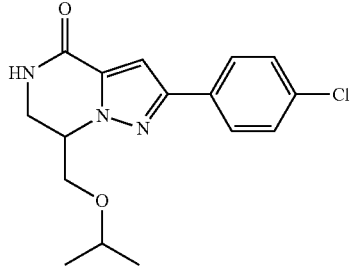 [SMILES: CC(C)OCC1CNC(=O)c2cc(-c3ccc(Cl)cc3)nn21] | B | 2.02 | 320 |
| I-0200 | 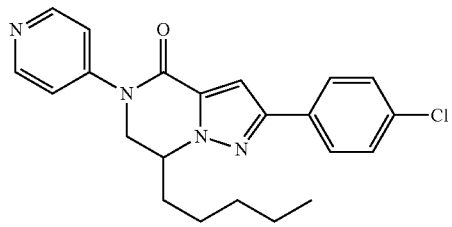 [SMILES: CCCCCC1CN(c2ccncc2)C(=O)c2cc(-c3ccc(Cl)cc3)nn21] | A | 2.44 | 395 |

TABLE 26
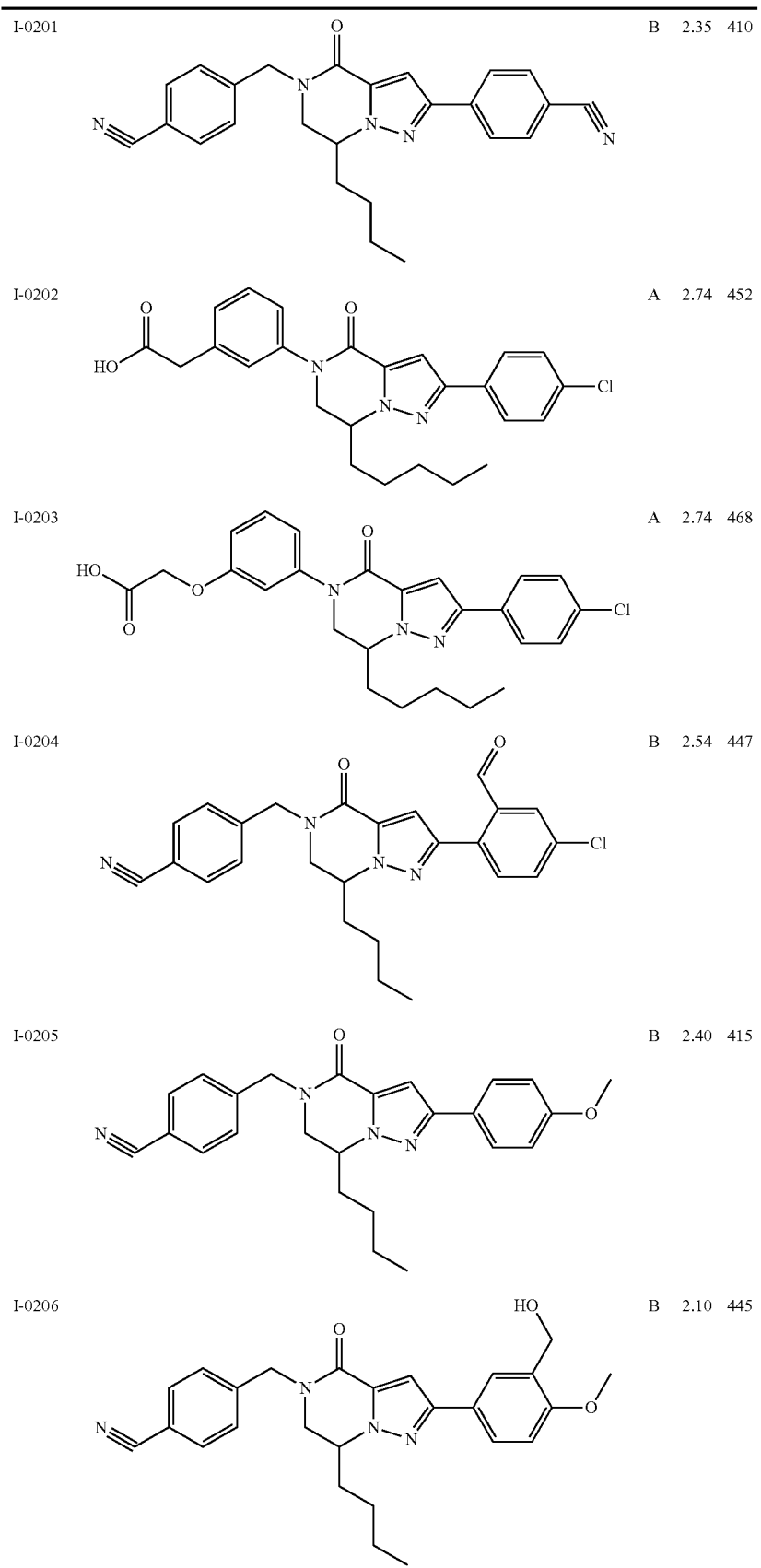
| | | | | |
|---|---|---|---|---|
| I-0201 | | B | 2.35 | 410 |
| I-0202 | | A | 2.74 | 452 |
| I-0203 | | A | 2.74 | 468 |
| I-0204 | | B | 2.54 | 447 |
| I-0205 | | B | 2.40 | 415 |
| I-0206 | | B | 2.10 | 445 |

TABLE 26-continued
| I-0207 | 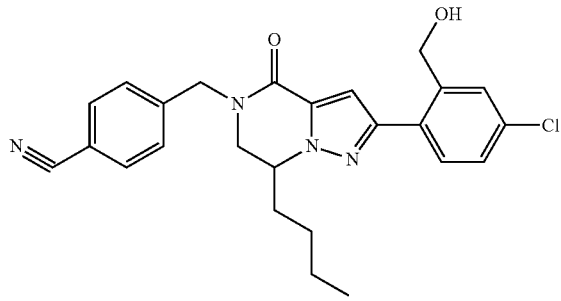 | B | 2.35 | 449 |
TABLE 27
| I-0208 | 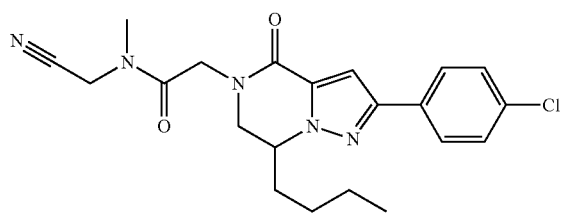 [SMILES: CCCCC1CN(CC(=O)N(C)CC#N)C(=O)c2cc(-c3ccc(Cl)cc3)nn21] | A | 2.50 | 414 |
| I-0209 | 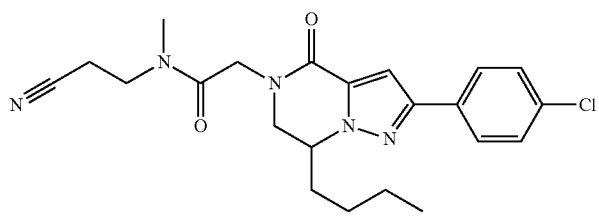 [SMILES: CCCCC1CN(CC(=O)N(C)CCC#N)C(=O)c2cc(-c3ccc(Cl)cc3)nn21] | A | 2.43 | 428 |
| I-0210 | 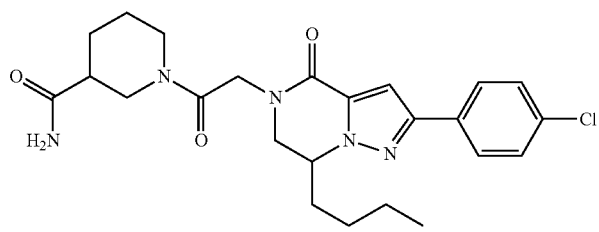 [SMILES: CCCCC1CN(CC(=O)N2CCCC(C(N)=O)C2)C(=O)c2cc(-c3ccc(Cl)cc3)nn21] | A | 2.20 | 472 |
| I-0211 | 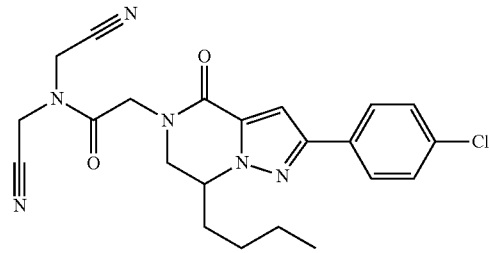 [SMILES: CCCCC1CN(CC(=O)N(CC#N)CC#N)C(=O)c2cc(-c3ccc(Cl)cc3)nn21] | A | 2.56 | 439 |
| I-0212 | 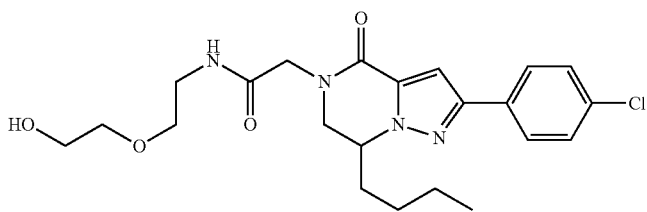 [SMILES: CCCCC1CN(CC(=O)NCCOCCO)C(=O)c2cc(-c3ccc(Cl)cc3)nn21] | A | 2.12 | 449 |

TABLE 27-continued

| ID | Structure | | | |
|---|---|---|---|---|
| I-0213 | (cyanomethyl-NH-C(O)-CH2-N[pyrazolopyrazinone-2-(4-Cl-phenyl)-7-butyl]) | A | 2.37 | 400 |
| I-0214 | (N-ethyl-N-(2-cyanoethyl)-NC(O)-CH2-N[pyrazolopyrazinone-2-(4-Cl-phenyl)-7-butyl]) | A | 2.55 | 442 |

TABLE 28

| ID | Structure | | | |
|---|---|---|---|---|
| I-0215 | (H2N-C(O)-CH2-NH-C(O)-CH2-N[pyrazolopyrazinone-2-(4-Cl-phenyl)-7-butyl]) | A | 2.05 | 418 |
| I-0216 | (CF3-CH(OH)-CH2-NH-C(O)-CH2-N[pyrazolopyrazinone-2-(4-Cl-phenyl)-7-butyl]) | A | 2.46 | 473 |
| I-0217 | (H2N-C(O)-N(piperazine)-C(O)-CH2-N[pyrazolopyrazinone-2-(4-Cl-phenyl)-7-butyl]) | A | 2.12 | 405 |
| I-0218 | (HO-CH2CH2-NH-C(O)-CH2-N[pyrazolopyrazinone-2-(4-Cl-phenyl)-7-butyl]) | A | 2.11 | 405 |

TABLE 28-continued

| I-0219 | [structure: 3-amino-1,2-propanediol-CH2NHC(O)CH2-N(pyrazolopyrazinone-butyl-4-chlorophenyl)] | A | 2.01 | 435 |
| I-0220 | [structure: 4-cyanopiperidinyl-C(O)CH2-N(pyrazolopyrazinone-butyl-4-chlorophenyl)] | A | 2.49 | 454 |
| I-0221 | [structure: trans-2-hydroxycyclopentyl-NHC(O)CH2-N(pyrazolopyrazinone-butyl-4-chlorophenyl)] | A | 2.33 | 445 |

TABLE 29

| I-0222 | [structure: H2N-C(O)CH2CH2-NHC(O)CH2-N(pyrazolopyrazinone-butyl-4-chlorophenyl)] | A | 2.04 | 432 |
| I-0223 | [structure: (3R,5S)-3,5-dimethylmorpholinyl-C(O)CH2-N(pyrazolopyrazinone-butyl-4-chlorophenyl)] | A | 2.60 | 459 |
| I-0224 | [structure: MeNH-C(O)CH2-NHC(O)CH2-N(pyrazolopyrazinone-butyl-4-chlorophenyl)] | A | 2.11 | 432 |

TABLE 29-continued
| I-0225 | 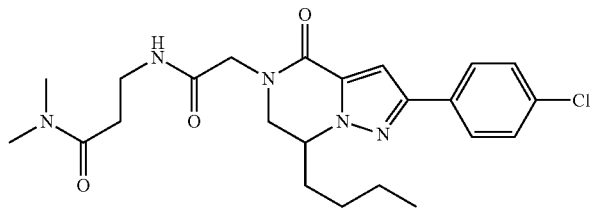 [SMILES: CCCCC1CN(CC(=O)NCCC(=O)N(C)C)C(=O)c2cc(-c3ccc(Cl)cc3)nn21] | A | 2.20 | 460 |
| I-0226 | 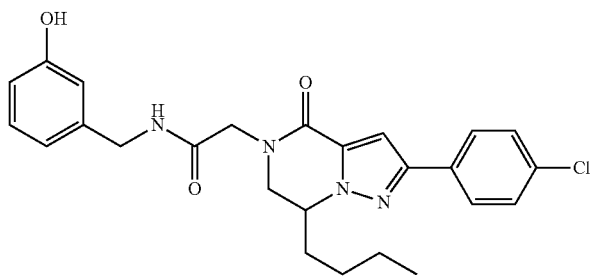 [SMILES: CCCCC1CN(CC(=O)NCc2cccc(O)c2)C(=O)c2cc(-c3ccc(Cl)cc3)nn21] | A | 2.44 | 467 |
| I-0227 | 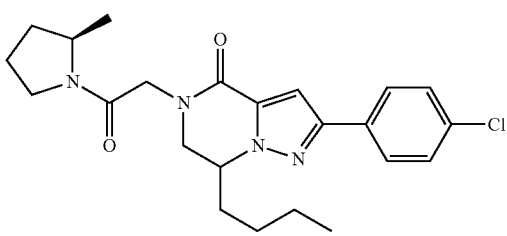 [SMILES: CCCCC1CN(CC(=O)N2CCC[C@H]2C)C(=O)c2cc(-c3ccc(Cl)cc3)nn21] | A | 2.62 | 429 |
| I-0228 | 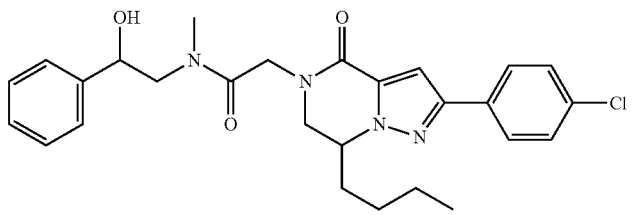 [SMILES: CCCCC1CN(CC(=O)N(C)CC(O)c2ccccc2)C(=O)c2cc(-c3ccc(Cl)cc3)nn21] | A | 2.62 | 496 |
TABLE 30
| I-0229 | 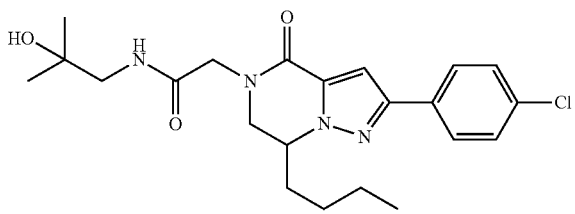 [SMILES: CCCCC1CN(CC(=O)NCC(C)(C)O)C(=O)c2cc(-c3ccc(Cl)cc3)nn21] | A | 2.25 | 433 |
| I-0230 | 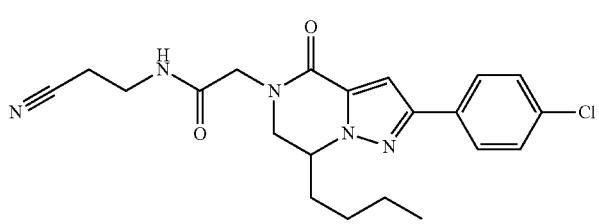 | A | 2.33 | 412 |

TABLE 30-continued

| I-0231 | [structure] | A | 2.46 | 425 |
| I-0232 | [structure] | A | 2.17 | 443 |
| I-0233 | [structure] | A | 2.25 | 458 |
| I-0234 | [structure] | A | 2.18 | 455 |
| I-0235 | [structure] | A | 2.49 | 467 |

TABLE 31

| I-0236 | [structure] | A | 2.06 | 468 |

TABLE 31-continued
| | | | | |
|---|---|---|---|---|
| I-0237 | 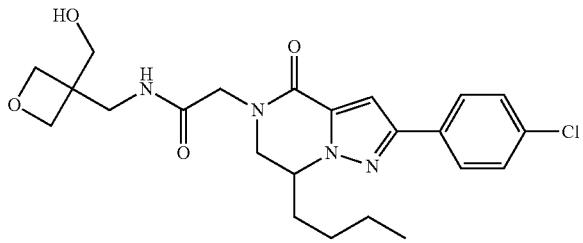 [SMILES: CCCCC1CN(CC(=O)NCC2(CO)COC2)C(=O)c2cc(-c3ccc(Cl)cc3)nn21] | A | 2.12 | 461 |
| I-0238 | 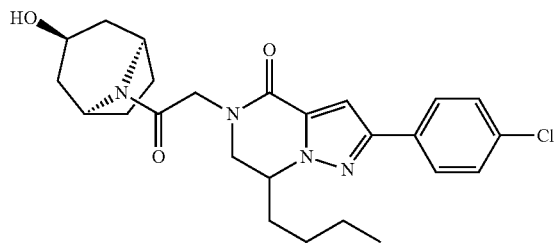 [SMILES: CCCCC1CN(CC(=O)N2[C@@H]3CC[C@H]2C[C@@H](O)C3)C(=O)c2cc(-c3ccc(Cl)cc3)nn21] | A | 2.34 | 471 |
| I-0239 | 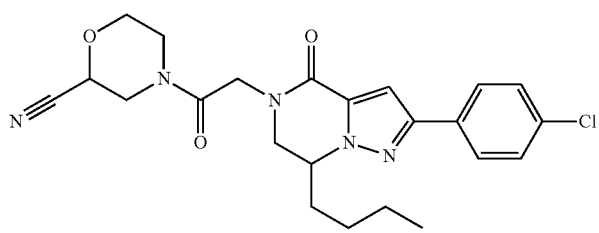 [SMILES: CCCCC1CN(CC(=O)N2CCOC(C#N)C2)C(=O)c2cc(-c3ccc(Cl)cc3)nn21] | A | 2.50 | 456 |
| I-0240 | 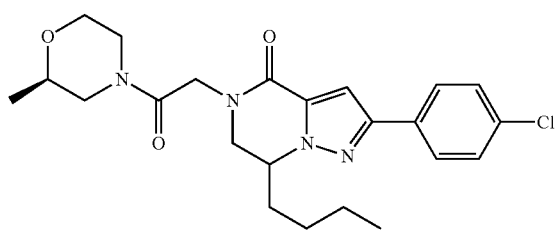 | A | 2.49 | 445 |
| I-0241 | 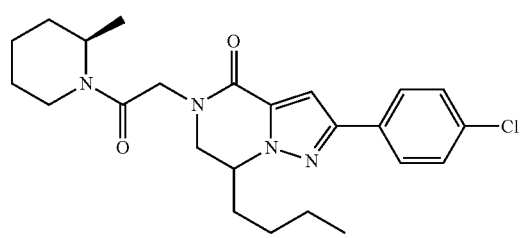 | A | 2.77 | 443 |
| I-0242 | 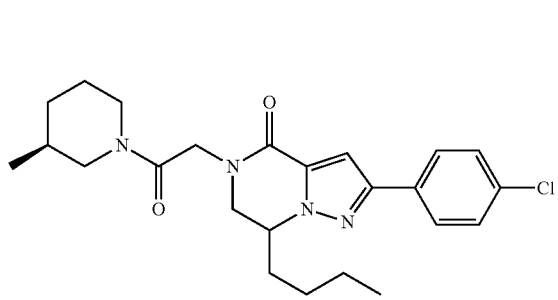 [SMILES: CCCCC1CN(CC(=O)N2CCO[C@H](C)C2)C(=O)c2cc(-c3ccc(Cl)cc3)nn21] | A | 2.80 | 443 |

TABLE 32
| | | | | |
|---|---|---|---|---|
| I-0243 | 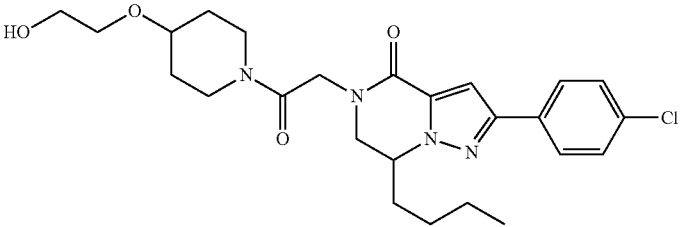 [SMILES: CCCCC1CN(CC(=O)N2CCC(OCCO)CC2)C(=O)c2cc(-c3ccc(Cl)cc3)nn21] | A | 2.25 | 490 |
| I-0244 | 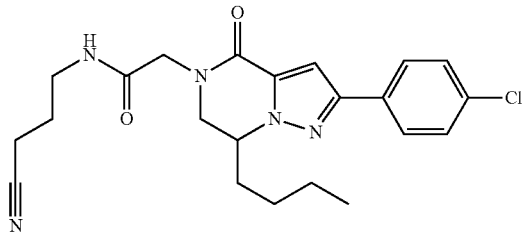 [SMILES: CCCCC1CN(CC(=O)NCCCC#N)C(=O)c2cc(-c3ccc(Cl)cc3)nn21] | A | 2.35 | 428 |
| I-0245 | 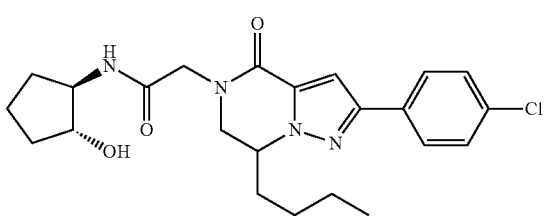 [SMILES: CCCCC1CN(CC(=O)N[C@@H]2CCC[C@H]2O)C(=O)c2cc(-c3ccc(Cl)cc3)nn21] | A | 2.29 | 445 |
| I-0246 | 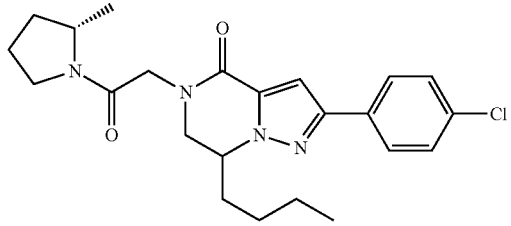 [SMILES: CCCCC1CN(CC(=O)N2CCC[C@@H]2C)C(=O)c2cc(-c3ccc(Cl)cc3)nn21] | A | 2.62 | 429 |
| I-0247 | 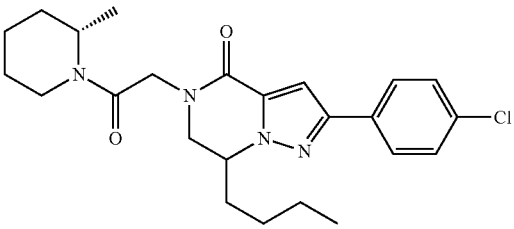 [SMILES: CCCCC1CN(CC(=O)N2CCCC[C@@H]2C)C(=O)c2cc(-c3ccc(Cl)cc3)nn21] | A | 2.77 | 443 |
| I-0248 | 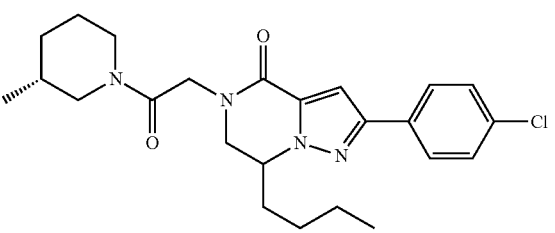 [SMILES: CCCCC1CN(CC(=O)N2CCC[C@@H](C)C2)C(=O)c2cc(-c3ccc(Cl)cc3)nn21] | A | 2.80 | 443 |
| I-0249 | 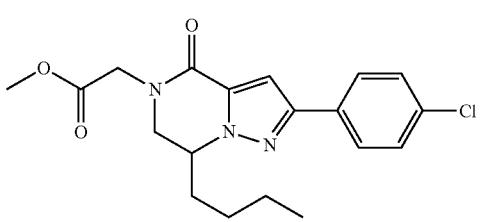 [SMILES: CCCCC1CN(CC(=O)OC)C(=O)c2cc(-c3ccc(Cl)cc3)nn21] | B | 2.63 | 390 |

TABLE 33
| | | | | |
|---|---|---|---|---|
| I-0250 | 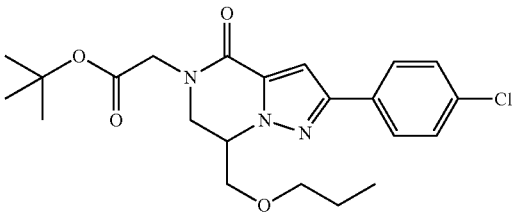 [SMILES: CCCOCC1CN(CC(=O)OC(C)(C)C)C(=O)c2cc(-c3ccc(Cl)cc3)nn21] | A | 2.81 | 434 |
| I-0251 | 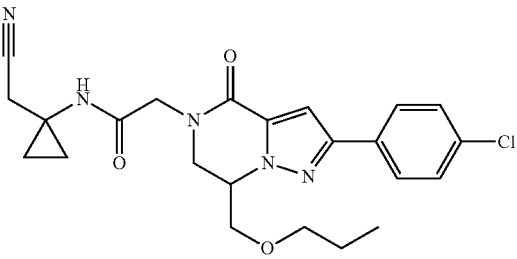 [SMILES: CCCOCC1CN(CC(=O)NC2(CC#N)CC2)C(=O)c2cc(-c3ccc(Cl)cc3)nn21] | A | 2.19 | 442 |
| I-0252 | 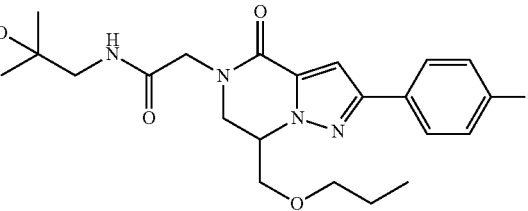 | A | 2.01 | 449 |
| I-0253 | 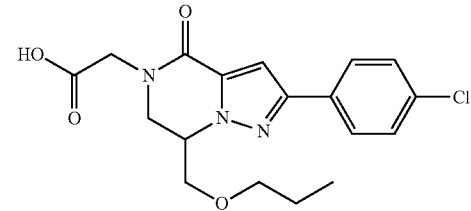 [SMILES: CCCOCC1CN(CC(=O)O)C(=O)c2cc(-c3ccc(Cl)cc3)nn21] | A | 2.12 | 378 |
| I-0254 | 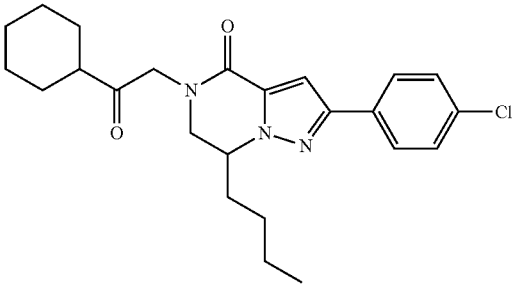 [SMILES: CCCCC1CN(CC(=O)C2CCCCC2)C(=O)c2cc(-c3ccc(Cl)cc3)nn21] | A | 2.96 | 428 |
| I-0255 | 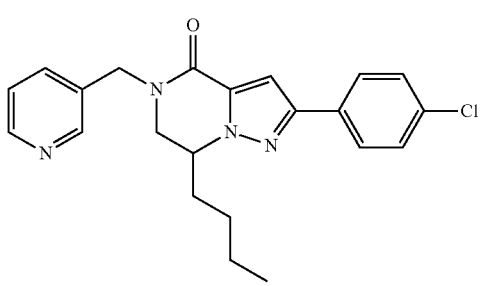 [SMILES: CCCCC1CN(Cc2cccnc2)C(=O)c2cc(-c3ccc(Cl)cc3)nn21] | A | 2.01 | 395 |

TABLE 33-continued
| I-0256 | 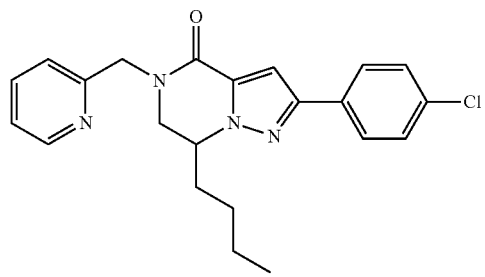 [SMILES: CCCCC1CN(Cc2ccccn2)C(=O)c2cc(-c3ccc(Cl)cc3)nn21] | A | 2.39 | 395 |
TABLE 34
| I-0257 | 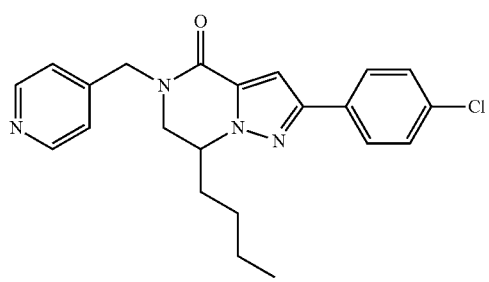 [SMILES: CCCCC1CN(Cc2ccncc2)C(=O)c2cc(-c3ccc(Cl)cc3)nn21] | A | 1.88 | 395 |
| I-0258 | 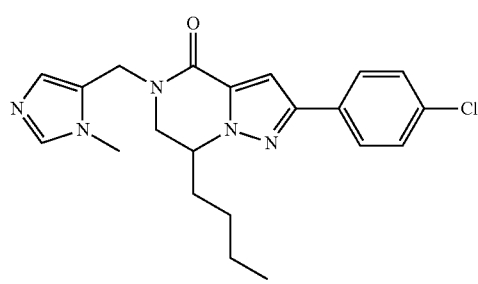 [SMILES: CCCCC1CN(Cc2cncn2C)C(=O)c2cc(-c3ccc(Cl)cc3)nn21] | A | 1.77 | 398 |
| I-0259 | 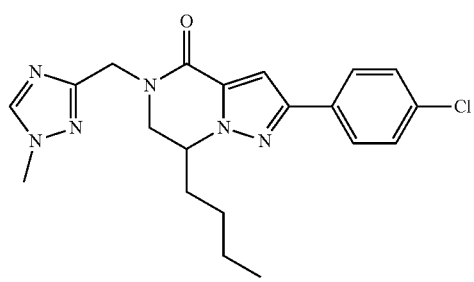 [SMILES: CCCCC1CN(Cc2ncn(C)n2)C(=O)c2cc(-c3ccc(Cl)cc3)nn21] | A | 2.24 | 399 |
| I-0260 | 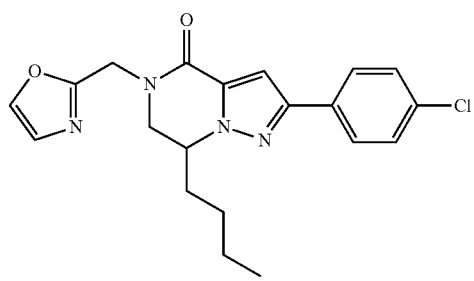 [SMILES: CCCCC1CN(Cc2ncco2)C(=O)c2cc(-c3ccc(Cl)cc3)nn21] | A | 2.44 | 385 |

TABLE 34-continued
| | | | | |
|---|---|---|---|---|
| I-0261 | 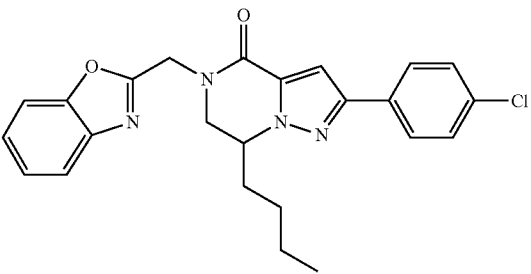 [SMILES: CCCCC1CN(Cc2nc3ccccc3o2)C(=O)c2cc(-c3ccc(Cl)cc3)nn21] | A | 2.80 | 435 |
| I-0262 | 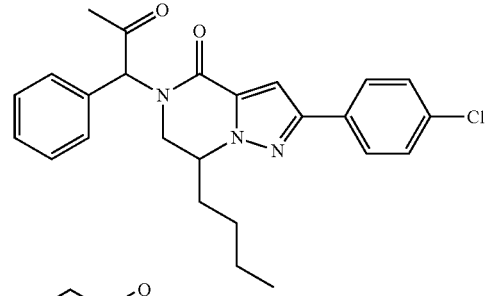 | A | 2.90 | 436 |
| I-0263 | 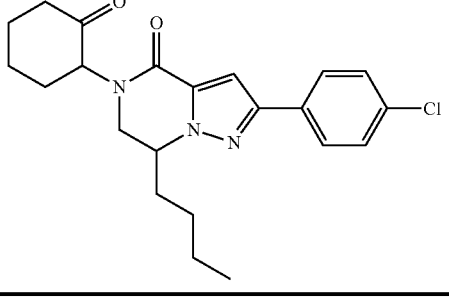 | A | 2.73 | 400 |
TABLE 35
| | | | | |
|---|---|---|---|---|
| I-0264 | 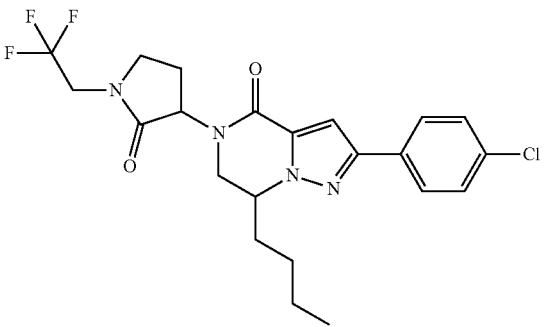 [SMILES: CCCCC1CN(C2CCN(CC(F)(F)F)C2=O)C(=O)c2cc(-c3ccc(Cl)cc3)nn21] | A | 2.59 | 469 |
| I-0265 | 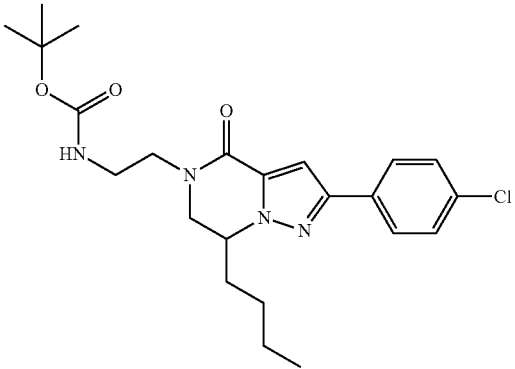 [SMILES: CCCCC1CN(CCNC(=O)OC(C)(C)C)C(=O)c2cc(-c3ccc(Cl)cc3)nn21] | A | 2.71 | 447 |

TABLE 35-continued
| I-0266 | 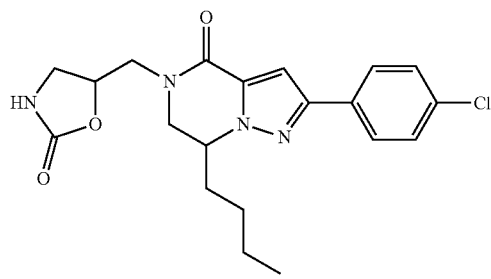 [SMILES: CCCCC1CN(CC2CNC(=O)O2)C(=O)c2cc(-c3ccc(Cl)cc3)nn21] | A | 2.12 | 403 |
| I-0267 | 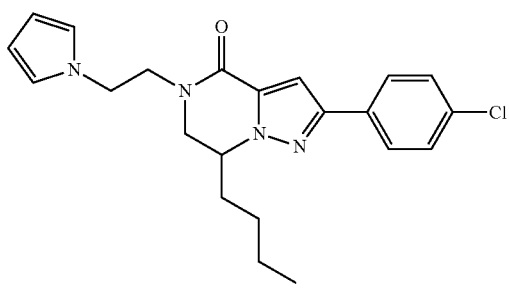 [SMILES: CCCCC1CN(CCn2cccc2)C(=O)c2cc(-c3ccc(Cl)cc3)nn21] | A | 2.82 | 397 |
| I-0268 | 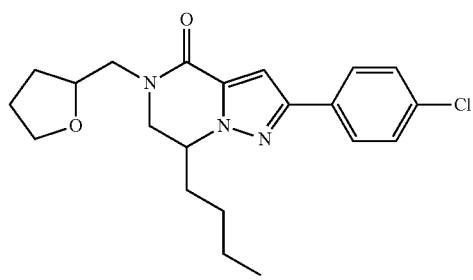 [SMILES: CCCCC1CN(CC2CCCO2)C(=O)c2cc(-c3ccc(Cl)cc3)nn21] | A | 2.63 | 388 |
| I-0269 | 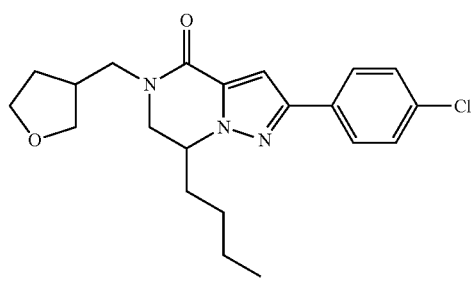 [SMILES: CCCCC1CN(CC2CCOC2)C(=O)c2cc(-c3ccc(Cl)cc3)nn21] | A | 2.46 | 388 |
TABLE 36
| I-0270 | 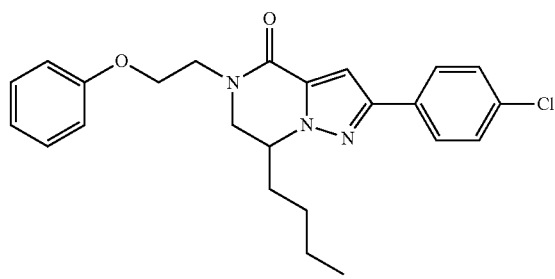 [SMILES: CCCCC1CN(CCOc2ccccc2)C(=O)c2cc(-c3ccc(Cl)cc3)nn21] | A | 2.93 | 424 |

TABLE 36-continued
| I-0271 | 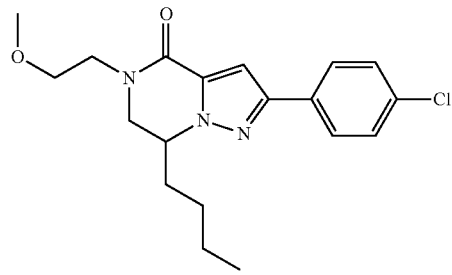 [SMILES: CCCCC1CN(CCOC)C(=O)c2cc(-c3ccc(Cl)cc3)nn21] | A | 2.52 | 362 |
| I-0272 | 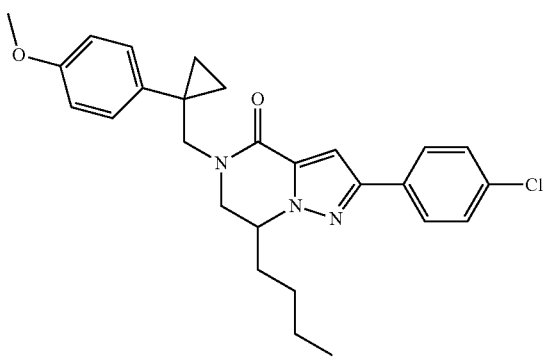 [SMILES: CCCCC1CN(CC2(c3ccc(OC)cc3)CC2)C(=O)c2cc(-c3ccc(Cl)cc3)nn21] | A | 3.03 | 464 |
| I-0273 | 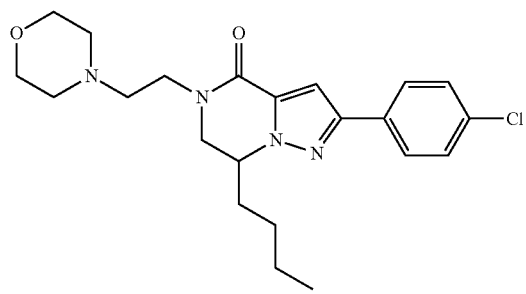 [SMILES: CCCCC1CN(CCN2CCOCC2)C(=O)c2cc(-c3ccc(Cl)cc3)nn21] | A | 1.71 | 417 |
| I-0274 | 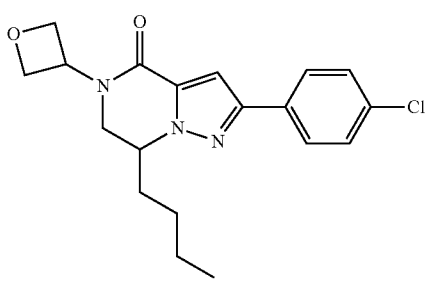 [SMILES: CCCCC1CN(C2COC2)C(=O)c2cc(-c3ccc(Cl)cc3)nn21] | A | 2.39 | 360 |
| I-0275 | 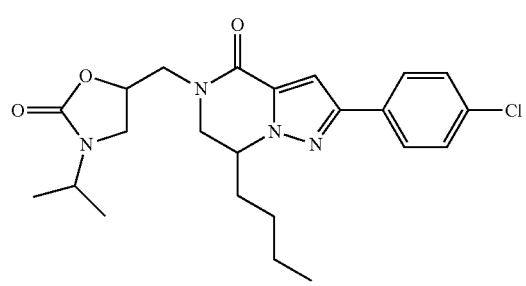 [SMILES: CCCCC1CN(CC2CN(C(C)C)C(=O)O2)C(=O)c2cc(-c3ccc(Cl)cc3)nn21] | A | 2.46 | 445 |

TABLE 37
| I-0276 | 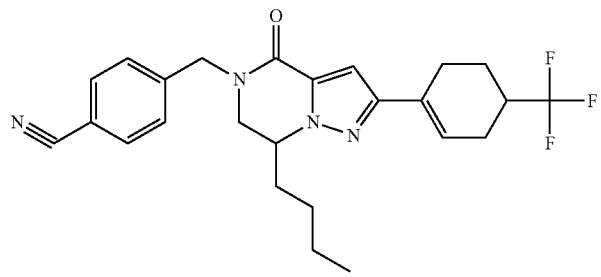 [SMILES: CCCCC1CN(Cc2ccc(C#N)cc2)C(=O)c2cc(C3=CCC(C(F)(F)F)CC3)nn21] | B | 2.66 | 457 |
| I-0277 | 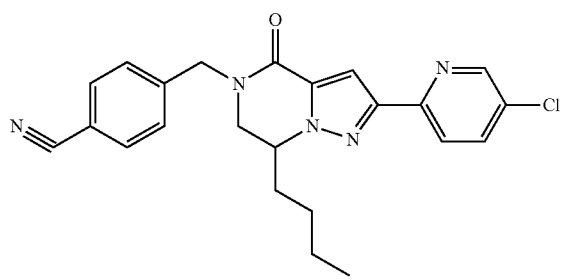 [SMILES: CCCCC1CN(Cc2ccc(C#N)cc2)C(=O)c2cc(-c3ccc(Cl)cn3)nn21] | B | 2.43 | 420 |
| I-0278 | 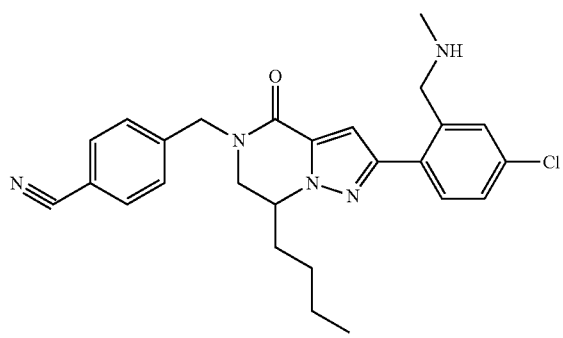 [SMILES: CCCCC1CN(Cc2ccc(C#N)cc2)C(=O)c2cc(-c3ccc(Cl)cc3CNC)nn21] | B | 1.74 | 462 |
| I-0279 | 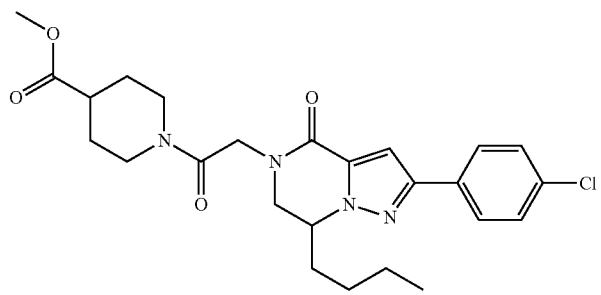 [SMILES: CCCCC1CN(CC(=O)N2CCC(C(=O)OC)CC2)C(=O)c2cc(-c3ccc(Cl)cc3)nn21] | B | 2.56 | 501 |
| I-0280 | 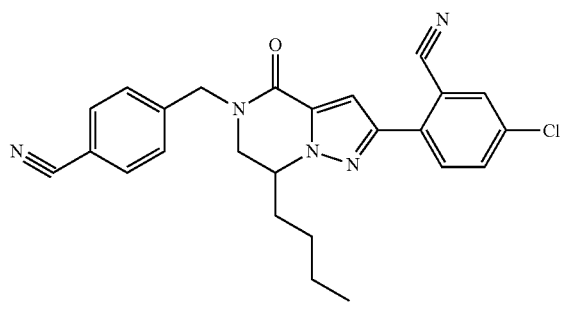 [SMILES: CCCCC1CN(Cc2ccc(C#N)cc2)C(=O)c2cc(-c3ccc(Cl)cc3C#N)nn21] | B | 2.56 | 444 |

TABLE 37-continued
| I-0281 | 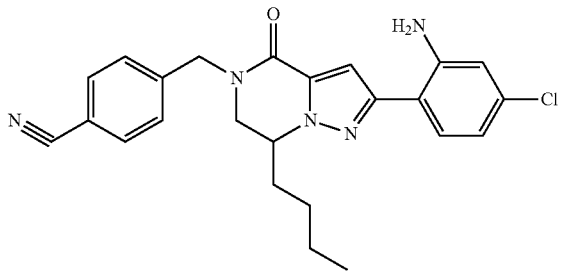 [SMILES: CCCCC1CN(Cc2ccc(C#N)cc2)C(=O)c2cc(-c3ccc(Cl)cc3N)nn21] | B | 2.47 | 434 |
TABLE 38
| I-0282 | 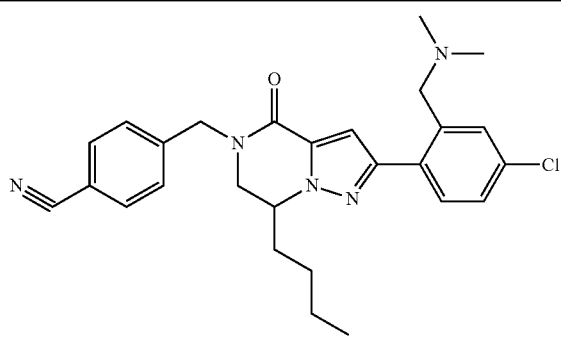 | B | 1.73 | 476 |
| I-0283 | 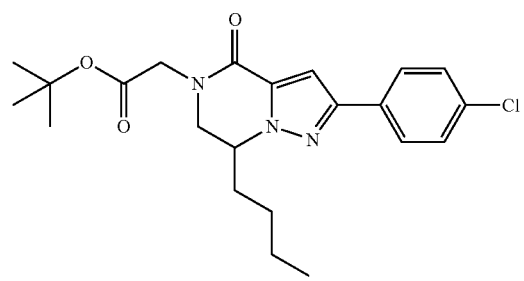 [SMILES: CCCCC1CN(CC(=O)OC(C)(C)C)C(=O)c2cc(-c3ccc(Cl)cc3)nn21] | B | 2.80 | 418 |
| I-0284 | 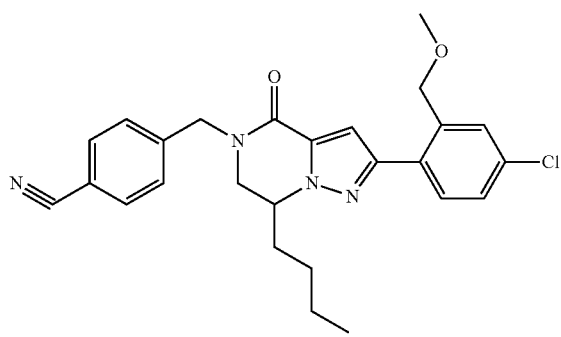 [SMILES: CCCCC1CN(Cc2ccc(C#N)cc2)C(=O)c2cc(-c3ccc(Cl)cc3COC)nn21] | B | 2.67 | 463 |
| I-0285 | 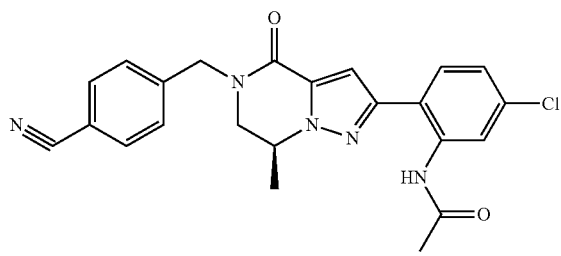 [SMILES: CC(=O)Nc1cc(Cl)ccc1-c1cc2n(n1)[C@@H](C)CN(Cc1ccc(C#N)cc1)C2=O] | B | 2.16 | 434 |

TABLE 38-continued
| I-0286 | 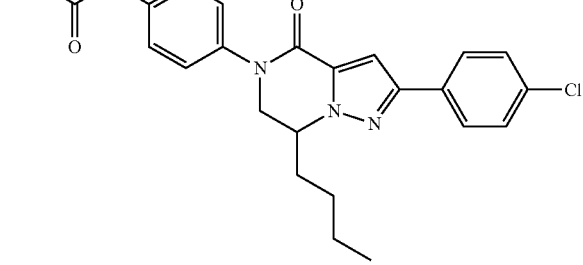 | A | 2.75 | 452 |
| I-0287 | 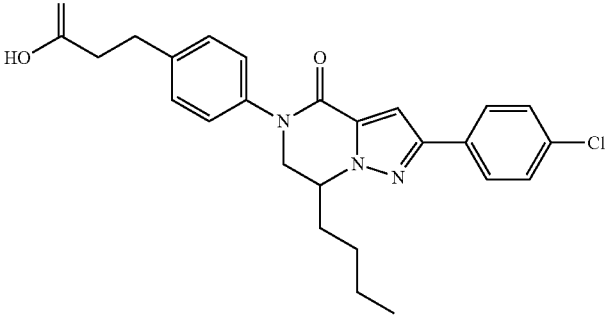 | A | 2.82 | 466 |
TABLE 39
| I-0288 | 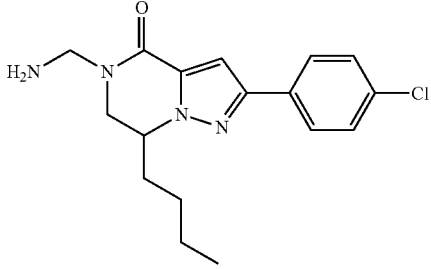 [SMILES: CCCCC1CN(CN)C(=O)c2cc(-c3ccc(Cl)cc3)nn21] | B | 1.77 | 333 |
| I-0289 | 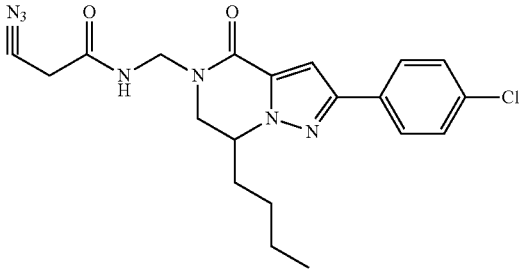 | B | 2.29 | 400 |
| I-0290 | 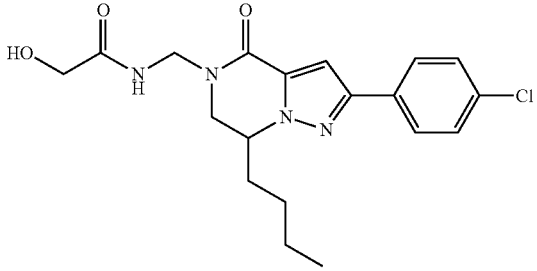 [SMILES: CCCCC1CN(CNC(=O)CO)C(=O)c2cc(-c3ccc(Cl)cc3)nn21] | B | 2.14 | 391 |

TABLE 39-continued
| I-0291 | 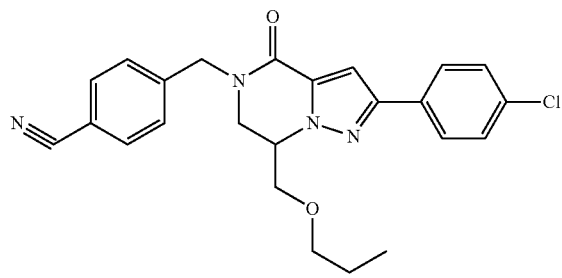 [SMILES: CCCOCC1CN(Cc2ccc(C#N)cc2)C(=O)c2cc(-c3ccc(Cl)cc3)nn21] | B | 2.53 | 435 |
| I-0292 | 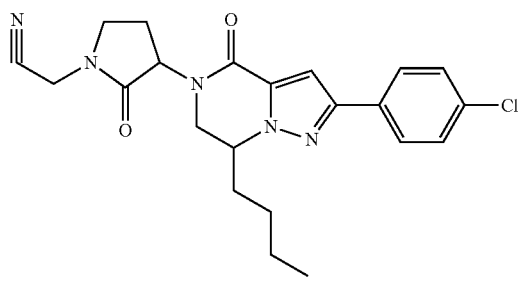 [SMILES: CCCCC1CN(C2CCN(CC#N)C2=O)C(=O)c2cc(-c3ccc(Cl)cc3)nn21] | B | 2.37 | 426 |
| I-0293 | 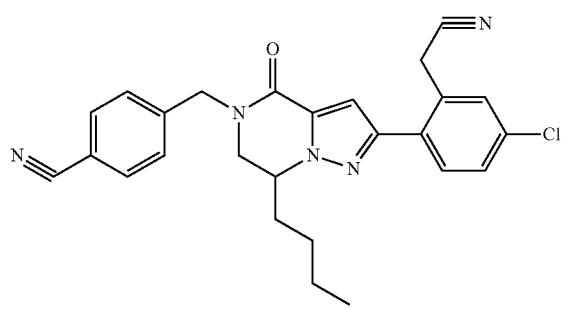 [SMILES: CCCCC1CN(Cc2ccc(C#N)cc2)C(=O)c2cc(-c3ccc(Cl)cc3CC#N)nn21] | B | 2.46 | 458 |
TABLE 40
| I-0294 | 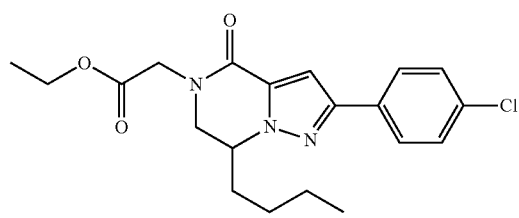 [SMILES: CCCCC1CN(CC(=O)OCC)C(=O)c2cc(-c3ccc(Cl)cc3)nn21] | B | 2.59 | 390 |
| I-0295 | 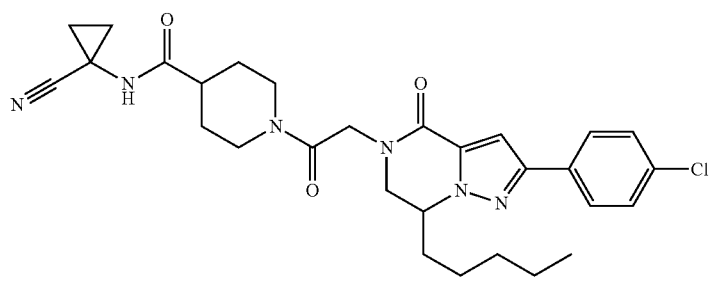 [SMILES: CCCCCC1CN(CC(=O)N2CCC(C(=O)NC3(C#N)CC3)CC2)C(=O)c2cc(-c3ccc(Cl)cc3)nn21] | B | 2.35 | 551 |

TABLE 40-continued
| | | | | |
|---|---|---|---|---|
| I-0296 | 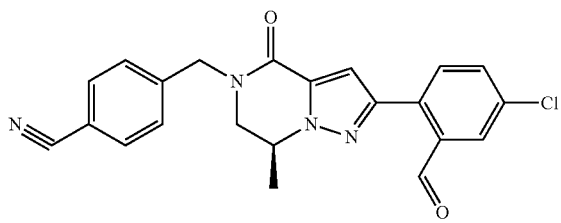 [SMILES: C[C@H]1CN(Cc2ccc(C#N)cc2)C(=O)c2cc(-c3ccc(Cl)cc3C=O)nn21] | B | 2.22 | 405 |
| I-0297 | 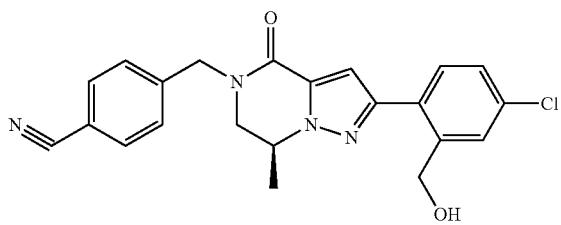 [SMILES: C[C@H]1CN(Cc2ccc(C#N)cc2)C(=O)c2cc(-c3ccc(Cl)cc3CO)nn21] | B | 2.03 | 407 |
| I-0298 | 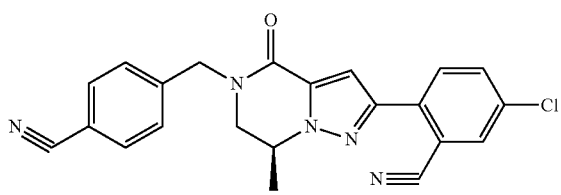 [SMILES: C[C@H]1CN(Cc2ccc(C#N)cc2)C(=O)c2cc(-c3ccc(Cl)cc3C#N)nn21] | B | 2.23 | 402 |
| I-0299 | 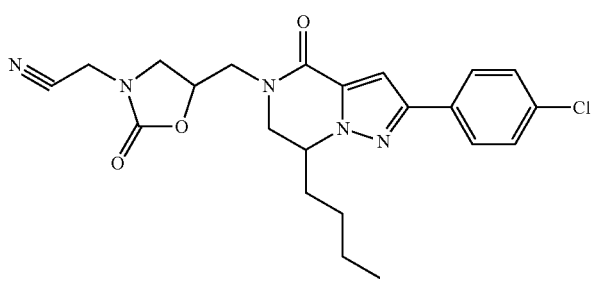 [SMILES: CCCCC1CN(CC2CN(CC#N)C(=O)O2)C(=O)c2cc(-c3ccc(Cl)cc3)nn21] | B | 2.34 | 442 |
| I-0300 | 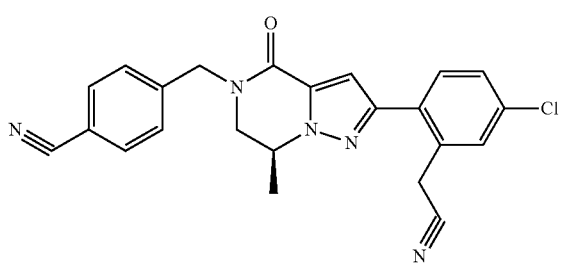 [SMILES: C[C@H]1CN(Cc2ccc(C#N)cc2)C(=O)c2cc(-c3ccc(Cl)cc3CC#N)nn21] | B | 2.19 | 416 |
TABLE 41
| | | | | |
|---|---|---|---|---|
| I-0301 | 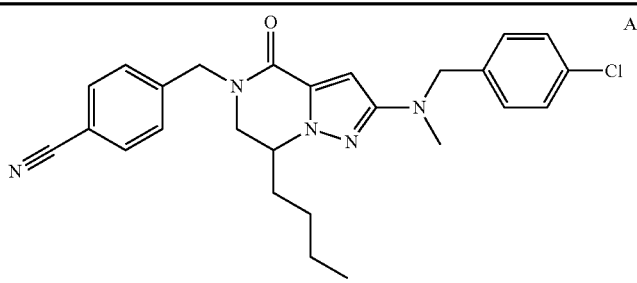 | A | 2.87 | 462 |

TABLE 41-continued
| I-0302 | 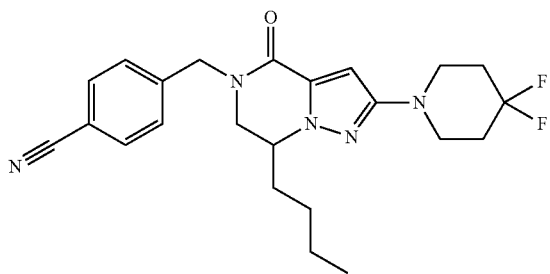 [SMILES: CCCCC1CN(Cc2ccc(C#N)cc2)C(=O)c2cc(N3CCC(F)(F)CC3)nn21] | A | 2.42 | 428 |
| I-0303 | 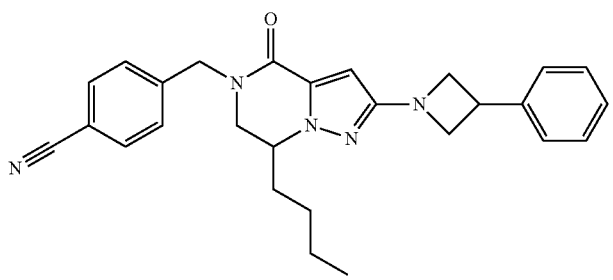 [SMILES: CCCCC1CN(Cc2ccc(C#N)cc2)C(=O)c2cc(N3CC(c4ccccc4)C3)nn21] | A | 2.59 | 440 |
| I-0304 | 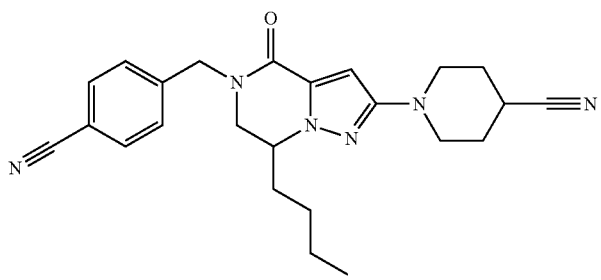 [SMILES: CCCCC1CN(Cc2ccc(C#N)cc2)C(=O)c2cc(N3CCC(C#N)CC3)nn21] | A | 2.17 | 417 |
| I-0305 | 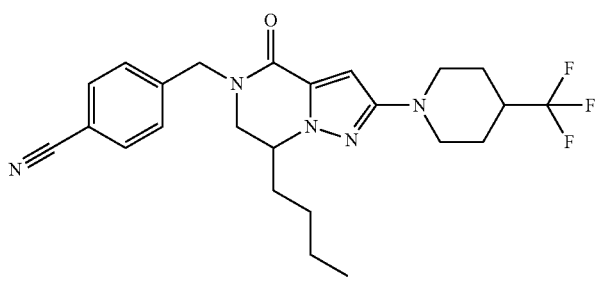 [SMILES: CCCCC1CN(Cc2ccc(C#N)cc2)C(=O)c2cc(N3CCC(C(F)(F)F)CC3)nn21] | A | 2.67 | 460 |
| I-0306 | 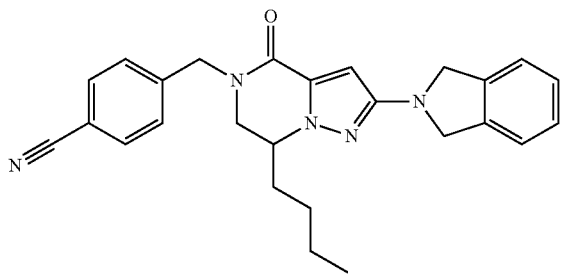 [SMILES: CCCCC1CN(Cc2ccc(C#N)cc2)C(=O)c2cc(N3Cc4ccccc4C3)nn21] | A | 2.63 | 426 |

TABLE 42
| | | | | |
|---|---|---|---|---|
| I-0307 | 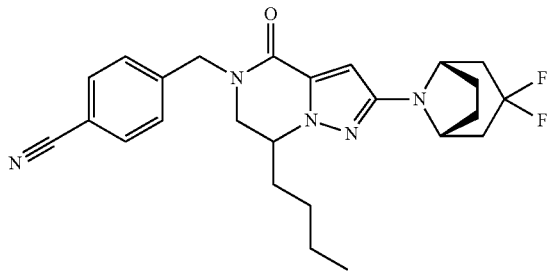 [SMILES: CCCCC1CN(Cc2ccc(C#N)cc2)C(=O)c2cc(N3[C@@H]4CC[C@H]3CC(F)(F)C4)nn21] | A | 2.58 | 454 |
| I-0308 | 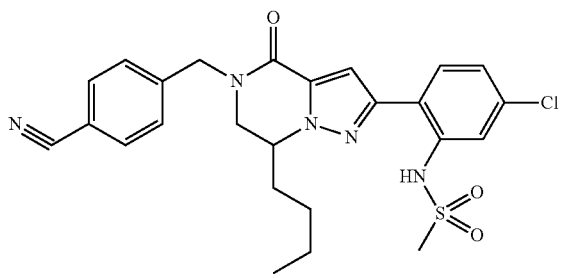 [SMILES: CCCCC1CN(Cc2ccc(C#N)cc2)C(=O)c2cc(-c3ccc(Cl)cc3NS(C)(=O)=O)nn21] | B | 2.45 | 512 |
| I-0309 | 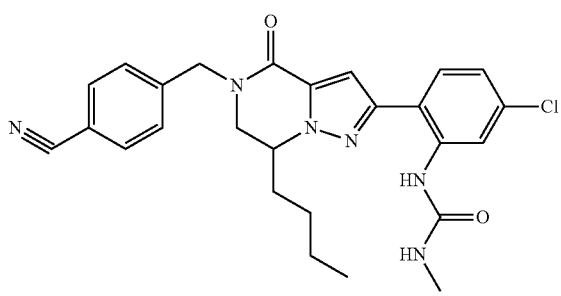 [SMILES: CCCCC1CN(Cc2ccc(C#N)cc2)C(=O)c2cc(-c3ccc(Cl)cc3NC(=O)NC)nn21] | B | 2.31 | 491 |
| I-0310 | 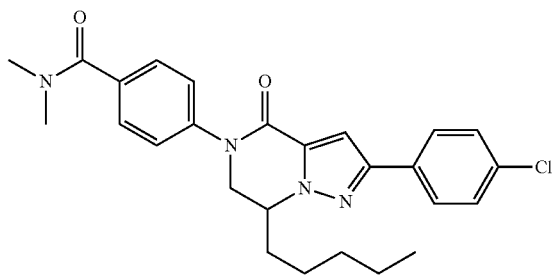 [SMILES: CCCCCC1CN(c2ccc(C(=O)N(C)C)cc2)C(=O)c2cc(-c3ccc(Cl)cc3)nn21] | A | 2.72 | 465 |
| I-0311 | 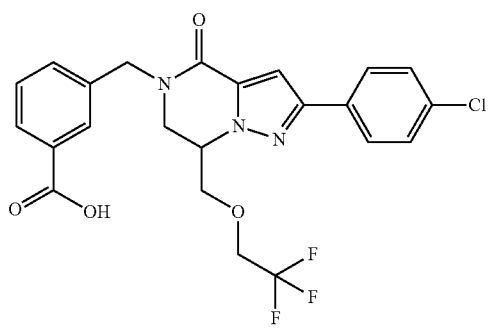 [SMILES: O=C(O)c1cccc(CN2CC(COCC(F)(F)F)n3nc(-c4ccc(Cl)cc4)cc3C2=O)c1] | A | 2.31 | 494 |

TABLE 42-continued
| I-0312 | 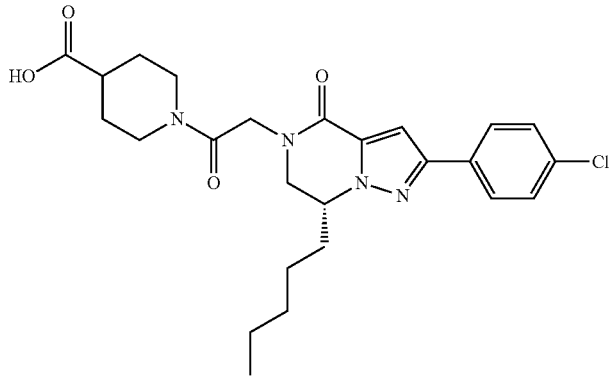 [SMILES: CCCCC[C@@H]1CN(CC(=O)N2CCC(C(=O)O)CC2)C(=O)c2cc(-c3ccc(Cl)cc3)nn21] | A | 2.33 | 487 |
TABLE 43
| I-0313 | 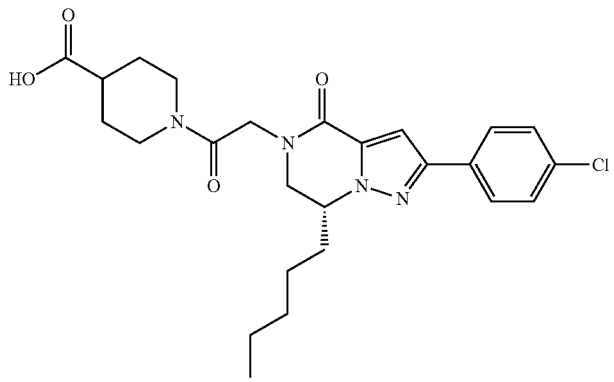 | A | 2.33 | 487 |
| I-0314 | | A | 2.16 | 482 |
| I-0315 | 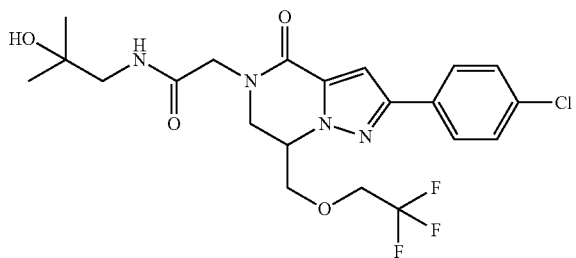 [SMILES: CC(C)(O)CNC(=O)CN1CC(COCC(F)(F)F)n2nc(-c3ccc(Cl)cc3)cc2C1=O] | A | 1.99 | 489 |

TABLE 43-continued
| I-0316 | 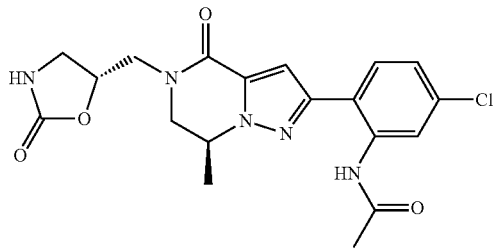 [SMILES: CC(=O)Nc1cc(Cl)ccc1-c1cc2n(n1)[C@@H](C)CN(C[C@H]1CNC(=O)O1)C2=O] | B | 1.70 | 418 |
| I-0317 | 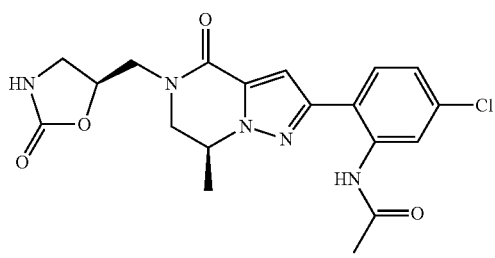 [SMILES: CC(=O)Nc1cc(Cl)ccc1-c1cc2n(n1)[C@@H](C)CN(C[C@@H]1CNC(=O)O1)C2=O] | B | 1.69 | 418 |
TABLE 44
| I-0318 | 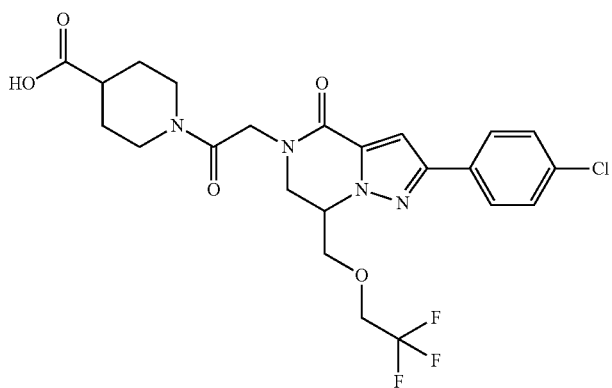 [SMILES: O=C(O)C1CCN(C(=O)CN2CC(COCC(F)(F)F)n3nc(-c4ccc(Cl)cc4)cc3C2=O)CC1] | A | 2.07 | 529 |
| I-0319 | 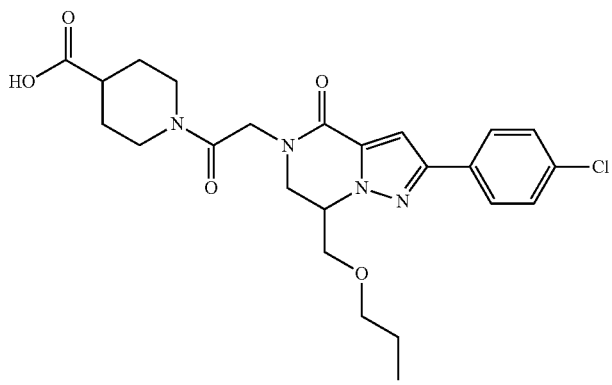 [SMILES: CCCOCC1CN(CC(=O)N2CCC(C(=O)O)CC2)C(=O)c2cc(-c3ccc(Cl)cc3)nn21] | A | 2.11 | 489 |
| I-0320 | 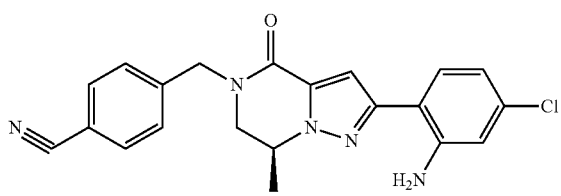 [SMILES: C[C@H]1CN(Cc2ccc(C#N)cc2)C(=O)c2cc(-c3ccc(Cl)cc3N)nn21] | B | 2.13 | 392 |

TABLE 44-continued

| | | | | |
|---|---|---|---|---|
| I-0321 | (structure) | B | 2.38 | 462 |
| I-0322 | (structure) | B | 2.33 | 460 |
| I-0323 | (structure) | B | 2.15 | 470 |
| I-0324 | (structure) | B | 2.52 | 475 |

TABLE 45

| | | | | |
|---|---|---|---|---|
| I-0325 | (structure) | B | 2.25 | 445 |

TABLE 45-continued
| | | | | |
|---|---|---|---|---|
| I-0326 | 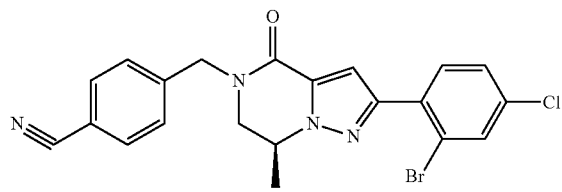 [SMILES: C[C@H]1CN(Cc2ccc(C#N)cc2)C(=O)c2cc(-c3ccc(Cl)cc3Br)nn21] | B | 2.45 | 456 |
| I-0327 | 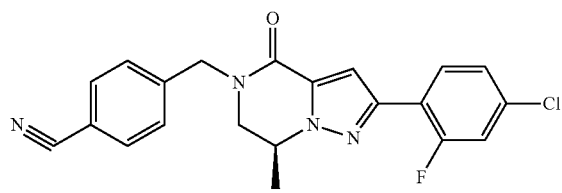 [SMILES: C[C@H]1CN(Cc2ccc(C#N)cc2)C(=O)c2cc(-c3ccc(Cl)cc3F)nn21] | B | 2.36 | 395 |
| I-0328 | 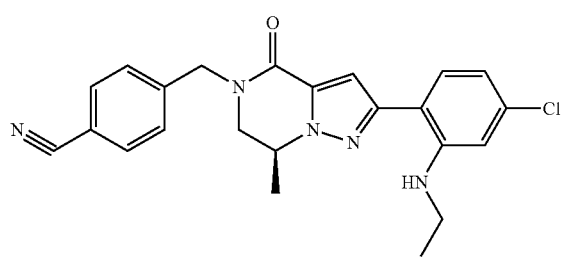 [SMILES: CCNc1cc(Cl)ccc1-c1cc2n(n1)[C@@H](C)CN(Cc1ccc(C#N)cc1)C2=O] | B | 2.55 | 420 |
| I-0329 | 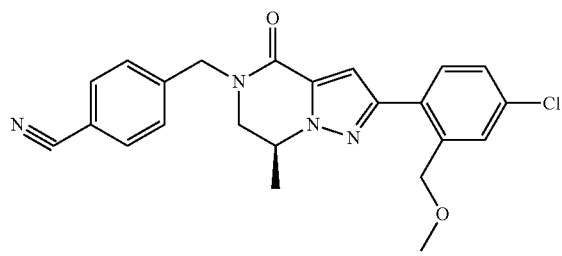 [SMILES: COCc1cc(Cl)ccc1-c1cc2n(n1)[C@@H](C)CN(Cc1ccc(C#N)cc1)C2=O] | B | 2.31 | 421 |
| I-0330 | 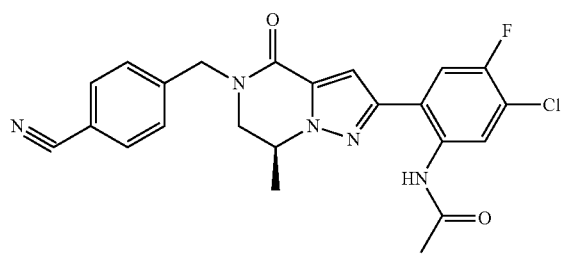 [SMILES: CC(=O)Nc1cc(Cl)c(F)cc1-c1cc2n(n1)[C@@H](C)CN(Cc1ccc(C#N)cc1)C2=O] | B | 2.16 | 452 |
| I-0331 | 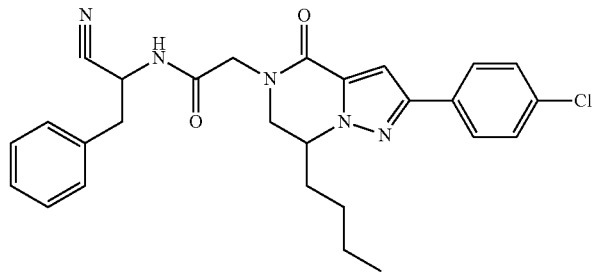 [SMILES: CCCCC1CN(CC(=O)NC(C#N)Cc2ccccc2)C(=O)c2cc(-c3ccc(Cl)cc3)nn21] | B | 2.57 | 490 |

TABLE 46

| ID | Structure | | | |
|---|---|---|---|---|
| I-0332 | (structure) | B | 1.54 | 477 |
| I-0333 | (structure) | B | 2.21 | 468 |
| I-0334 | (structure) | B | 2.26 | 484 |
| I-0335 | (structure) | B | 1.90 | 425 |
| I-0336 | (structure) | B | 1.86 | 448 |
| I-0337 | (structure) | B | 2.07 | 435 |

TABLE 47

| ID | Structure | | | |
|---|---|---|---|---|
| I-0338 | 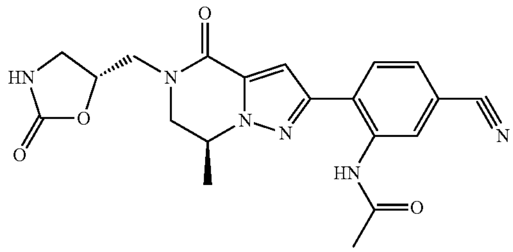 [SMILES: CC(=O)Nc1cc(C#N)ccc1-c1cc2n(n1)[C@@H](C)CN(C[C@H]1CNC(=O)O1)C2=O] | B | 1.45 | 409 |
| I-0339 | 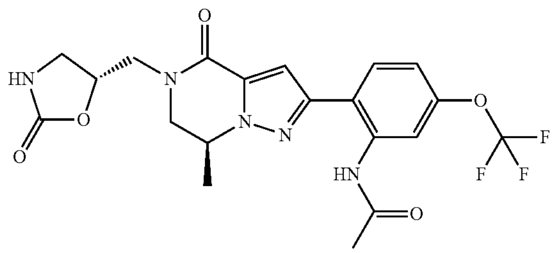 [SMILES: CC(=O)Nc1cc(OC(F)(F)F)ccc1-c1cc2n(n1)[C@@H](C)CN(C[C@H]1CNC(=O)O1)C2=O] | B | 1.85 | 468 |
| I-0340 | 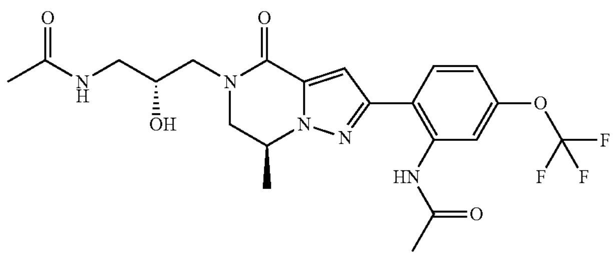 [SMILES: CC(=O)NC[C@@H](O)CN1C[C@H](C)n2nc(-c3ccc(OC(F)(F)F)cc3NC(C)=O)cc2C1=O] | B | 1.78 | 484 |
| I-0341 | 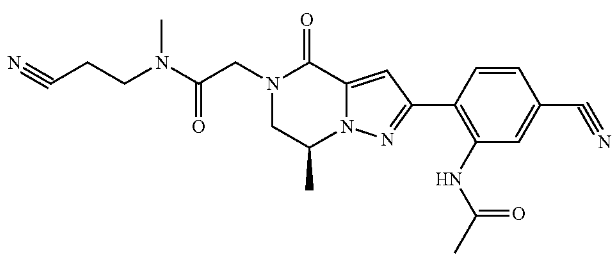 [SMILES: CC(=O)Nc1cc(C#N)ccc1-c1cc2n(n1)[C@@H](C)CN(CC(=O)N(C)CCC#N)C2=O] | B | 1.54 | 434 |
| I-0342 | 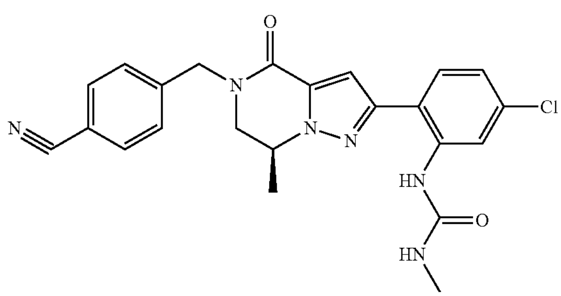 [SMILES: CNC(=O)Nc1cc(Cl)ccc1-c1cc2n(n1)[C@@H](C)CN(Cc1ccc(C#N)cc1)C2=O] | B | 2.04 | 449 |
| I-0343 | 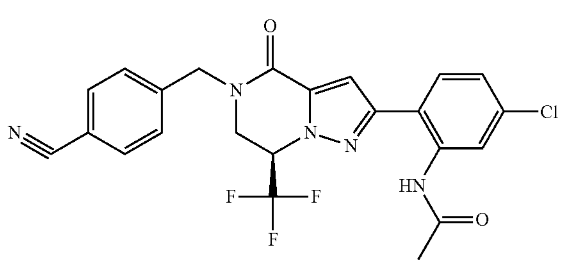 [SMILES: CC(=O)Nc1cc(Cl)ccc1-c1cc2n(n1)[C@@H](C(F)(F)F)CN(Cc1ccc(C#N)cc1)C2=O] | B | 2.25 | 487 |

TABLE 48

| | | | | |
|---|---|---|---|---|
| I-0344 | [structure] | B | 1.80 | 444 |
| I-0345 | [structure] | B | 2.17 | 503 |
| I-0346 | [structure] | B | 1.78 | 422 |
| I-0347 | [structure] | B | 1.73 | 464 |
| I-0348 | [structure] | B | 1.55 | 455 |
| I-0349 | [structure] | B | 2.65 | 434 |

TABLE 49
I-0350 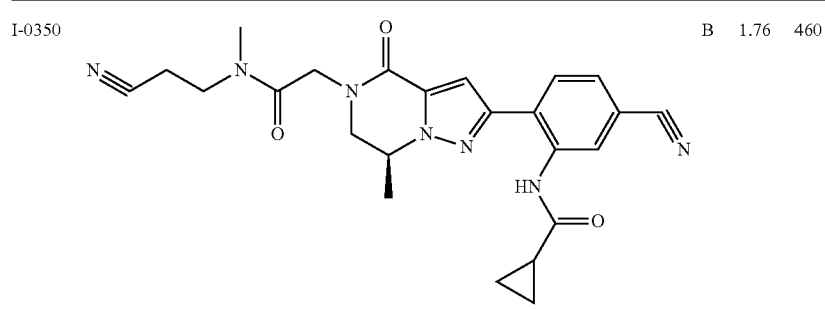 B 1.76 460
I-0351 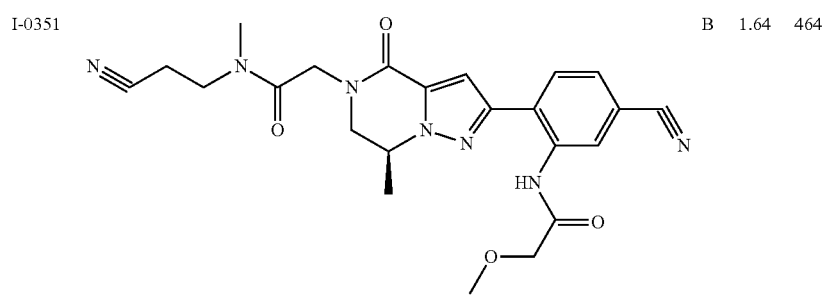 B 1.64 464
I-0352 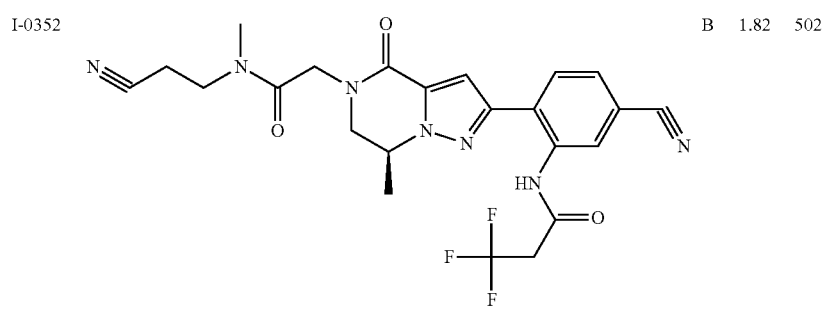 B 1.82 502
I-0353 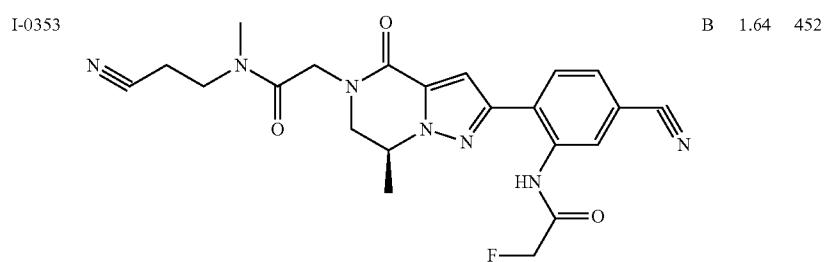 B 1.64 452
I-0354 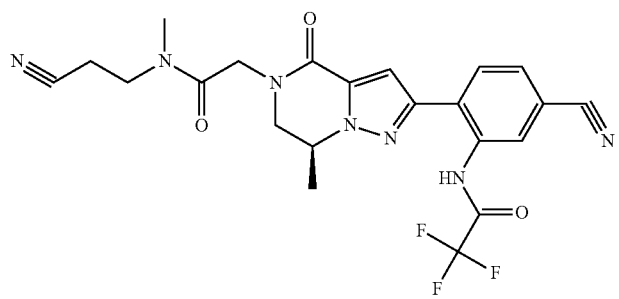 [SMILES: C[C@H]1CN(CC(=O)N(C)CCC#N)C(=O)c2cc(-c3ccc(C#N)cc3NC(=O)C(F)(F)F)nn21] B 1.97 488

TABLE 50
| | | | | |
|---|---|---|---|---|
| I-0355 | 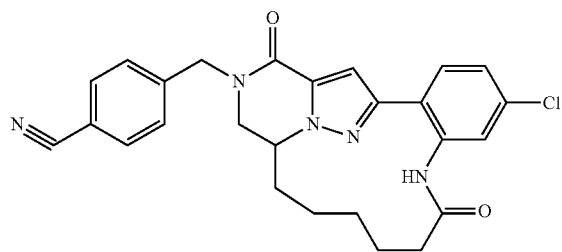 [SMILES: N#Cc1ccc(CN2CC3CCCCCC(=O)Nc4cc(Cl)ccc4-c4cc(n3n4)C2=O)cc1] | B | 2.21 | 474 |
| I-0356 | 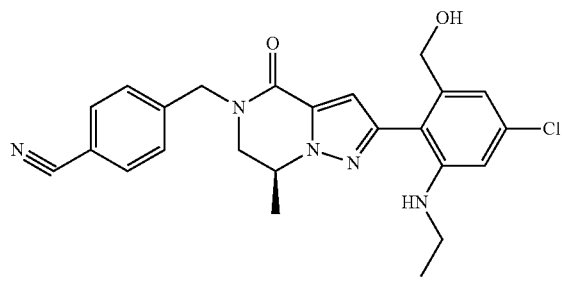 [SMILES: CCNc1cc(Cl)cc(CO)c1-c1cc2n(n1)[C@@H](C)CN(Cc1ccc(C#N)cc1)C2=O] | B | 2.1 | 450 |
| I-0357 | 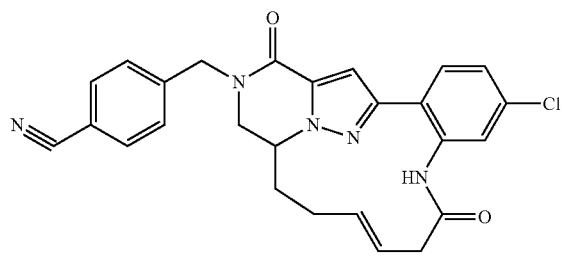 [SMILES: N#Cc1ccc(CN2CC3CC/C=C/CC(=O)Nc4cc(Cl)ccc4-c4cc(n3n4)C2=O)cc1] | B | 2.29 | 472 |
| I-0358 | 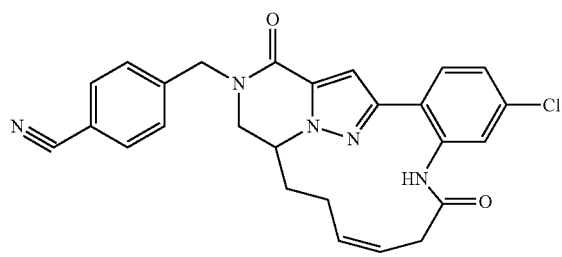 [SMILES: N#Cc1ccc(CN2CC3CC/C=C\CC(=O)Nc4cc(Cl)ccc4-c4cc(n3n4)C2=O)cc1] | B | 2.23 | 472 |
| I-0359 | 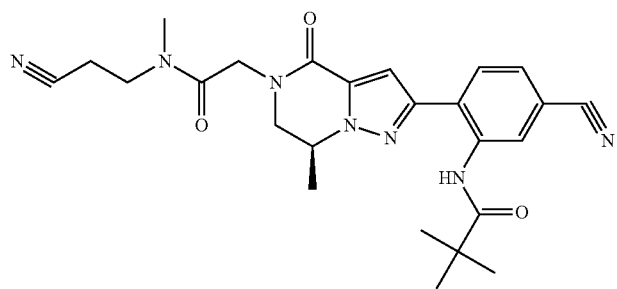 [SMILES: C[C@H]1CN(CC(=O)N(C)CCC#N)C(=O)c2cc(-c3ccc(C#N)cc3NC(=O)C(C)(C)C)nn21] | B | 1.94 | 476 |

TABLE 51
| I-0360 | 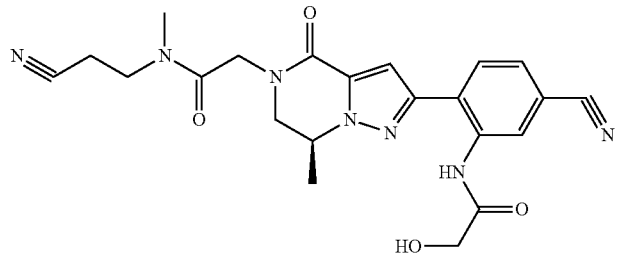 [SMILES: C[C@H]1CN(CC(=O)N(C)CCC#N)C(=O)c2cc(-c3ccc(C#N)cc3NC(=O)CO)nn21] | B | 1.42 | 450 |
| --- | --- | --- | --- | --- |
| I-0361 | 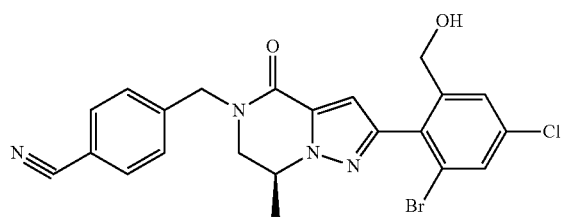 [SMILES: C[C@H]1CN(Cc2ccc(C#N)cc2)C(=O)c2cc(-c3c(Br)cc(Cl)cc3CO)nn21] | B | 2.11 | 486 |
TABLE 52
| I-0362 | 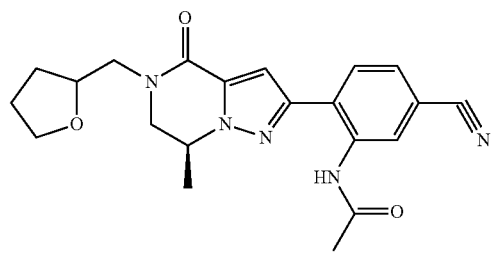 [SMILES: CC(=O)Nc1cc(C#N)ccc1-c1cc2n(n1)[C@@H](C)CN(CC1CCCO1)C2=O] | B | 1.80 | 394 |
| --- | --- | --- | --- | --- |
| I-0363 | 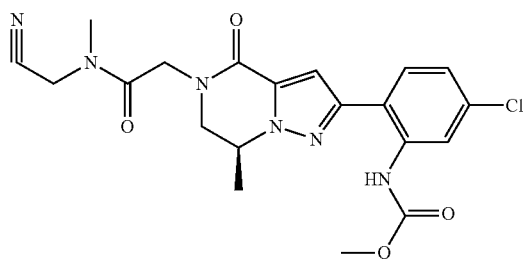 [SMILES: COC(=O)Nc1cc(Cl)ccc1-c1cc2n(n1)[C@@H](C)CN(CC(=O)N(C)CC#N)C2=O] | B | 2.04 | 445 |
| I-0364 | 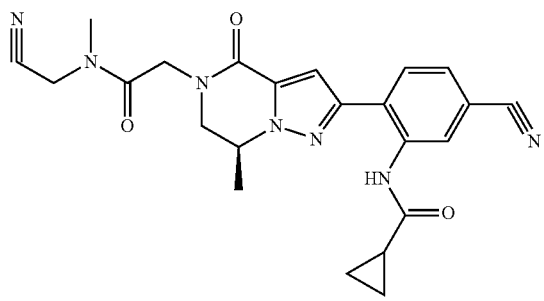 [SMILES: C[C@H]1CN(CC(=O)N(C)CC#N)C(=O)c2cc(-c3ccc(C#N)cc3NC(=O)C3CC3)nn21] | B | 1.79 | 446 |

TABLE 52-continued
| I-0365 | 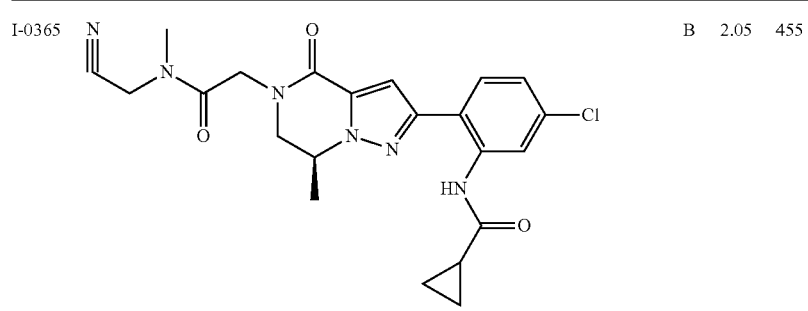 | B | 2.05 | 455 |
| I-0366 | 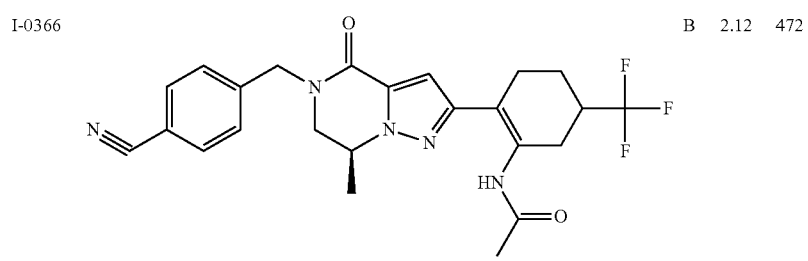 | B | 2.12 | 472 |
TABLE 53
| I-0367 | 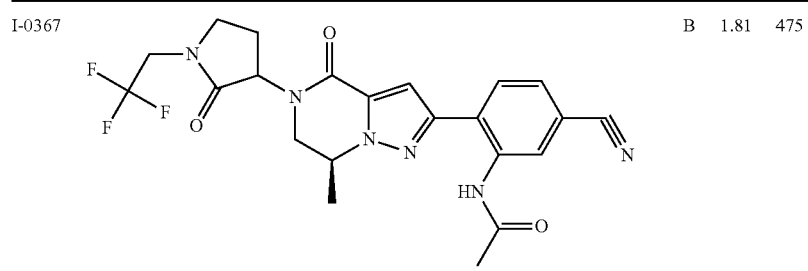 | B | 1.81 | 475 |
| I-0368 | 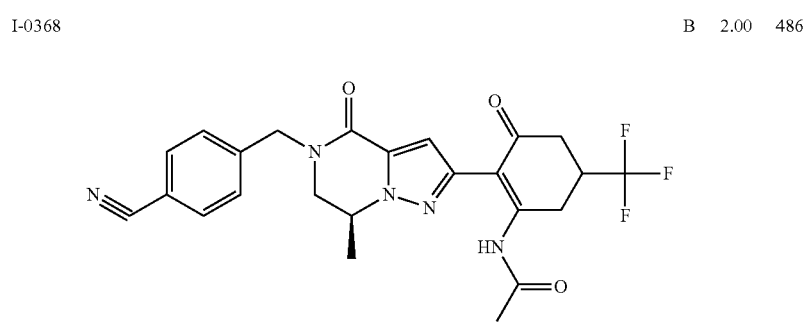 | B | 2.00 | 486 |
| I-0369 | 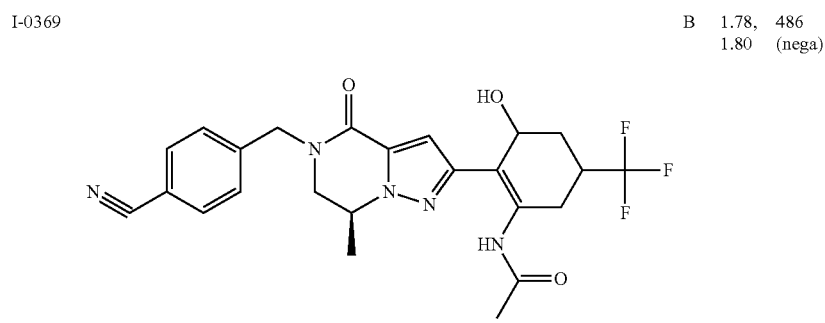 | B | 1.78, 1.80 | 486 (nega) |

TABLE 53-continued

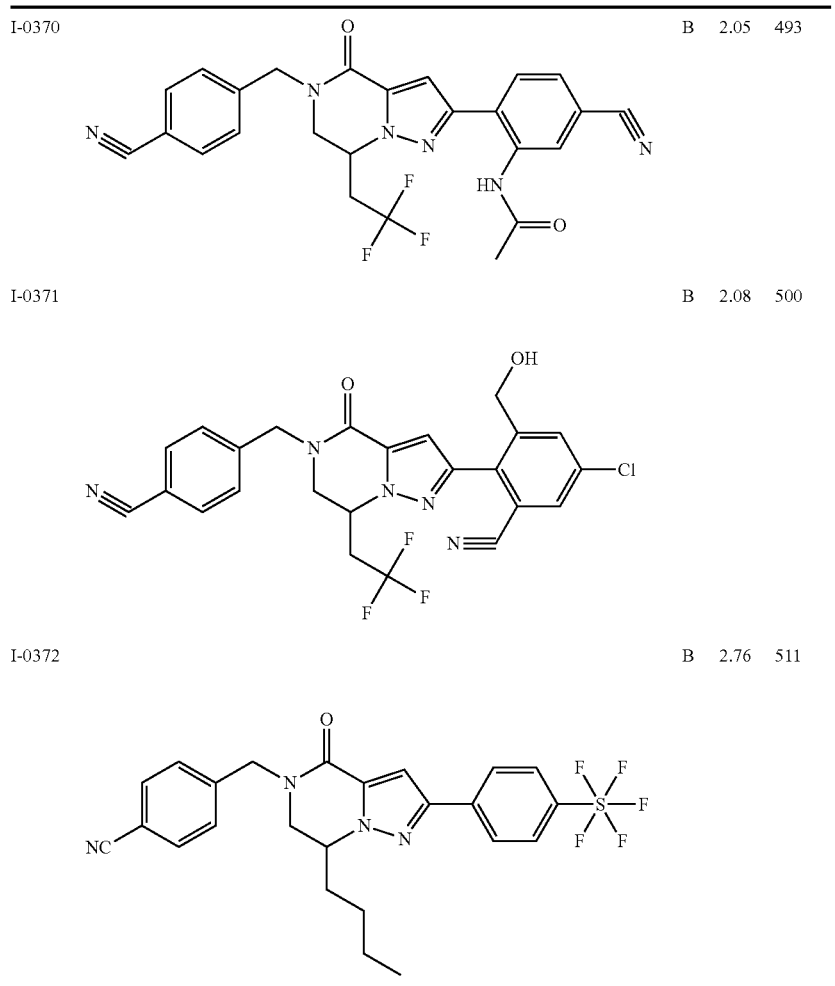

| | | | |
|---|---|---|---|
| I-0370 | | B 2.05 493 | |
| I-0371 | | B 2.08 500 | |
| I-0372 | | B 2.76 511 | |

Test Example 1 (Method A) Evaluation of Aoutotaxin Inhibitor

Solution A containing 25 mM Tris-HCl buffer (pH7.5), 100 mM NaCl, 5 mM MgCl2, and 0.1% BSA was prepared. Mouse autotaxin enzyme (purchased from R&D system) was diluted with Solution A, and 5 µl of which was added to a solution of test compound in DMSO. Furthermore, 5 µl of 0.5 µM TG-mTMP in Solution A was added and allowed react at room temperature for 2 hours. 5 µl of 150 mM EDTA in Solution A was added to quench the reaction, and a fluorescent dye TokyoGreen, which was produced by the reaction, was detected. The fluorescence was detected using ViewLux (PerkinElmer, Inc.) with an excitation wavelength of 480 nm and a fluorescence wavelength of 540 nm. The percent inhibition of the test compound was calculated by assuming the sample with no test compound as 0% inhibition and the test sample with no enzyme as 100% inhibition, and the percent inhibitions at different concentrations of the test compound were plotted to obtain a concentration-dependent curve. The IC50 value, which is the concentration of the test compound that resulted in 50% inhibition, was determined from the curve.

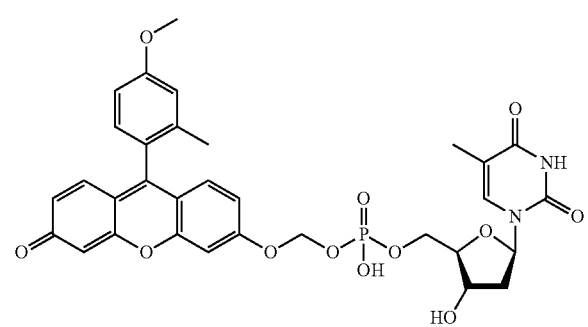

TG-mTMP

Test Example 2 (Method B) Evaluation of Autotaxin Inhibitor

Solution A containing 25 mM Tris-HCl buffer (pH7.5), 100 mM NaCl, 5 mM MgCl2, 0.1% BSA was prepared. Human autotaxin enzyme (purchased from R&D System) was diluted with Solution A, and 5 µl of which was added to a solution of test compound in DMSO. Furthermore, 5 µl of 0.5 µM TG-mTMP in Solution A was added and allowed to react at room temperature for 2 hours. 5 µl of 150 mM EDTA in Solution A was added to quench the reaction, and the fluorescent dye TokyoGreen, which was produced by the reaction, was detected. The fluorescence was detected using ViewLux (PerkinElmer, Inc.) with an excitation wavelength of 480 nm and a fluorescence wavelength of 540 nm.

The percent inhibition of the test compound was calculated by assuming the sample with no test compound as 0% inhibition and the sample with no enzyme as 100% inhibition, and the percent inhibitions at different concentrations of the test compound were plotted to obtain a concentration-dependent curve. The IC50 value, which is the concentration of the test compound that resulted in 50% inhibition, was determined from the curve.

Test Example 3 (Method C) Evaluation of Autotaxin Inhibitor

Solution B containing 100 mM Tris-HCl buffer (pH7.5), 150 mM NaCl, 5 mM MgCl2, and 0.05% Triton X-100 was prepared. Human autotaxin enzyme (purchased from R&D System) was diluted with Solution B, and 2.5 µl of which was added to a solution of test compound in DMSO. Furthermore, 2.5 µl of 200 µM 18:0 Lyso PC (purchased from Avanti Polar Lipids) in Solution B was added and allowed to react at room temperature for 2 hours. After completion of the reaction, 15 µl of the coline assay reagent (100 mM Tris-HCl buffer (pH7.5), 5 mM MgCl2, 77 µg/ml coline oxidase, 10 µg/ml peroxydase, 25 µM 10-acetyl-3,7-dihydroxyphenoxazine, and excess autotaxin inhibitor) was added and allowed to react at room temperature for 20 minutes. The fluorescent dye Resorufin, which was produced by the reaction, was detected. The fluorescence was detected using ViewLux (PerkinElmer, Inc.) with a excitation wavelength of 531 nm and a fluorescence wavelength of 598 nm.

The percent inhibition of the test compound was calculated by assuming the sample with no test compound as 0% inhibition and the sample with no enzyme as 100% inhibition, and the percent inhibitions at different concentrations of the test compound were plotted to obtain a concentration-dependent curve. The IC50 value, which is the concentration of the test compound that resulted in 50% inhibition, was determined from the curve.

The results obtained by the test method described the above Test Example 3 are shown in the following tables.
Test Method:
Method A: Test Example 1; Method B: Test Example 2; Method C: Test Example 3 Enzyme inhibitory activity:
A: IC50<10 nM, B: 10 nM≤ IC50<100 nM, C: 100 nM≤IC50<1000 nM, D: 1000 nM≤IC50

TABLE 54

| Compound No. | Inhibitory activity |
|---|---|
| I-0001 | D |
| I-0002 | B |
| I-0003 | D |
| I-0004 | B |
| I-0005 | C |
| I-0006 | C |
| I-0007 | A |
| I-0008 | B |
| I-0009 | C |
| I-0010 | D |
| I-0011 | D |
| I-0012 | C |
| I-0013 | D |
| I-0014 | D |
| I-0015 | D |
| I-0016 | D |
| I-0017 | D |
| I-0018 | D |
| I-0019 | D |
| I-0020 | D |
| I-0021 | D |
| I-0022 | D |
| I-0023 | D |
| I-0024 | D |
| I-0025 | C |
| I-0026 | D |
| I-0027 | D |
| I-0028 | D |
| I-0029 | D |
| I-0030 | D |
| I-0031 | D |
| I-0032 | C |
| I-0033 | D |
| I-0034 | D |
| I-0035 | C |
| I-0036 | B |
| I-0037 | B |
| I-0038 | C |
| I-0039 | C |
| I-0040 | C |
| I-0041 | B |
| I-0042 | C |
| I-0043 | B |
| I-0044 | B |
| I-0045 | C |
| I-0046 | C |
| I-0047 | B |
| I-0048 | B |
| I-0049 | B |
| I-0050 | B |
| I-0051 | C |
| I-0052 | A |
| I-0053 | B |
| I-0054 | C |
| I-0055 | A |
| I-0056 | B |
| I-0057 | C |
| I-0058 | C |
| I-0059 | B |
| I-0060 | C |
| I-0061 | B |
| I-0062 | A |
| I-0063 | B |
| I-0064 | A |
| I-0065 | B |
| I-0066 | B |
| I-0067 | C |
| I-0068 | A |
| I-0069 | A |
| I-0070 | B |
| I-0071 | C |
| I-0072 | D |
| I-0073 | D |
| I-0074 | C |
| I-0075 | B |
| I-0076 | C |
| I-0077 | C |
| I-0078 | D |
| I-0079 | C |
| I-0080 | B |
| I-0081 | C |
| I-0082 | B |
| I-0083 | C |
| I-0084 | D |
| I-0085 | D |
| I-0086 | C |
| I-0087 | D |
| I-0088 | C |
| I-0089 | B |
| I-0090 | B |
| I-0091 | C |
| I-0092 | C |

TABLE 54-continued

| Compound No. | Inhibitory activity |
|---|---|
| I-0093 | C |
| I-0094 | B |
| I-0095 | B |
| I-0096 | C |
| I-0097 | C |
| I-0098 | C |
| I-0099 | C |
| I-0100 | C |
| I-0101 | C |
| I-0102 | D |
| I-0103 | D |
| I-0104 | D |
| I-0105 | C |
| I-0106 | C |
| I-0107 | C |
| I-0108 | C |
| I-0109 | D |
| I-0110 | C |
| I-0111 | D |
| I-0112 | C |
| I-0113 | B |
| I-0114 | D |
| I-0115 | C |
| I-0116 | B |
| I-0117 | C |
| I-0118 | D |
| I-0119 | B |
| I-0120 | B |

TABLE 55

| Compound No. | Inhibitory activity |
|---|---|
| I-0121 | B |
| I-0122 | B |
| I-0123 | D |
| I-0124 | A |
| I-0125 | D |
| I-0126 | D |
| I-0127 | D |
| I-0128 | D |
| I-0129 | D |
| I-0130 | C |
| I-0131 | C |
| I-0132 | B |
| I-0133 | D |
| I-0134 | D |
| I-0135 | C |
| I-0136 | D |
| I-0137 | B |
| I-0138 | C |
| I-0139 | D |
| I-0140 | D |
| I-0141 | C |
| I-0142 | C |
| I-0143 | D |
| I-0144 | D |
| I-0145 | C |
| I-0146 | D |
| I-0147 | C |
| I-0148 | A |
| I-0149 | C |
| I-0150 | A |
| I-0151 | B |
| I-0152 | D |
| I-0153 | D |
| I-0154 | D |
| I-0155 | D |
| I-0156 | D |
| I-0157 | D |
| I-0158 | C |
| I-0159 | D |
| I-0160 | B |
| I-0161 | C |
| I-0162 | D |

TABLE 55-continued

| Compound No. | Inhibitory activity |
|---|---|
| I-0163 | C |
| I-0164 | C |
| I-0165 | D |
| I-0166 | D |
| I-0167 | D |
| I-0168 | D |
| I-0169 | D |
| I-0170 | B |
| I-0171 | D |
| I-0172 | D |
| I-0173 | C |
| I-0174 | D |
| I-0175 | B |
| I-0176 | A |
| I-0177 | D |
| I-0178 | C |
| I-0179 | C |
| I-0180 | D |
| I-0181 | C |
| I-0182 | D |
| I-0183 | B |
| I-0184 | A |
| I-0185 | B |
| I-0186 | D |
| I-0187 | C |
| I-0188 | B |
| I-0189 | B |
| I-0190 | B |
| I-0191 | C |
| I-0192 | C |
| I-0193 | C |
| I-0194 | C |
| I-0195 | C |
| I-0196 | C |
| I-0197 | D |
| I-0198 | D |
| I-0199 | D |
| I-0200 | D |

TABLE 56

| Compound No. | Inhibitory activity |
|---|---|
| I-0201 | B |
| I-0202 | D |
| I-0203 | D |
| I-0204 | B |
| I-0205 | C |
| I-0206 | D |
| I-0207 | B |
| I-0208 | B |
| I-0209 | B |
| I-0210 | B |
| I-0211 | B |
| I-0212 | C |
| I-0213 | B |
| I-0214 | B |
| I-0215 | C |
| I-0216 | C |
| I-0217 | C |
| I-0218 | C |
| I-0219 | C |
| I-0220 | C |
| I-0221 | C |
| I-0222 | C |
| I-0223 | C |
| I-0224 | C |
| I-0225 | C |
| I-0226 | C |
| I-0227 | C |
| I-0228 | C |
| I-0229 | C |
| I-0230 | B |
| I-0231 | D |
| I-0232 | B |

TABLE 56-continued

| Compound No. | Inhibitory activity |
| --- | --- |
| I-0233 | B |
| I-0234 | C |
| I-0235 | B |
| I-0236 | D |
| I-0237 | C |
| I-0238 | C |
| I-0239 | B |
| I-0240 | C |
| I-0241 | C |
| I-0242 | C |
| I-0243 | C |
| I-0244 | C |
| I-0245 | C |
| I-0246 | B |
| I-0247 | B |
| I-0248 | C |
| I-0249 | B |
| I-0250 | B |
| I-0251 | C |
| I-0252 | B |
| I-0253 | D |
| I-0254 | B |
| I-0255 | B |
| I-0256 | C |
| I-0257 | C |
| I-0258 | C |
| I-0259 | C |
| I-0260 | C |
| I-0261 | C |
| I-0262 | D |
| I-0263 | C |
| I-0264 | B |
| I-0265 | B |
| I-0266 | B |
| I-0267 | C |
| I-0268 | B |
| I-0269 | B |
| I-0270 | C |
| I-0271 | C |
| I-0272 | D |
| I-0273 | C |
| I-0274 | C |
| I-0275 | B |
| I-0276 | C |
| I-0277 | C |
| I-0278 | D |
| I-0279 | B |
| I-0280 | B |
| I-0281 | C |
| I-0282 | D |
| I-0283 | C |
| I-0284 | D |
| I-0285 | A |
| I-0286 | D |
| I-0287 | D |
| I-0288 | D |
| I-0289 | B |
| I-0290 | C |
| I-0291 | B |
| I-0292 | B |
| I-0293 | C |
| I-0294 | B |
| I-0295 | B |
| I-0296 | C |
| I-0297 | C |
| I-0298 | C |
| I-0299 | B |
| I-0300 | D |
| I-0301 | D |
| I-0302 | C |
| I-0303 | D |
| I-0304 | D |
| I-0305 | C |
| I-0306 | D |
| I-0307 | D |
| I-0308 | D |
| I-0309 | C |
| I-0310 | D |

TABLE 56-continued

| Compound No. | Inhibitory activity |
| --- | --- |
| I-0311 | A |
| I-0312 | B |
| I-0313 | A |
| I-0314 | C |
| I-0315 | C |
| I-0316 | B |
| I-0317 | C |
| I-0318 | A |
| I-0319 | A |
| I-0320 | D |

TABLE 57

| Compound No. | Inhibitory activity |
| --- | --- |
| I-0321 | B |
| I-0322 | B |
| I-0323 | C |
| I-0324 | D |
| I-0325 | D |
| I-0326 | D |
| I-0327 | D |
| I-0328 | C |
| I-0329 | D |
| I-0330 | A |
| I-0331 | C |
| I-0332 | B |
| I-0333 | B |
| I-0334 | A |
| I-0335 | A |
| I-0336 | D |
| I-0337 | B |
| I-0338 | B |
| I-0339 | A |
| I-0340 | B |
| I-0341 | B |
| I-0342 | C |
| I-0343 | B |
| I-0344 | A |
| I-0345 | A |
| I-0346 | C |
| I-0347 | B |
| I-0348 | B |
| I-0349 | C |
| I-0350 | A |
| I-0351 | A |
| I-0352 | B |
| I-0353 | A |
| I-0354 | A |
| I-0355 | A |
| I-0356 | A |
| I-0357 | A |
| I-0358 | B |
| I-0359 | B |
| I-0360 | C |
| I-0361 | C |

TABLE 58

| Compound No. | Inhibitory activity |
| --- | --- |
| I-0362 | B |
| I-0363 | B |
| I-0364 | B |
| I-0365 | B |
| I-0366 | B |
| I-0367 | B |
| I-0368 | B |
| I-0369 | C |
| I-0370 | B |
| I-0371 | C |
| I-0372 | C |

Test Example 4: CYP Inhibition Test

Using commercially available pooled human hepatic microsome, the compound was tested to assess inhibitory effect on the typical substrate metabolism reactions of human main five CYP enzyme forms (CYP1A2, 2C9, 2C19, 2D6, 3A4), specifically, 7-ethoxyresorufin O-deethylation (CYP1A2), tolbutamide methyl-hydroxylation (CYP2C9), mephenyloin 4'-hydroxylation (CYP2C19), dextromethorphan O-demethylation (CYP2D6) terfenedine hydroxylation (CYP3A4).

The reaction conditions were as follows.
Substrates:
  0.5 µmol/L ethoxyresorufin (CYP1A2),
  100 µmol/L tolbutamide (CYP2C9),
  50 µmol/L S-mephenitoin (CYP2C19),
  5 µmol/L dextromethorphan (CYP2D6),
  1 µmol/L terfenadine (CYP3A4);
Reaction Time: 15 minutes;
Reaction Temperature: 37° C.;
Enzyme: pooled human hepatic microsome 0.2 mg protein/mL;
Concentration of Test Compound: 1, 5, 10, 20 µmol/L (four points).

A test sample, which contains the substrate, human hepatic microsome and test compound at the amounts as described above in 50 mM Hepes buffer, was added to a 96-well plate. The cofactor NADPH was added to initiate metabolism reaction. After the incubation at 37° C. for 15 minutes, a methanol/acetonitrile=1/1 (v/v) solution was added to stop the reaction. After centrifugation at 3000 rpm for 15 minutes, resotufin (CYP1A2 metabolite) in the supernatant was quantified by fluorescent multilabel counter. Tributamide hydroxide (CYP2C9 metabolite), mephenyloin 4' hydroxide (CYP2C19 metabolite), dextromethorphan (CYP2D6 metabolite) and terfenadine alcohol (CYP3A4 metabolite) were determined by LC/MS/MS.

Only DMSO, which was the solvent for the test compound, was added to the reaction system as the control (100%). For each concentration of the test compound, the remaining activity (%) was calculated, and the IC50 was calculated by reverse presumption by a logistic model using the concentration and the inhibition rate.

Test Example 5: Metabolic Stability

Assessment of Metabolic Stability in Hepatic Microsomes:

To tris-hydrochloric acid buffer (pH 7.4), were added NADPH (the final concentration was 1 mM in case of oxidative metabolism), hepatic microsomes (the final concentration was 0.5 mg protein/mL) and test compound (the final concentration was 2 µM), and the mixture was reacted at 37° C. for 0 and 30 minutes. In case of conjugated glucuronic acid, UDPGA (the final concentration was 5 mM) was added instead of NADPH. The reaction was stopped by addition of acetonitrile/methanol=1/1(v/v) (2 parts by volume of the reaction solution). After the centrifugation, the supernatant was measured by HPLC. By comparing the results obtained from the reactions for 0 and 30 minutes, the loss of the compound by metabolic reaction was calculated to assess the metabolic stability of the compound of the invention.

Test Example 6: Powder Solubility Test

Appropriate amount of test sample was put into appropriate container. To the container was added 200 µL each of JP-1 solution (sodium chloride 2.0 g, hydrochloric acid 7.0 mL and water to reach 1000 mL), JP-2 solution (phosphate buffer (pH 6.8) 500 mL and water 500 mL) and 20 mmol/L TCA (sodium taurocholate)/JP-2 solution (TCA 1.08 g and water to reach 100 mL). In the case that the test compound was dissolved after the addition of the test solution, bulk powder was added as appropriate. The container was sealed and shaken for 1 hour at 37° C. The mixture was filtered, and 100 µL of methanol was added to each 100 µL aliquot of the filtrate to make the filtrates two-fold diluted. The dilution ratio was changed if necessary. After checking if any bubble or precipitate occurred, the container was sealed and shaken. Quantification was performed by absolute calibration method using HPLC.

FORMULATION EXAMPLES

The following Formulation Examples are only exemplified and not intended to limit the scope of the invention.

Formulation Example 1: Tablets

| | |
|---|---|
| Compound of formula (I) | 15 mg |
| Starch | 15 mg |
| Lactose | 15 mg |
| Crystalline cellulose | 19 mg |
| Polyvinyl alcohol | 3 mg |
| Distilled water | 30 ml |
| Calcium stearate | 3 mg |

The above ingredients except calcium stearate are uniformly mixed and milled to granylate, and dried to obtain a suitable size of granules. Then, the granules are added with calcium stearate and compressed to form a tablet.

Formulation Examples 2: Capsules

| | |
|---|---|
| Compound of formula (I) | 10 mg |
| Magnesium stearate | 10 mg |
| Lactose | 80 mg |

The above ingredients are mixed uniformly to obtain powders or fine granules, which are then filled in a capsule.

Formulation Examples 3: Granules

| | |
|---|---|
| Compound of formula (I) | 30 g |
| Lactose | 265 g |
| Magnesium stearate | 5 g |

The above ingredients are mixed uniformly and compressed. The compressed mixture is milled, granulated and stirred to obtain the desired size of granules.

INDUSTRIAL APPLICABILITY

The present invention is applicable in the pharmaceutical field, for example, in the development and production of medicaments for the treatment of fibrotic diseases.

The invention claimed is:
1. A compound of formula (I) or a pharmaceutical acceptable salt thereof:

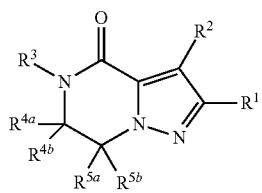

(I)

wherein
R$^1$ is substituted or unsubstituted phenyl,
R$^2$ is hydrogen,
R$^3$ is hydrogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkylcarbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclyl carbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkyl sulfonyl, substituted or unsubstituted alkenylsulfonyl, substituted or unsubstituted alkynylsulfonyl, substituted or unsubstituted non-aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl,
R$^{4a}$ and R$^{4b}$ are each independently hydrogen, halogen, hydroxy, cyano, formyl, carboxy, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted amino, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy, substituted or unsubstituted aromatic heterocyclyloxy, substituted or unsubstituted alkylthio, substituted or unsubstituted alkenylthio, substituted or unsubstituted alkynylthio, substituted or unsubstituted non-aromatic carbocyclylthio, substituted or unsubstituted aromatic carbocyclylthio, substituted or unsubstituted non-aromatic heterocyclylthio, substituted or unsubstituted aromatic heterocyclylthio, substituted or unsubstituted alkyl carbonyl, substituted or unsubstituted alkenylcarbonyl, substituted or unsubstituted alkynylcarbonyl, substituted or unsubstituted non-aromatic carbocyclylcarbonyl, substituted or unsubstituted aromatic carbocyclylcarbonyl, substituted or unsubstituted non-aromatic heterocyclylcarbonyl, substituted or unsubstituted aromatic heterocyclylcarbonyl, substituted or unsubstituted alkyloxycarbonyl, substituted or unsubstituted alkenyloxycarbonyl, substituted or unsubstituted alkynyloxycarbonyl, substituted or unsubstituted non-aromatic carbocyclyloxycarbonyl, substituted or unsubstituted aromatic carbocyclyloxycarbonyl, substituted or unsubstituted non-aromatic heterocyclyloxycarbonyl, substituted or unsubstituted aromatic heterocyclyloxycarbonyl, substituted or unsubstituted carbamoyl, substituted or unsubstituted sulfamoyl, substituted or unsubstituted alkyl sulfinyl, substituted or unsubstituted alkenylsulfinyl, substituted or unsubstituted alkynylsulfinyl, substituted or unsubstituted non-aromatic carbocyclylsulfinyl, substituted or unsubstituted aromatic carbocyclylsulfinyl, substituted or unsubstituted non-aromatic heterocyclylsulfinyl, substituted or unsubstituted aromatic heterocyclylsulfinyl, substituted or unsubstituted alkyl sulfonyl, substituted or unsubstituted alkenyl sulfonyl, substituted or unsubstituted alkynylsulfonyl, substituted or unsubstituted aromatic carbocyclylsulfonyl, substituted or unsubstituted aromatic carbocyclylsulfonyl, substituted or unsubstituted non-aromatic heterocyclylsulfonyl or substituted or unsubstituted aromatic heterocyclylsulfonyl,
R$^{5a}$ is hydrogen, halogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy,
R$^{5b}$ is halogen, substituted or unsubstituted alkyl, substituted or unsubstituted alkenyl, substituted or unsubstituted alkynyl, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted alkyloxy, substituted or unsubstituted alkenyloxy, substituted or unsubstituted alkynyloxy, substituted or unsubstituted non-aromatic carbocyclyloxy, substituted or unsubstituted aromatic carbocyclyloxy, substituted or unsubstituted non-aromatic heterocyclyloxy or substituted or unsubstituted aromatic heterocyclyloxy, or
R$^{4b}$ and R$^{5a}$ may be taken together to form a bond, R$^{5b}$ may be taken together with the substituent on R$^1$ to form substituted or unsubstituted non-aromatic carbocycle or substituted or unsubstituted non-aromatic heterocycle, or R$^{4b}$ and R$^{5b}$ may be taken together to form substituted or unsubstituted non-aromatic carbocycle or substituted or unsubstituted non-aromatic heterocycle,
provided that
(i) a compound wherein R$^1$ is substituted or unsubstituted phenyloxymethyl or substituted or unsubstituted pyridyloxymethyl, R$^2$ is hydrogen, R$^{5a}$ is hydrogen or substituted or unsubstituted methyl, and $R^{5b}$ is substituted or unsubstituted methyl, (ii) a compound wherein $R^3$ is hydrogen or unsubstituted methyl, and either one of $R^{5a}$ and $R^{5b}$ or each of them are each independently unsubstituted methyloxy or unsubstituted ethyloxy, and (iii) a compound represented as follows:

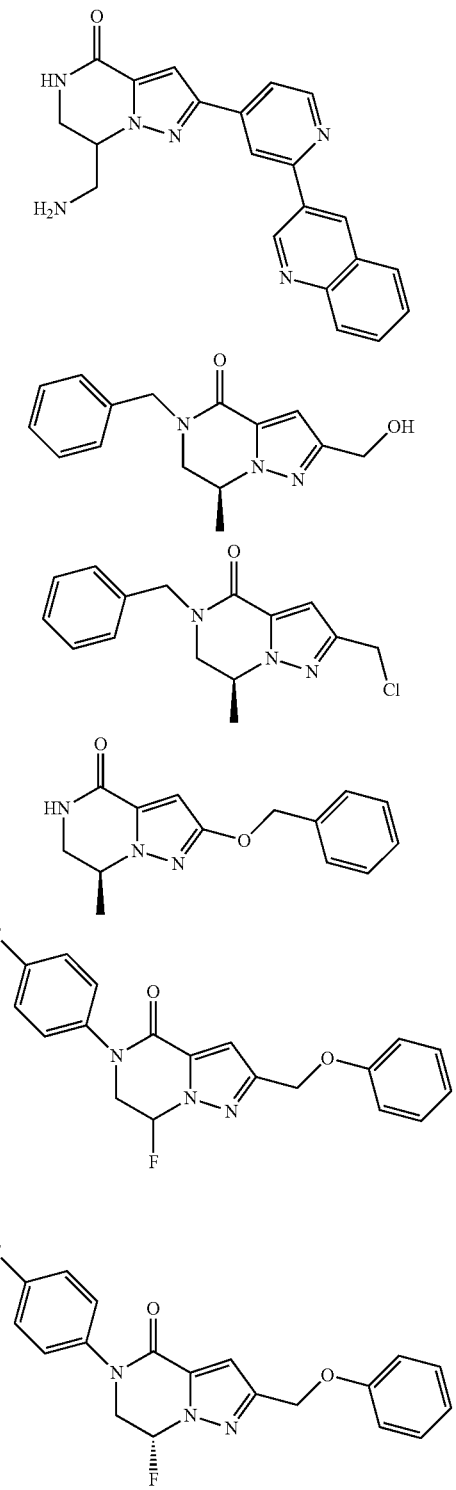

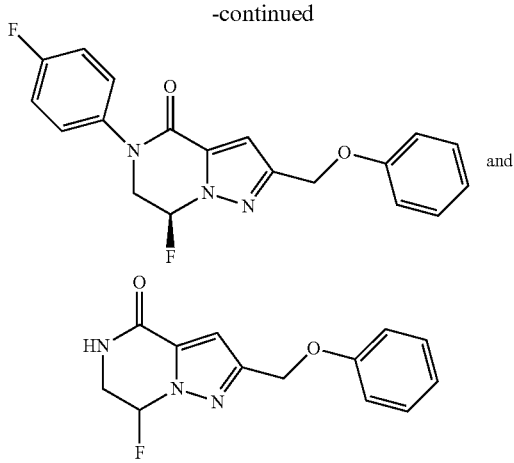

are excluded.

2. The compound according to claim 1, wherein $R^1$ is substituted phenyl, wherein the substituent(s) is(are) each dependently one or more substituent(s) selected from halogen, cyano, formyl, carboxy, trihaloalkyl, cyanoalkyl, hydroxyalkyl, alkenyl, alkyloxy, trihaloalkyloxy, alkyloxyalkyl, alkylcarbamoylalkyl, alkylaminoalkyl, dialkylaminoalkyl, amino, alkylamino, dialkylamino, cyanoalkylamino, trihaloalkylamino, alkylcarbonylamino, monohaloalkylcarbonylamino, trihaloalkylcarbonylamino, non-aromatic carbocyclylcarbonylamino, hydroxyalkylcarbonylamino, alkyloxycarbonylamino, alkyloxyalkylcarbonylamino, alkylaminocarbonylamino, dialkylaminocarbonylamino, alkylsulfonylamino, aromatic heterocyclylamino, trihaloalkylcarbamoyl, alkyloxyalkylcarbamoyl, pentafluorothio and aromatic carbocycly, or a pharmaceutically acceptable salt thereof.

3. The compound according to claim 1, wherein $R^3$ is alkyl substituted with one or more substituent(s) selected from the Substituent group A",
wherein the Substituent group A" consists of hydroxy, carboxy, substituted or unsubstituted alkyloxy, substituted or unsubstituted alkenyloxy, substituted or unsubstituted alkynyloxy, substituted or unsubstituted non-aromatic carbocyclyl, substituted or unsubstituted aromatic carbocyclyl, substituted or unsubstituted non-aromatic heterocyclyl, substituted or unsubstituted aromatic heterocyclyl, substituted or unsubstituted aromatic carbocyclyloxy, substituted or unsubstituted alkyl carbonyl, substituted or unsubstituted alkenylcarbonyl, substituted or unsubstituted alkynyl carbonyl, substituted or unsubstituted aromatic carbocyclyl carbonyl, substituted or unsubstituted non-aromatic carbocyclylcarbonyl, substituted or unsubstituted aromatic heterocyclylcarbonyl, substituted or unsubstituted non-aromatic heterocyclylcarbonyl, substituted or unsubstituted alkyloxycarbonyl, substituted or unsubstituted amino, substituted or unsubstituted carbamoyl and substituted or unsubstituted sulfamoyl,
alkenyl substituted with one or more substituent(s) selected from the Substituent group A", substituted or unsubstituted aromatic carbocyclyl or substituted or unsubstituted aromatic heterocyclyl,
or a pharmaceutically acceptable salt thereof.

4. The compound according to claim 3, wherein the substituent(s) selected from the Substituent group A" is(are) hydroxy, carboxy, aromatic carbocyclyl optionally substituted with one or more substituent(s) selected from the Substituent group α", non-aromatic heterocyclyl optionally substituted with one or more substituent(s) selected from the Substituent group α", aromatic heterocyclyl optionally substituted with carboxy, carbamoyl optionally substituted with one or more substituent(s) selected from the Substituent group β", carbonyl optionally substituted with one or more substituent(s) selected from the Substituent group γ" and amino optionally substituted with one or more substituent(s) selected from the Substituent group δ", wherein the Substituent group α" consists of hydroxy, carboxy, cyano, alkyl, hydroxyalkyl, carboxyalkyl, carboxyalkyl, cyanoalkyl, carbamoyl, alkyloxycarbonyl, alkyloxycarbonylalkyl, aromatic carbocyclylsulfonylalkyl, alkyloxy, alkylcarbonyloxy, alkylaminoalkyloxy, dialkylaminoalkyloxy, aromatic carbocyclyloxy, alkylcarbonyl, hydroxy non-aromatic heterocyclyl carbonyl, alkylcarbonylamino, alkyl sulfonyl and non-aromatic heterocyclylsulfonyl, the Substituent group β" consists of alkyl, cyanoalkyl, dicyanoalkyl, carboxyalkyl, hydroxyalkyl, di(hydroxy)alkyl, trihalo(hydroxy)alkyl, hydroxyalkyloxyalkyl, aromatic carbocyclyl alkyl, aromatic carbocyclyl(cyano)alkyl, hydroxy aromatic carbocyclyl alkyl, aromatic heterocyclylalkyl, hydroxy aromatic heterocyclylalkyl, aromatic carbocyclylalkyl (carboxy), oxo non-aromatic heterocyclylalkyl, hydroxyalkyl non-aromatic heterocyclylalkyl, carboxyalkyl(alkyl), alkylaminoalkyl, dialkylaminoalkyl, alkylaminoalkyl(alkyl), carbamoylalkyl, alkylcarbamoylalkyl, dialkylcarbamoylalkyl, carboxy non-aromatic carbocyclyl alkyl, aromatic carbocyclyl (carboxy) alkyl, aromatic carbocyclyl(hydroxy)alkyl, carboxy aromatic carbocyclylalkyl, carboxy aromatic carbocyclyl, carboxyalkyl aromatic carbocyclyl, cyano non-aromatic carbocyclyl, hydroxy non-aromatic carbocyclyl, carboxy non-aromatic carbocyclyl, aromatic heterocyclyl, non-aromatic carbocyclyl, aromatic carbocyclyl, carboxy aromatic carbocyclyl, alkyloxycarbonyl non-aromatic carbocyclyl and alkyloxycarbonyl, the Substituent group γ" consists of alkyl, alkyloxy, non-aromatic heterocyclylalkyloxy, carbamoyl aromatic carbocyclyl, non-aromatic carbocyclyl, carboxy aromatic heterocyclyl, non-aromatic heterocyclyl, hydroxy non-aromatic heterocyclyl, cyano non-aromatic heterocyclyl, alkyl non-aromatic heterocyclyl, dialkyl non-aromatic heterocyclyl, hydroxyalkyl non-aromatic heterocyclyl, hydroxyalkyloxy non-aromatic heterocyclyl, carboxyalkyl non-aromatic heterocyclyl, aromatic carbocyclylalkyl non-aromatic heterocyclyl, non-aromatic heterocyclylalkyl non-aromatic heterocyclyl, non-aromatic heterocyclylcarbonyl non-aromatic heterocyclyl, alkyloxycarbonyl non-aromatic heterocyclyl, carboxy non-aromatic heterocyclyl, carbamoyl non-aromatic heterocyclyl, cyanoalkylcarbamoyl non-aromatic carbocyclyl, cyano non-aromatic carbocyclylcarbamoyl non-aromatic heterocyclyl, alkylamino non-aromatic heterocyclyl, dialkyl amino non-aromatic heterocyclyl, oxo non-aromatic heterocyclyl and aromatic carbocyclyl non-aromatic heterocyclyl, the Substituent group δ" consists of alkyl, carboxyalkyl, alkylcarbonyl, hydroxyalkylcarbonyl, cyanoalkylcarbonyl and alkyloxycarbonyl, or a pharmaceutically acceptable salt thereof.

5. The compound according to claim 1, wherein $R^{4a}$ and $R^{4b}$ are hydrogen, or a pharmaceutically acceptable salt thereof.

6. The compound according to claim 1, wherein $R^{4b}$ and $R^{5b}$ are taken together to form substituted or unsubstituted non-aromatic carbocycle or substituted or unsubstituted non-aromatic heterocycle, or a pharmaceutically acceptable salt thereof.

7. The compound according to claim 1, wherein $R^{5a}$ is hydrogen, substituted or unsubstituted alkyl, substituted or unsubstituted alkenyl or substituted or unsubstituted alkynyl, $R^{5b}$ is substituted or unsubstituted alkyl, substituted or unsubstituted alkenyl or substituted or unsubstituted alkynyl, or a pharmaceutically acceptable salt thereof.

8. The compound according to claim 1, wherein $R^{5a}$ is hydrogen or substituted or unsubstituted alkyl, $R^{5b}$ is substituted or unsubstituted C2-C10 alkyl, or a pharmaceutically acceptable salt thereof.

9. The compound according to claim 1, wherein $R^{5a}$ is hydrogen, $R^{5b}$ is substituted or unsubstituted C2-C10 alkyl, or a pharmaceutically acceptable salt thereof.

10. The compound according to claim 1, wherein $R^{5a}$ is hydrogen, $R^{5b}$ is substituted alkyl, wherein the substituent(s) is(are) each dependently selected from the group consisting of hydroxy, halogen, alkyloxy optionally substituted with halogen, aromatic carbocyclyl and aromatic carbocyclylalkyloxy, or a pharmaceutically acceptable salt thereof.

11. A pharmaceutical composition comprising the compound according to claim 1 or a pharmaceutically acceptable salt thereof.

* * * * *